US011555033B2

(12) United States Patent
Drummond et al.

(10) Patent No.: US 11,555,033 B2
(45) Date of Patent: Jan. 17, 2023

(54) OXAZOLIDINONE COMPOUNDS, LIPOSOME COMPOSITIONS COMPRISING OXAZOLIDINONE COMPOUNDS AND METHOD OF USE THEREOF

(71) Applicant: Akagera Medicines, Inc., Boxford, MA (US)

(72) Inventors: Daryl C. Drummond, Lincoln, MA (US); Suresh K. Tipparaju, Arlington, MA (US); Charles O. Noble, San Francisco, CA (US); Alexander Koshkaryev, Newton, MA (US); Dmitri B. Kirpotin, San Francisco, CA (US)

(73) Assignee: Akagera Medicines, Inc., Boxford, MA (US)

(*) Notice: Subject to any disclaimer, the term of this patent is extended or adjusted under 35 U.S.C. 154(b) by 0 days.

(21) Appl. No.: 17/351,631

(22) Filed: Jun. 18, 2021

(65) Prior Publication Data
US 2021/0403463 A1 Dec. 30, 2021

Related U.S. Application Data

(60) Provisional application No. 63/040,810, filed on Jun. 18, 2020.

(51) Int. Cl.
| | | |
|---|---|---|
| *C07D 413/14* | (2006.01) |
| *A61K 47/02* | (2006.01) |
| *A61K 47/28* | (2006.01) |
| *A61K 9/127* | (2006.01) |
| *A61K 47/26* | (2006.01) |
| *A61K 47/24* | (2006.01) |

(52) U.S. Cl.
CPC ............ *C07D 413/14* (2013.01); *A61K 9/127* (2013.01); *A61K 9/1271* (2013.01); *A61K 9/1277* (2013.01); *A61K 47/02* (2013.01); *A61K 47/24* (2013.01); *A61K 47/26* (2013.01); *A61K 47/28* (2013.01)

(58) Field of Classification Search
CPC ...... C07D 413/14; A61K 47/26; A61K 9/127; A61K 9/1271; A61K 9/1277; A61K 47/24; A61K 47/28
USPC ....................................................... 548/229
See application file for complete search history.

(56) References Cited

U.S. PATENT DOCUMENTS

| | | | |
|---|---|---|---|
| 5,316,771 | A | 5/1994 | Barenholz et al. |
| 5,800,833 | A | 9/1998 | Hope et al. |
| 6,110,491 | A | 8/2000 | Kirpotin |
| 6,689,779 | B2 | 2/2004 | Lee et al. |
| 7,498,350 | B2 | 3/2009 | Gravestock et al. |
| 7,744,921 | B2 | 6/2010 | Tardi et al. |
| 7,759,351 | B2 | 7/2010 | Cano et al. |
| 7,816,379 | B2 | 10/2010 | Rhee et al. |
| 8,147,867 | B2 | 4/2012 | Hong et al. |
| 8,349,360 | B2 | 1/2013 | Bally et al. |
| 8,420,676 | B2 | 4/2013 | Rhee et al. |
| 9,549,939 | B2 | 1/2017 | Weers |
| 2004/0009126 | A1 | 1/2004 | Pilkiewicz et al. |
| 2008/0021071 | A1 | 1/2008 | Gravestock et al. |
| 2010/0022772 | A1 | 1/2010 | Wu et al. |
| 2018/0369143 | A1 | 12/2018 | Bally et al. |
| 2020/0078345 | A1 | 3/2020 | Rhee et al. |

FOREIGN PATENT DOCUMENTS

| | | |
|---|---|---|
| WO | 1990001405 | 2/1990 |
| WO | 1994001110 A1 | 1/1994 |
| WO | 1995025106 A1 | 9/1995 |
| WO | 2002006278 A1 | 1/2002 |
| WO | 2003007870 A2 | 1/2003 |
| WO | 2003097059 A1 | 11/2003 |
| WO | 20040014392 A1 | 2/2004 |
| WO | 2004056818 A1 | 7/2004 |
| WO | 2004099199 A1 | 11/2004 |
| WO | 2005058886 A1 | 6/2005 |
| WO | 2005082899 A1 | 9/2005 |
| WO | 2005116022 A1 | 12/2005 |
| WO | 2006035283 A1 | 4/2006 |
| WO | 2006051408 A1 | 5/2006 |
| WO | 2010036000 A2 | 4/2010 |

(Continued)

OTHER PUBLICATIONS

International Search Report and Written Opinion in PCT International Application No. PCT/US2021/038131 dated Oct. 1, 2021.
Allen et al., "Pharmacokinetics and Anti-Tumor Activity of Vincristine Encapsulated in Sterically Stabilized Liposomes", Int. J. Cancer, vol. 62, No. 2, pp. 199-204, Jul. 17, 1995.
Bigelow et al., "Pharmacodynamic Correlates of Linezolid Activity and Toxicity in Murine Models of Tuberculosis", Journal of Infectious Diseases, vol. 223, pp. 1855-1864, Jun. 2021.
Cheng et al., "Multiplex PCR Amplimer Conformation Analysis for Rapid Detection of gyrA Mutations in Fluoroquinolone-Resistant *Mycobacterium tuberculosis* Clinical Isolates", Antimicrobial Agents and Chemotherapy, vol. 48, No. 2, pp. 596-601, Feb. 2004.

(Continued)

*Primary Examiner* — Kahsay Habte
(74) *Attorney, Agent, or Firm* — Greenberg Traurig, LLP; David J. Dykeman; Natalie Salem

(57) ABSTRACT

Compositions and methods for the treatment of tuberculosis, as well as other mycobacterial and gram positive bacterial infections are disclosed. These compositions contain a highly potent and selective oxazolidinone encapsulated with high efficiency to maximize dosing potential of low toxicity drugs, and are stable in the presence of plasma. The compositions are long circulating and retain their encapsulated drug while in the circulation following intravenous dosing to allow for efficient accumulation at the site of the bacterial or mycobacterial infection. The high doses that can be achieved when combined with the long circulating properties and highly stable retention of the drug allow for a reduced frequency of administration when compared to daily or twice daily administrations of other drugs typically utilized to treat these infections.

26 Claims, 30 Drawing Sheets

(56) References Cited

FOREIGN PATENT DOCUMENTS

| | | | |
|---|---|---|---|
| WO | 2010042887 A2 | 4/2010 | |
| WO | 2010091131 A1 | 8/2010 | |
| WO | 2010138649 A1 | 12/2010 | |
| WO | 2012033952 A1 | 3/2012 | |
| WO | 2013044845 A1 | 4/2013 | |
| WO | 2016009401 A2 | 1/2016 | |
| WO | 2016041505 A1 | 3/2016 | |
| WO | 2016041508 A1 | 3/2016 | |
| WO | 2016058467 A1 | 4/2016 | |
| WO | 2016088100 A1 | 6/2016 | |
| WO | 2016088101 A1 | 6/2016 | |
| WO | 2016088102 A1 | 6/2016 | |
| WO | 2016088103 A1 | 6/2016 | |
| WO | 2017066964 A1 | 4/2017 | |
| WO | 2017070024 A1 | 4/2017 | |
| WO | 2017076285 A1 | 5/2017 | |
| WO | 2017099530 A1 | 6/2017 | |
| WO | 2017143112 A3 | 8/2017 | |
| WO | 2018170664 A1 | 9/2018 | |
| WO | 2018175185 A1 | 9/2018 | |
| WO | 2020021468 A1 | 1/2020 | |
| WO | 2020147504 A1 | 7/2020 | |
| WO | 2021188606 A1 | 9/2021 | |

OTHER PUBLICATIONS

Collins et al., "Microplate Alamar Blue Assay versus BACTEC 460 System for High-Throughput Screening of Compounds against *Mycobacterium tuberculosis* and *Mycobacterium avium*", Antimicrobial Agents and Chemotherapy, vol. 41, No. 5, pp. 1004-1009, May 1997.

Conradie et al., "Treatment of Highly Drug-Resistant Pulmonary Tuberculosis", N Engl J Med, vol. 382, No. 10, pp. 893-902, Mar. 2020.

Doxil © drug information package insert, updated Aug. 2019.

Driver et al., "Evaluation of a Mouse Model of Necrotic Granuloma Formation Using C3HeB/FeJ Mice for Testing of Drugs against *Mycobacterium tuberculosis*", Antimicrobial Agents and Chemotherapy, vol. 56, No. 6, pp. 3181-3195, Jun. 2012.

Drummond et al. "Development of a Highly Active Nanoliposomal Irinotecan Using a Novel Intraliposomal Stabilization Strategy" Cancer Res, vol. 66, No. 6, pp. 3271-3277, Mar. 15, 2006.

Drummond et al., "Pharmacokinetics and In Vivo Dug Release Rates in Liposomal Nanocarrier Development", J. Pharm Sci, vol. 97, No. 11, pp. 4696-4740, Nov. 2008.

Drummond, et al. "Intraliposomal Trapping Agents for Improving in Vivo Liposomal Drug Formulation Stability" Liposome Technology, Third Edition (Ed. Gregoriadis, G.) vol. 2, p. 149-168, 2006.

Flanagan et al. , "Nonclinical and Pharmacoinetic Assessments to Evaluate the Potential of Tedizolid and Linezolid to Affect Mitochondrial Function", Antimicrob Agents Chemotherapy, vol. 59, No. 1, pp. 178-185, Jan. 2015.

Gregoriadis (editor), Liposome Technology, vol. 1-3, 1st edition, 1983; 2nd edition, 1993; 3rd edition, 2006; CRC Press, Boca Raton, Florida.

Gruppo et al., "Rapid Microbiologic and Pharmacologic Evaluation of Experimental Compounds against *Mycobacterium tuberculosis*", Antimicrob Agents Chemotherapy, vol. 50, No. 4, pp. 1245-1250, Apr. 2006.

Irwin et al., "Presence of Multiple Lesion Types with Vastly Different Microenvironments in C3HeB/FeJ Mice Following Aerosol Infection with *Mycobacterium tuberculosis*", Dis Model Meeh, vol. 8, pp. 591-602, Mar. 2015.

Ishida et al., "Accelerated Blood Clearance of PEGylated Liposomes Following Preceding Liposome Injection: Effects of Lipid Dose and PEG Surface-Density and Chain Length of the First-Dose Liposomes", Journal of Controlled Release vol. 105, pp. 305-317, Apr. 2005.

Lanoix et al., "Heterogeneous Disease Progression and Treatment Response in a C3HeB/FeJ Mouse Model of Tuberculosis", Disease Models & Mechanisma, vol. 8, pp. 603-610, Mar. 2015.

Laverman et al., "Factors Affecting the Accelerated Blood Clearance of Polyethylene Glycol-Liposomes Upon Repeated Injection", JPET, vol. 298, No. 2, pp. 607-612, 2001.

Lenaerts et al., "Preclinical Testing of the Nitroimidazopyran PA-824 for Activity against *Mycobacterium tuberculosis* in a Series of In Vitro and In Vivo Models", AAC, vol. 49, No. 6, pp. 2294-2301, Jun. 2005.

Obregón-Henao et al. "Susceptibility of *Mycobacterium abscessus* to Antimycobacterial Drugs in Preclinical Models" Antimicrobial Agents and Chemotherapy, vol. 59, No. 11, pp. 6904-6912, Nov. 2015.

Palanisamy et al., "Disseminated Disease Severity as a Measure of Virulence of *Mycobacterium tuberculosis* in the Guinea Pig Model", Tuberculosis, vol. 88, Issue 4, pp. 295-306, Jul. 2008.

Reddy et al., "In Vitro Interactions Between New Antitubercular Drug Candidates SQ109 and TMC207", Antimicrob Agents Chemother., vol. 54, No. 7, pp. 2840-2846, Jul. 2010.

Renslo, Adam R., "Antibacterial Oxazolidinones: Emerging Structure-Toxicity Relationships", Expert Review Anti Infect Therapy, vol. 8, No. 5, pp. 565-574, 2010.

Ruiz et al., "In Vitro Activity of Tedizolid Against *Mycobacterium tuberculosis*", Antimicrobial Agents and Chemotherapy, vol. 63, Issue 4, pp. 1-3, Apr. 2019.

Santini et al. , "Linezolid-Induced Lactic Acidosis: the Thin Line Between Bacterial and Mitochondrial Ribosomes", Exp. Opinion on Drug Safety, vol. 16, No. 7, pp. 833-843, Jun. 2017.

Shirley et al., "Amikacin Liposome Inhalation Suspension: a Review in *Mycobacterium avium* Complex Lung Disease", Drugs, vol. 79, No. 5, pp. 555-562, Apr. 2019.

Torrea et al., Bedaquiline Susceptability Testing of *Mycobacterium tuberculosis* in an Automated Liquid Culture System, J Antimicrob Chemother., vol. 70, pp. 2300-2305, Aug. 2015.

Tweed et al., "Bedaquiline, Moxifloxacin, Pretomanid, and Pyrazinamide During the First 8 Weeks of Treatment of Patients with Drug-Susceptible or Drug-Resistant Pulmonary Tuberculosis: a Multicentre, Open-Label, Partially Randomised, Phase 2B Trial", Lancet Respir Med, vol. 7, No. 12, pp. 1048-1058, Dec. 2019.

Non-Final Office Action in U.S. Appl. No. 17/738,216 dated Jul. 27, 2022.

Response to Non-Final Office Action in U.S. Appl. No. 17/738,216 dated Jul. 27, 2022, filed Aug. 18, 2022.

Final Office Action in U.S. Appl. No. 17/738,216 dated Aug. 26, 2022.

OXAZOLIDINONE COMPOUNDS, LIPOSOME COMPOSITIONS COMPRISING OXAZOLIDINONE COMPOUNDS AND METHOD OF USE THEREOF

RELATED APPLICATIONS

This application claims priority to and the benefit of U.S. Application No. 63/040,810, filed Jun. 18, 2020, the entire contents of which is hereby incorporated herein by reference.

FIELD

The present disclosure relates to novel aminoalkyl oxazolidinone compounds, liposome compositions comprising novel aminoalkyl oxazolidinone compounds and use of the aminoalkyl oxazolidinone compounds in the treatment of *Mycobacterium tuberculosis* and other gram-positive bacterial infections.

BACKGROUND

Mycobacteria is a genus of bacteria responsible for tuberculosis (TB). According to the World Health Organization, worldwide, TB is one of the top 10 causes of death and the leading cause of death from a single infectious agent. Rifampicin is the most effective first-line drug to treat TB. However, there is a growing number of cases infected with *Mycobacterium tuberculosis* that is resistant to rifampicin. Multidrug-resistant tuberculosis (MDR-TB) is a form of TB caused by bacteria that do not respond to isoniazid and rifampicin.

SUMMARY

Compositions and methods for the treatment of tuberculosis, as well as other mycobacterial and gram positive bacterial infections are disclosed.

One aspect of the disclosure provides a compound of Formula I or pharmaceutically acceptable salts thereof:

Formula I

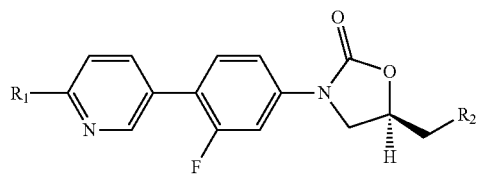

wherein $R_2$ is an amine ($NH_2$) or an acetamide ($NHCOCH_3$), and wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In some embodiments, a compound of Formula 1a is provided:

Formula 1a

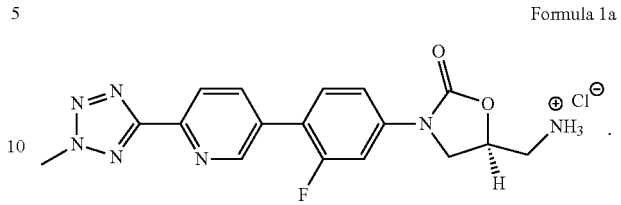

In some embodiments, a compound of Formula 1b is provided:

Formula 1b

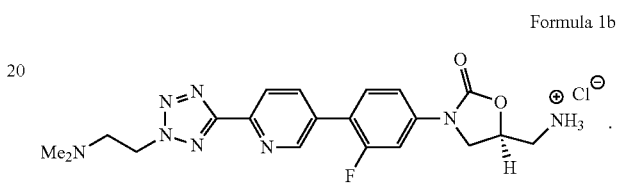

In some embodiments, a compound of Formula 1c or pharmaceutically acceptable salts thereof is provided:

Formula 1c

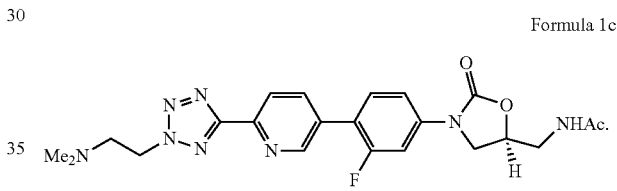

In some embodiments, a compound of Formula 1d or pharmaceutically acceptable salts thereof is provided:

Formula 1d

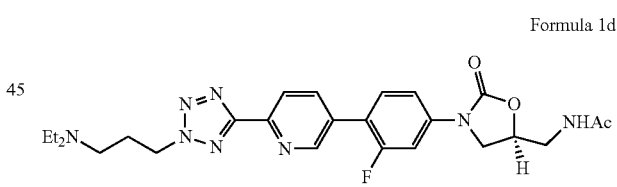

In some embodiments, a compound of Formula 1e is provided:

Formula 1e

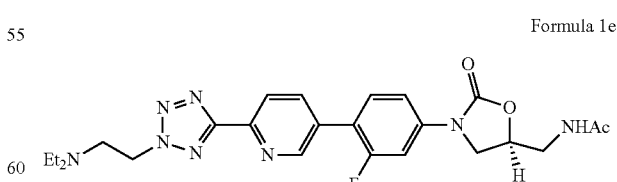

In some embodiments, the compound has a Selectivity Index (SI) index for Erd/HepG2 and H37Rv/HepG2 ranges from 100 to 1700.

In some embodiments, the compound has a SI index for Erd/HepG2 and H37Rv/HepG2 ranges from 200 to 1700.

In some embodiments, the compound has a SI index for Erd/HepG2 and H37Rv/HepG2 ranges from 300 to 1700.

Another aspect of the disclosure provides a liposomal composition comprising liposome vesicles, the liposome vesicles comprising a compound of Formula I or pharmaceutically acceptable salts thereof therein

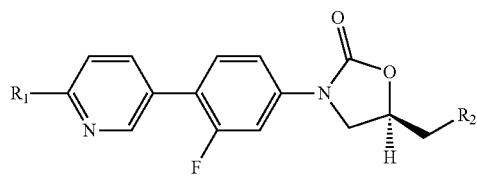

Formula I wherein $R_2$ is an amine ($NH_2$) or an acetamide ($NHCOCH_3$), and wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In some embodiments, a liposomal composition is provided comprising liposome vesicles, the liposome vesicles comprising a compound of Formula 1a:

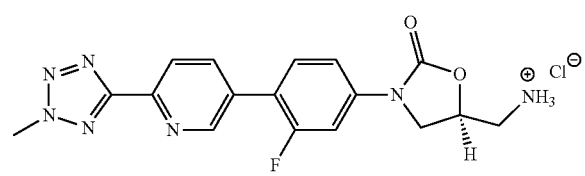

Formula 1a

In some embodiments, a liposomal composition is provided comprising liposomes vesicles, the liposome vesicles comprising a compound of Formula 1b:

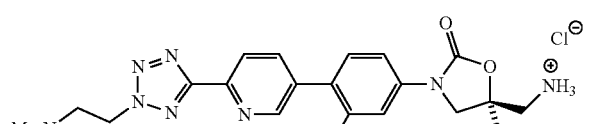

Formula 1b

In some embodiments, a liposomal composition is provided comprising liposomes vesicles, the liposome vesicles comprising a compound of Formula 1c or a pharmaceutically acceptable salt thereof:

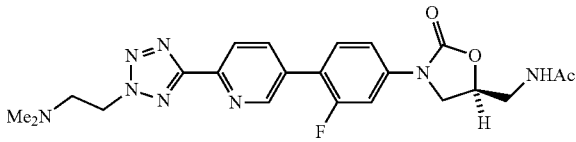

Formula 1c

In some embodiments, a liposomal composition is provided comprising liposomes vesicles, the liposome vesicles comprising a compound of Formula 1d:

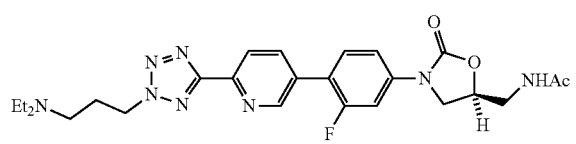

Formula 1d

In some embodiments, a liposomal composition is provided comprising liposomes vesicles, the liposome vesicles comprising a compound of Formula 1e:

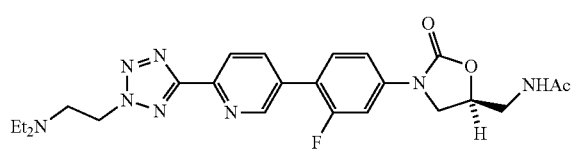

Formula 1e

In some embodiments, the liposome vesicles are in an aqueous medium.

In some embodiments, the compound is entrapped in the liposome vesicle with a trapping agent, wherein the trapping agent comprises a polyanion. In some embodiments, the trapping agent is triethylammonium sucrose octasulfate or ammonium sulfate. In some embodiments, the trapping agent is triethylammonium sucrose octasulfate. In some embodiments, the trapping agent is ammonium sulfate.

In some embodiments, the liposomal composition comprises a salt of the compound, wherein the salt is sulfate, citrate, sucrosofate, a salt with a phosphorylated or sulfated polyol, or a salt with a phosphorylated or sulfated polyanionic polymer. In some embodiments, the liposomal composition comprises a sulfate salt of the compound.

In some embodiments, the compound in the liposome vesicle has an aqueous solubility less than 1 mg/mL. In some embodiments, the compound in the liposome vesicle has an aqueous solubility less than 0.1 mg/mL.

In some embodiments, the liposome vesicle comprises a membrane comprising phosphatidylcholine and cholesterol. In some embodiments, the liposome vesicle comprises a membrane comprising phosphatidylcholine and cholesterol, wherein the membrane separates the inside of the liposome vesicles from the aqueous medium. In some embodiments, the phosphatidylcholine is distearoylphosphatidylcholine (DSPC) or hydrogenated soy phosphatidylcholine (HSPC). In some embodiments, the phosphatidylcholine to cholesterol molar ratios is from about 60:40 to 35:65. In some embodiments, the phosphatidylcholine to cholesterol molar ratio is from about 55:45 to about 35:65. In some embodiments, the phosphatidylcholine to cholesterol molar ratio is from about 50:50 to about 40:60.

In some embodiments, the phosphatidylcholine to cholesterol molar ratio is from about 50:50 to about 45:55.

In some embodiments, the membrane further comprises a polymer-conjugated lipid.

In some embodiments, the liposome vesicle comprises HSPC, cholesterol and polymer-conjugated lipid in a about 55:45:2.75 molar ratio.

In some embodiments, the polymer-conjugated lipid is PEG(Mol. weight 2,000)-distearoylglycerol (PEG-DSG) or PEG(Mol. weight 2,000)-distearoylphosphatidylethanolamine (PEG-DSPE).

In some embodiments, the liposomes in the liposome composition have Z-average particle size from about 80 to about 130 nm.

In some embodiments, the composition is a liquid pharmaceutical formulation for parenteral administration.

Other aspects of the disclosure relate to a method of treating bacterial infection, the method comprising administering to a subject in need thereof a therapeutically effective amount of the liposomal composition provided herein.

In some embodiments, the bacterial infection is *Mycobacterium tuberculosis* infection. In some embodiments, the compound in the liposome vesicle has a minimum inhibitory concentration (MIC) ranging from about 0.01 µg/ml to about 0.25 µg/ml. In some embodiments, the compound in the liposome vesicle has a minimum inhibitory concentration (MIC) ranging from about 0.01 µg/ml to about 0.1 µg/ml.

In some embodiments, the liposomal composition is administered parenterally.

In some embodiments, the method comprises administering simultaneously or sequentially one or more additional active agent. In some embodiments, the one or more active agents comprise bedaquiline, pretomanid, pyrazinamide, moxifloxacin, a pharmaceutically acceptable salt thereof or a combination thereof.

In some embodiments, the liposomal composition is administered once a week to once every six weeks.

In some embodiments, the percentage of compound remaining in blood is greater than 20% of the administered amount at 6 hours following administration to the subject in need thereof. In some embodiments, the percentage of compound remaining in blood is greater than 10% of the administered amount.

Aspects of the disclosure relate to method of making liposome composition comprising the steps of: (i) preparing the liposomes comprising phospholipid, cholesterol, and PEG-lipid, and having an interior space containing a trapping agent, in a medium substantially free from the trapping agent; (ii) contacting the liposomes with a compound of any one of claims 1 to 8 in an aqueous medium to effect encapsulation of the compound in the liposomes; (iii) removing unencapsulated compound; and (iv) providing the liposomes in a physiologically acceptable medium suitable for parenteral use.

BRIEF DESCRIPTION OF THE DRAWINGS

FIG. 2A shows the effect of the added drug-to-lipid (DL0) ratio, in grams of the drug per mole of liposome phospholipid (PhL), on the liposome payload, expressed as post-load drug-to-lipid ratio (DL). FIG. 2B shows the effect the DL0 ratio (drug-to-lipid input ratio) on liposome loading efficiency, calculated as percent of post-load DL relative to DL0.

FIG. 3A shows the effect the DL0 ratio on liposome payload for AKG-5, and AKG-16. FIG. 3B shows the effect the DL0 ratio on liposome loading efficiency for AKG-5, and AKG-16. FIG. 3C shows the effect the DL0 ratio on liposome payload for AKG-3. FIG. 3D shows the effect the DL0 ratio on liposome loading efficiency for AKG-3.

FIG. 4A shows the effect the DL0 ratio on liposome payload. FIG. 4B shows the effect the DL0 ratio on loading efficiency.

Figure 11A:
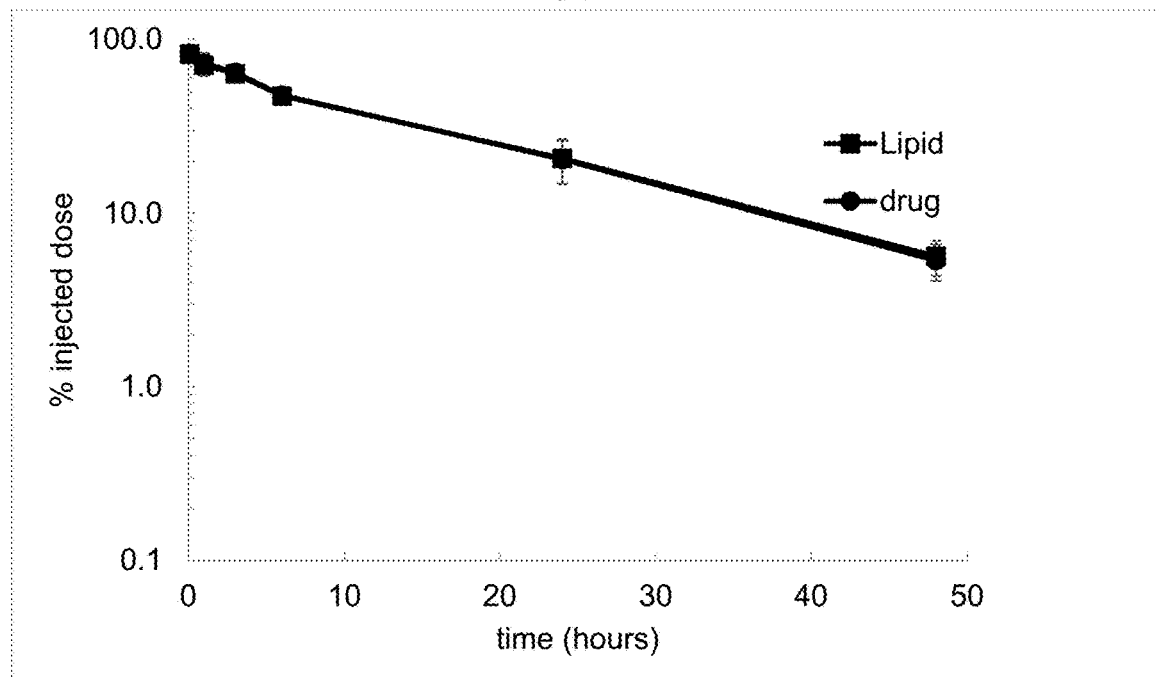
FIG. 11A, FIG. 11B, and FIG. 11C are graphs showing the plasma concentration versus time profiles of both lipid (using nonexchangeable DiIC18(3)-DS label), drug for liposomal AKG-28 (FIG. 11A) and liposomal AKG-38 (FIG.
Figure 11B:
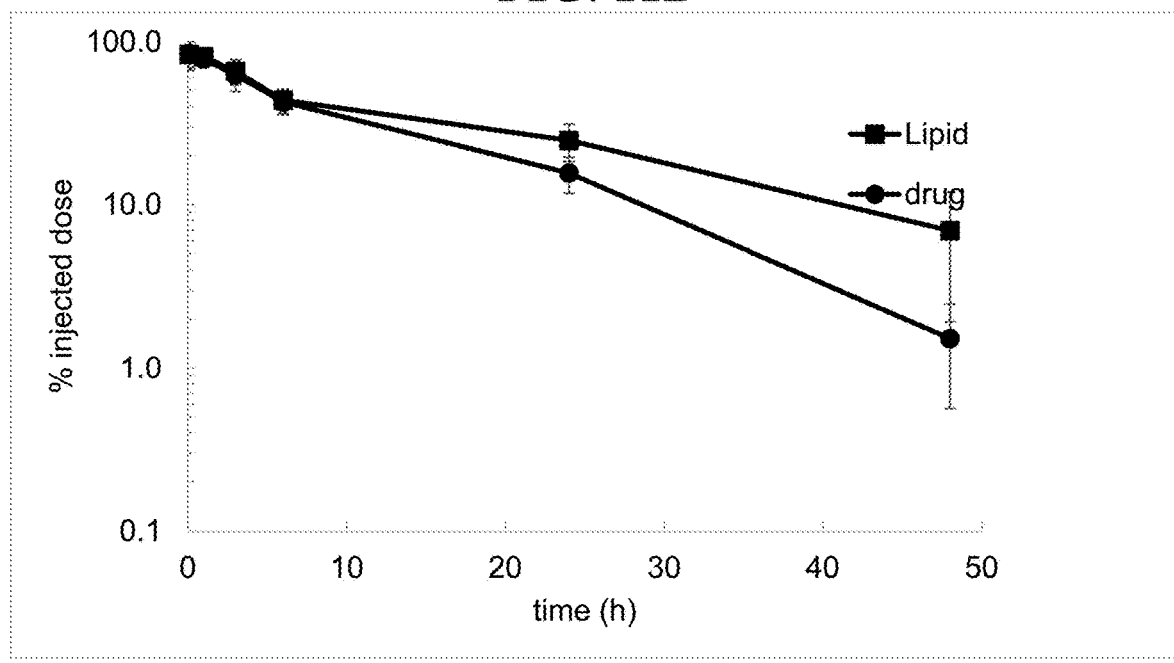
Figure 11C:
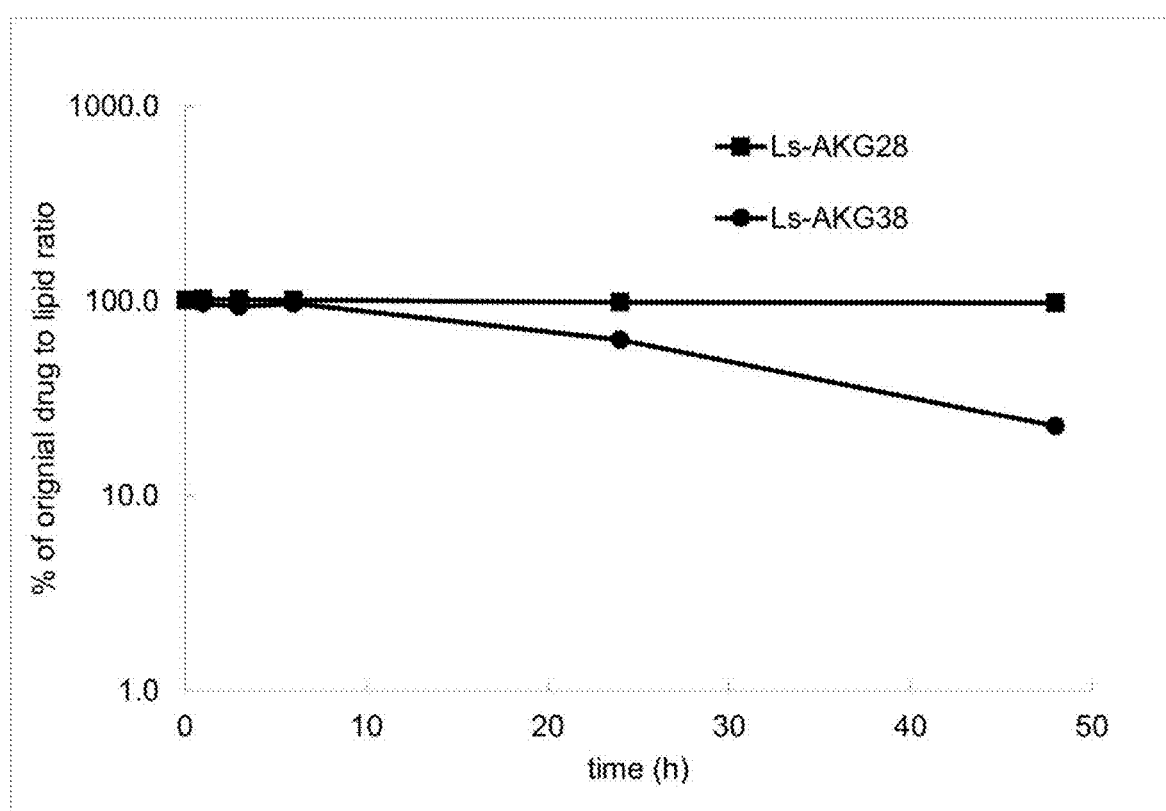

11B), and the change in plasma drug-to-lipid ratio, a measure of drug release rate from the liposomes, for both Ls-AKG28 and Ls-AKG38 (FIG. 11C) in CD-1 mice after single intravenous injection in CD-1 mice. The mean and SD are presented at each time point.

Figure 12:
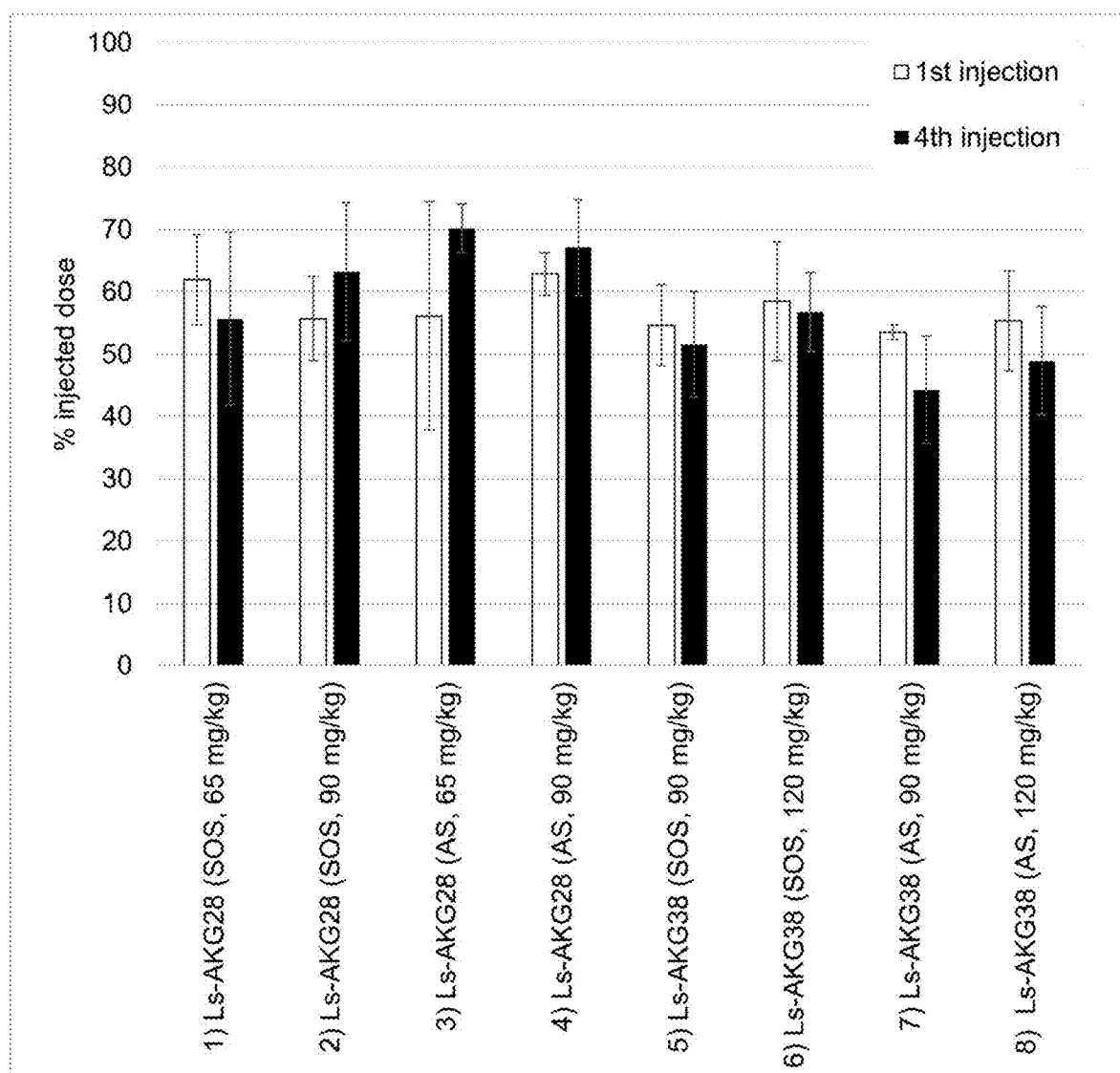

FIG. 12 is a graph showing the plasma drug concentration presented as % injected dose for Ls-AKG28 and Ls-AKG38 were compared were multiple formulations of liposomal AKG-28 and liposomal AKG-38 after the first and fourth weekly doses. Mice were injected with the indicated dose and formulation once per week for a total of 4 injections.

Figure 13A:
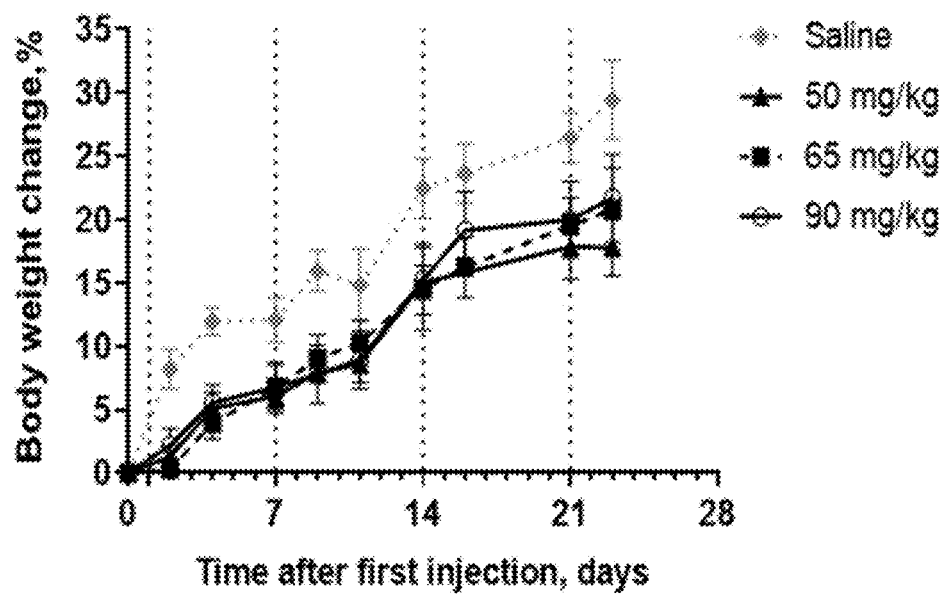

FIG. 13A is a graph showing the effect of Ls-AKG28 dose escalation on female CD-1 mice body weight over time.

Figure 13B:
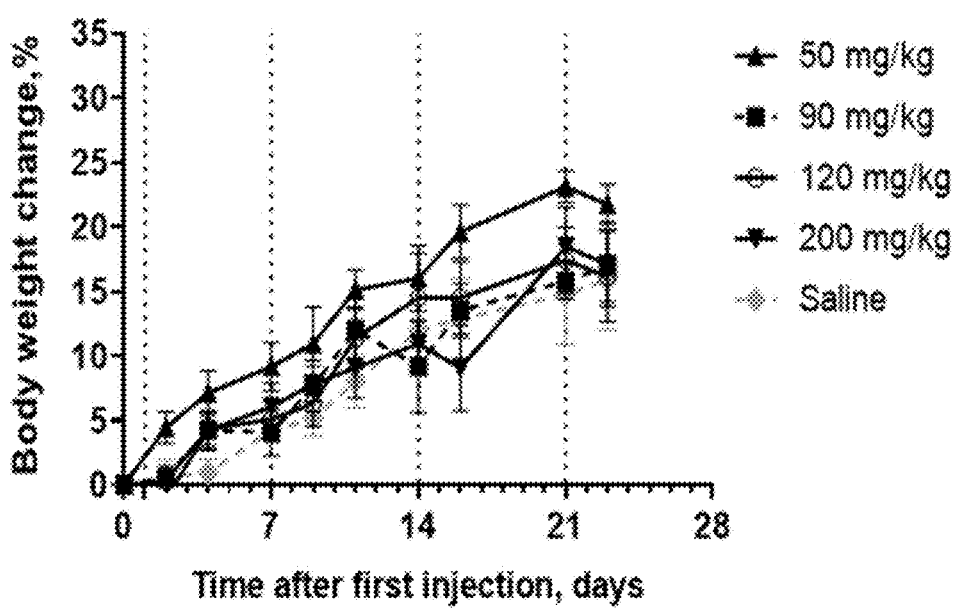

FIG. 13B is a graph showing the effect of Ls-AKG38 dose escalation on female CD-1 body weight in mice over time.

Figure 13C:
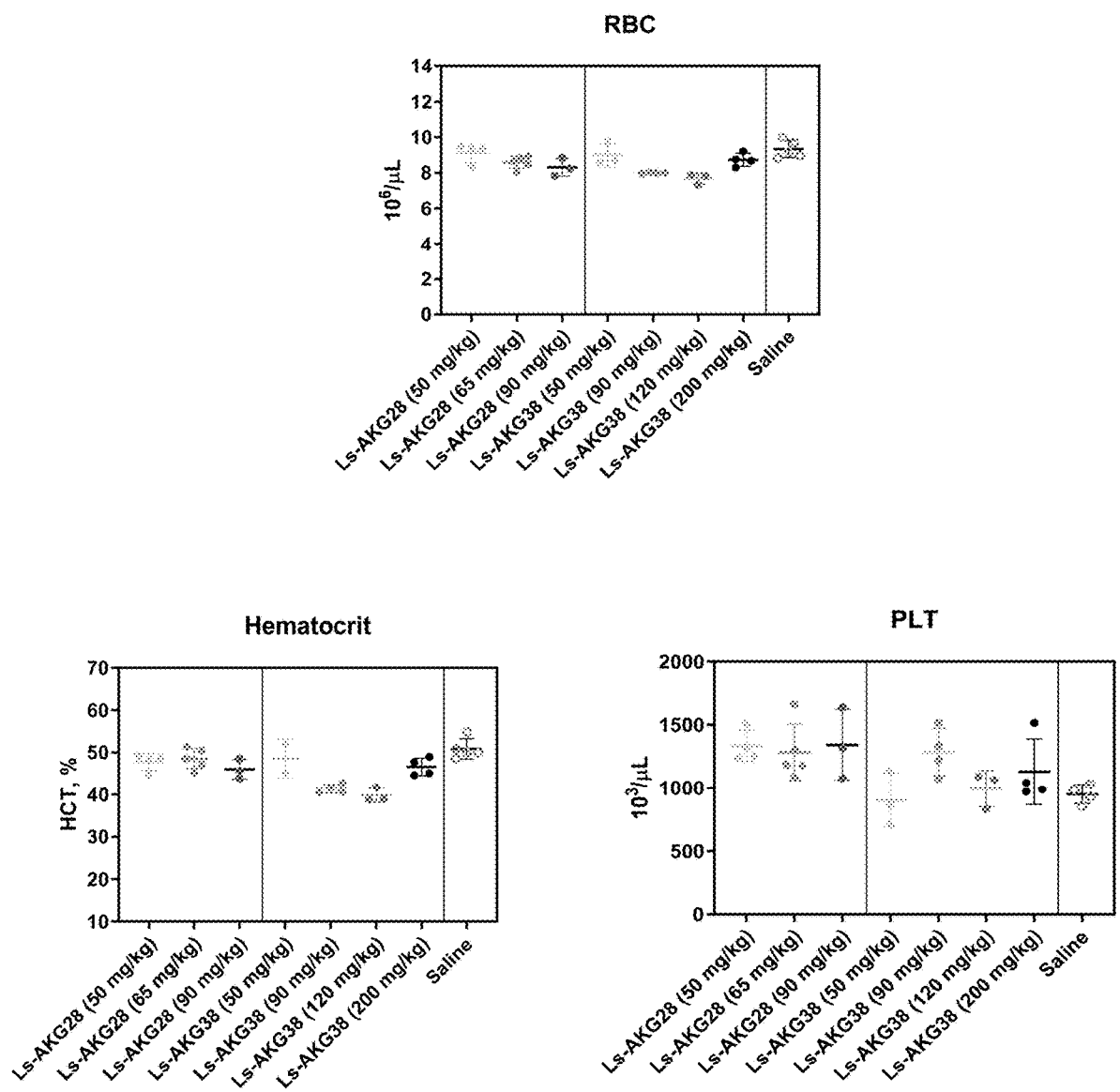
Figure 13C:
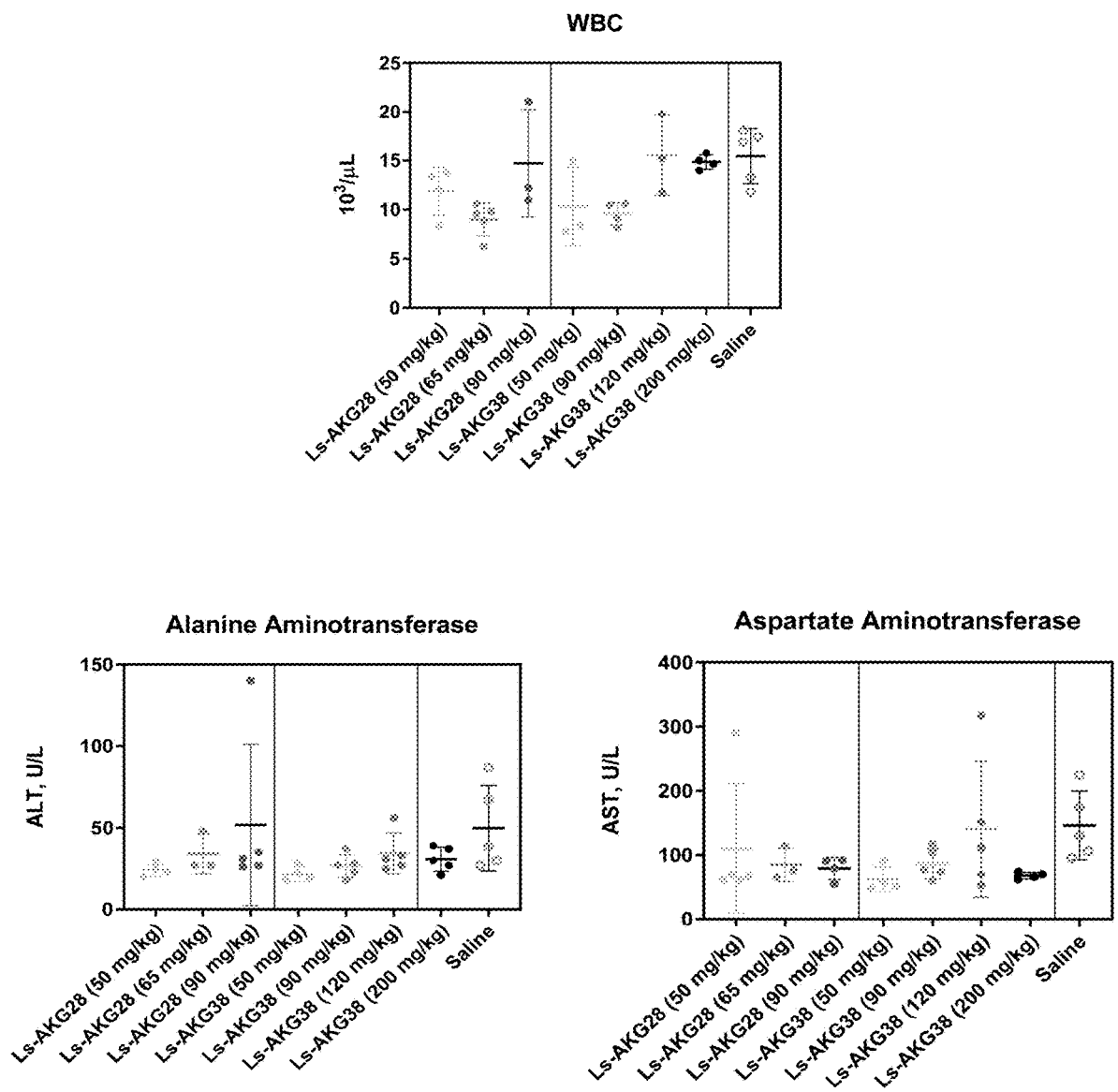

FIG. 13C are graphs showing the effects of Ls-AKG28 and Ls-AKG38 in combination with BP or BPM on hematology (RBC, HTC, PLT, WBC) and blood biochemistry (ALT, AST) parameters in female CD-1 mice.

Figure 13D:
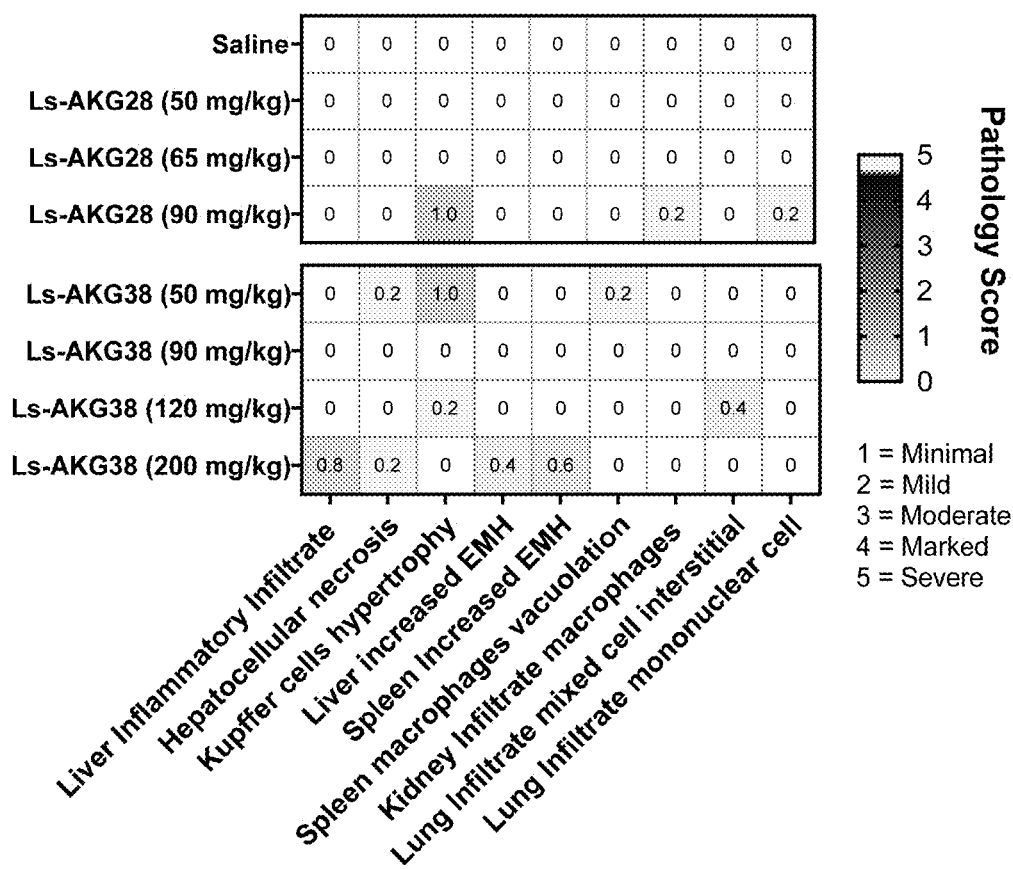

FIG. 13D is a heat map showing the effect of monotherapy Ls-AKG28 or Ls-AKG38 on tissue pathological findings in female CD-1 mice.

Figure 14A:
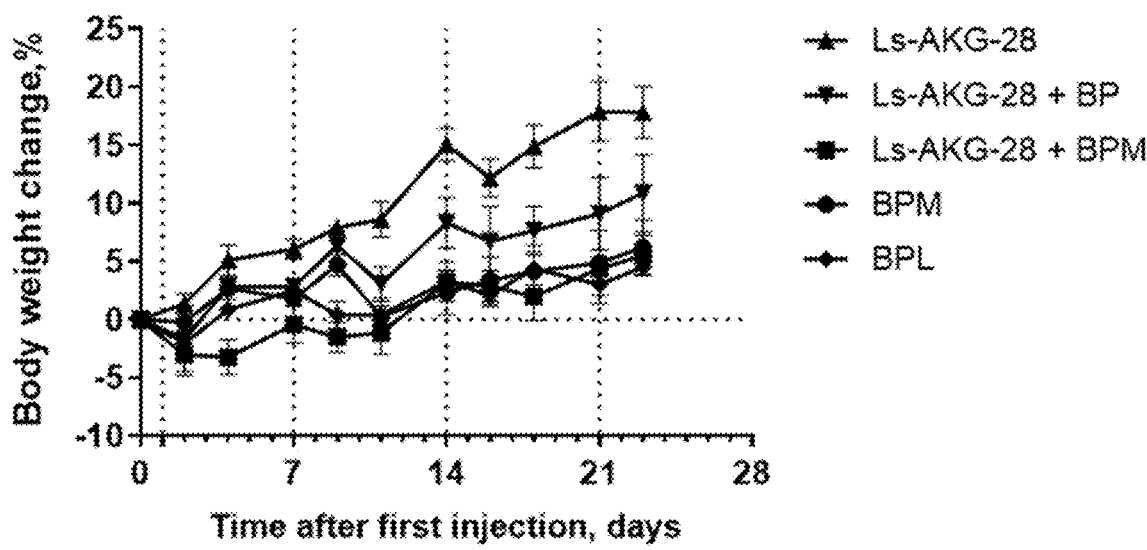

FIG. 14A is a graph showing the effect of Ls-AKG28 in combination with bedaquiline and pretomanid (BP) or bedaquiline, pretomanid, and moxifloxacin (BPM) on female CD-1 mice body weight over time.

Figure 14B:
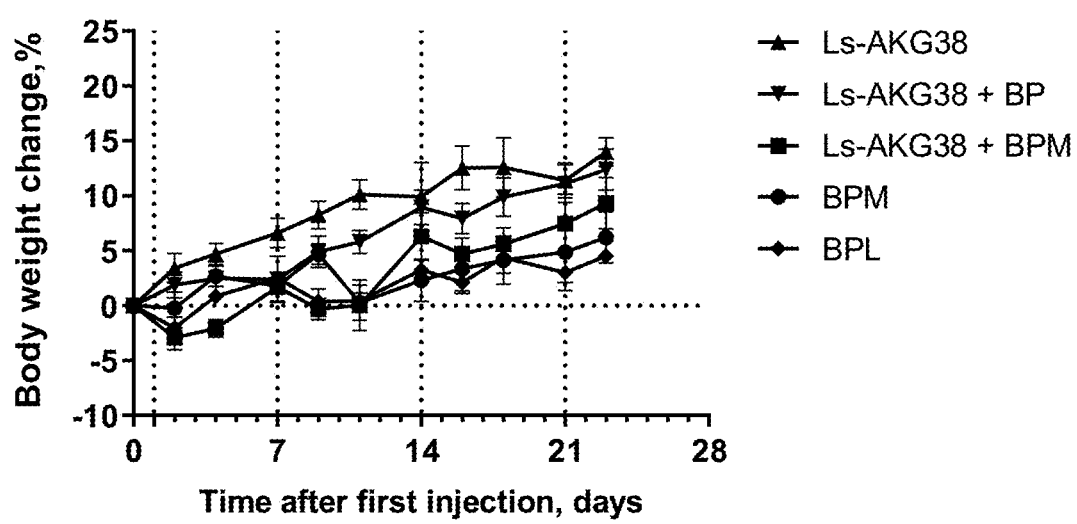

FIG. 14B is a graph showing the effect of Ls-AKG38 in combination with BP or BPM on female CD-1 mice body weight over time.

Figure 14C:
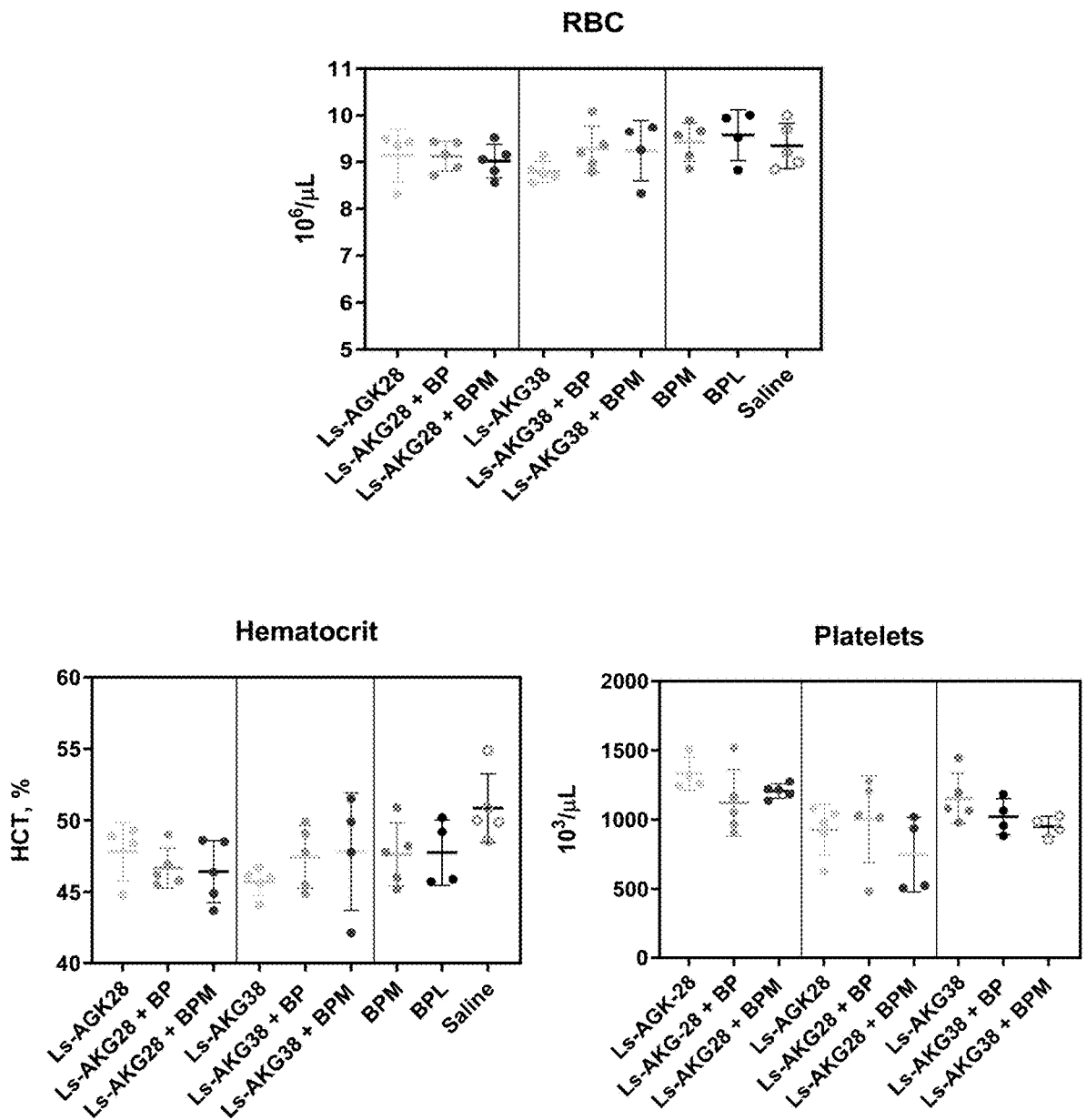
Figure 14C:
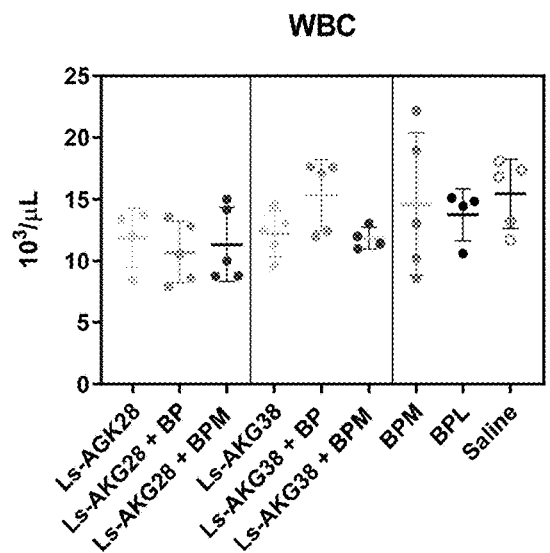
Figure 14C:
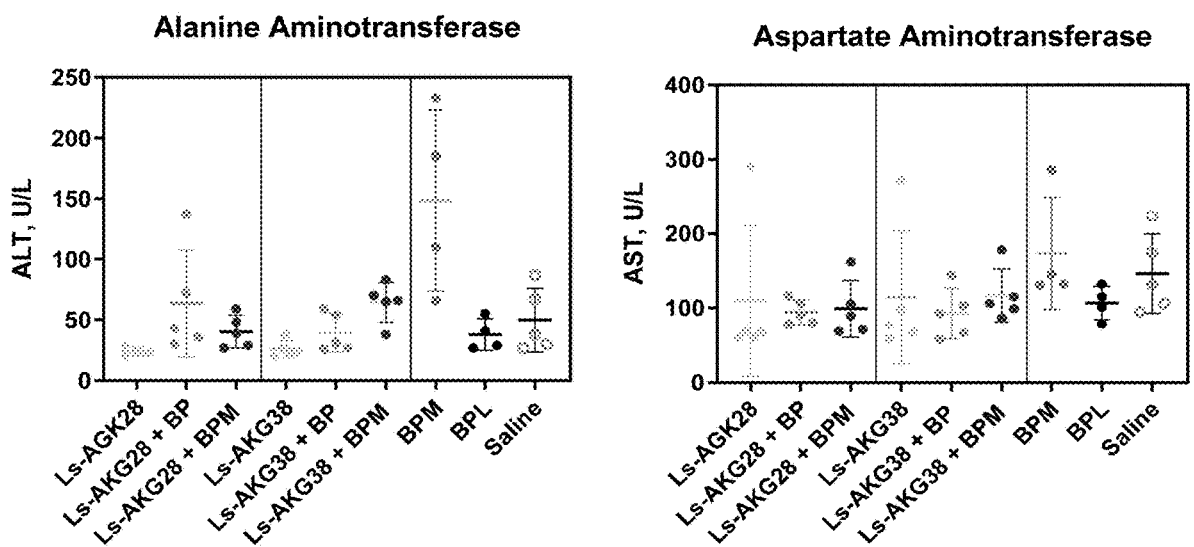

FIG. 14C are graphs showing the effect of Ls-AKG28 and Ls-AKG38 in combination with BP or BPM on hematology (RBC, HTC, PLT, WBC) and blood biochemistry (ALT, AST) parameters in female CD-1 mice.

Figure 14D:
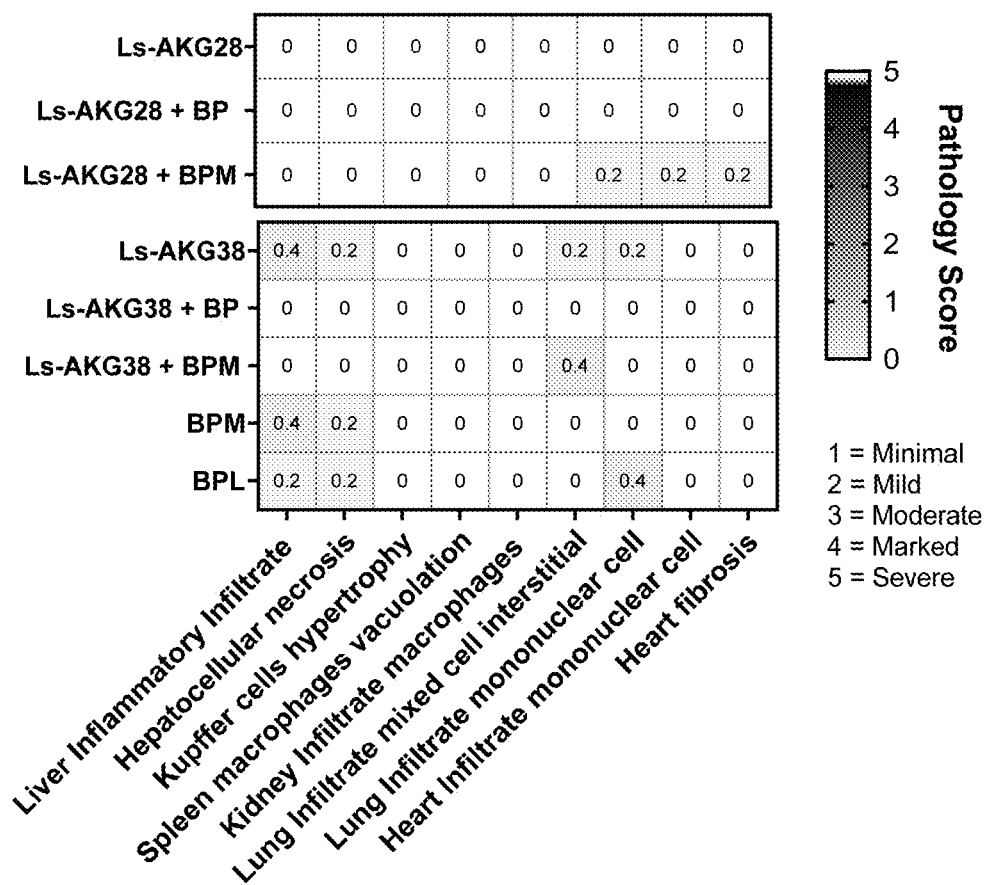

FIG. 14D is a heat map showing the effect of Ls-AKG28 and Ls-AKG38 in combination with BP or BPM on tissue pathology findings in female CD-1 mice.

Figure 15A:
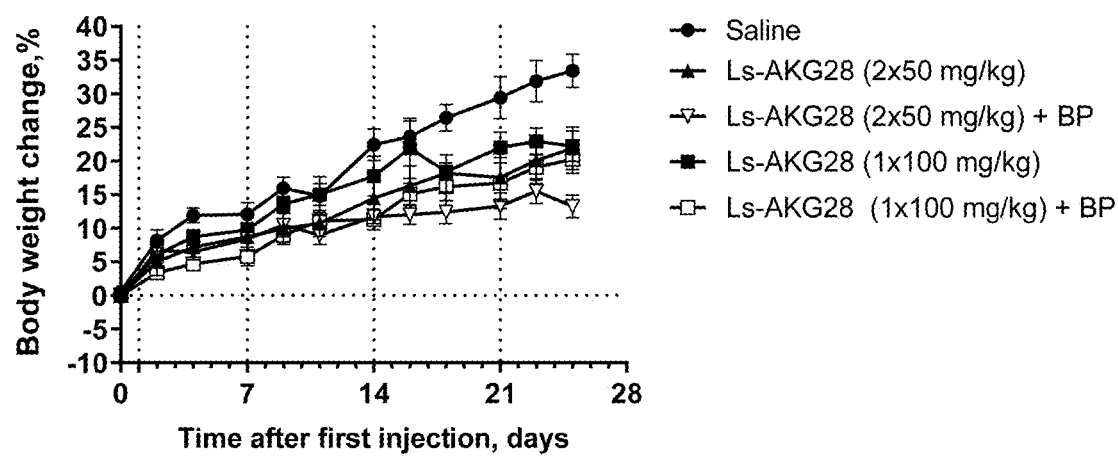

FIG. 15A is a graph showing the body weight change in female CD-1 mice treated with Ls-AKG28 injected twice a week (2qw) at 50 mg/kg or once a week (1qw) at 100 mg/kg alone or in in combination with BP over time.

Figure 15B:
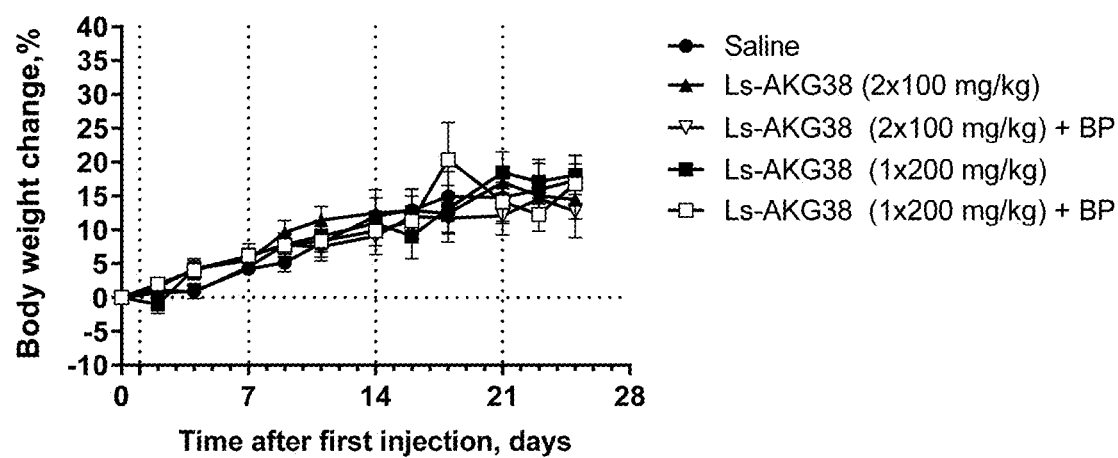

FIG. 15B is a graph showing the body weight change in female CD-1 mice treated with Ls-AKG38 injected 2qw at 100 mg/kg or 1qw at 200 mg/kg alone or in combination with BP.

Figure 15C:
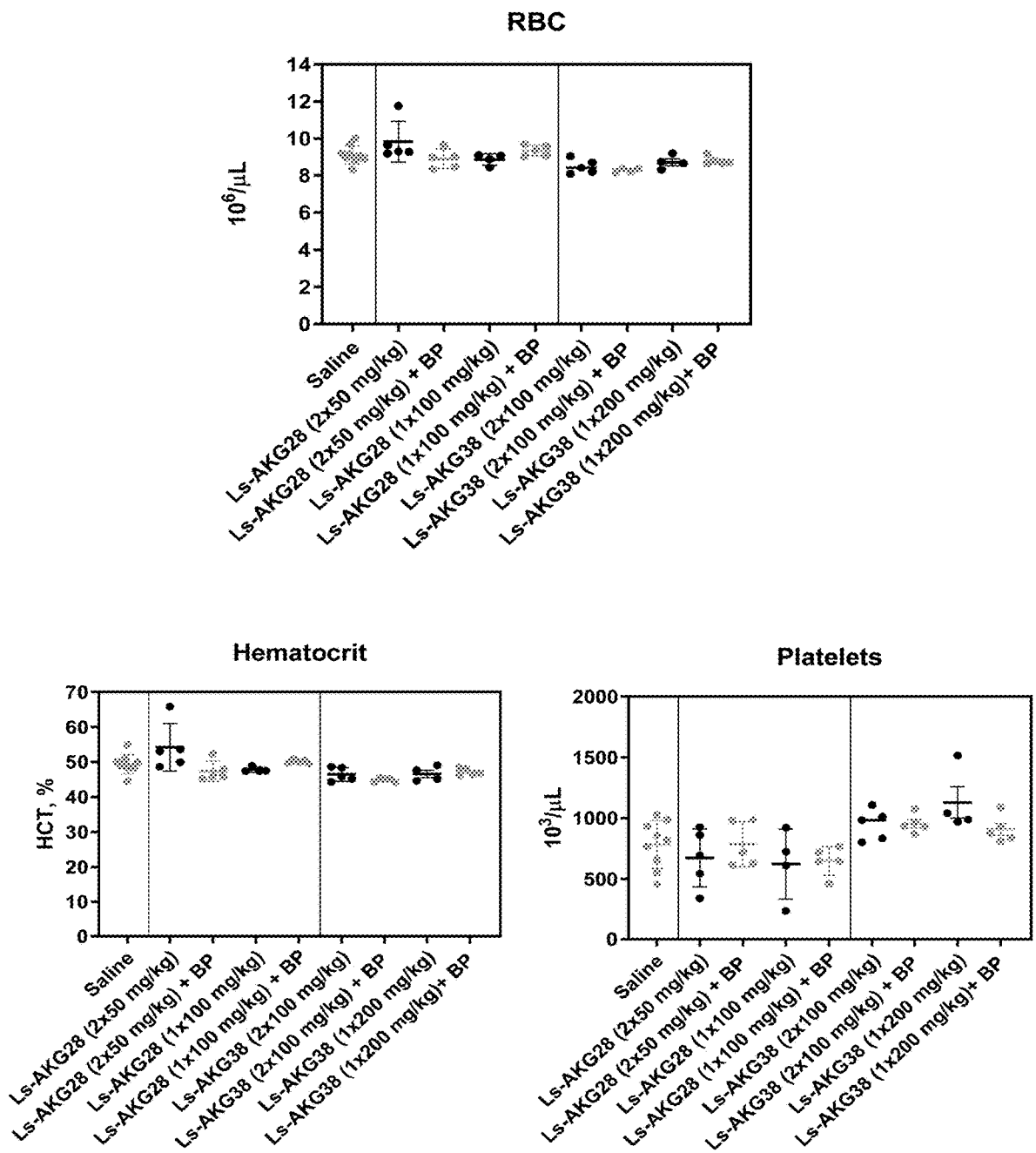
Figure 15C:
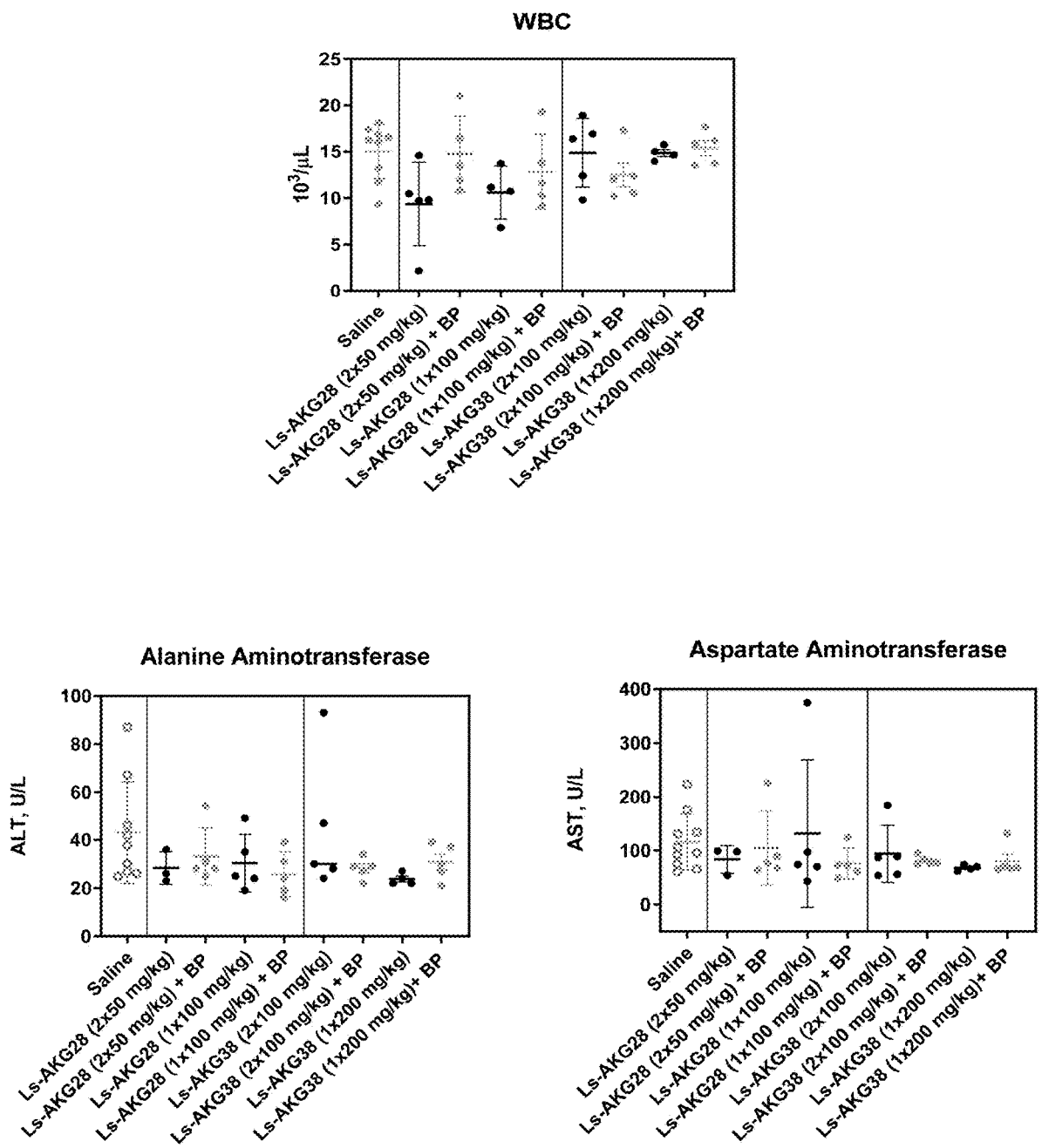

FIG. 15C are graphs showing the hematology and blood biochemistry parameters in female CD-1 mice treated with Ls-AKG28 (2qw at 50 mg/kg or 1qw at 100 mg/kg) or Ls-AKG28 (2qw at 100 mg/kg or 1qw at 200 mg/kg) alone or in combination with BP.

Figure 15D:
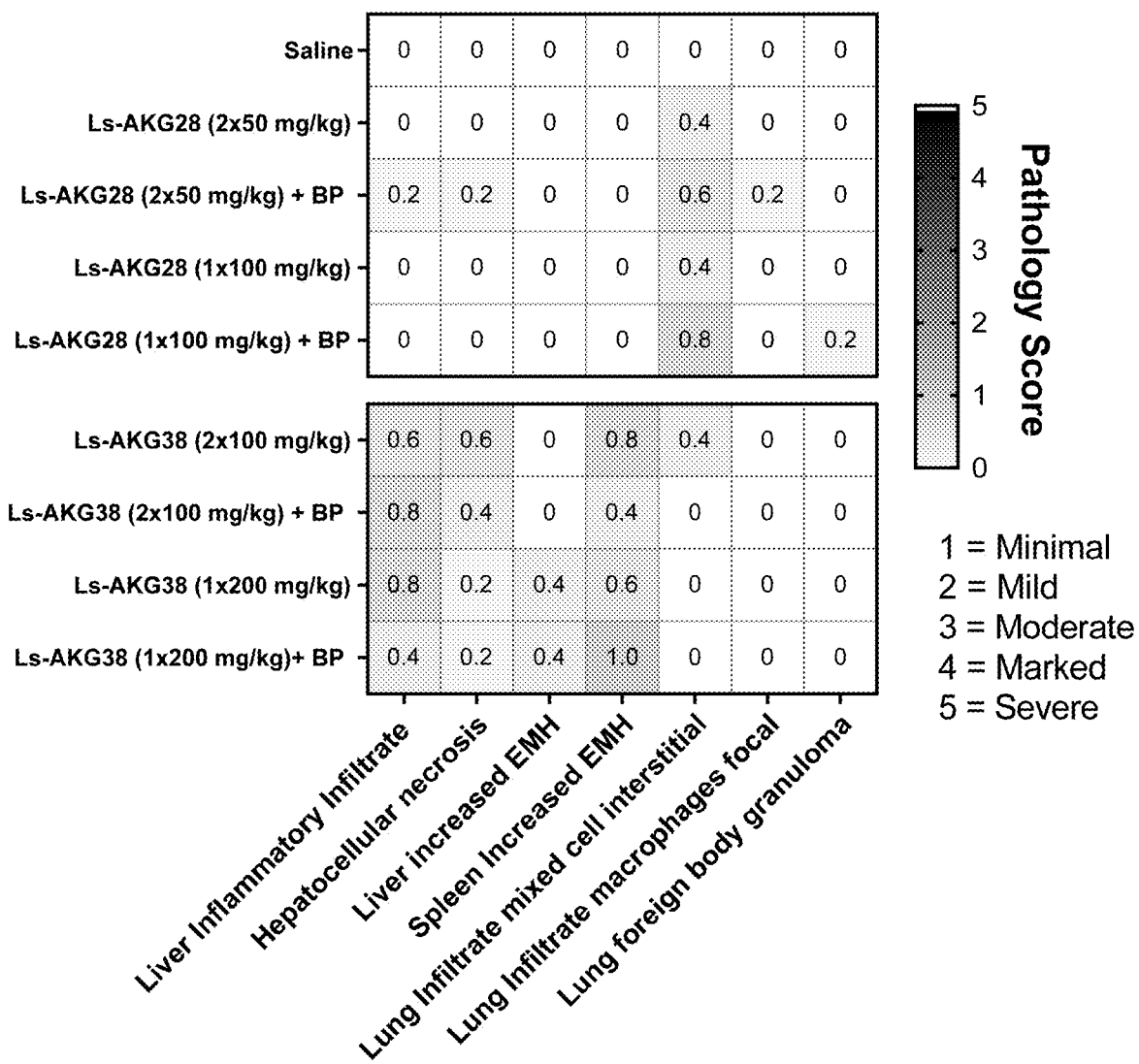

FIG. 15D is a heat map showing the histopathology results of female CD-1 mice treated with Ls-AKG28 (2qw at 50 mg/kg or 1qw at 100 mg/kg) or Ls-AKG28 (2qw at 100 mg/kg or 1qw at 200 mg/kg) alone, or in combination with BP.

Figure 16A:
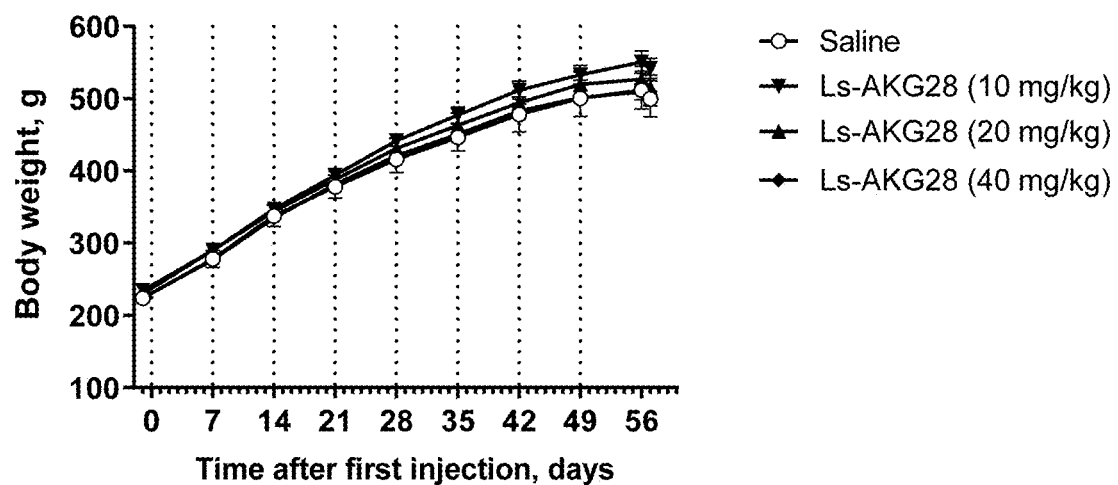

FIG. 16A is a graph showing the effect of Ls-AKG28 on body weight in male Sprague-Dawley rats treated chronically for a total of eight weeks over time.

Figure 16B:
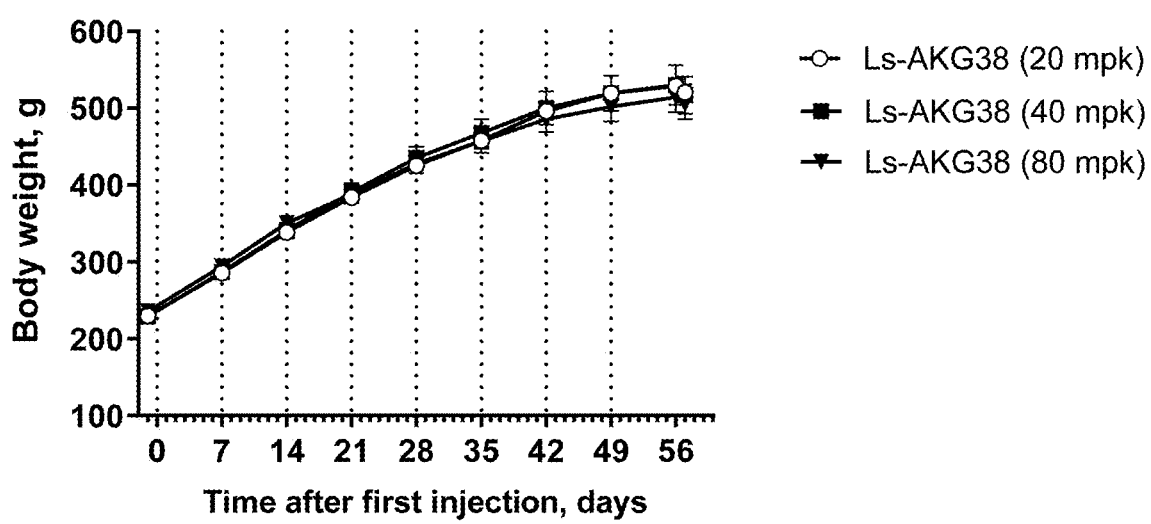

FIG. 16B is a graph showing the effect of Ls-AKG38 on body weight in male Sprague-Dawley rats treated chronically for a total of eight weeks over time.

DETAILED DESCRIPTION

It is to be understood that both the foregoing general description and the following detailed description are exemplary and explanatory only and are not restrictive of the compositions and methods of the present disclosure.

Disclosed herein are compounds, compositions and methods related to the treatment of bacterial infections. As used herein, the term "compound" and "drug" are used interchangeably. Some aspects of the disclosure relate to novel aminoalkyl derivatives of oxazolidinones. Some aspects of the disclosure relate to the process for the synthesis of the novel aminoalkyl derivatives of oxazolidinone compounds. Other aspects relate to compositions comprising aminoalkyl derivatives of oxazolidinone compounds in liposomes. Other aspects of the disclosure relate to the use of aminoalkyl derivatives of oxazolidinone compounds or liposome compositions comprising aminoalkyl derivatives of oxazolidinone compounds in the treatment of bacterial infections. In some embodiments, the compounds and compositions described herein can be used to treat infections from mycobacteria and gram-positive bacteria. In some embodiments, the bacterial infection is *Mycobacterium tuberculosis*. In some embodiments, the compounds and compositions described herein inhibits growth of mycobacteria and gram-positive bacteria. These include, but are not limited to, *Mycobacterium tuberculosis, Mycobacterium avium* complex, *Mycobacterium leprae, Mycobacterium gordonae, Mycobacterium abscessus, Mycobacterium* mucogenicum, streptococci, vancomycin-resistant enterococci (VRE), methicillin-resistant *Staphylococcus aureus* (MRSA), *Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium*.

In some embodiments, the aminoalkyl derivatives of oxazolidinone compounds described herein are selectively active against *Mycobacterium tuberculosis*, when compared to mammalian cells, such as human kidney or hepatocyte cells. In some embodiments, the aminoalkyl derivatives of oxazolidinone compounds described herein exhibit an unexpectedly high selectivity of at least 1000-fold towards *Mycobacterium tuberculosis* compared to mammalian cells, such as kidney or hepatocyte mammalian cells. In some embodiments, the aminoalkyl derivatives of oxazolidinone compounds described herein exhibit an unexpectedly high selectivity of at least 100-fold. In some embodiments, the aminoalkyl derivatives of oxazolidinone compounds described herein exhibit an unexpectedly high selectivity of from 100 to 6,500 folds, 100 to 6,000 folds, 100 to 5,500 folds, 100 to 5,000 folds, 100 to 4,500 folds, 100 to 4,000 folds, 100 to 3,500 folds, 100 to 3,000 folds, 100 to 2,500 folds, 100 to 2,000 folds, 100 to 1,500 folds, 100 to 1,000 folds, 500 to 6,500 folds, 500 to 6,000 folds, 500 to 5,500 folds, 500 to 5,000 folds, 500 to 4,500 folds, 500 to 4,000 folds, 500 to 3,500 folds, 500 to 3,000 folds, 500 to 2,500 folds, 500 to 2,000 folds, 500 to 1,500 folds, 500 to 1,000 folds, 1,000 to 6,500 folds, 1,000 to 6,000 folds, 1,000 to 5,500 folds, 1,000 to 5,000 folds, 1,000 to 4,500 folds, 1,000 to 4,000 folds, 1,000 to 3,500 folds, 1,000 to 3,000 folds, 1,000 to 2,500 folds, 1,000 to 2,000 folds, 1,000 to 1,500 folds towards *Mycobacterium tuberculosis* compared to mammalian cells, such as kidney or hepatocyte mammalian cells.

In some embodiments, the compounds and compositions described herein may promote selective uptake in *Mycobacterium*-residing macrophages in the liver, spleen, or lungs, helping to provide potent intracellular killing. Macrophages are responsible for the clearance of foreign particles via phagocytosis, including both foreign infectious agent like *Mycobacterium*, as well as laboratory-derived nanoparticles such as liposomes. This results in the opportunity for both to be co-localized in the same biological reservoir, effectively concentrating the active agent at an important depot for the disease.

Aspects of the disclosure relate to compounds that are aminoalkyl derivatives of oxazolidinones (see FIG. 6). In some embodiments, the compounds having the following chemical Formula I and pharmaceutically, acceptable salts thereof:

Formula I 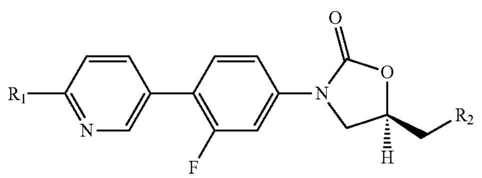 wherein $R_2$ is an amine ($NH_2$) or an acetamide ($NHCOCH_3$), and wherein $R_1$ is a tetrazole ring substituted at position 2' with an aminoalkyl.

In other embodiments, the compounds having the following chemical Formula I and pharmaceutically acceptable salts thereof:

Formula I wherein $R_2$ is an amine ($NH_2$) or an acetamide ($NHCOCH_3$), and wherein $R_1$ is a tetrazole ring substituted at 1' with an aminoalkyl group.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

The present disclosure shows a very specific structure-activity relationship (SAR) for the aminoalkyl derivatives of oxazolidinone compounds described herein that included either an amine or acetamide group at the $R_2$ positions of the oxazolidinone ring and a dimethylaminoethyl group on the tetrazole ring. These compounds are (1) highly selective against *Mycobacterium tuberculosis* when compared to activity in mammalian cells (for example human kidney or hepatocyte cells), (2) highly active against *Mycobacterium tuberculosis*, and (3) efficiently loaded into liposomes.

In some embodiments, the aminoalkyl derivatives of oxazolidinones described herein load in liposomes with 85% or better efficiency using gradient-based drug loading methods. In some embodiments, the loading efficiency of these derivatives is 90% or more. In some embodiments, the loading of these derivatives is 95% or more, or even quantitative. In some embodiments, methods for loading the aminoalkyl derivatives of oxazolidinones in liposomes are described. In some embodiments, the loading methods employs transmembrane gradients and trapping agents to efficiently load, and subsequently stabilize, weakly basic amphipathic drugs in the liposomal interior aqueous space. The gradients can include (1) simple pH gradients formed, for example, using citric acid solutions, (2) ammonium ion gradients employing citrate or sulfate ammonium salts, (3) alkyl, dialkyl, or trialkylammonium salts, (4) gradients of transition metals ($Cu^{2+}$, $Mn^{2+}$, $Zn^{2+}$, $Mg^{2+}$), or even (5) transmembrane gradients of drug solubility. See U.S. Pat. Nos. 5,316,771, 5,800,833, 8,147,867, 7,744,921, 8,349,360, 6,110,491, U.S. Patent Application Publication No. 20180369143A1 and International Patent Application Publication No. WO199001405, which are incorporated herein by reference in their entireties. See also Allen et al. (1995) Int J Cancer 62:199-204. Without being bound by the theory, the cation contained in the liposome interior plays a role in establishing a pH gradient across the membrane that helps drive the accumulation of weakly basic drugs into the liposome interior, or directly exchanges with the drug molecule. This results in some embodiments, in a quantitative loading of the drug below the total capacity of the gradient. The counterion can play an important role in stabilizing the formulation to premature leakage in the circulation or during storage by forming stable complexes with the drugs in the liposome interior (see Drummond et al. (2008) J. Pharm Sci 97, 4696-4740).

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "comprising" when used in the specification includes "consisting of" and "consisting essentially of".

If it is referred to "as mentioned above" or "mentioned above", "supra" within the description it is referred to any of the disclosures made within the specification in any of the preceding pages.

If it is referred to "as mentioned herein", "described herein", "provided herein," or "as mentioned in the present text," or "stated herein" within the description it is referred to any of the disclosures made within the specification in any of the preceding or subsequent pages.

As used herein, the term "about" means acceptable variations within 20%, within 10% and within 5% of the stated value. In certain embodiments, "about" can mean a variation of +/−1%, 2%, 3%, 4%, 5%, 10% or 20%.

The term "effective amount" as used herein with respect to a compound or the composition means the amount of active compound (also referred herein as active agent or drug) sufficient to cause a bactericidal or bacteriostatic effect. In one embodiment, the effective amount is a "therapeutically effective amount" meaning the amount of active compound that is sufficient alleviate the symptoms of the bacterial infection being treated.

The term "subject" (or, alternatively, "patient") as used herein refers to an animal, preferably a mammal, most preferably a human that receives either prophylactic or therapeutic treatment.

The term "administration" or "administering" as used herein includes all means of introducing the compounds or the pharmaceutical compositions to the subject in need thereof, including but not limited to, oral, intravenous, intramuscular, intraperitoneal, subcutaneous, transdermal, inhalation, buccal, ocular, sublingual, vaginal, rectal and the like. Administration of the compound or the composition is suitably parenteral. For example, the compounds or the composition can be preferentially administered intravenously, but can also be administered intraperitoneally or via inhalation like is currently used in the clinic for liposomal amikacin in the treatment of *Mycobacterium avium* (see Shirley et al., Amikacin Liposome Inhalation Suspension: A Review in *Mycobacterium avium* Complex Lung Disease. Drugs. 2019 April; 79(5):555-562)

The terms "treat," "treating," and "treatment," as used herein, refer to therapeutic or preventative measures such as those described herein.

The terms "synergy" and "synergistic" as used herein, means that the effect achieved with the compounds used together is greater than the sum of the effects that results from using the compounds separately, i.e. greater than what would be predicted based on the two active ingredients administered separately.

The term "pharmaceutically acceptable salt" refers to a relatively non-toxic, inorganic or organic acid addition salt of a compound of the present disclosure which salt possesses the desired pharmacological activity.

The term "alkyl" means saturated carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

The term "aminoalkyl" means an alkyl wherein at least one carbon of an alkyl carbon chain forms the bond with an amino group, wherein said amino group is primary amino group, mono-alkyl-substituted (secondary) amino group, di-alkyl-substituted (tertiary) amino group, or an alkyl-substituted amino group where the amine nitrogen atom and the alkyl chain that substitutes for amine hydrogens form a heterocycle.

The term "liposomes" means vesicles composed of a bilayer (unilamellar) and/or a concentric series of multiple bilayers (multi-lamellar) separated by aqueous compartments formed by amphipathic molecules such as phospholipids that enclose a central aqueous compartment. In a liposome drug product, the drug substance is generally contained in liposomes. Typically, water soluble drugs are contained in the aqueous compartment(s) and hydrophobic drugs are contained in the lipid bilayer(s) of the liposomes. Release of drugs from liposome formulations, among other characteristics such as liposomal clearance and circulation half-life, can be modified by the presence of polyethylene glycol and/or cholesterol or other potential additives in the liposome.

"Unilamellar liposomes," also referred to as "unilamellar vesicles," are liposomes that include one lipid bilayer membrane which defines a single closed aqueous compartment. The bilayer membrane includes two layers of lipids; an inner layer and an outer layer (leaflet). Lipid molecules in the outer layer are oriented with their hydrophilic ("head") portions toward the external aqueous environment and their hydrophobic ("tail") portions pointed downward toward the interior of the liposome. The inner layer of the lipid lays directly beneath the outer layer, the lipids are oriented with their heads facing the aqueous interior of the liposome and their tails toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments.

The terms "encapsulation" and "entrapped," as used herein, refer to the incorporation or association of the oxazolidinone pharmaceutical agent in or with a liposome.

The terms "DL", "DL ratio", "D/L", or "D/L ratio" are used interchangeably and refer to the ratio of the drug to the liposome lipid. Unless indicated otherwise, it is expressed as grams of the drug per mole of liposome phospholipid (PhL).

The term "mol %" with regard to cholesterol refers to the molar amount of cholesterol relative to the sum of the molar amounts of cholesterol and non-PEGylated phospholipid expressed in percentage points. For example, "55 mol. % cholesterol" in a liposome containing cholesterol and HSPC refers to the composition of 55 mol. parts of cholesterol per 45 mol. parts of HSPC.

The term "mol %" with regard to PEG-lipid refers to the ratio of the molar amount of PEG-lipid and non-PEGylated phospholipid expressed in percentage points. For example, "5 mol. % PEG-DSPE" in a liposome containing HSPC and PEG-DSPE refers to the composition having 5 mol. parts of PEG-DSPE per 100 mol. parts of HSPC.

The terms "sucrose octasulfate", "sucrosofate", and "sucrooctasulfate" refer the same compound, sucrose octasulfuric acid or an anion thereof, and are used herein interchangeably.

The symbols "Ac", "Me", and "Et", as found in chemical formulas, refer to acetyl group ($CH_3CO$), methyl group ($CH_3$), and ethyl group ($C_2H_5$), respectively.

Various aspects and embodiments are described in further detail in the following subsections.

Compounds

Oxazolidinones are synthetic antibiotics that exert their function by inhibiting protein synthesis. Linezolid (LZD) is an oxazolidinone compound that exhibits bacteriostatic activity against *M. tuberculosis*. However, administration of LZD may cause severe side effects such as anemia, thrombocytopenia, and peripheral neuropathy. Tedizolid is an oxazolidinone compound which has been shown to inhibit gram positive bacteria. The side effects for tedizolid phosphate are similar, but generally less severe than observed for linezolid, although the experience with prolonged dosing such as that required for the treatment of tuberculosis has been limited for tedizolid phosphate compared to the extensive experience with linezolid.

Figure 6:
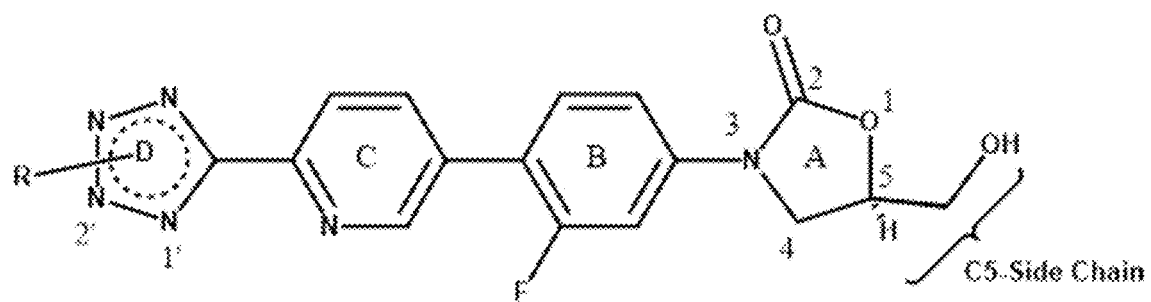
FIG. 6 represents the numbered ring structure of a compound of Formula I.

Aspects of the disclosure relate to compounds that are aminoalkyl derivatives of oxazolidinone (see FIG. 6). In some embodiments, the compounds having the following chemical Formula I and pharmaceutically acceptable salts thereof:

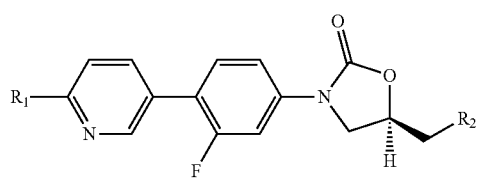

Formula I wherein $R_2$ is an amine ($NH_2$) or an acetamide ($NHCOCH_3$), wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In other embodiments, the compounds having the following chemical Formula I and pharmaceutically acceptable salts thereof:

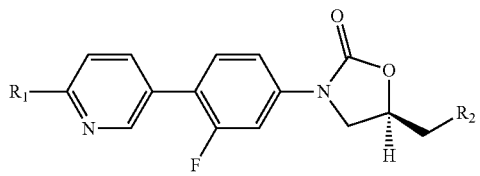

Formula I wherein $R_2$ is an amine ($NH_2$) or an acetamide ($NHCOCH_3$), and wherein $R_1$ is a tetrazole ring substituted 1' with an aminoalkyl.

The aminoalkyl derivatives of oxazolidinone compounds having the chemical structure of the Table 1 below were synthesized as described in Example 1.

The compounds of the present disclosure can exist in free form, e.g. as a free base, or as a free acid, or as a zwitterion, or can exist in the form of a salt. Said salt may be any salt, either an organic or inorganic addition salt or a cocrystal, particularly any pharmaceutically acceptable organic or inorganic addition salt or a cocrystal, customarily used in pharmacy. It is understood that the chemical formula showing a compound in a particular salt form or ionic form also discloses this compound in its non-dissociated, free base (or free acid) form.

The present disclosure encompasses all stereoisomeric forms of the compounds. In some embodiments, the compounds of Table 1 below are substantially pure (i.e. at least 60%, 70%, 80%, 90%, 91%, 92%, 93%, 94%, 95%, 96%, 97%, 98%, 99%, e.g. 100%)

TABLE 1

| Name | Structure |
|---|---|
| AKG-1 | 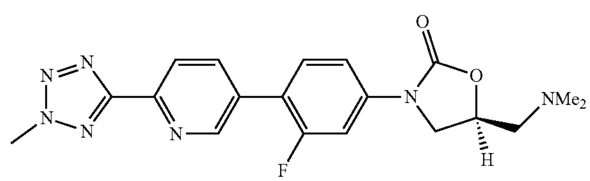 [SMILES: CN(C)C[C@H]1CN(c2ccc(-c3ccc(-c4nnn(C)n4)nc3)c(F)c2)C(=O)O1] |
| AKG-2 | 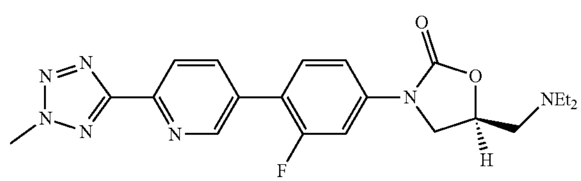 |
| AKG-3 | 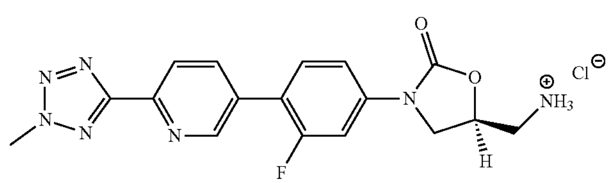 [SMILES: Cn1nnc(-c2ccc(-c3ccc(N4C[C@H](C[NH3+])OC4=O)cc3F)cn2)n1 ; [Cl-]] |
| AKG-5 | 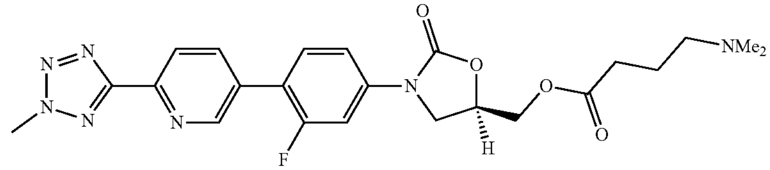 [SMILES: CN(C)CCCC(=O)OC[C@H]1CN(c2ccc(-c3ccc(-c4nnn(C)n4)nc3)c(F)c2)C(=O)O1] |

TABLE 1-continued

| Name | Structure |
|---|---|
| AKG-6 | (2-methyltetrazolyl)-pyridyl-(fluoro)phenyl-oxazolidinone-CH2-piperidinyl-CH2CH2NMe2 |
| AKG-7 | (2-methyltetrazolyl)-pyridyl-(fluoro)phenyl-oxazolidinone-CH2-O-CH2CH2NEt2 |
| AKG-8 | (2-methyltetrazolyl)-pyridyl-(fluoro)phenyl-oxazolidinone-CH2-NH-CH2CH2CH2NEt2 |
| AKG-9 | (2-methyltetrazolyl)-pyridyl-(fluoro)phenyl-oxazolidinone-CH2-NH-CH2CH2NEt2 |
| AKG-11 | Me2N-CH2CH2-piperidinyl-pyridyl-(fluoro)phenyl-oxazolidinone-CH2OH |
| AKG-12 | Me2N-CH2CH2-NH-pyridyl-(fluoro)phenyl-oxazolidinone-CH2OH |
| AKG-13 | Et3N-CH2CH2-NH-pyridyl-(fluoro)phenyl-oxazolidinone-CH2OH |
| AKG-14 | Me2N-CH2CH2CH2-NH-pyridyl-(fluoro)phenyl-oxazolidinone-CH2OH |

TABLE 1-continued

| Name | Structure |
|---|---|
| AKG-15 | 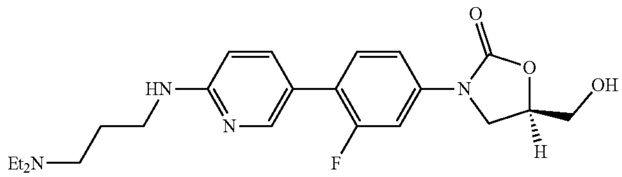 |
| AKG-16 | 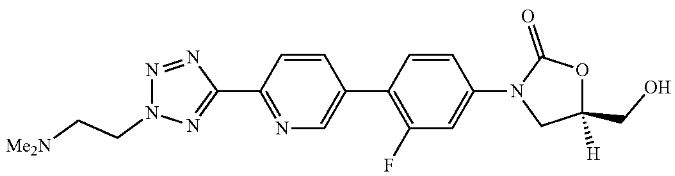 [SMILES: CN(C)CCn1nnc(-c2ccc(-c3ccc(N4C[C@H](CO)OC4=O)cc3F)cn2)n1] |
| AKG-17 | 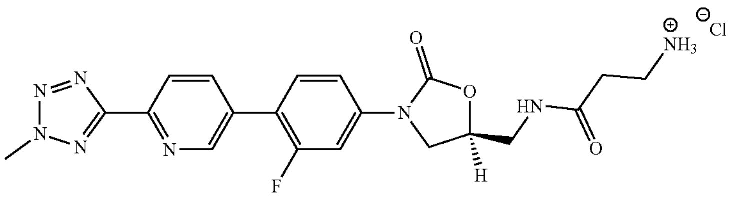 [SMILES: [Cl-] ; Cn1nnc(-c2ccc(-c3ccc(N4C[C@H](CNC(=O)CC[NH3+])OC4=O)cc3F)cn2)n1] |
| AKG-18 | 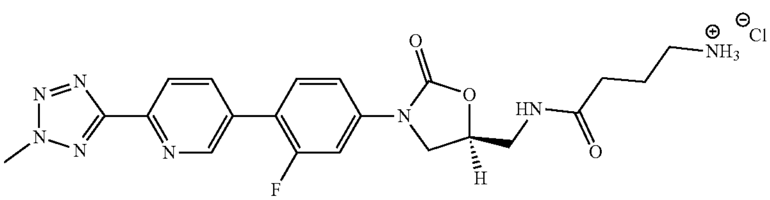 [SMILES: [Cl-] ; Cn1nnc(-c2ccc(-c3ccc(N4C[C@H](CNC(=O)CCC[NH3+])OC4=O)cc3F)cn2)n1] |
| AKG-19 | 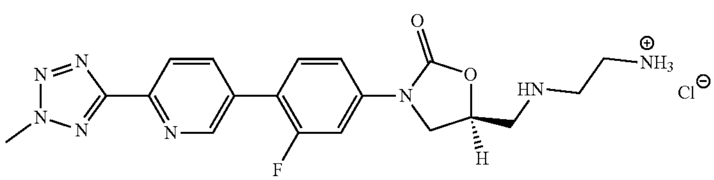 [SMILES: Cn1nnc(-c2ccc(-c3ccc(N4C[C@H](CNCC[NH3+])OC4=O)cc3F)cn2)n1 ; [Cl-]] |
| AKG-20 | 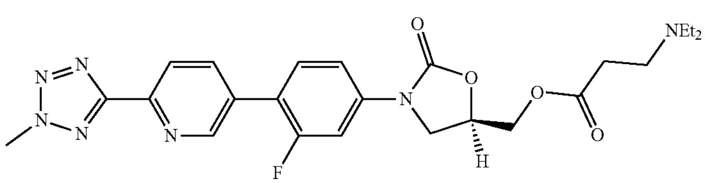 |
| AKG-21 | 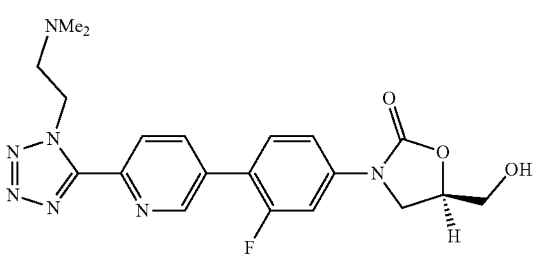 [SMILES: CN(C)CCn1nnnc1-c1ccc(-c2ccc(N3C[C@H](CO)OC3=O)cc2F)cn1] |

TABLE 1-continued

| Name | Structure |
|---|---|
| AKG-22 | 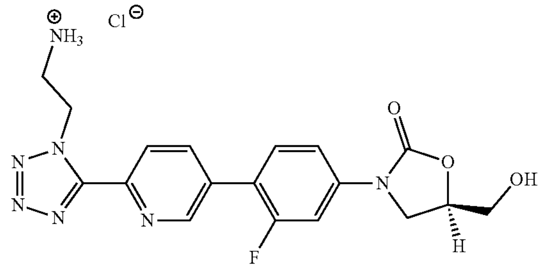 [SMILES: [Cl-] ; [NH3+]CCn1nnnc1-c1ccc(-c2ccc(N3C[C@H](CO)OC3=O)cc2F)cn1] |
| AKG-23 | 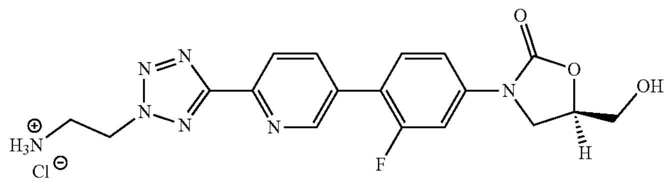 [SMILES: [NH3+]CCn1nnc(-c2ccc(-c3ccc(N4C[C@H](CO)OC4=O)cc3F)cn2)n1 ; [Cl-]] |
| AKG-24 | 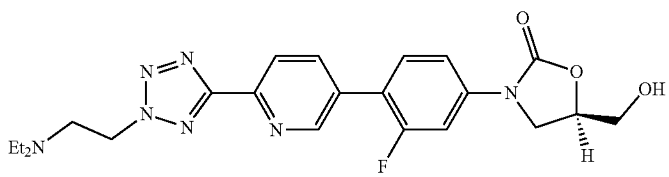 |
| AKG-25 | 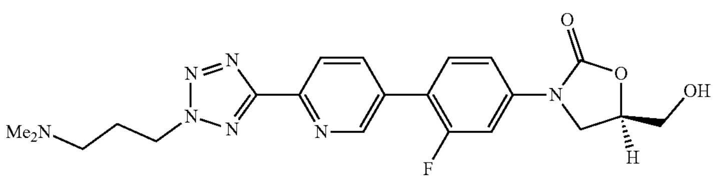 [SMILES: CN(C)CCCn1nnc(-c2ccc(-c3ccc(N4C[C@H](CO)OC4=O)cc3F)cn2)n1] |
| AKG-26 | 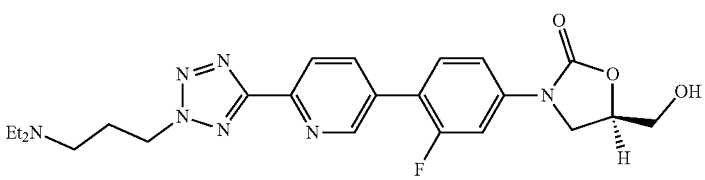 |
| AKG-27 | 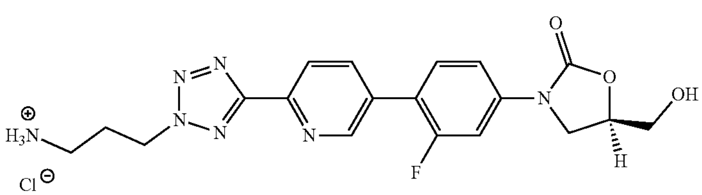 [SMILES: [NH3+]CCCn1nnc(-c2ccc(-c3ccc(N4C[C@H](CO)OC4=O)cc3F)cn2)n1 ; [Cl-]] |
| AKG-28 | 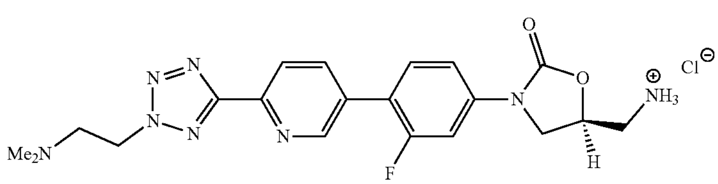 [SMILES: CN(C)CCn1nnc(-c2ccc(-c3ccc(N4C[C@H](C[NH3+])OC4=O)cc3F)cn2)n1 ; [Cl-]] |
| AKG-29 | 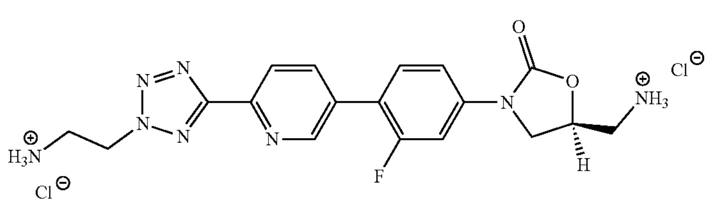 [SMILES: [NH3+]CCn1nnc(-c2ccc(-c3ccc(N4C[C@H](C[NH3+])OC4=O)cc3F)cn2)n1 ; [Cl-] ; [Cl-]] |

TABLE 1-continued

| Name | Structure |
|---|---|
| AKG-30 | 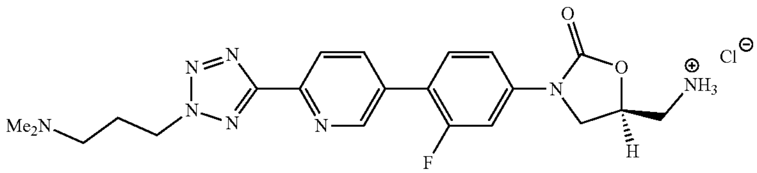 [SMILES: CN(C)CCCn1nnc(-c2ccc(-c3ccc(N4C[C@H](C[NH3+])OC4=O)cc3F)cn2)n1 ; [Cl-]] |
| AKG-31 | 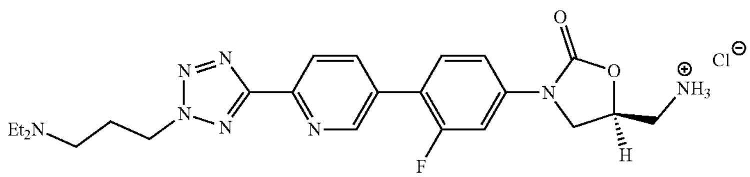 |
| AKG-38 | 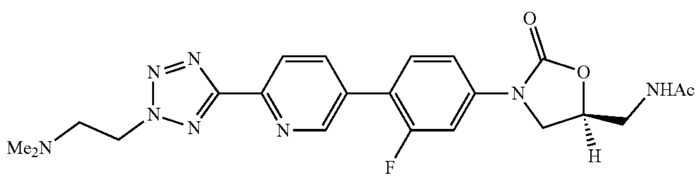 [SMILES: CC(=O)NC[C@H]1CN(c2ccc(-c3ccc(-c4nnn(CCN(C)C)n4)nc3)c(F)c2)C(=O)O1] |
| AKG-39 | 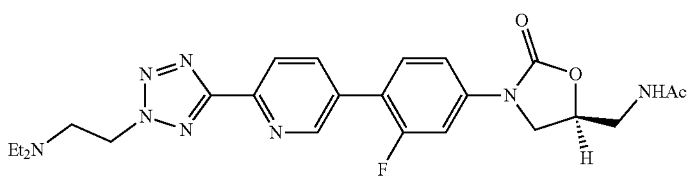 |
| AKG-40 | 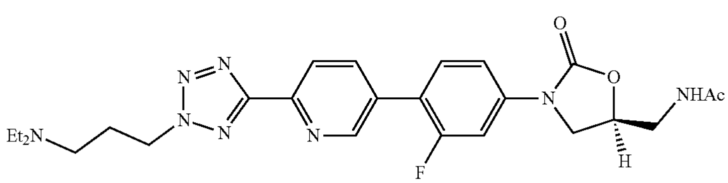 |

In some embodiments, the compound has the following chemical formula:

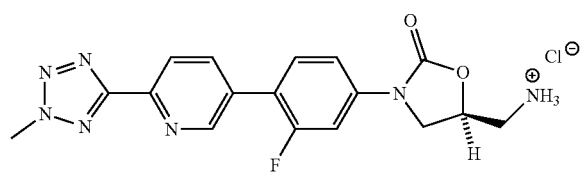

Formula 1a

In some embodiments, the compound has the following chemical formula:

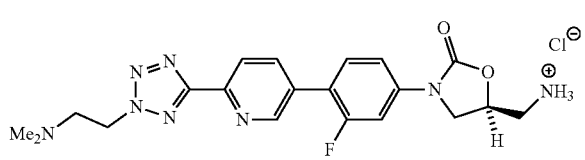

Formula 1b

In some embodiments, the compound has the following chemical formula:

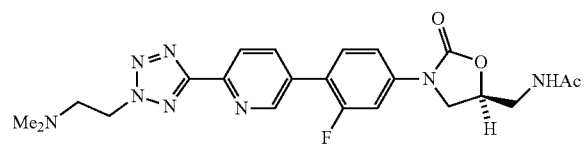

Formula 1c

In some embodiments, the compound has the following chemical formula:

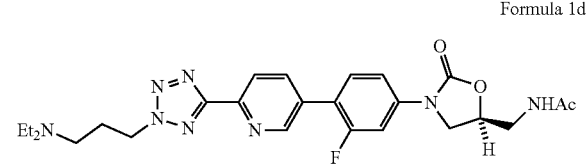

Formula 1d

In some embodiments, the compound has the following chemical formula:

Formula 1e

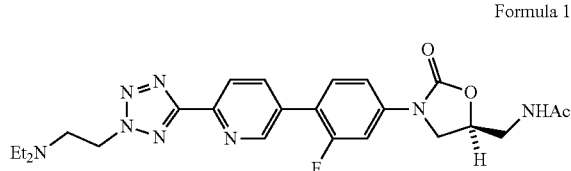

Disclosed herein are compounds of Formula I or pharmaceutically acceptable salts thereof that are useful for the treatment of *Mycobacterium* infections. In some embodiments, the compounds have the chemical formula 1a, 1b, 1c, 1d or 1e. In some embodiments, the compounds have the chemical formula 1b. In some embodiments, the compounds of Formula I have a minimum inhibitory concentration (MIC), for example against *Mycobacterium tuberculosis*, ranging from 0.1 µg/ml to 1 µg/ml, from 0.25 µg/ml to 1 µg/ml, from 0.5 µg/ml to 1 µg/ml, from 0.1 µg/ml to 0.25 µg/ml, from 0.1 µg/ml to 0.5 µg/ml, from 0.25 µg/ml to 0.5 µg/ml, from 0.01 µg/ml to 1 µg/ml, from 0.01 µg/ml to 0.25 µg/ml, from 0.01 µg/ml to 0.5 µg/ml, from 0.01 µg/ml to 0.1 µg/ml. In some embodiments, the compounds of Formula I have a minimum inhibitory concentration (MIC), for example against *Mycobacterium tuberculosis* of less than 1 µg/ml, less than 0.25 µg/ml, or less than 0.1 µg/ml. In some embodiments, the compounds of Formula I have a MIC ranging from 0.01 µg/ml to 0.25 µg/ml. In some embodiments, the compound of Formula I have a MIC ranging from 0.01 µg/ml to 0.1 µg/ml. It should be appreciated that the MIC values can be lower or than the ranges provided herein depending on the bacteria.

In some embodiments for the treatment of *Mycobacterium*, for example *M. tuberculosis*, the compound (AKG-28 or AKG-38) has a MIC below 0.1 µg/mL. In some embodiments for the treatment of *Mycobacterium*, for example *M. tuberculosis*, the compound has a selectivity index (SI) for killing *M. tuberculosis* vs human kidney cells (VERO) of at least 1,000. In some embodiments for the treatment of *Mycobacterium*, for example *M. tuberculosis*, the compound has a MIC below 0.1 µg/mL and a selectivity index (SI) for killing *M. tuberculosis* vs human kidney cells (VERO) of at least 1,000. In some embodiments, the compound has the structure of AKG-28 (Formula 1b) or AKG-38 (Formula 1c). In some embodiments, the MIC is less than 0.05 µg/mL and the selectivity index for MIC in *M. tuberculosis* relative to mitochondrial protein synthesis inhibition (SI-MPS) is greater than 20, such as for AKG-28.

In some embodiments, the compounds described herein have a 2-to-20 fold increase (about 2, about 3, about 4, about 5, about 6, about 7, about 8, about 9, about 10, about 11, about 12, about 13, about 14, about 15, about 16, about 17, about 18, about 19, about 20) in potency adjusted dose compared to linezolid for *M. tuberculosis*.

In some embodiments for the treatment of methicillin-resistant *Staphylococcus aureus* (MRSA), the compound has a MIC against MRSA strains of less than 2 µg/mL. In some embodiments for the treatment of methicillin-resistant *Staphylococcus aureus* (MRSA), the compound has an IC50 of greater than 100 µg/mL against human VERO kidney cells. In some embodiments for the treatment of methicillin-resistant *Staphylococcus aureus* (MRSA), the compound has a MIC against MRSA strains of less than 2 µg/mL and an IC50 of greater than 100 µg/mL against human VERO kidney cells. In some embodiments, the compound has the structure of AKG-38 (Formula 1c), AKG-39 (Formula 1e), and AKG-40 (Formula 1d).

Aqueous Solubility

In some embodiments, the compounds are in the form of salts, e.g., a hydrochloride or mesylate salt and are soluble in water at greater than 1 mg/ml, and preferably greater than 10 mg/ml (and up to 1 g/ml) prior to encapsulation in liposomes. Additional salts prior to encapsulation can include, but are not limited to, besylate, bitartrate, carbonate, citrate, esylate, gluconate, glutamate, glycolate, lactate, malate, maleate, mandelate, methylsulfate, napsylate, phosphate, propionate, salicylate, succinate, tartrate, and tosylate. In some embodiments, the compounds are in the form of hydrate or solvate or a cocrystal prior to encapsulation in the liposomes.

In some embodiments, the drug is entrapped in the interior of the liposomes in a different salt form with a reduced aqueous solubility, for example less than 1 mg/mL and preferably less than 0.1 mg/mL (0.1-0.001 mg/mL). The salt of the compound once entrapped in the liposomes includes, but not limited to sulfate, citrate, phosphate, sucrosofate, or various phosphorylated or sulfated polyols or polyanionic polymers. Exemplary polyols include, but not limited to, sucrose, erythritol, mannitol, xylitol, sorbitol, inositol, and combinations thereof. Exemplary polyanionic polymers include but not limited to, polyvinylsulfonate, polyvinylsulfate, polyphosphate, copolymers of acrylic acid and vinyl-alcohol sulfate, and combinations thereof.

Working stocks of the compounds were prepared as follows: to an aliquot of a compound (free base) in a powder form 1-1.5 equivalents of HCl in the form of 1 N aqueous solution was added, and the mixture was vortexed until homogeneity. To the resulting cake or syrup, water was added typically to the final 10 mg/ml, and complete dissolution was observed. In some instances, 0.95 equivalents of HCl were added to the free base form of the drug, and 20 mg/ml stock solution was prepared.

Aqueous solubility of the compounds of the present disclosure is illustrated by the following observations of obtaining visually clear solutions:

| Compound | Amount, mg | Volume of 1N HCl added, ml | Volume of water added, ml | Concentration % (w/w) of free base |
|---|---|---|---|---|
| AKG-16 (free base) | 22.3 | 0.052 | — | 30.0 |
| AKG-28 (2HCl) | 32.5 | — | 0.35 | 7.3 |
| AKG-38 (free base) | 31.7 | 0.067 | 0.35 | 7.1 |

These results show that the compounds provided herein have an aqueous solubility that is higher than the known aqueous solubilities of:

linezolid (3 mg/ml) (www.drugbank.ca/drugs/DB00601)

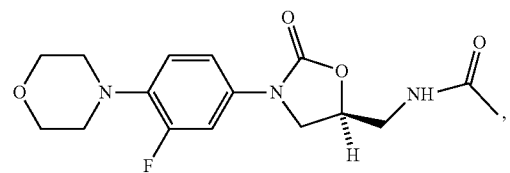 [SMILES: CC(=O)NC[C@H]1CN(c2ccc(N3CCOCC3)c(F)c2)C(=O)O1]

sutezolid (0.237 mg/ml) (www.drugbank.ca/drugs/DB11905)

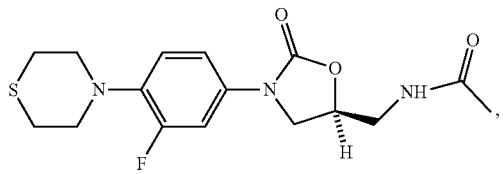 [SMILES: CC(=O)NC[C@H]1CN(c2ccc(N3CCSCC3)c(F)c2)C(=O)O1]

and
tedizolid (0.382 mg/ml) (www.drugbank.ca/drugs/DB14569)

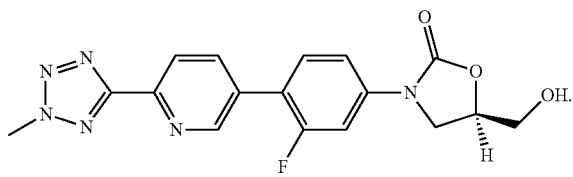 [SMILES: Cn1nnc(-c2ccc(-c3ccc(N4C[C@H](CO)OC4=O)cc3F)cn2)n1]

In some embodiments, the aqueous solubility of the compounds described herein, prior to encapsulation into the liposomes, is at least 5 times, at least 10 times, at least 20 times, at least 30 times, or at least 40 times of the above oxazolidinones.

The excellent aqueous solubility of the compounds of described herein and their properties of amphiphilic weak bases allows efficient use of transmembrane-gradient-based and intraliposomal complexation (active loading) approach to creating liposome-encapsulated forms of these compounds with high drug/carrier (drug/lipid) ratio and pharmacokinetic properties favorable for encapsulated drug delivery to the infected tissues after systemic administration of the drug. As used herein, an amphiphilic weak base has a pKa of between 7 and 12 and a log P between 1 and 6.

Liposome Loading Properties and Antimycobacterial Activity.

An important feature of the compounds described herein is their weak amphiphilic base property that facilitates transmembrane gradient-driven loading of these compounds into liposomes. In some embodiments, a weak base property of the compounds of the present disclosure is characterized by an electrolytic dissociation constant in the pKa range of 7.0-12.0, 7.5-11.0, 7.8-10.5, or 8.0-10.0. In some embodiments, the amphiphilic property of the compounds described herein is characterized by a log P parameter in the range of 0.5-5.0, 1.0-4.0, 1.0-3.5, or 1.0-3.0. It was unexpectedly discovered that certain embodiments having these favorable properties with regard to the liposome loading, also have superior activity against mycobacteria that matches or surpasses the activity of similar compounds in the same class of drugs whose properties are less favorable for efficient and stable liposome encapsulation.

Liposome Compositions

Compositions and use of the compositions for the treatment of tuberculosis, as well as other mycobacterial and gram positive bacterial infections are disclosed. These compositions provided herein contain a highly potent and selective oxazolidinone encapsulated with high efficiency to maximize dosing potential of low toxicity drugs, and are stable in the presence of plasma. In some embodiments, the compositions are long circulating and retain their encapsulated drug while in the circulation following intravenous dosing to allow for efficient accumulation at the site of the bacterial or mycobacterial infection. In some embodiments, high doses that can be achieved when combined with the long circulating properties and highly stable retention of the drug allow for a reduced frequency of administration when compared to daily or twice daily administrations of other drugs typically utilized to treat these infections.

Disclosed herein are pharmaceutical compositions for treating bacterial infections, in particular a *Mycobacterium tuberculosis* infection. In some embodiments, the pharmaceutical composition is a liposomal composition comprising a polyanion or a sulfate containing polyanion and an aminoalkyl oxazolidinone compound.

In some embodiments, the composition comprises liposomes in a medium, wherein the intraliposomal space comprises an aqueous phase with a polyanion and the compound of Formula I. In some embodiments, the composition comprises liposomes in a medium, wherein the intraliposomal space comprises a polyanion or a sulfate containing polyanion and the compound AKG-16, AKG-28, or AKG-38. In some embodiments, the medium is an aqueous medium, where the primary composition in that media is the compound of formula I and a corresponding trapping agent.

The compound of Formula I can be entrapped within the liposome with a suitable polyanion, such as sucrose octasulfate (e.g. derived from triethylammonium sucrose octasulfate, (TEA-SOS) gradients) or sulfate (e.g. derived from ammonium sulfate gradients). Additional polyanion trapping agents include but are not limited to inositol hexaphosphate, inositol hexasulfate, polyvinylsulfonate, dextran sulfate, citrate, polyphosphate, and suramin.

The exterior aqueous medium is typically composed of a suitable buffer and an isotonicity agent. Suitable buffers may include histidine, citrate, HEPES, MOPS, MES, TRIS, phosphate, glycine, and imidazole, borate, carbonate, and succinate. Isotonicity agents may include salts such as sodium chloride, potassium chloride, sucrose, glycerin, dextrose, or mannitol.

In some embodiments, the composition comprises a compound of Formula I or the Formula 1a, 1b, 1c, or 1d or pharmaceutical acceptable salt thereof, encapsulated with a polyanion in a primarily unilamellar vesicle formed from one or more phospholipid, a sterol and optionally a lipid conjugated to a hydrophilic polymer (a polymer-conjugated lipid). In some embodiments, the composition can comprise a compound of Formula I or the Formula 1a, 1b 1c, or 1d, or pharmaceutical acceptable salt thereof, encapsulated with a polyanion in unilamellar and multilamellar vesicles (e.g. having two or three lamella). It should be appreciated that multilamellar vesicles can be cleared more quickly from circulation than unilamellar vesicles. In some embodiments, the phospholipid is hydrogenated soy phosphatidyl choline (HSPC), distearoylphosphatidylcholine (DSPC), or egg sphingomyelin (ESM). The term "phospholipid as used herein refers to any one phospholipid or combination of phospholipids capable of forming liposomes. Neutral phospholipids can include diacylphosphatidylcholines, dialkylphosphatidylcholines, sphingomyelins, and diacylphosphatidylethanolamines. Phosphatidylcholines (PC), including those obtained from egg, soybeans or other plant sources or those that are partially or wholly synthetic, or of variable lipid chain length and unsaturation are suitable for use in the present compositions. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this disclosure. Charged phospholipids can include phosphatidylserines, phosphatidic acids, phosphatidylinositols, phosphatidylglycerols, cardiolipins, or headgroup modified lipids such as N-succinyl-phosphatidylethanolamines, N-glutaryl-phosphatidylethanolamines, and PEG-derivatized phosphatidylethanolamines.

Polymer-conjugated lipids may include poly(ethylene glycol)-conjugated (pegylated)phospholipids (PEG-lipids) such as PEG(Mol. weight 2,000) methoxy-poly(ethylene glycol)-1,2-distearoyl-sn-glycerol (PEG(2000)-distearoylglycerol, PEG-DSG), PEG(Mol. weight 2,000) 1,2-distearoyl-sn-glycero-3-phosphoethanolamine-N-[methoxy (polyethylene glycol)-2000] (PEG(Mol. weight 2,000)-distearoylphosphatidylethanolamine, PEG-DSPE), or PEG (Mol. weight 2,000)N-palmitoyl-sphingosine-1-{succinyl [methoxy(polyethylene glycol)-2000]} (PEG-ceramide). The molecular weight of the PEG portion in the PEG-lipid component can also vary from 500-10,000 g/mol, from 1,500-6000 g/mol, but is preferably about 2,000 MW. Other polymers used for conjugation to lipid anchors may include poly(2-methyl-2-oxazoline) (PMOZ), poly(2-ethyl-2-oxazoline) (PEOZ), poly-N-vinylpyrrolidone (PVP), polyglycerol, poly(hydroxyethyl L-asparagine) (PHEA), and poly (hydroxyethyl L-glutamine) (PHEG).

In some embodiments, the sterol is cholesterol. Other exemplary sterols include, but are not limited to, ergosterol, phytosterols such as β-sitosterol, and hopanoids. In some embodiments, the ratio of the phospholipid(s) and the cholesterol is selected to provide a desired amount of liposome membrane rigidity while maintaining a sufficiently reduced amount of leakage of the compound of formula I from the liposome. In some embodiments, the optional polymer-conjugated lipid can be added to reduce the tendency of the liposomes to aggregate. The type and amount of polymer-conjugated lipid can be selected to provide desirable levels of protein binding, liposome stability and circulation time in the blood stream. For example, the liposome vesicle comprises phosphatidylcholine (e.g. DSPC or HSPC) and cholesterol in an about 45:55 molar ratio. Phosphatidylcholine to cholesterol molar ratios can vary from about 60:40 to 35:65, about 50:50 to 35:65, about 50:50 to about 45:55. In particular, the liposome can comprise a vesicle consisting of HSPC, cholesterol and polymer-conjugated lipid (PEG-DSG or PEG-DSPE) in a about 55:45:2.75 molar ratio, corresponding to a PEG-lipid concentration of 5 mol % relative to the concentration of phospholipid. The concentration of PEG-lipid can vary from 0.5-to-10 mol % relative to (non-PEGylated) phospholipid, with a preferred ratio of 3-10 mol %, and an even more preferred ratio of 4-8 mol %.

In some embodiments, liposomes compositions provide desirable pharmacokinetic properties such as extended plasma half-life, measured as the percentage of the injected dose (ID) (or injected amount) remaining in blood after 6 or 24 hours following injection intravenously in immunocompetent mice, and stable encapsulation of drug over 24 hours in plasma as determined by changes in the drug-to-lipid ratio (DL ratio) following iv administration in mice. In some embodiments, the percentage of drug remaining in blood is greater than 20%, preferably greater than 30%, and most preferably greater than 40% of the injected dose at 6 hours. The percent retained in blood after 24 h is preferably greater than 10%, and more preferably greater than 20% of the injected dose. The DL ratio is greater than 20% at 24 hours, preferably greater than 50%, and most preferably greater than 80% of the originally injected liposomal drug. Desirable liposome compositions also display stable encapsulation in the presence of human plasma in vitro using a burst release method, with liposomes retaining greater than 50% of the drug over 20 min, greater than 60%, greater than 70%, preferably greater than 80%, and most preferably greater than 90% of encapsulated drug over 20 min.

Liposomes of the present disclosure can be made by any method known in the art. See, for example, G. Gregoriadis (editor), Liposome Technology, vol. 1-3, 1st edition, 1983; 2nd edition, 1993; $3^{rd}$ edition, 2006; CRC Press, Boca Raton, Fla. Examples of methods suitable for making liposome composition of the present disclosure include membrane extrusion, reverse phase evaporation, sonication, solvent (e.g., ethanol) injection (including microfluidic, Y-junction and T-junction mixing), microfluidization, detergent dialysis, ether injection, and dehydration/rehydration. The size of liposomes can be controlled by controlling the pore size of membranes used for extrusions or the pressure and number of passes utilized in microfluidization or any other suitable methods. In some embodiments, the desired lipids are first hydrated by thin-film hydration or by ethanol injection and subsequently sized by extrusion through membranes of a defined pore size, such as, 50 nm, 80 nm, 100 nm, or 200 nm, or the combinations thereof, producing the liposomes with the average size in the range of 70-150 nm, or 80-130 nm, and polydispersity index of 0.1 or less. The drug compound to be encapsulated can be added to the liposome lipids prior to the liposome formation, dissolved in the aqueous medium in which the liposomes are formed by the above methods, whereby the drug is sequestered within the liposomes. In some embodiments, the drug compound is encapsulated in the liposomes using a trapping agent incorporated into the interior space of the liposomes (see Drummond, D. C., et al. (2006) in: Liposome Technology, Third Edition (Ed. Gregoriadis, G.) Volume 2, p. 149-168).

In some embodiments, the method of making liposome composition of the present disclosure comprises the steps of: (i) preparing the liposomes comprising phospholipid, cholesterol, and PEG-lipid, and having an interior space containing a trapping agent, in a medium substantially free from said trapping agent; (ii) contacting said liposomes with the compound of the present disclosure in an aqueous medium to effect encapsulation of the compound in the liposomes; (iii) removing unencapsulated compound; and (iv) providing the liposomes in a physiologically acceptable medium suitable for parenteral use. In some embodiments, the process to generate the liposomes with the compound therein includes the steps of (a) preparing a liposome containing a trapping agent composed of an ammonium or substituted ammonium salt of a polyanion, (b) subsequently removing extra-liposomal trapping agent to form an electrochemical gradients across the membrane, and (c) contacting the liposome with the compound under conditions effective for the compound to enter the liposome and to permit a corresponding amount of the ammonia or substituted ammonia to leave the liposome (thereby exhausting or reducing the pH gradient across the resulting liposome). Liposome compositions containing a trapping agent in the interior of the liposome can be made by formation of the liposomes in a solution of the trapping agent. The transmembrane concentration gradient of the trapping agent can be formed across the liposome by the removal of the trapping agent outside of the or dilution of the liposomes either following liposome formation or before loading (entrapping) of the drug.

In some embodiments said contacting includes incubation of the liposomes with the drug in an aqueous medium at the temperature above ambient and below the boiling point of water, preferably between 30° C. and 90° C., between 40° C.

and 80° C., between 50° C. and 80° C., or between 60° C. and 75° C. In some embodiments, the incubation is carried at ionic strength of less than that equivalent to 50 mM NaCl, or more preferably, less than that equivalent to 30 mM NaCl. Following the incubation, a concentrated salt, e.g., NaCl, solution may be added to raise the ionic strength to higher than that of 50 mM NaCl, or of about 100 mM NaCl. The increase of ionic strength after the drug loading incubation step aided in reducing post-loading aggregation of the liposomes. The incubation times may range from few minutes to several hours. In some embodiments, the incubation times are from 5 to 40 min, from 10 to 30 min, or from 15-25 min. After the incubation, the liposomes are cooled down and then allowed to reach the ambient temperature. In some embodiments, the liposomes are cooled down to 2-15° C. In some embodiments, the liposomes are cooled down to 4-10° C. Following the cooling step, a concentrated salt, e.g., NaCl, solution may be added to raise the ionic strength to higher than that of 50 mM NaCl, or of about 100 mM NaCl. The increase of ionic strength after the drug loading incubation step aided in reducing post-loading aggregation of the liposomes.

In some embodiments, said contacting also included incubation of the liposomes with the drug in aqueous medium in the presence of an osmotic (tonicity) balancing agent. In some embodiments, the osmotic balancing agent (osmotic agent) is a non-ionic agent. Exemplary non-ionic osmotic agents include, but are not limited to, dextrose (glucose), sucrose, trehalose, lactose, mannitol, sorbitol, and polyvinylpyrrolidone. In some embodiments, the concentration of osmotic agent has osmotic concentration (expressed as osmolarity or osmolality) equal to the osmotic concentration of the trapping agent solution in the interior space of the liposomes prior to drug loading. The osmotic concentration of the trapping agent solution can be measured by any known method before the solution is combined with the lipids to form liposomes. In another embodiment, the concentration of osmotic agent provides osmotic concentration that is lower than the osmotic concentration of the trapping agent solution, and is less than about 90%, less than about 80%, less than about 70%, less than about 60%, less than about 50%, less than about 40%, less than about 30%, less than about 20%, or less than about 10% of the osmotic concentration of the trapping agent solution. In yet another embodiment, the concentration of osmotic agent during the drug loading process is in the range of 200-400 mmol/kg, preferably 250-350 mmol/kg. In yet another embodiment, the osmotic agent is dextrose, and the concentration is 45 g/L. In yet another embodiment, no osmotic agent is used during the incubation of the liposomes with the drug. In yet another embodiment, said incubation is performed in the presence of ionic strength adjusting agent. An example of the ionic strength adjusting agent is sodium chloride, added to the liposome-drug solution for example at the concentration between 5 and 50 mM, between 10 and 20 mM, or about 10 mM. Contrary to the convention in the field of liposomes, the compounds of the present disclosure, for example, AKG-28 and AKG-38, are loaded into the liposomes of the present disclosure in a stable and highly efficient manner even if, during the drug-liposome contacting step, the amount of osmotic agent provides osmotic concentration that is lower than the osmotic concentration of the trapping agent solution (osmotically imbalanced liposomes), up to complete absence of the added osmotic agent.

Methods of Use

Disclosed herein are methods for inhibiting the growth of mycobacteria, such as *Mycobacterium tuberculosis*, or gram positive bacteria, such as methicillin-resistant *Staphylococcus aureus* (MRSA). Additional mycobacteria and gram positive bacteria include, but are not limited to, *Mycobacterium avium* complex, *Mycobacterium leprae*, *Mycobacterium gordonae*, *Mycobacterium abscessus*, *Mycobacterium abscessus*, *Mycobacterium mucogenicum*, streptococci, vancomycin-resistant enterococci (VRE), *Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium*. In some embodiments, the compounds and compositions provided herein inhibit the growth of drug resistant strains of *Mycobacterium tuberculosis*. In some embodiments, methods of treating mycobacterial infections are provided. In some embodiments, the compounds and compositions provided herein can be used to treat nontuberculosis mycobacteria infections. In some embodiments, the method comprises administering a therapeutically effective amount of an aminoalkyl oxazolidinone of the disclosure and/or a pharmaceutical acceptable salt thereof to a subject in need thereof. In some embodiments, the method comprises administering a therapeutically effective amount of a liposomal composition comprising an aminoalkyl oxazolidinone compound of the disclosure and/or a pharmaceutical acceptable salt thereof to a subject in need thereof.

In some embodiments, the composition is a liquid pharmaceutical formulation for parenteral administration. In some embodiments, the liquid pharmaceutical formulation is a liposomal formulation containing a suitable amount of the oxazolidinone compound described herein, wherein the oxazolidinone compound is encapsulated in the interior of the liposomes. In another embodiment, that compound is in a salt form in the interior of the liposome with a polyanion such as sulfate, citrate, sucrose octasulfate, inositol hexaphosphate. In some embodiments, the compound is an precipitated or gelated salt with sulfate inside a liposome composed of multiple lipid excipients, including but not limited to, phosphatidylcholine, cholesterol, and pegylated phosphatidylethanolamine. The liposomes of the present disclosure show entrapment efficiencies of more than 85%, more than 90%, and more than 95%. In some embodiments, the residual amount of the unentrapped drug is removed from the liposome composition. This can be achieved by various means, such as size exclusion chromatography, ion exchange, dialysis, ultrafiltration, tangential flow filtration, adsorption, or precipitation. During or after the unentrapped drug removal step, the liposomes may be brought into a desired pharmaceutically acceptable carrier, for example, normal saline, isotonic dextrose, isotonic sucrose, Ringer's solution, or Hanks' solution. A buffer substance can be added to provide desired physiologically acceptable pH. The liposomal composition may be adjusted for desired drug concentration, and sterilized, e.g., by aseptic filtration through 0.2-0.22 μm filters. In some embodiments, the compound concentration in the liposomal composition is in the range of 1-50 mg/ml, 3-30 mg/ml, or 5-25 mg/ml.

In some embodiments, the liposomes are mixed with one or more additional excipients for isotonicity or pH control. In some embodiments, the excipients include but are not limited to sodium chloride, Hepes buffer, phosphate buffer, and histidine buffer.

In other embodiments, the composition is an oral formulation. In some embodiments, the composition is a liquid formulation. In some embodiments, the composition is a solid formulation (e.g. tablet, capsule, pill, dragees, caplets etc. . . . ). When used for oral use for example, tablets, troches, lozenges, aqueous or oil suspensions, dispersible powders or granules, emulsions, hard or soft capsules, syrups or elixirs may be prepared (Remington's Pharmaceutical Sciences (Mack Publishing Co., Easton, Pa.). Compositions intended for oral use may be prepared according to any method known to the art for the manufacture of pharmaceutical compositions. The compositions may contain one or more agents including antioxidants, sweetening agents, flavoring agents, coloring agents and preserving agents, in order to provide a palatable preparation. Tablets containing the active ingredient in admixture with non-toxic pharmaceutically acceptable excipient or auxiliary agents which are suitable for manufacture of tablets are acceptable. Suitable excipients or auxiliary agents include but are not limited to, for example, inert diluents, solubilizers, suspending agents, adjuvants, wetting agents, sweeteners, perfuming or flavoring substances, isotonic substances, colloidal dispersants and surfactants.

Tablets, dragees, capsules, pills, granules, suppositories, solutions, suspensions and emulsions, pastes, ointments, gels, creams, lotions, powders and sprays can be suitable pharmaceutical compositions.

The compound or the composition can be administered locally, orally, parenterally, intraperitoneally and/or rectally.

Dosage regimens are adjusted to provide the optimum desired response (e.g., a therapeutic response). For example, one or more doses may be administered over time or the dose may be proportionally reduced or increased as indicated by the exigencies of the therapeutic situation.

The dosage of the compounds and/or of their pharmaceutically acceptable salts or the liposomes comprising the compounds and/or of their pharmaceutically acceptable salts may vary within wide limits and should naturally be adjusted, in each particular case, to the individual conditions and to the pathogenic agent to be controlled.

In some embodiments, for a use in the treatment of bacterial infections, the compound or the pharmaceutical liposomal composition is administered once every 7 days (i.e., once every week), once every 14 days (i.e., once every two weeks), once every 21 days (i.e., once every three weeks), once every 28 days (i.e., once every four weeks) and once every 42 days (i.e., once every six weeks) to the subject in need thereof. In some embodiments, the average weekly dosage is from about 1 mg to about 1500 mg, about 10 to about 700 mg, about 25 to about 500 mg, or about 70 to about 250 mg. In some embodiments, the average weekly dosage is from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg. In some embodiments, the compound or composition is administered for up to one month, up to two months, up to three months, up to four months or more. The specific therapeutically effective amount will depend on a variety of factors, including the bacterial infection being treated, the activity of the specific compound being administered, the pharmaceutical composition employed, the age, body eight, gender etc. of the subject, the route of administration, the severity of the bacterial infection, the optional drugs/active agents used in combination (sequentially or simultaneously) with the specific compound, and the like factors known to the medical doctor of ordinary skill. In some embodiments, the compounds or the composition can be used for the treatment of tuberculosis or other *Mycobacterium* infections. In some embodiments, the compound can be used as a monotherapy. In some embodiments, the treatment can include administering simultaneously and/or sequentially an effective amount of the compound described herein and an effective amount of one or more additional active agents to treat *Mycobacterium tuberculosis* and other gram-positive bacterial infections. In some embodiments, the treatment can include administering simultaneously and/or sequentially an effective amount of the compound described herein and an effective amount of two or more additional active agents (two, three, four, etc.) to treat *Mycobacterium tuberculosis* and other gram-positive bacterial infections. A synergistic antibacterial effect denotes an antibacterial effect which is greater than the predicted purely additive effects of the individual compounds of the combination. When administered simultaneously, the compound and the active agent can be contained in the same composition or in separate compositions. When administered sequentially, the composition comprising the compound and the composition comprising the additional active agent can be administered with a time separation (e.g. 20 minutes, 40 minutes, 60 minutes or more). In some embodiments, the additional active agents can be administered using a different administration route or by different injections. For example, the compounds of the disclosure can be administered intravenously and one or more additional agents can be administered orally.

In some embodiments, the administration of the compounds with one or more (e.g. one, two, three or four) additional active agents can result in a reduction of the length of the treatment duration. For example, administration of the compounds with one or more (e.g. one, two, three or four) additional active agent can result in a treatment duration at least three times, at least twice, at least 1.5 times shorter than compared to the treatment with only one active agent. In some embodiments, the additional agent(s) is an antibacterial agent. In some embodiments, the additional active agent can include, but are not limited to, fluoroquinolines, such as moxifloxacin, gatifloxacin, or levofloxacin, bedaquiline and other diaryl quinoline analogs (e.g. TBAJ-587 and TBAJ-876), delamanid, pretomanid, isoniazid, rifampicin, rifapentine, pyrazinamide, clofazimine, spectinamide, ethambutol, streptomycin, kanamycin, capreomycin, amikacin, the Leucyl-tRNA Synthetase (LeuRS) inhibitor GSK 3036656, tryptophan synthase inhibitor GSK839, DprE1 inhibitors OPC-167832 and Macozinone (PBTZ-169), Telacebec, GSK-656, TBA-7371, and amoxicillin plus clavulanate, a pharmaceutically acceptable salt of each thereof and any combinations thereof. For the treatment of gram positive bacterial infections, the additional active agent can include, but are not limited to, vancomycin, gentamycin, daptomycin, teicoplanin, ceftaroline, ceftrobiprole, telavancin, dalbavancin, oritavancin, fluoroquinolines (e.g. delafloxacin), tetracyclines (e.g. eravacycline and omadacycline), sulfonamides (e.g. sulfamethoxazole), trimethoprim, lefamulin, and any combinations thereof. In some embodiments, the treatment can include administering simultaneously and/or sequentially an effective amount of the compound described herein and an effective amount of bedaquiline, pretomanid, pyrazinamide, moxifloxacin or a pharmaceutically acceptable salt of each thereof or a combination of the foregoing.

Actual dosage levels of the active ingredients in the pharmaceutical compositions disclosed herein may be varied so as to obtain an amount of the active ingredient which is effective to achieve the desired therapeutic response for a particular patient, composition, and mode of administration, without being toxic to the patient.

"Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, inhalation, subcapsular, subarachnoid, intraspinal, epidural and intrasternal injection and infusion. Intravenous injection and infusion are often (but not exclusively) used for liposomal drug administration.

In some embodiments, the liquid composition is injected intravenously. In some embodiments, the compound or the pharmaceutical composition is administered once every 7 days (i.e., once every week), once every 14 days (i.e., once every two weeks), once every 21 days (i.e., once every three weeks), once every 28 days (i.e., once every four weeks) and once every 42 days (i.e., once every six weeks) to the subject in need thereof. In some embodiments, the average weekly dosage is from about 1 mg to about 1500 mg, about 10 to about 700 mg, about 25 to about 500 mg, or about 70 to about 250 mg. In some embodiments, the average weekly dosage is from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg. The specific therapeutically effective amount will depend on a variety of factors, including the bacterial infection being treated, the activity of the specific compound being administered, the pharmaceutical composition employed, the age, body weight, gender etc. of the subject, the route of administration, the severity of the bacterial infection, the optional drugs/active agents used in combination (sequentially or simultaneously) with the specific compound, and the like factors known to the medical doctor of ordinary skill in the art.

In some embodiments, for a use in the treatment of bacterial infections, the compound or the pharmaceutical oral composition is administered once or twice daily. The specific therapeutically effective amount will depend on a variety of factors, including the bacterial infection being treated, the activity of the specific compound being administered, the pharmaceutical composition employed, the age, body eight, gender etc. of the subject, the route of administration, the severity of the bacterial infection, the optional drugs/active agents used in combination (sequentially or simultaneously) with the specific compound, and the like factors known to the medical doctor of ordinary skill.

EXAMPLES

The following examples, including the experiments conducted and results achieved are provided for illustrative purposes only and are not to be construed as limiting the disclosure.

Example 1—Synthesis of Oxazolidinone Derivatives

Compounds AKG-1, AKG-2, AKG-6, AKG-8, AKG-9 and AKG-19 were synthesized by reacting Tedizolid mesylate (Tedizolid-MS) with respective amines at 60° C. in N-methyl-2-pyrrolidone (NMP) as a solvent (Scheme-1). Tedizolid-MS was obtained by mesylation of the 1° hydroxyl group of Tedizolid with methanesulfonyl chloride in the presence of a base at room temperature (RT). Treatment of Tedizolid-MS with sodium azide followed by reduction of the resulting azide (AKG-3-A) gave either Intermediate-1 as a free base or AKG-3 as a hydrochloride salt depending on eluant selected for purification. Amidation of Intermediate-1 with the corresponding acid followed by hydrochloride salt formation using HCl/EtOAc resulted in compounds AKG-17 and AKG-18. Reacting Tedizolid with the corresponding dialkylamino acid under standard esterification conditions resulted in compounds AKG-5 and AKG-20. O-alkylation of Tedizolid with 2-chloro-N,N-diethylamino ethylamine using sodium hydride as a base gave compounds AKG-7.

Intermediate-2 was synthesized by boronation of commercially available aryl bromide using bis(pinocolato)diboron (Scheme-2). Suzuki coupling of Intermediate-2 with readily available 5-bromo-2-fluoropyridine resulted in Intermediate-3, which was heated in NMP in a sealed tube with the corresponding amine to give compounds AKG-11 to AKG-15.

Compounds AKG-16, AKG-21 to AKG-27 were prepared in a convergent synthesis starting from Intermediate-4 (Schemes-3 and 4). Click chemistry using sodium azide on 5-bromo-2-cyanopyridine gave Intermediate-4. N-alkylation of the tetrazole in Intermediate-4 resulted in Intermediates 5 and 6 in 3:1 ratio. The structure of these intermediates was deduced from HMBC analysis. Intermediates 7 to 12 were synthesized and the regioisomers were obtained in a similar manner (Only desired isomers are shown in Scheme-4). Suzuki coupling of Intermediates 5 to 12 with Intermediate 2 and deprotection of amine group where applicable resulted in compounds AKG-16, AKG-21 to AKG-27.

Intermediate-13 was synthesized by mesylation of readily available aryl bromide. Intermediate-15 was obtained by reducing Intermediate-14 with hydrazine (Scheme-5). Boc protection or acetylation of the primary amine in Intermediate-15 followed by boronation resulted in Intermediates-18 and 19, respectively. Suzuki (U.S. Pat. Appl. Publ. No. 20100022772, PCT Int. Appl. Publ. No. WO2013044845, which are incorporated herein by reference in their entireties) coupling of the boronate intermediates with the corresponding aryl bromide intermediates and deprotection of the amine group where applicable resulted in compounds AKG-28 to AKG-31 and AKG-38 to AKG-40.

Synthetic Schemes

See U.S. Pat. Appl. Publ. No. 20100022772, PCT Int. Appl. No. 2013044845 which are incorporated herein by reference in their entireties, for the synthesis of Intermediate-19.

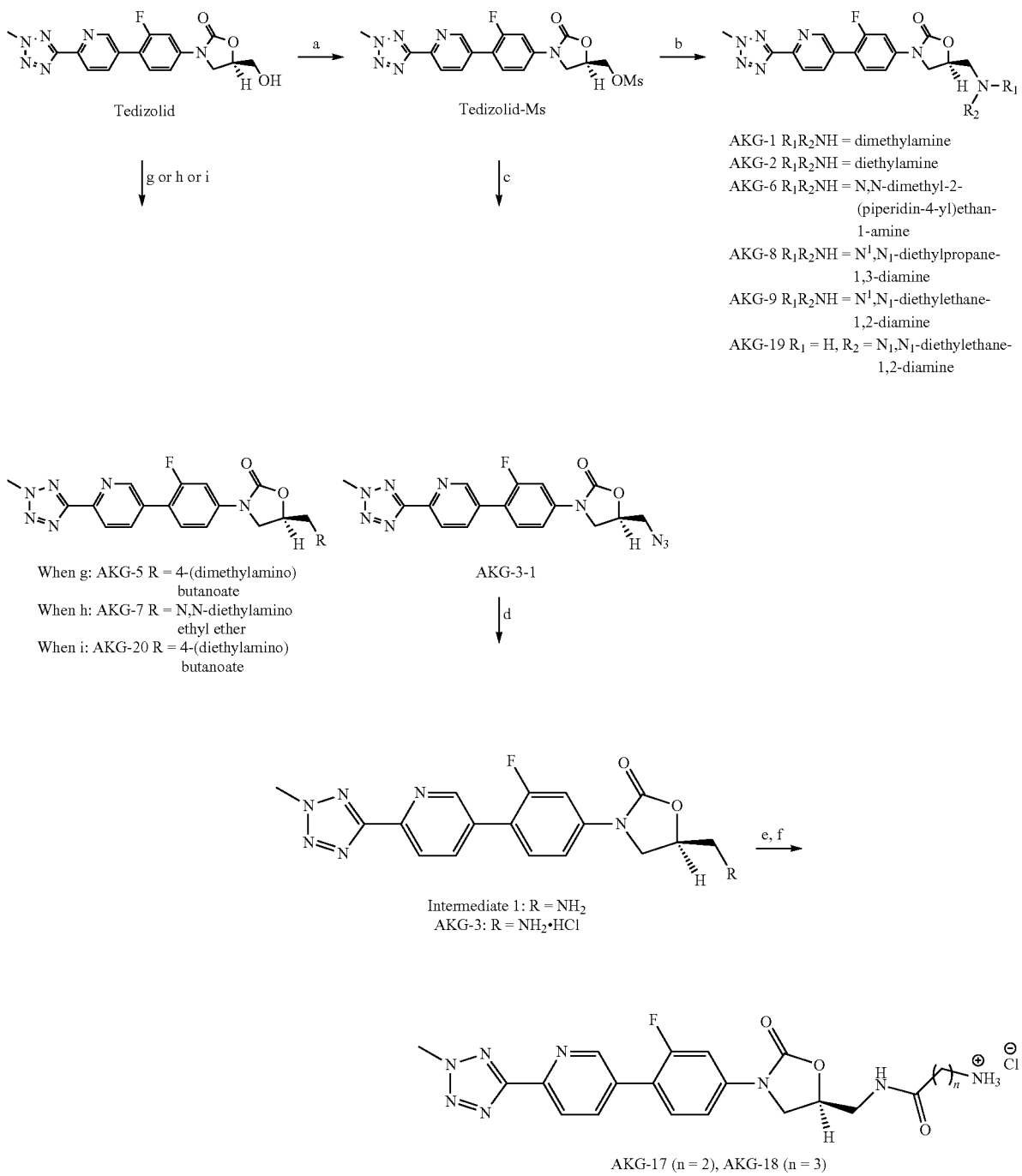

Conditions: (a) CH$_2$Cl$_2$, MsCl, TEA, r.t 2 h; (b) R$_2$R$_2$NH, NMP, 60° C. 16 h; (c) NaN$_3$, DMF, 90° C., 3 h; (d) Ph$_3$P, THF/H$_2$O, reflux 1 h; (e) HATU, acid, DMF; (f) HCl/EtOAc; (g) DCC, DMF, TEA, DMAP, 4-(dimethylamino)butanoic acid hydrogen chloride, r.t, 16 h; (h) NaH, DMF, 2-chloro-N,N-diethylethan-1-amine, 0° C. r.t, 3 h; (i) DCC, DMF, DMAP, 4-(diethylamino)butanoic acid hydrogen chloride, r.t, 16 h.

Scheme 2

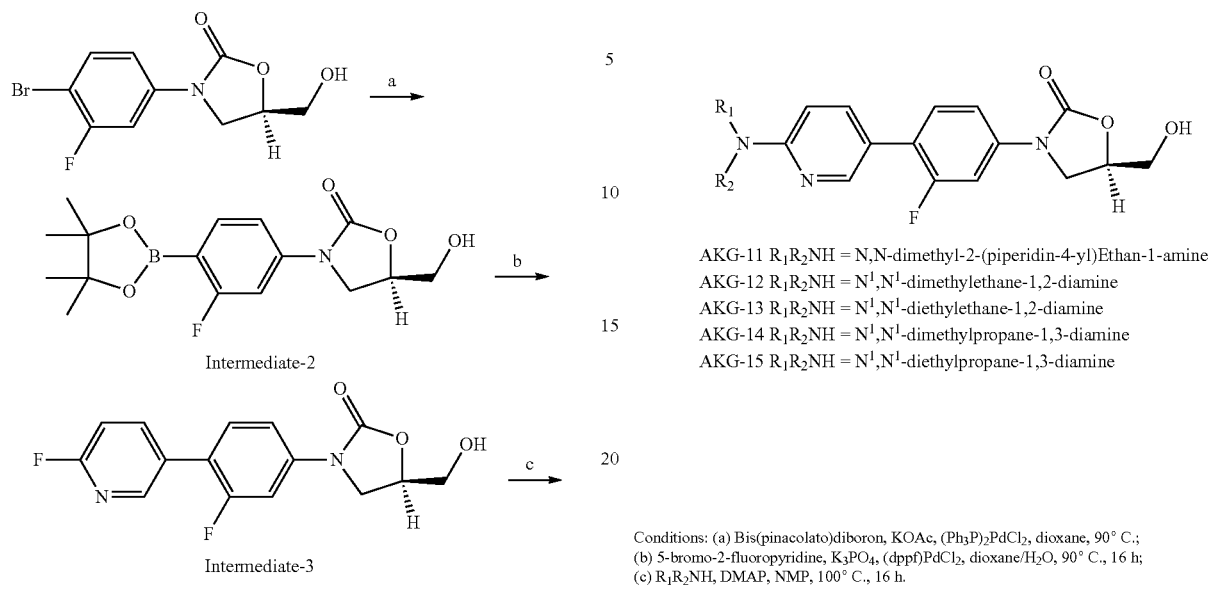

AKG-11 R$_1$R$_2$NH = N,N-dimethyl-2-(piperidin-4-yl)Ethan-1-amine
AKG-12 R$_1$R$_2$NH = N$^1$,N$^1$-dimethylethane-1,2-diamine
AKG-13 R$_1$R$_2$NH = N$^1$,N$^1$-diethylethane-1,2-diamine
AKG-14 R$_1$R$_2$NH = N$^1$,N$^1$-dimethylpropane-1,3-diamine
AKG-15 R$_1$R$_2$NH = N$^1$,N$^1$-diethylpropane-1,3-diamine Conditions: (a) Bis(pinacolato)diboron, KOAc, (Ph$_3$P)$_2$PdCl$_2$, dioxane, 90° C.;
(b) 5-bromo-2-fluoropyridine, K$_3$PO$_4$, (dppf)PdCl$_2$, dioxane/H$_2$O, 90° C., 16 h;
(c) R$_1$R$_2$NH, DMAP, NMP, 100° C., 16 h.

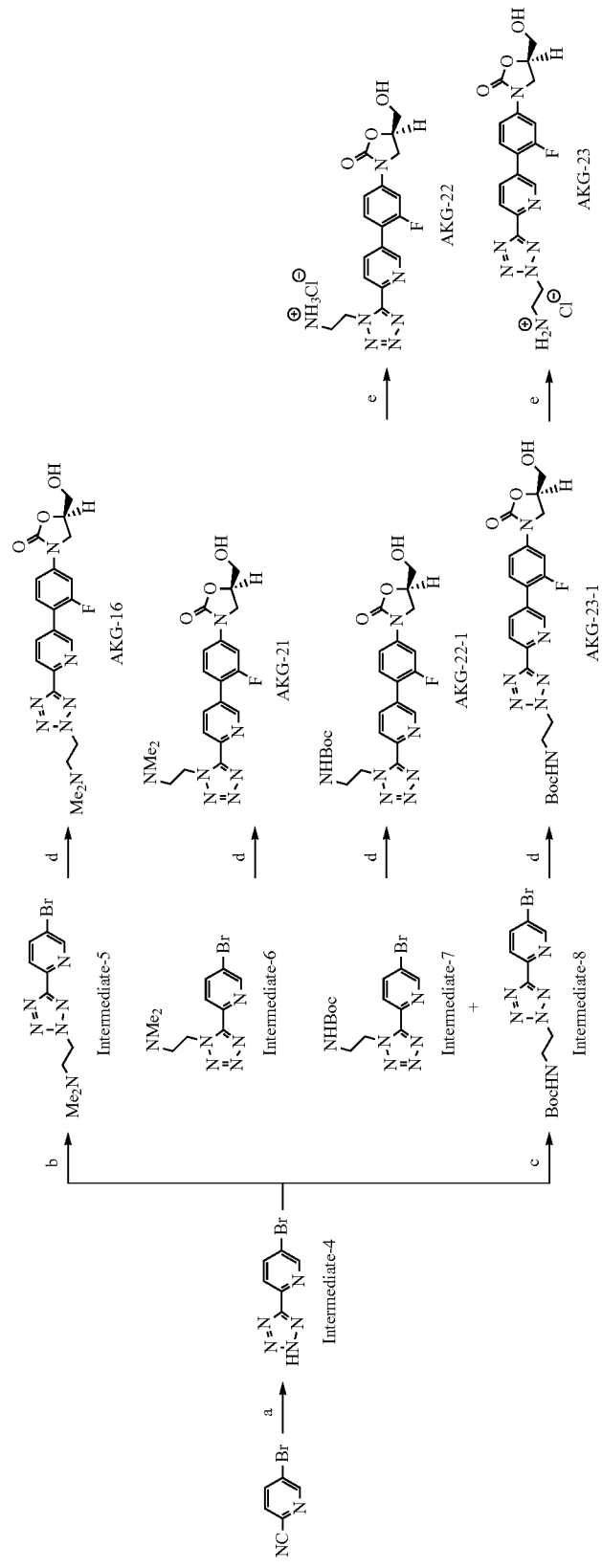
Conditions: (a) NaN₃·ZnCl₂, pyridine, 120° C., 2 h; (b) (2-Bromoethyl)® hydroxymide, Ca(OH)₂, H₂O/DMF, 80° C., 24 h; (c) NHBoc(CH₂)₂Br, Ca(OH)₂, H₂O/DMF, 80° C., 24 h; (d) Intermediate-2, (dppf)PdCl₂, K₃PO₄, dioxane, 90° C., 16 h, (e) HCl/Dioxane, r.t., 5h.

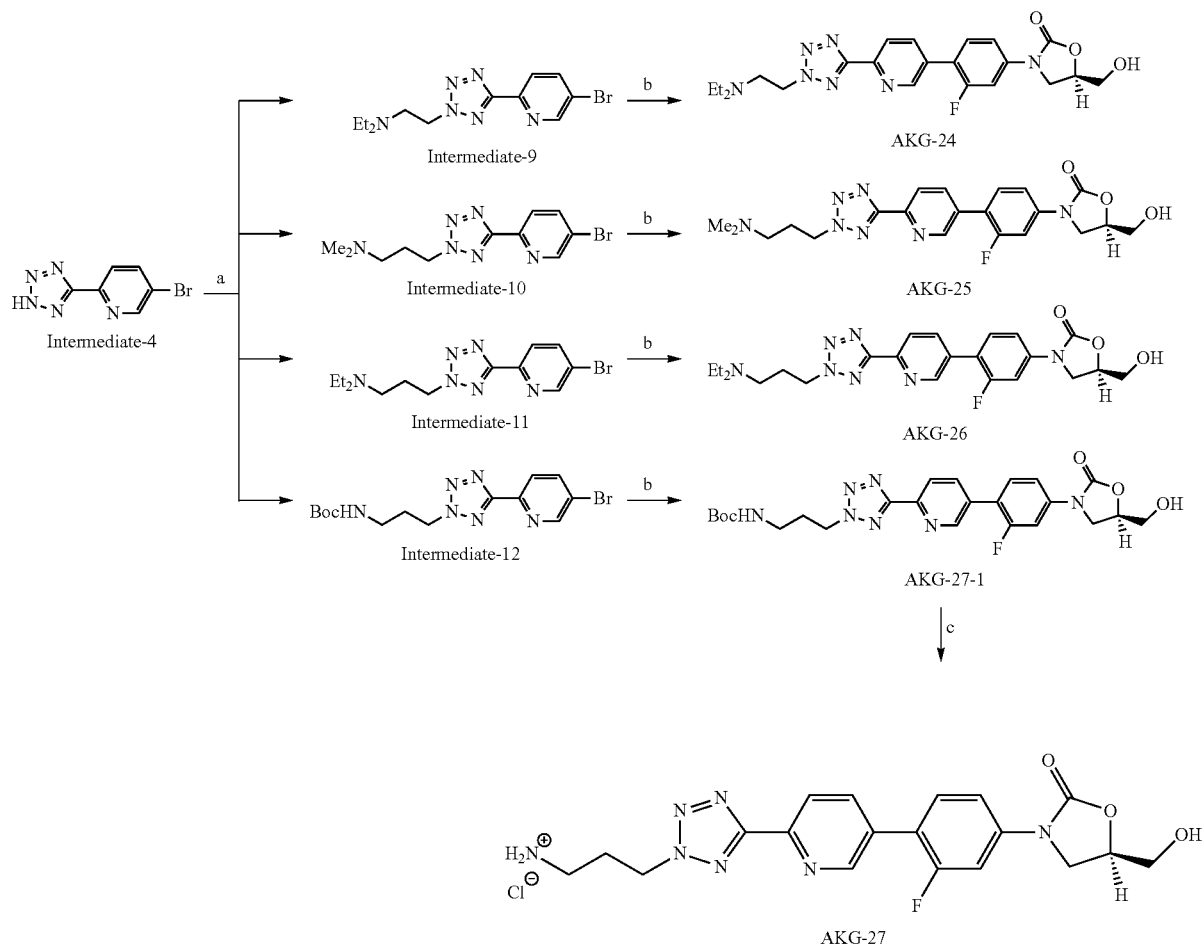
Conditions: (a) Amine, Ca(OH)₂, H₂O/DMF, 80° C., 24 h; (b) Intermediate-2, (dppf)PdCl₂, K₃PO₄, dioxane, 90° C., 16 h; (c) HCl/Dioxane, r.t., 5 h.
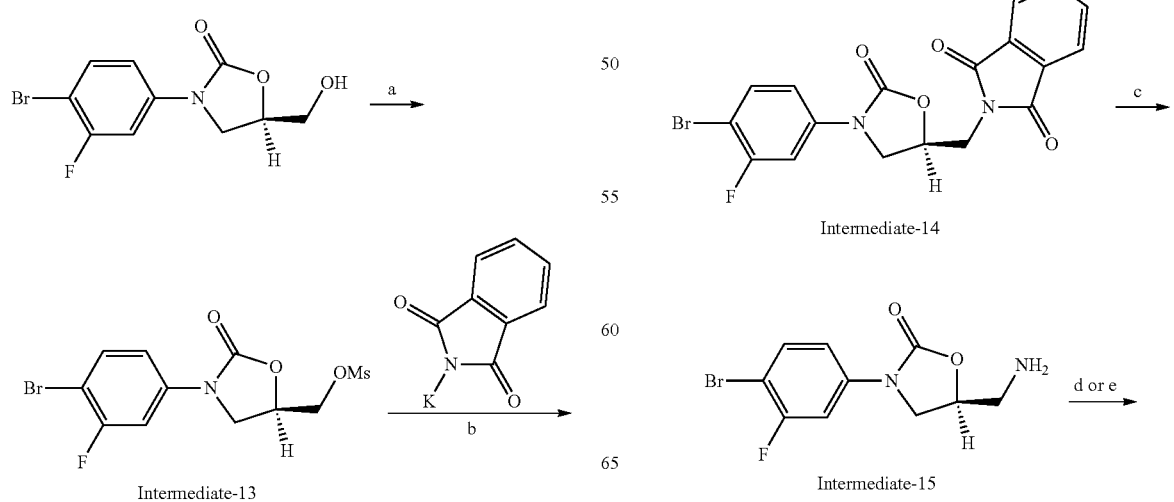

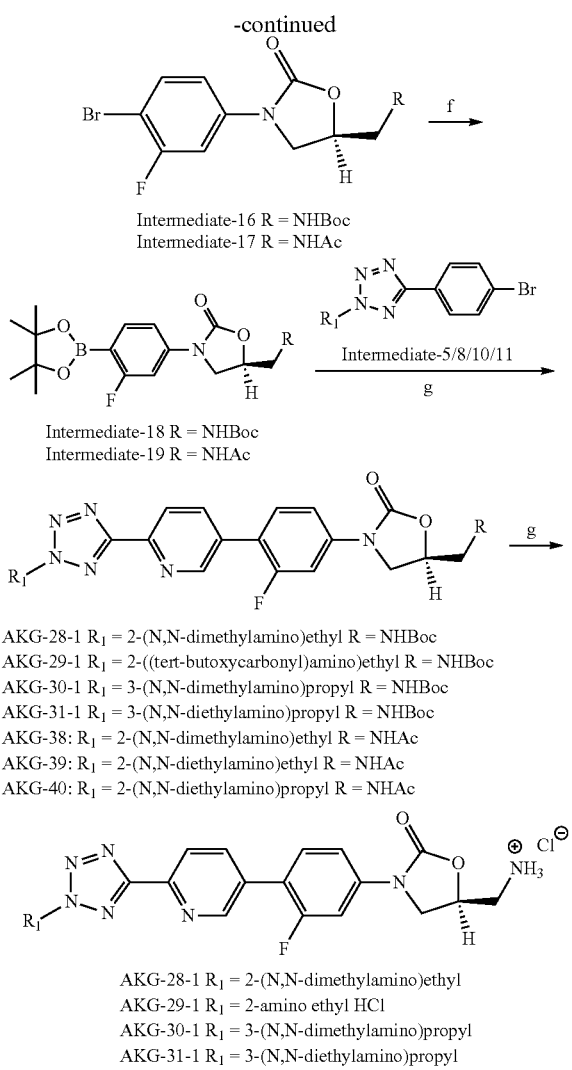

Intermediate-16 R = NHBoc
Intermediate-17 R = NHAc

Intermediate-18 R = NHBoc
Intermediate-19 R = NHAc

AKG-28-1 R₁ = 2-(N,N-dimethylamino)ethyl R = NHBoc
AKG-29-1 R₁ = 2-((tert-butoxycarbonyl)amino)ethyl R = NHBoc
AKG-30-1 R₁ = 3-(N,N-dimethylamino)propyl R = NHBoc
AKG-31-1 R₁ = 3-(N,N-diethylamino)propyl R = NHBoc
AKG-38: R₁ = 2-(N,N-dimethylamino)ethyl R = NHAc
AKG-39: R₁ = 2-(N,N-diethylamino)ethyl R = NHAc
AKG-40: R₁ = 2-(N,N-diethylamino)propyl R = NHAc AKG-28-1 R₁ = 2-(N,N-dimethylamino)ethyl
AKG-29-1 R₁ = 2-amino ethyl HCl
AKG-30-1 R₁ = 3-(N,N-dimethylamino)propyl
AKG-31-1 R₁ = 3-(N,N-diethylamino)propyl Conditions: (a) MsCl, TEA, DCM, RT, 2 h; (b) DMF, 80° C., 16 h; (c) NH₂NH₂, EtOH, 80° C.; (d) Eoc₂O, THF/H₂O, NaHCO₃, RT, (e) AcCl, TEA, DCM, RT, (f) Bis(pinacolato)diboron, KOAc, (Ph₃P)₂PdCl₂, dioxane, 90° C.; (g) K₃PO₄, (dppf)PdCl₂, dioxane:H₂O, 90° C., 16 h; (h) HCl in EtOAc, DCM, RT, 2 h.

Synthesis
Materials and Methods.

Tedizolid, (R)-3-(4-bromo-3-fluorophenyl)-5-(hydroxymethyl)oxazolidin-2-one were purchased from Skychemical and Dimethyl-(2-piperdin-4-yl-ethyl)-amine was purchased from Enamine, the other reagents and solvents were purchased from Adams and were used as received. The chemical structures of final products were characterized by nuclear magnetic resonance spectra ($^{1}$H NMR, $^{13}$C NMR) determined on a Bruker NMR spectrometer (500 MHz or 400 MHz). $^{13}$C NMR spectra were fully decoupled. Chemical shifts were in parts per millions (ppm) using deuterated solvent peak or tetramethylsilane (internal) as the internal standards. Data for $^{1}$H NMR are recorded as follows: chemical shift (d, ppm), multiplicity (s, singlet; br s, broad singlet; d, doublet; t, triplet; m, multiplet), integration, coupling constant (Hz). Data for $^{13}$C NMR are recorded in terms of chemical shift (d, ppm).

The purity of final products (>95%) was confirmed by analytical HPLC. Analytical HPLC was performed on an Agilent analytical HPLC system using a Sunfire column, 3.5 μm (150 cm×4.6 mm) and a gradient system (water (0.01% TFA)/ACN (0.01% TFA)) and a flow rate of 1 mL/min with detection at 254 and 214 nm. Flash Chromatographic (FC) purifications were performed with Silica Gel 60 from Santai Technologies (0.04-0.063 nm; 230-400 mesh).

Procedure A. The reaction mixture of Tedizolid-Ms (1.0 eq), R₁R₂NH (4.0 eq) in NMP (10 mL) was heated to 60° C. for 15 h in a sealed tube. Upon completion (LCMS), the reaction was diluted with H₂O (40 mL) and extracted with EtOAc (2×50 mL). The combined extracts were washed with saturated brine dried over Na₂SO₄ and filtered. The solvent was removed in vacuo and the residue was purified using FC to give the product with >95% purity.

1. Synthesis of Tedizolid-Ms

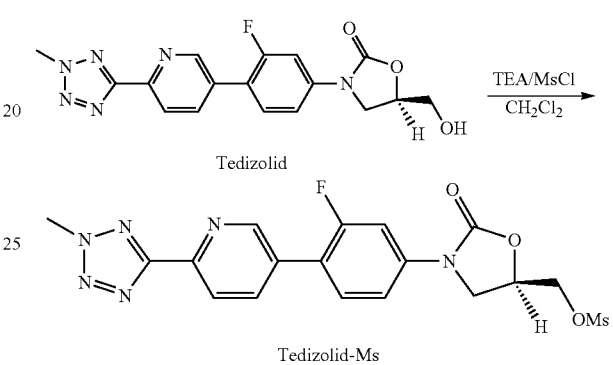

Tedizolid

Tedizolid-Ms

To a solution of Tedizolid (7.00 g, 18.90 mmol) and triethylamine (3.83 g, 37.80 mmol) in CH₂Cl₂ (50 mL) at 0° C. was added dropwise methanesulfonyl chloride (3.25 g, 28.36 mmol) at 0° C. under Ar. After stirring at RT for 2 h, the reaction mixture was poured into water and extracted with CH₂Cl₂. The organic layer was washed with brine, dried over Na₂SO₄ and collected by filtration. The solvent was removed in vacuum to give the pure product Tedizolid-Ms (7.0 g, 82.6% yield) as a yellow solid. $^{1}$H NMR (400 MHz, DMSO-d₆) δ 8.95 (s, 1H), 8.31-8.14 (m, 2H), 7.88-7.65 (m, 2H), 7.53 (d, J=8.6 Hz, 1H), 5.14-4.96 (m, 1H), 4.59-4.39 (m, 5H), 4.28 (t, J=9.4 Hz, 1H), 3.92 (dd, J=9.2, 6.3 Hz, 1H), 3.28 (s, 3H). MS (ESI+) m/z 449.1 ([M+1]⁺).

2. Synthesis of AKG-1, 2, 6, 8, 9 and 19

AKG-1

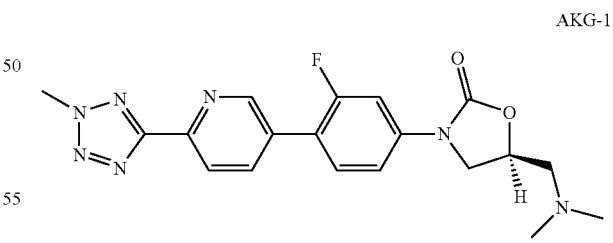

Using procedure A, AKG-1 was obtained from Tedizolid-Ms and dimethylamine as a white solid (0.5 g, 56.4% yield). $^{1}$H NMR (400 MHz, DMSO-d₆) δ 8.94 (s, 1H), 8.32-8.13 (m, 2H), 7.83-7.64 (m, 2H), 7.54 (d, J=7.6 Hz, 1H), 4.87 (s, 1H), 4.49 (s, 3H), 4.21 (t, J=8.6 Hz, 1H), 3.84 (t, J=7.4 Hz, 1H), 2.62 (s, 2H), 2.25 (s, 6H). $^{13}$C NMR (101 MHz, DMSO-d₆) δ 164.3, 161.0, 158.6, 154.6, 149.9, 145.5, 140.9, 137.6, 132.1, 131.4, 122.6, 119.1, 114.6, 106.0, 72.0, 62.1, 48.7, 46.4, 40.2. MS (ESI+) m/z 398.2 ([M+1]⁺).

AKG-2

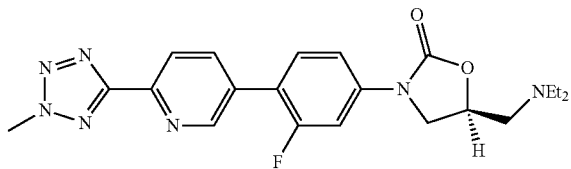

Using procedure A, AKG-2 was obtained from Tedizolid-Ms and diethylamine as a white solid (0.52 g, 54.8% yield). $^1$H NMR (400 MHz, DMSO-$d_6$) δ 8.94 (s, 1H), 8.29-8.11 (m, 2H), 7.81-7.65 (m, 2H), 7.52 (dd, J=8.6, 1.8 Hz, 1H), 4.89-4.73 (m, 1H), 4.49 (s, 3H), 4.19 (t, J=8.8 Hz, 1H), 3.82 (dd, J=8.7, 7.0 Hz, 1H), 2.75 (dd, J=5.1, 3.7 Hz, 2H), 2.57 (q, J=6.9 Hz, 4H), 0.97 (t, J=7.1 Hz, 6H). $^{13}$C NMR (101 MHz, DMSO-$d_6$) δ 164.3, 161.0, 158.6, 154.7, 149.9, 145.5, 141.0, 137.6, 132.1, 131.3, 122.5, 119.1, 114.6, 106.1, 72.6, 56.1, 48.6, 47.7, 40.3, 12.3. MS (ESI+) m/z 426.3 ([M+1]$^+$).

AKG-6

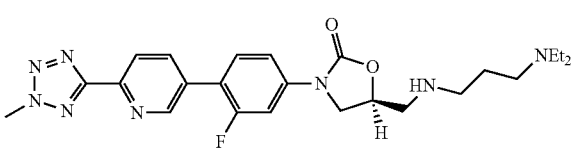

Using procedure A, AKG-6 was obtained from Tedizolid-Ms and N,N-Dimethyl-2-(piperidin-4-yl)ethan-1-amine as a white solid (0.66 g, 58.2% yield). $^1$H NMR (400 MHz, CDCl$_3$) δ 8.93 (s, 1H), 8.30 (dd, J=8.1, 2.4 Hz, 1H), 8.05 (d, J=7.8 Hz, 1H), 7.62 (d, J=12.9 Hz, 1H), 7.56-7.47 (m, 1H), 7.45-7.37 (m, 1H), 4.89-4.74 (m, 1H), 4.48 (s, 3H), 4.11 (t, J=8.6 Hz, 1H), 3.86 (t, J=7.8 Hz, 1H), 2.93 (dd, J=28.8, 10.9 Hz, 2H), 2.80-2.64 (m, 2H), 2.50-2.04 (m, 11H), 1.69 (d, J=10.8 Hz, 2H), 1.48 (d, J=7.1 Hz, 2H), 1.37-1.19 (m, 4H). $^{13}$C NMR (101 MHz, CDCl$_3$) δ 164.7, 161.3, 158.8, 154.3, 149.9, 145.4, 140.2, 137.0, 132.3, 130.5, 122.0, 120.0, 113.8, 106.4, 71.5, 61.4, 57.0, 55.3, 54.3, 48.9, 45.0, 39.7, 33.6, 32.4. MS (ESI+) m/z 509.2 ([M+1]$^+$).

AKG-8

Using procedure A, AKG-8 was obtained from Tedizolid-Ms and N$^1$,N$^1$-diethylpropane-1,3-diamine as a white solid (0.62 g, 57.6% yield). $^1$H NMR (400 MHz, DMSO-$d_6$) S 8.94 (s, 1H), 8.34-8.11 (m, 2H), 7.84-7.59 (m, 2H), 7.52 (dd, J=8.6, 2.0 Hz, 1H), 4.80 (dd, J=8.3, 5.7 Hz, 1H), 4.49 (s, 3H), 4.18 (t, J=8.9 Hz, 1H), 3.90 (dd, J=8.8, 6.5 Hz, 1H), 2.94-2.77 (m, 2H), 2.66-2.53 (m, 7H), 1.65-1.51 (m, 2H), 0.99 (t, J=7.1 Hz, 6H). $^{13}$C NMR (101 MHz, DMSO-$d_6$) δ 164.3, 161.0, 158.6, 154.6, 149.9, 145.5, 141.0, 137.6, 132.1, 131.4, 122.6, 119.1, 114.6, 106.1, 73.2, 52.1, 50.7, 48.2, 48.0, 46.7, 40.3, 26.4, 11.4. m/z 483.2 ([M+1]$^+$).

AKG-9

Using procedure A, AKG-9 was obtained from Tedizolid-Ms and N$^1$,N$^1$-diethylethane-1,2-diamine as a white solid (0.36 g, 34.4% yield). $^1$H NMR (500 MHz, DMSO-$d_6$) δ 8.94 (s, 1H), 8.26-8.16 (m, 2H), 7.78-7.66 (m, 2H), 7.53 (d, J=8.5 Hz, 1H), 4.85-4.73 (m, 1H), 4.49 (s, 3H), 4.18 (t, J=8.8 Hz, 1H), 3.90 (t, J=7.5 Hz, 1H), 2.88 (t, J=5.4 Hz, 2H), 2.65 (t, J=6.1 Hz, 2H), 0.95 (t, J=7.0 Hz, 6H). $^{13}$C NMR (101 MHz, DMSO-$d_6$) δ 164.3, 161.0, 158.6, 154.7, 149.9, 145.5, 141.0, 137.6, 132.1, 131.4, 122.6, 119.1, 114.6, 106.1, 73.3, 52.6, 52.2, 48.1, 47.6, 47.1, 40.3, 12.0. m/z 469.3 ([M+1]$^+$).

Using procedure A, AKG-19 was obtained from Tedizolid-Ms and ethane-1,2-diamine as a white solid (0.60 g, 55% yield). $^1$H NMR (500 MHz, DMSO-$d_6$) δ 10.33 (s, 1H), 9.89 (s, 1H), 8.95 (s, 1H), 8.58 (s, 3H), 8.23 (q, J=8.3 Hz, 2H), 7.79 (t, J=8.8 Hz, 1H), 7.69 (d, J=13.5 Hz, 1H), 7.49 (d, J=8.7 Hz, 1H), 5.25-5.19 (m, 1H), 4.49 (s, 3H), 4.33 (t, J=9.2 Hz, 1H), 4.05 (dd, J=9.1, 6.7 Hz, 1H), 3.52 (s, 2H), 3.43-3.23 (m, 4H). $^{13}$C NMR (101 MHz, DMSO-$d_6$) δ 164.26, 160.94, 158.50, 153.79, 149.84, 145.51, 140.58, 137.78, 132.04, 131.42, 122.61, 119.50, 114.94, 106.46, 69.38, 49.59, 47.87, 45.16, 40.34, 35.58.

3. Synthesis of AKG-3

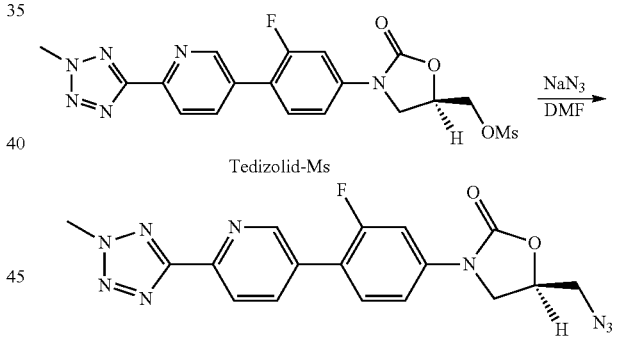

To a solution of Tedizolid-Ms (1.00 g, 2.23 mmol) in DMF (20 mL) was added NaN$_3$ (0.44 g, 6.69 mmol). After stirring at 90° C. for 3 h, the reaction mixture was poured into water and extracted with EtOAc. The organic layer was washed with brine, dried over anhydrous MgSO$_4$, filtered and concentrated in vacuo. The residue was further purified by column chromatography to obtain the title compound AKG-3-1 (0.7 g, 79.4% yield) as white solid.

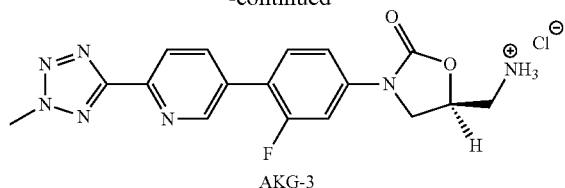

AKG-3

The reaction mixture of AKG-3-1 (0.7 g, 1.77 mmol) and Ph₃P (1.39 g, 5.31 mmol) in H₂O (2 mL) and THF (20 mL) was heated to reflux for 1 h. After completion of (LCMS), the reaction was concentrated in vacuo and purified using reverse phase FC. While purification using MeOH in DCM 0-10% as eluant and freeze drying gave freebase Intermediate-1 (2.5 g, 76.5% yield) as a yellow solid, FC purification with MeCN in 0.006M HCl in H₂O/0-30% as eluant gave hydrochloride salt AKG-3 (0.35 g, 48.8% yield) as a yellow solid after freeze drying. $^1$H NMR (400 MHz, DMSO-$d_6$) δ 8.95 (s, 1H), 8.61 (s, 3H), 8.28-8.18 (m, 2H), 7.79 (t, J=8.8 Hz, 1H), 7.69 (dd, J=13.5, 2.1 Hz, 1H), 7.48 (dd, J=8.6, 2.1 Hz, 1H), 5.13-5.00 (m, 1H), 4.49 (s, 3H), 4.29 (t, J=9.2 Hz, 1H), 4.02 (dd, J=9.3, 6.6 Hz, 1H), 3.34-3.23 (m, 2H). $^{13}$C NMR (101 MHz, DMSO-$d_6$) δ 163.8, 160.4, 158.0, 153.4, 149.4, 145.1, 140.2, 137.2, 131.5, 130.9, 122.1, 118.9, 114.3, 105.9, 69.8, 47.1, 41.4, 39.8. m/z 370.3 ([M−HCl+1]$^+$).

4. Synthesis of AKG-17

To a solution of 3-((tert-butoxycarbonyl)amino)propanoic acid (0.62 g, 3.25 mmol, 1.2 eq) and TEA (0.63 g, 6.25 mmol, 2.5 eq) in DMF (10 mL) was added HATU (1.44 g, 3.78 mmol, 1.4 eq) at RT under Ar. The mixture was stirred for 0.5 h and then Intermediate 1 (1.0 g, 2.70 mmol, 1.0 eq) was added. The whole mixture was stirred at RT overnight. LCMS showed the reaction was complete, it was poured into H₂O and the solid was collected by filtration and washed with H₂O. The solid was dried in vacuo and the residue was used in the next step directly by dissolving it into EtOAc and then HCl/EtOAc (4 M, 20 mL) was added. The whole mixture was stirred for 16 h and the solvent was removed by N2. The residue was purified by reverse phase FC (eluant with MeCN in 0.006M HCl in H₂O/0-30%) to give the product AKG-17 (0.5 g, 39.5% yield) after freeze drying as a yellow solid. $^1$H NMR (500 MHz, DMSO-$d_6$) δ 8.95 (s, 1H), 8.67 (s, 1H), 8.23 (q, J=8.3 Hz, 2H), 8.14 (s, 3H), 7.77 (t, J=8.6 Hz, 1H), 7.69 (d, J=13.5 Hz, 1H), 7.50 (d, J=8.6 Hz, 1H), 4.87-4.78 (m, 1H), 4.49 (s, 3H), 4.22 (t, J=9.0 Hz, 1H), 3.89 (dd, J=9.0, 6.5 Hz, 1H), 3.50 (t, J=5.3 Hz, 2H), 2.98 (dd, J=12.5, 6.4 Hz, 2H), 2.58 (t, J=7.1 Hz, 2H). $^{13}$C NMR (101 MHz, DMSO-$d_6$) δ 170.60, 164.22, 160.97, 158.53, 154.42, 149.78, 145.42, 140.89, 137.79, 132.11, 131.41, 122.61, 119.19, 114.72, 106.23, 105.95, 72.13, 47.77, 40.33, 35.58, 32.58.

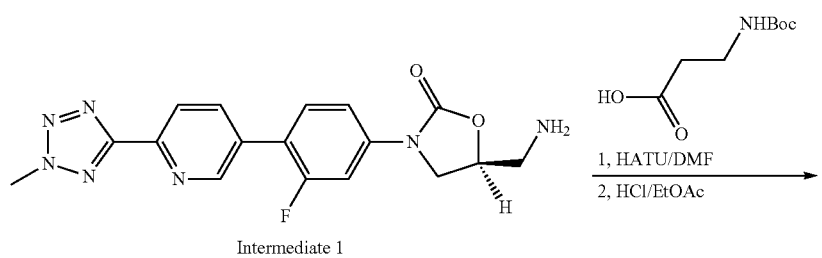

Intermediate 1

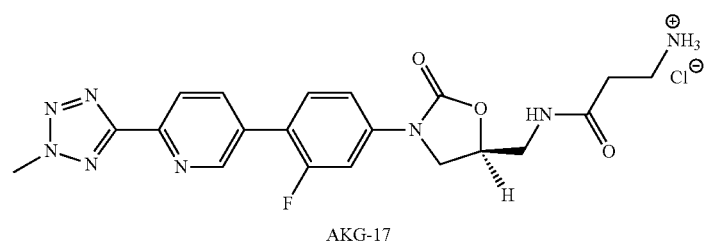

AKG-17

5. Synthesis of AKG-18

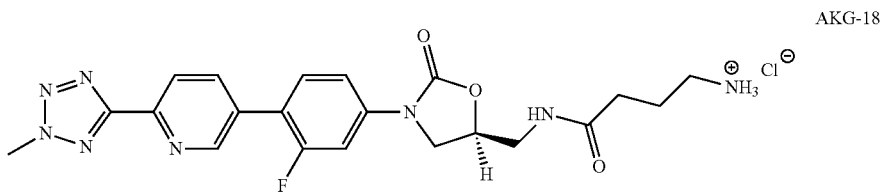 [SMILES: Cn1nnc(-c2ccc(-c3ccc(N4C[C@H](CNC(=O)CCC[NH3+])OC4=O)cc3F)cn2)n1 ; [Cl-]]
AKG-18

Using the procedure of AKG-17, AKG-18 was obtained from Intermediate-1 and 4-((tert-butoxycarbonyl)amino)butanoic acid as a yellow solid (0.5 g, 37.6% yield). $^1$H NMR (500 MHz, DMSO-$d_6$) δ 8.95 (s, 1H), 8.52 (t, J=5.7 Hz, 1H), 8.29-8.08 (m, 5H), 7.77 (t, J=8.8 Hz, 1H), 7.69 (d, J=13.6 Hz, 1H), 7.50 (d, J=8.7 Hz, 1H), 4.87-4.76 (m, 1H), 4.50 (s, 3H), 4.22 (t, J=9.0 Hz, 1H), 3.93-3.83 (m, 1H), 3.49 (t, J=5.3 Hz, 2H), 2.83-2.72 (m, 2H), 2.28 (t, J=7.2 Hz, 2H), 1.88-1.75 (m, 2H). $^{13}$C NMR (101 MHz, DMSO-$d_6$) δ 172.59, 164.23, 160.96, 158.52, 154.44, 149.00, 145.39, 140.88, 137.78, 132.10, 131.40, 122.61, 119.17, 114.70, 106.21, 72.17, 47.78, 41.88, 40.37, 38.78, 32.44, 23.60.

6. Synthesis of AKG-5

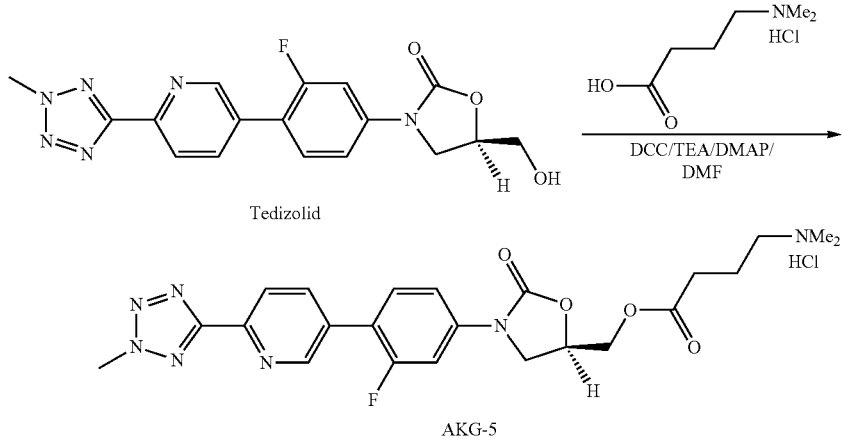

To a mixture of Tedizolid (1.0 g, 2.70 mmol), 4-(dimethylamino)butanoic acid hydrogen chloride (0.57 g, 3.37 mmol) and TEA (0.27 g, 2.70 mmol), cat amount of DMAP in DMF (20 mL) was added DCC (0.84 g, 4.05 mmol) at under N2. The mixture was stirred at RT for 16 h. Upon completion of reaction (LCMS), it was diluted with H$_2$O (100 mL) and filtrated. The filtrate was acidified with 0.02 M HCl to pH=5-6 and then purified using RP-FC (eluant with MeCN in 0.5% formic acid/H$_2$O) to give the product AKG-5 as a formic acid salt after freeze drying. The product was re-dissolved into H$_2$O and 1 eq of aq. HCl (0.02 M) was added. Freeze drying the product resulted in AKG-5 as a HCl salt (600 mg, 42.7% yield). $^1$H NMR (400 MHz, DMSO-$d_6$) δ 10.40 (br, 1H), 8.95 (s, 1H), 8.23 (q, J=8.5 Hz, 2H), 7.78 (t, J=8.8 Hz, 1H), 7.71 (dd, J=13.6, 2.1 Hz, 1H), 7.53 (dd, J=8.6, 2.1 Hz, 1H), 5.03 (dd, J=5.6, 3.1 Hz, 1H), 4.48 (s, 3H), 4.36 (qd, J=12.4, 4.2 Hz, 2H), 4.26 (t, J=9.3 Hz, 1H), 3.95 (dd, J=9.2, 6.2 Hz, 1H), 2.99-2.86 (m, 2H), 2.64 (s, 6H), 2.45 (t, J=7.3 Hz, 2H), 1.87 (m, 2H). $^{13}$C NMR (126 MHz, DMSO-$d_6$) δ 172.3, 164.3, 158.8, 154.3, 149.9, 145.6, 140.8, 137.7, 132.0, 131.5, 122.6, 119.4, 114.7, 106.2, 71.1, 64.8, 56.3, 46.7, 40.3, 30.9, 19.9. m/z 469.3 ([M+1]$^+$). m/z 484.1 ([M−HCl+1]$^+$).

7. Synthesis of AKG-7

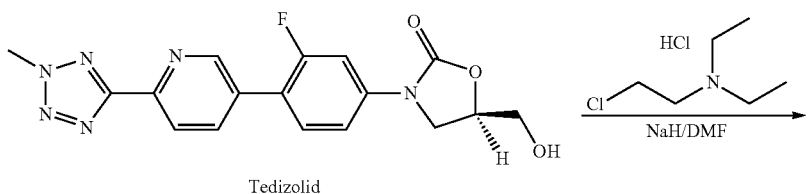

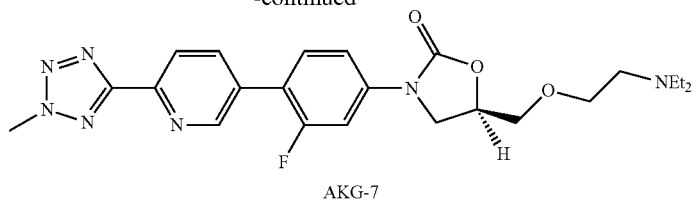

AKG-7

To a mixture of Tedizolid (1.0 g, 2.70 mmol in DMF (20 mL) was added NaH (0.13 g, 60%, 5.40 mmol) at RT under N2. The mixture was stirred at 0° C. for 0.5 h and then 2-Diethylaminoethylchloride hydrochloride (930 mg, 5.40 mmol) was added in one portion. The whole mixture was stirred at RT for 3 h. LCMS showed completion of the reaction. The reaction was carefully poured into ice/H$_2$O (20 mL) and extracted with DCM (2×50 mL). The combined organic extracts were washed with saturated brine followed by the drying over Na$_2$SO$_4$. The solvent was removed in vacuo and the residue was purified using FC (eluant with MeOH in DCM 0-15%) to give AKG-7 as a white solid (0.5 g, 39.4% yield). $^1$H NMR (500 MHz, CDCl$_3$) δ 8.93 (s, 1H), 8.30 (d, J=8.2 Hz, 1H), 8.05 (d, J=8.2 Hz, 1H), 7.72 (d, J=12.9 Hz, 1H), 7.53 (t, J=8.5 Hz, 1H), 7.42 (d, J=8.5 Hz, 1H), 4.88 (d, J=3.5 Hz, 1H), 4.48 (s, 3H), 4.34-4.26 (m, 1H), 4.18-4.08 (m, 2H), 4.00-3.93 (m, 1H), 3.87 (qd, J=10.8, 2.9 Hz, 2H), 3.19-3.11 (m, 2H), 3.06 (q, J=7.1 Hz, 4H), 1.26 (t, J=7.2 Hz, 6H). $^{13}$C NMR (126 MHz, CDCl$_3$) δ 164.7, 161.1, 159.1, 154.3, 149.8, 145.5, 140.0, 137.0, 132.2, 130.6, 122.0, 120.1, 113.8, 106.3, 71.3, 71.3, 66.9, 51.9, 48.2, 46.6, 39.7, 8.9. m/z 470.3 ([M+1]$^+$).

8. Synthesis of AKG-20

AKG-20

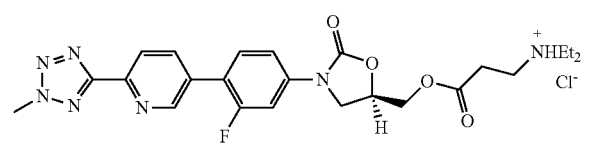

To a reaction mixture of Tedizolid (1.0 g, 2.70 mmol), 4-(diethylamino)butanoic acid hydrogen chloride (0.61 g, 3.37 mmol) and DMAP (0.05 g) in DMF (20 mL) was added DCC (0.84 g, 4.05 mmol) at RT under N2. The mixture was stirred at RT for 16 h. Upon completion (LCMS), the reaction was diluted with H$_2$O (100 mL) and filtrated. The filtrate was acidified with 0.02 M HCl to pH=5-6 and then purified using RP-FC (eluant with MeCN in 0.5% FA/H$_2$O) to give the product as a formic acid salt after freeze drying. The salt was then re-dissolved into H$_2$O and 1 eq of HCl (0.02 M) was added, after freeze drying the product AKG-20 as a HCl salt was obtained (0.61 g, 42% yield). $^1$H NMR (400 MHz, DMSO-d$_6$) δ 8.94 (s, 1H), 8.28-8.14 (m, 2H), 7.82-7.66 (m, 2H), 7.53 (d, J=8.7 Hz, 1H), 5.11-4.97 (m, 1H), 4.49 (s, 3H), 4.43-4.33 (m, 2H), 4.27 (t, J=9.3 Hz, 1H), 4.01-3.91 (m, 1H), 3.08-2.99 (m, 2H), 2.90-2.69 (m, 6H), 1.08 (t, J=7.2 Hz, 6H). $^{13}$C NMR (101 MHz, DMSO-d$_6$) δ 171.00, 164.33, 158.55, 154.32, 149.90, 145.58, 140.71, 137.63, 132.02, 131.45, 122.58, 119.33, 114.69, 106.21, 71.01, 65.04, 46.86, 46.63, 40.31, 29.99, 9.95(s).

9. Synthesis of Intermediate-3

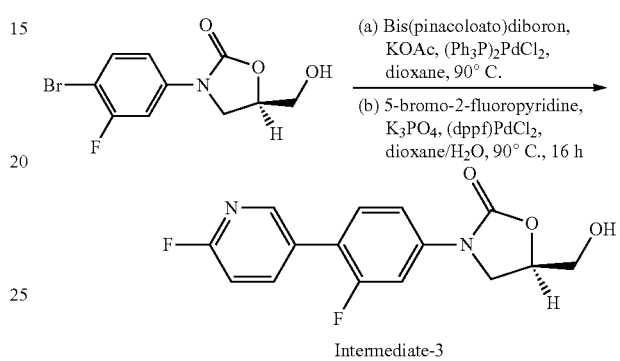

Intermediate-3

A mixture of (R)-3-(4-bromo-3-fluorophenyl)-5-(hydroxymethyl)oxazolidin-2-one (9.0 g, 31.02 mmol), Bis(pinacolato)diboron (11.88 g, 46.54 mmol) and KOAc (4.56 g, 46.54 mmol) in dioxane (200 mL) was purged with Ar for 10 min and then (Ph$_3$P)$_2$PdCl$_2$ (1.09 g, 1.55 mmol) was added. After purging the mixture with Ar again, it was heated to 90° C. for 15 h. LCMS showed completion of reaction. It was cooled to RT and filtrated over Celite to give Intermediate-2 as a filtrate. To the filtrate, 5-bromo-2-fluoropyridine (6.55 g, 37.22 mmol), K$_3$PO$_4$ (14.47 g, 6.80 mmol) and H$_2$O (20 mL) were added. The mixture was purged with Ar for 10 min. and (dppf) PdCl$_2$ (2.27 g, 3.10 mmol) was added. The mixture was purged with Ar again. It was then heated to 90° C. for 15 h. Reaction was monitored by LCMS. Upon completion, it was concentrated in vacuo and the residue was diluted with H$_2$O (200 mL) and extracted with EtOAc (2×200 mL). The combined extracts were washed with saturated brine followed by the drying over Na$_2$SO$_4$. Filtering and solvent removal in vacuo resulted in a residue that was purified using FC (eluant with MeOH in DCM 0-15%) to give the product Intermediate-3 (6.8 g, 71.6% yield for two steps) as a yellow solid. $^1$H NMR (400 MHz, DMSO-d$_6$) δ 8.43 (s, 1H), 8.23-8.14 (m, 1H), 7.72-7.61 (m, 2H), 7.49 (dd, J=8.6, 2.2 Hz, 1H), 7.32 (dd, J=8.6, 2.7 Hz, 1H), 5.27 (t, J=5.6 Hz, 1H), 4.80-4.71 (m, 1H), 4.15 (t, J=9.1 Hz, 1H), 3.90 (dd, J=8.9, 6.1 Hz, 1H), 3.75-3.67 (m, 1H), 3.63-3.55 (m, 1H). MS (ESI+) m/z 307 ([M+1]$^+$).

10. Synthesis of AKG-11, 12, 13, 14, 15

Procedure B. A mixture of Intermediate-3 (1.0 eq), R$_1$R$_2$NH (4.0 eq) and cat. amount of DMAP in NMP (10 mL) was heated to 100° C. for 16 h in a sealed tube. On completion of reaction (LCMS), it was diluted with H$_2$O (50 mL) and extracted with EtOAc (2×50 mL). The combined organic extracts were washed with saturated brine followed by drying over Na$_2$SO$_4$ and filtering. The solvent was removed in vacuo and the residue was purified using RPFC (Eluant with MeCN in 0.1% NH$_4$HCO$_3$/H$_2$O, 0-40%, C18) to give the product.

AKG-11

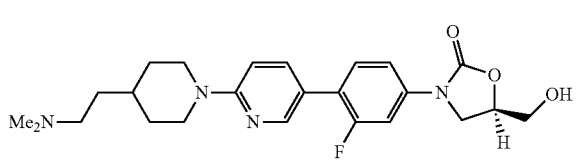

Using procedure B. AKG-11 was obtained from Intermediate-3 and N,N-Dimethyl-2-(piperidin-4-yl)ethan-1-amine as a white solid (0.40 g, 30.1% yield). $^1$H NMR (400 MHz, DMSO-d$_6$) δ 8.28 (s, 1H), 7.73-7.65 (m, 1H), 7.60 (dd, J=13.6, 2.1 Hz, 1H), 7.54 (t, J=8.9 Hz, 1H), 7.41 (dd, J=8.6, 2.1 Hz, 1H), 6.89 (d, J=9.0 Hz, 1H), 5.25 (t, J=5.6 Hz, 1H), 4.78-4.68 (m, 1H), 4.33 (d, J=13.0 Hz, 2H), 4.12 (t, J=9.0 Hz, 1H), 3.87 (dd, J=8.9, 6.2 Hz, 1H), 3.74-3.64 (m, 1H), 3.62-3.52 (m, 1H), 2.87-2.71 (m, 2H), 2.23 (t, J=7.3 Hz, 2H), 2.11 (s, 6H), 1.72 (d, J=11.5 Hz, 2H), 1.64-1.49 (m, 1H), 1.34 (dd, J=14.3, 7.0 Hz, 2H), 1.18-1.04 (m, 2H). 13C NMR (101 MHz, DMSO-d$_6$) δ 160.68, 158.33, 154.81, 147.54, 139.15, 137.82, 130.32, 120.72, 119.11, 114.35, 106.97, 106.03, 105.74, 73.82, 62.09, 56.98, 46.45, 45.73, 45.39, 34.29, 34.15, 31.94. MS (ESI+) m/z 443.1 ([M+1]$^+$).

AKG-12

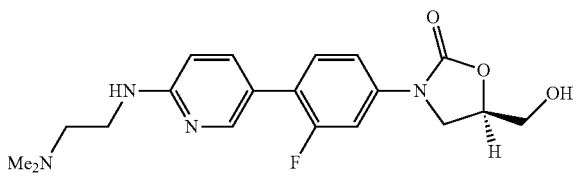

Using procedure B. AKG-12 was obtained from Intermediate-3 and N$^1$,N$^1$-dimethylethane-1,2-diamine as a white solid (0.52 g, 42.6% yield). $^1$H NMR (400 MHz, DMSO-d$_6$) δ 8.16 (s, 1H), 7.64-7.46 (m, 3H), 7.39 (dd, J=8.6, 2.2 Hz, 1H), 6.58 (dd, J=9.9, 5.6 Hz, 2H), 5.25 (t, J=5.6 Hz, 1H), 4.80-4.66 (m, 1H), 4.11 (t, J=9.0 Hz, 1H), 3.86 (dd, J=8.9, 6.2 Hz, 1H), 3.76-3.65 (m, 1H), 3.61-3.49 (m, 1H), 3.37 (dd, J=12.3, 6.5 Hz, 2H), 2.42 (t, J=6.6 Hz, 2H), 2.18 (s, 6H). $^{13}$C NMR (101 MHz, DMSO-d$_6$) δ 160.60, 158.48, 158.19, 154.82, 147.57, 138.92, 137.10, 130.22, 121.18, 118.53, 114.30, 108.37, 106.02, 105.74, 73.81, 62.10, 58.76, 46.45, 45.76, 39.21. MS (ESI+) m/z 375.1 ([M+1]$^+$).

AKG-13

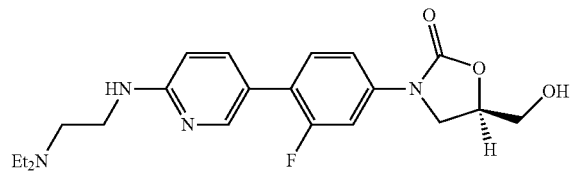

Using procedure B. AKG-13 was obtained from Intermediate-3 and N$^1$,N$^1$-diethylethane-1,2-diamine as a white solid (0.68 g, 51.9% yield). $^1$H NMR (400 MHz, DMSO-d$_6$) δ 8.17 (s, 1H), 7.67-7.46 (m, 3H), 7.39 (dd, J=8.6, 2.1 Hz, 1H), 6.63-6.44 (m, 2H), 5.25 (s, 1H), 4.74 (dd, J=9.2, 5.8 Hz, 1H), 4.12 (t, J=9.0 Hz, 1H), 3.87 (dd, J=8.9, 6.2 Hz, 1H), 3.76-3.65 (m, 1H), 3.63-3.52 (m, 1H), 3.34 (dd, J=13.2, 6.2 Hz, 2H), 2.60-2.55 (m, 2H), 2.54-2.50 (m, 4H), 0.97 (t, J=7.1 Hz, 6H). $^{13}$C NMR (101 MHz, DMSO-d$_6$) δ 160.60, 158.53, 158.18, 154.81, 147.62, 138.91, 137.13, 130.20, 121.16, 118.54, 114.29, 108.24, 105.87, 73.80, 62.10, 52.19, 47.13, 46.45, 39.48, 12.31. MS (ESI+) m/z 417.1 ([M+1]$^+$).

AKG-14

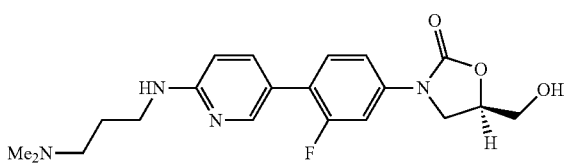

Using procedure B. AKG-14 was obtained from Intermediate-3 and N$^1$,N$^1$-dimethylpropane-1,3-diamine as a white solid (0.6 g, 47.3% yield). $^1$H NMR (400 MHz, DMSO-d$_6$) S 8.16 (s, 1H), 7.63-7.54 (m, 2H), 7.50 (t, J=8.9 Hz, 1H), 7.39 (dd, J=8.6, 2.2 Hz, 1H), 6.73 (t, J=5.6 Hz, 1H), 6.54 (d, J=8.7 Hz, 1H), 5.25 (t, J=5.5 Hz, 1H), 4.78-4.68 (m, 1H), 4.11 (t, J=9.0 Hz, 1H), 3.87 (dd, J=8.9, 6.2 Hz, 1H), 3.75-3.66 (m, 1H), 3.64-3.53 (m, 1H), 3.33-3.23 (m, 2H), 2.28 (t, J=7.1 Hz, 2H), 2.13 (s, 6H), 1.72-1.62 (m, 2H). $^{13}$C NMR (101 MHz, DMSO-d$_6$) δ 160.60, 158.62, 158.18, 154.81, 147.62, 138.89, 137.08, 130.19, 121.21, 118.39, 114.29, 108.10, 106.02, 105.74, 73.81, 62.10, 57.44, 46.45, 45.72, 39.58, 27.54. MS (ESI+) m/z 389.1 ([M+1]$^+$).

AKG-15

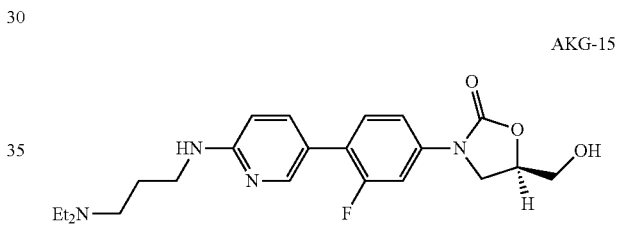

Using procedure B. AKG-15 was obtained from Intermediate-3 and N$^1$,N$^1$-diethylpropane-1,3-diamine as a white solid (0.65 g, 48.0% yield). $^1$H NMR (400 MHz, DMSO-d$_6$) S 8.16 (s, 1H), 7.63-7.54 (m, 2H), 7.50 (t, J=8.9 Hz, 1H), 7.39 (dd, J=8.6, 2.2 Hz, 1H), 6.75 (t, J=5.5 Hz, 1H), 6.54 (d, J=8.7 Hz, 1H), 5.25 (t, J=5.4 Hz, 1H), 4.79-4.68 (m, 1H), 4.12 (t, J=9.0 Hz, 1H), 3.87 (dd, J=8.9, 6.2 Hz, 1H), 3.75-3.66 (m, 1H), 3.63-3.54 (m, 1H), 3.32-3.23 (m, 2H), 2.49-2.40 (m, 6H), 1.70-1.61 (m, 2H), 0.95 (t, J=7.1 Hz, 6H). $^{13}$C NMR (101 MHz, DMSO-d$_6$) δ 160.60, 158.65, 158.18, 154.81, 147.64, 138.89, 137.05, 130.18, 121.21, 118.37, 114.29, 108.01, 106.02, 105.74, 73.80, 62.09, 50.81, 46.80, 46.45, 40.11, 27.10, 12.23. MS (ESI+) m/z 417.1 ([M+1]$^+$).

11. Synthesis of AKG-16

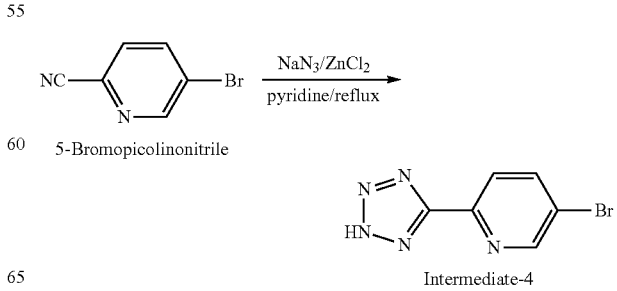

5-Bromopicolinonitrile

Intermediate-4

ZnCl$_2$ (11.2 g, 81.9 mmol) was added portion wise to pyridine (40 mL) followed by the addition of NaN$_3$ (8.90 g, 137 mmol) and 5-bromo-2-cyanopyridine (10.0 g, 54.6 mmol) at RT, and the reaction mixture was heated to reflux at 120° C. for 2 h. After the mixture was cooled to RT it was diluted with water (200 mL), stirred at RT for 1 h, filtered and washed with water (200 mL). The filtered solid was collected and suspended into HCl (200 mL, 6 M) at RT for 2 h. The product was collected by filtration and washed with H$_2$O. It was dried in vacuo to give Intermediate-4 (10.0 g, 81.3% yield) as a white solid. $^1$H NMR (400 MHz, DMSO-d$_6$) δ 8.96 (s, 1H), 8.36 (dd, J=8.4, 2.2 Hz, 1H), 8.18 (d, J=8.4 Hz, 1H). MS (ESI+) m/z 225.9 227.9 ([M+1]$^+$).

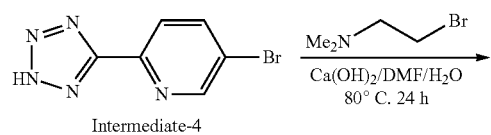

A mixture of Intermediate-4 (10.0 g, 44.25 mmol) and Ca(OH)$_2$ (7.20 g, 97.35 mmol) in H$_2$O (150 mL) and DMF (20 mL) was stirred at r,t for 0.5 h and then (2-bromoethyl) dimethylamine hydrobromide (25.0 g, 107.3 mmol) was added. The mixture was heated at 80° C. for 24 h. LCMS showed 3:1 mixture of Intermediates 5 and 6, respectively. The mixture was diluted with H$_2$O (40 mL) and extracted with EtOAc (2×50 mL). The combined extracts were washed with saturated brine, dried over Na$_2$SO$_4$ and filtered. The solvent was removed in vacuo and the residue was purified using FC (eluant with MeOH in DCM 0-15%) to give the crude product. The crude product was further purified by RPFC (MeCN in 0.1% NH$_4$HCO$_3$/H$_2$O 0-30%, C18, Intermediate-5 eluted first followed by Intermediate-6) to give Intermediate-5 (0.74 g, 5.6% yield) as a white solid and Intermediate-6 (0.25 g as light yellow solid).

Intermediate-5: $^1$H NMR (400 MHz, DMSO-d$_6$) δ 8.89 (dd, J=2.3, 0.6 Hz, 1H), 8.27 (dd, J=8.4, 2.4 Hz, 1H), 8.10 (dd, J=8.4, 0.6 Hz, 1H), 4.87 (t, J=6.1 Hz, 2H), 2.87 (t, J=6.1 Hz, 2H), 2.17 (s, 6H). $^{13}$C NMR (101 MHz, DMSO-d$_6$) δ 163.74, 151.48, 145.51, 140.81, 124.40, 122.21, 57.73, 51.54, 45.29. MS (ESI+) m/z 297.1, 299.1 ([M+1]$^+$). Intermediate-6: $^1$H NMR (400 MHz, DMSO-d$_6$) δ 8.98 (s, 1H), 8.38 (dd, J=8.4, 2 Hz, 1H), 8.20 (d, J=8.4 Hz, 1H), 5.00 (t, J=6.4 Hz, 2H), 2.75 (t, J=6 Hz, 2H), 2.10 (s, 6H), MS (ESI+) m/z 297.1, 299.1 ([M+1]$^+$).

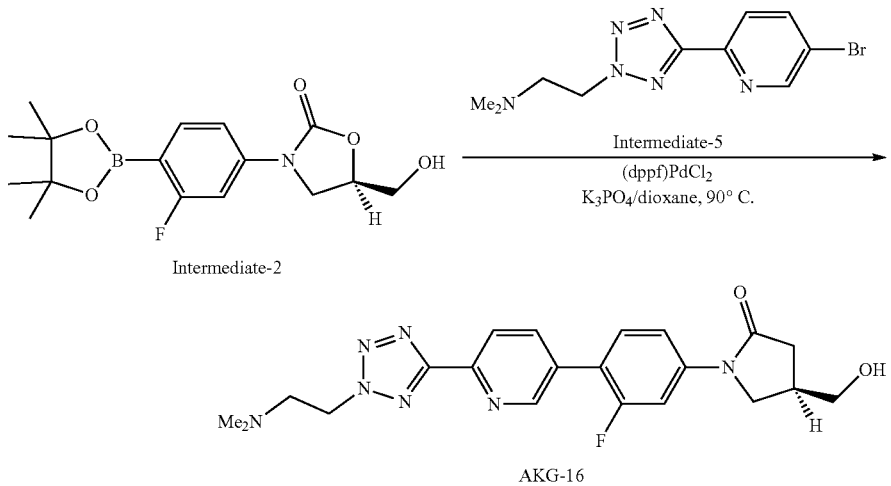

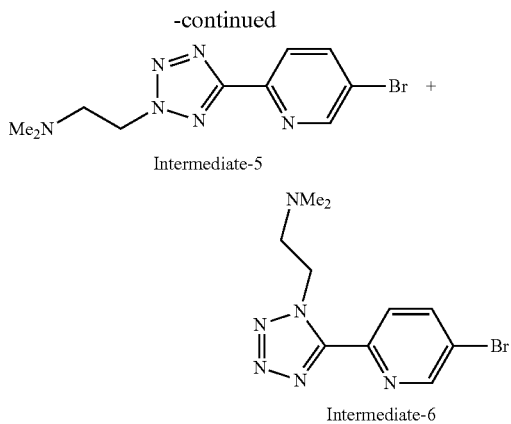

A mixture of freshly prepared Intermediate-2 (1.68 g, 4.98 mmol) (from 1.44 g of (R)-3-(4-bromo-3-fluorophenyl)-5-(hydroxymethyl)oxazolidin-2-one using the procedure of Intermediate-3), Intermediate-5 (740 mg, 2.49 mmol) and K$_3$PO$_4$ (1.16 g, 5.48 mmol) in dioxane (50 mL) and H$_2$O (5 mL) was purged with Ar for 10 min. To this (dppf)PdCl$_2$ (182 mg, 0.25 m mol) was added. The mixture was purged with Ar again. It was then heated to 90° C. for 15 h. LCMS showed completion of reaction. It was concentrated in vacuo and the residue was diluted with H$_2$O (200 mL) and extracted with EtOAc (2×200 mL). The combined extracts were washed with saturated brine, dried over Na$_2$SO$_4$ and filtered. The solvent was removed in vacuo and the residue was purified using RPFC (Eluant with MeCN in H$_2$O, 0-40%) to give the product AKG-16 (520 mg, 49.0% yield) as a white solid. $^1$H NMR (400 MHz, DMSO-d$_6$) δ 8.95 (s, 1H), 8.23 (dd, J=18.3, 8.2 Hz, 2H), 7.82-7.66 (m, 2H), 7.54 (dd, J=8.6, 2.1 Hz, 1H), 5.28 (s, 1H), 4.89 (t, J=6.1 Hz, 2H), 4.82-4.71 (m, 1H), 4.17 (t, J=9.0 Hz, 1H), 3.98-3.87 (m, 1H), 3.77-3.65 (m, 1H), 3.64-3.53 (m, 1H), 2.90 (t, J=6.1 Hz, 2H), 2.19 (s, 6H). $^{13}$C NMR (101 MHz, DMSO-d$_6$) S 164.17, 161.02, 158.58, 154.81, 149.91, 145.59, 141.03, 137.63, 132.10, 131.39, 122.59, 119.05, 114.47, 105.97, 105.69, 73.95, 62.07, 57.72, 51.46, 46.46, 45.26. MS (ESI+) m/z 428.1 ([M+1]⁺).

12. Synthesis of AKG-21

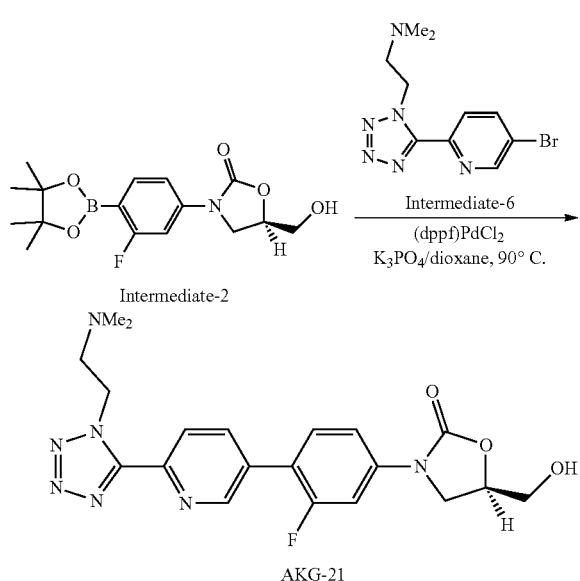

A solution of Intermediate-2 (1.5 g, 4.5 mmol), Intermediate-6 (0.9 g, 3 mmol), Pd(dppf)Cl₂ (247 mg, 0.3 mmol) and K₃PO₄ (1.3 g, 6 mmol) in dioxane (30 mL) and H₂O (5 mL) was purged with Ar for 10 min. and heated to 100° C. for 15 h. On completion of reaction (LCMS), it was concentrated in vacuo and the residue was diluted with H₂O (100 mL) and extracted with EtOAc (2×50 mL). The combined extracts were washed with saturated brine, dried over Na₂SO₄ and filtered. The solvent was removed in vacuo and the residue was purified using FC (eluant with MeOH in DCM (10% of NH₄₀H) from 0 to 10%) to give AKG-21 (450 mg as white solid) in 35% yield. ¹H NMR (400 MHz, DMSO-d₆) δ 9.01 (s, 1H), 8.36 (d, J=8.4 Hz, 1H), 8.30 (d, J=8.4 Hz, 1H), 7.81 (t, J=8.8 Hz, 1H), 7.74 (dd, J=13.6, 2.0 Hz, 1H), 7.55 (dd, J=8.4, 2.0 Hz, 1H), 5.26 (t, J=5.6 Hz, 1H), 5.08 (t, J=6.4 Hz, 2H), 4.79-4.75 (m, 1H), 4.18 (t, J=9.2 Hz, 1H), 3.93-3.89 (m, 1H), 3.74-3.68 (m, 1H), 3.62-3.56 (m, 1H), 2.80 (t, J=6.4 Hz, 2H), 2.13 (s, 6H). ¹³C NMR (101 MHz, DMSO-d₆): δ 161.09, 158.64, 154.80, 152.10, (149.45, 149.40), 143.46, (141.35, 141.23), (138.19, 138.15), (132.77, 132.76), (131.53, 131.48), 124.58, (118.69, 118.56), (114.51, 114.49), (105.97, 105.68), 73.96, 62.06, 58.38, 47.26, 46.47, 45.42.

13. Synthesis of AKG-22

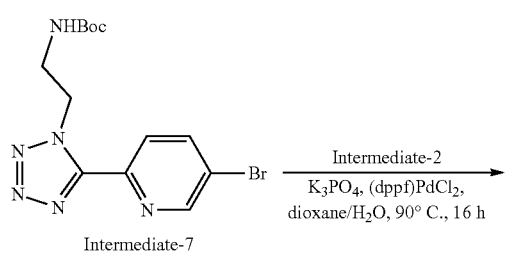

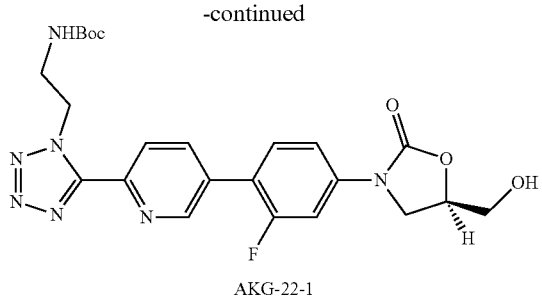

To a mixture of Intermediate-7 (500 mg, 1.354 mmol) in H₂O (2 mL) and dioxane (8 mL) was added Intermediate-2 (685 mg, 2.03 mmol), K₃PO₄ (862 mg, 4.06 mmol) and (dppf)PdCl₂ (99 mg, 0.135 mmol). The flask was evacuated and backfilled with Ar. Then the mixture was stirred at 90° C. for 16 h. Water (20 mL) was added, extracted with EtOAc (2×20 mL). The organic phase was washed with brine, dried over Na₂SO₄, filtered and concentrated. The residue was purified by silica gel column chromatography (Biotage, 40 g silica gel column @30 mL/min, eluting with 0-100% EtOAc in Petroleum Ether) to give the desired product AKG-22-1 (450 mg, yield: 66%) as a gray solid.

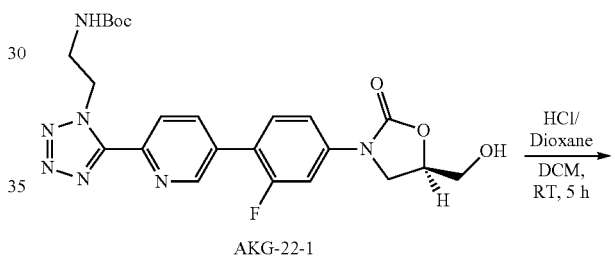

To a mixture of AKG-22-1 (450 mg, 0.9 mmol) in DCM (8 mL) was added 4M HCl/Dioxane (2 mL). Then the mixture was stirred at RT. for 5 h. The solvent was removed under vacuum to give the desired product AKG-22 (390 mg, yield: 99%) as a gray solid. ¹H NMR (400 MHz, DMSO-d₆) δ 9.03 (s, 1H), 8.39 (d, J=8.0 Hz, 1H), 8.32 (d, J=8.0 Hz, 1H), 8.19 (brs, 3H), 7.82-7.70 (m, 2H), 7.57 (dd, J=8.8, 2.0 Hz, 1H), 5.18 (t, J=5.8 Hz, 2H), 4.81-4.74 (m, 1H), 4.17 (t, J=9.2 Hz, 1H), 3.93 (dd, J=9.2, 6.4 Hz, 1H), 3.71 (dd, J=12.4, 3.2 Hz, 1H), 3.59 (dd, J=12.4, 4.0 Hz, 1H), 3.53-3.47 (m, 2H). ¹³C NMR (400 MHz, DMSO-d₆) S (161.07, 158.63), 154.82, 152.52, 149.54, 143.25, (141.39, 141.28), 138.24, 124.54, (118.66, 118.53), 114.60, (106.01, 105.73), 73.97, 62.02, 47.37, 46.48, 38.84.

14. Synthesis of AKG-23

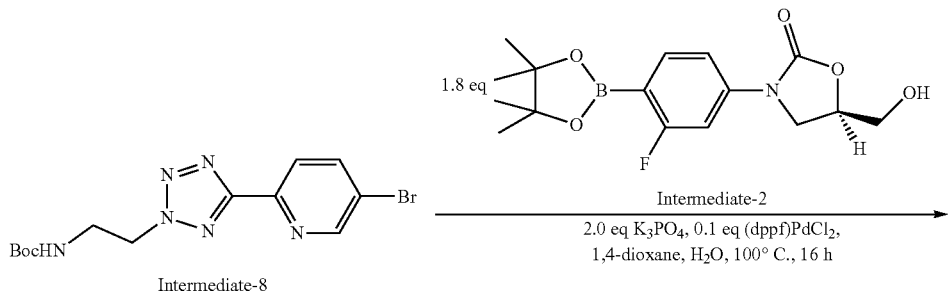

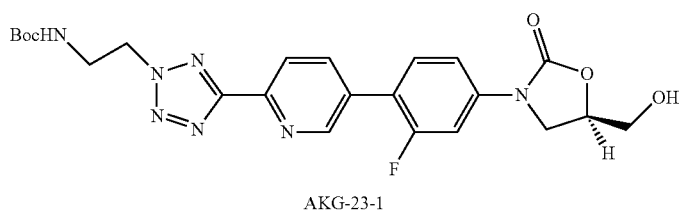

To Intermediate-8 (1.0 g, 2.71 mmol) in 20 mL 1,4-dioxane and 5 mL H₂O Intermediate-2 (4.86 mmol, 1.63 g), K₃PO₄ (1.14 g, 5.42 mmol) and (dppf)PdCl₂ (0.23 g, 0.27 mmol) were added and the mixture was stirred at 100° C. for 16 h. After starting material was consumed, 100 mL sat NaHCO₃ was added. The aqueous phase was extracted with EtOAc (3×30 mL), combined organic extracts were washed with H₂O, concentrated in vacuo and purified by FC to afford desired compound AKG-23-1 (1.0 g, 70% yield).

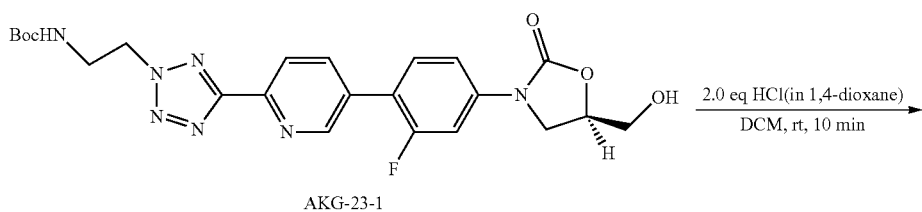

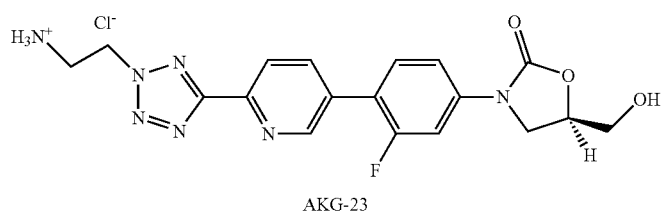

To AKG-23-1 (1.0 g, 2 mmol) in 30 mL DCM was added 1 mL HCl (4M in 1,4-dioxane) and the mixture was allowed to stir at for 1 h. After starting material was consumed, the mixture was flittered to afford crude product. The crude was stirred in 3 mL MeOH at for 1 h, flittered to afford desired product AKG-23 as a white solid (0.53 g, 63% yield). $^1$H NMR (400 MHz, DMSO-$d_6$) δ 8.97 (s, 1H), 8.26 (m, 5H), 7.83-7.64 (m, 2H), 7.54 (dd, J=8.6, 1.9 Hz, 1H), 5.09 (s, 2H), 4.77 (m, 1H), 4.16 (t, J=9.1 Hz, 1H), 3.92 (dd, J=8.8, 6.2 Hz, 1H), 3.71 (dd, J=12.3, 3.2 Hz, 1H), 3.61-3.57 (dd, J=12.3, 3.2 Hz, 1H), 3.53 (m, 3H). $^{13}$C NMR (125 MHz, DMSO-$d_6$) S 38.31, 46.49, 50.86, 62.01, 73.96, [105.69, 105.97], 114.46, [118.90, 119.03], 122.73, [131.37, 131.47], 132.21, [137.66, 137.70], [140.99, 141.10], 145.42, 149.86, 154.82, [158.57, 161.02], 164.50.

15. Synthesis of AKG-24

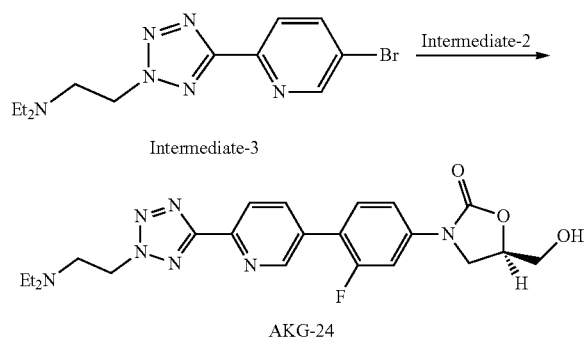

A mixture of Intermediate-2 (1.66 g, 4.98 mmol), Intermediate-9 (800 mg, 2.49 mmol) and $K_3PO_4$ (1.16 g, 5.48 mmol) in dioxane (50 mL) and $H_2O$ (5 mL) was purged with Ar for 10 min. and (dppf)PdCl$_2$ (182 mg, 0.25 mmol) was added. The mixture was purged again with Ar. It was then heated to 90° C. for 15 h. LCMS showed completion of the reaction; it was concentrated in vacuo and the residue was diluted with $H_2O$ (200 mL) and extracted with EtOAc (2×200 mL). The combined extracts were washed with saturated brine followed by the drying over $Na_2SO_4$ and filtered. The solvent was removed in vacuo and the residue was purified using RPFC (Eluant with MeCN in $H_2O$, 0-40%) to give the product AKG-24 (440 mg, 39.0% yield) as a white solid. $^1$H NMR (400 MHz, DMSO-$d_6$) δ 8.95 (s, 1H), 8.28-8.16 (m, 2H), 7.81-7.67 (m, 2H), 7.54 (dd, J=8.6, 2.1 Hz, 1H), 5.27 (t, J=5.6 Hz, 1H), 4.93-4.70 (m, 3H), 4.17 (t, J=9.1 Hz, 1H), 3.92 (dd, J=8.9, 6.1 Hz, 1H), 3.72 (m, 1H), 3.60 (m, 1H), 3.04 (s, 2H), 0.87 (t, J=6.9 Hz, 6H). $^{13}$C NMR (101 MHz, DMSO-$d_6$) δ 164.13, 161.03, 158.59, 154.81, 149.94, 149.90, 145.66, 141.09, 140.98, 137.66, 137.62, 132.10, 132.08, 131.41, 131.37, 122.54, 119.15, 119.02, 114.50, 114.47, 105.99, 105.71, 73.95, 62.08, 52.09, 51.60, 46.85, 46.48, 12.26. MS (ESI+) m/z 456 ([M+H]$^+$).

16. Synthesis of AKG-25

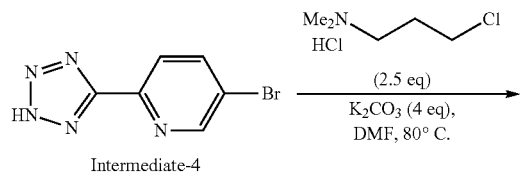

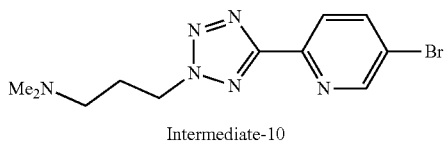

Intermediate-10

To a mixture of Intermediate-4 (2.25 g, 10 mmol) and $K_2CO_3$ (5.52 g, 40 mmol) in DMF (20 mL) 3-chloro-N,N-dimethylpropan-1-amine hydrogen chloride (3.95 g, 25 mmol) was added and the mixture was heated to 80° C. for 4 h. It was diluted with $H_2O$ (40 mL) and extracted with EtOAc (2×100 mL). The combined extracts were washed with saturated brine followed by the drying over $Na_2SO_4$ and filtered. The solvent was removed in vacuo and the residue indicated presence of two regioisomers of N-alkylation. The isomers were separated using FC (eluant with MeOH in DCM 0-15%) to give the Intermediate-10 (0.98 g, 31.6% yield) as a white solid. $^1$H NMR (400 MHz, CDCl$_3$) δ 8.83 (dd, J=2.4, 0.8 Hz, 1H), 8.16 (dd, J=8.0, 0.4 Hz, 1H), 8.01 (dd, J=8.4, 2.4 Hz, 1H), 4.78 (t, J=6.8 Hz, 2H), 2.38 (t, J=3.2 Hz, 2H), 2.27-2.22 (m, 8H). MS (ESI+) m/z 311.1, 313.1 ([M+1]$^+$).

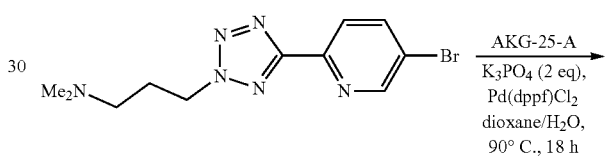

A mixture of Intermediate-10 (0.74 g, 2.4 mmol), Intermediate-2 (1.62 g, 4.8 mmol) and $K_3PO_4$ (1 g, 4.8 mmol) in dioxane (30 mL) and $H_2O$ (5 mL) was purged with Ar for 10 min. and Pd(dppf)Cl$_2$ (175 mg, 0.24 mmol) was added. The mixture was purged with Ar again and heated to 90° C. for 15 h. It was concentrated in vacuo and the residue was diluted with $H_2O$ (80 mL) and extracted with EtOAc (2×100 mL). The combined extracts were washed with saturated brine followed by the drying over $Na_2SO_4$ and filtered. The solvent was removed in vacuo and the residue was purified using FC (eluant with MeOH in DCM 0-15%) to give the product AKG-25 (0.73 g, 69.5% yield) as a grey solid. $^1$H NMR (400 MHz, DMSO-$d_6$) δ 8.94 (s, 1H), 8.24-8.26 (m, 1H), 8.19-8.21 (m, 1H), 7.78-7.70 (m, 2H), 7.54 (dd, J=8.4, 2.0 Hz, 1H), 5.27 (t, J=5.6 Hz, 1H), 4.80 (t, J=6.8 Hz, 2H), 4.77-4.75 (m, 1H), 4.16 (t, J=9.2 Hz, 1H), 3.92 (dd, J=8.8 Hz, 6.0 Hz, 1H), 3.74-3.69 (m, 1H), 3.63-3.58 (m, 1H), 2.28 (t, J=7.2 Hz, 2H), 2.10-2.17 (m, 8H). $^{13}$C NMR (101 MHz, DMSO-$d_6$) δ 164.26, 161.03, 158.58, 154.81, 149.92, 145.58, 141.09, 137.65, 132.10, 131.37, 122.60, 119.12, 118.99, 114.46, 105.98, 105.70, 73.95, 62.07, 55.96, 51.65, 46.47, 45.53, 27.21. MS (ESI+) m/z 442.1 ([M+1]$^+$).

17. Synthesis of AKG-26

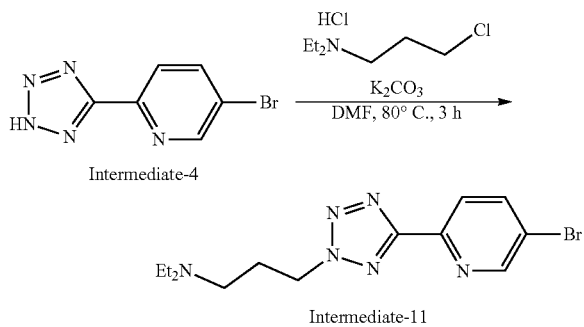

Intermediate-4

Intermediate-11

To a solution of Intermediate-4 (5.0 g, 22.12 mmol) in DMF (30 mL) was added (3-chloropropyl)diethylamine hydrochloride (8.23 g, 55.30 mmol) and $K_2CO_3$ (9.17 g, 66.36 mmol) at 80° C. for 3 h. The reaction was cooled down and poured into an ice-water bath and extracted with EA (2×200 mL). Combined organic phases was washed with brine (2×50 mL), dried over $Na_2SO_4$. Upon removal of solvent, the crude product with N-alkylation regioisomers was purified by FC (PE/EA=1:10) to give Intermediate-11 (1.70 g, 22.65%) as a white solid. $^1H$ NMR (500 MHz, $CDCl_3$) δ 8.34 (d, J=2.0 Hz, 1H), 8.15 (d, J=8.0 Hz, 1H), 8.00 (dd, J=8.0, 2.0 Hz, 2H), 4.77 (t, J=7.0 Hz, 2H), 2.53-2.49 (m, 6H), 2.26-2.20 (m, 2H), 0.99 (t, J=7.5 Hz, 6H). MS (ESI*) m/z 339.1, 341.1 ([M+1]$^+$).

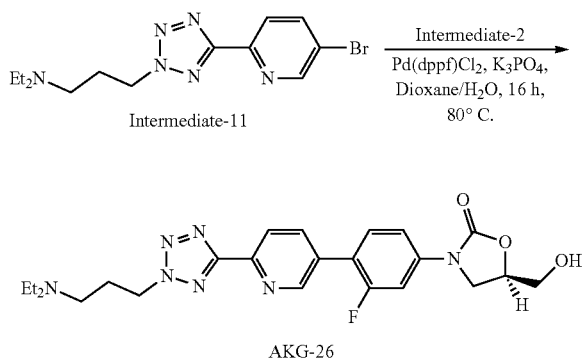

Intermediate-11

AKG-26

A mixture of Intermediate-11 (0.68 g, 2.00 mmol), Intermediate-2 (1.07 g, 3.99 mmol), tripotassium phosphate (0.85 g, 3.985 mmol) and $Pd(dppf)Cl_2$ (0.15 g, 0.20 mmol) were suspended in 1,4-dioxane:water (12 mL, 6:1). The reaction was stirred at reflux for 16 h. The mixture was partitioned between EtOAc (2×100 mL) and water, washed with brine, dried over $Na_2SO_4$ and filtered. Up to removal of solvent, the residue containing regioisomers was purified using FC eluting with (DCM/MeOH=20/1) to afford AKG-26 (0.54 g, 56.04%) as a grey solid. $^1H$ NMR (500 MHz, DMSO-$d_6$) δ 8.95 (s, 1H), 8.26-8.19 (m, 2H), 7.78-7.70 (m, 2H), 7.53 (dd, J=10.5, 2.5 Hz, 1H), 5.27 (d, J=7.5 Hz, 1H), 4.83-4.75 (m, 2H), 4.17 (t, J=11.5 Hz, 1H), 3.92 (dd, J=11.0, 7.5 Hz, 1H), 3.74-3.69 (m, 1H), 3.62-3.58 (m, 1H), 3.51-3.28 (m, 8H), 2.14 (t, J=8.0 Hz, 2H), 0.93 (t, J=8.5 Hz, 6H). $^{13}C$ NMR (101 MHz, DMSO-$d_6$) δ 164.24, 161.03, 158.59, 154.52, 149.91, (d, J=3.2 Hz), 145.59, 141.03 (d, J=11.8 Hz), 137.64 (d, J=3.2 Hz), 132.12, 131.40 (d, J=4.5 Hz), 122.57, 119.06 (d, J=12.8 Hz), 114.47 (d, J=2.8 Hz), 105.97, 105.70, 73.96, 62.07, 51.70, 49.19, 46.75, 46.48. MS (ESI*) m/z 470.1 ([M+1]$^+$).

18. Synthesis of AKG-27

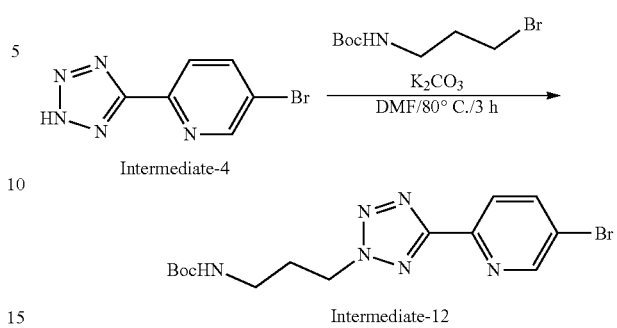

Intermediate-4

Intermediate-12

To a solution of Intermediate-4 (6.3 g, 27.87 mmol) in DMF (42 mL) was added $BocNH(CH_2)_3Br$ (16.6 g, 69.71 mmol) and $K_2CO_3$ (11.1 g, 80.02 mmol) at 80° C. for 3 hours. The reaction was cooled down and poured into an ice-water bath and extracted with EtOAc (2×200 mL). The organic phase was washed with brine (2×50 mL), dried over $Na_2SO_4$ and filtered, evaporating the solvent under reduced pressure. The crude product with regioisomers of N-alkylation was purified by FC (PE/EA=2:1) to give Intermediate-12 (14 g, 13.1%) as a yellow solid. $^1H$ NMR (400 MHz, DMSO-$d_6$) δ 8.89 (d, J=2.4 Hz, 1H), 8.28 (dd, J=8.4 Hz, 1H), 8.11 (d, J=8.4 Hz, 1H), 6.97 (s, 1H), 4.77 (t, J=6.8 Hz, 2H), 3.03 (q, J=12.4 Hz, 2H), 2.15-2.08 (m, 2H), 1.37 (s, 9H) ppm. MS (ESI+) m/z 383.0 ([M+1]$^+$).

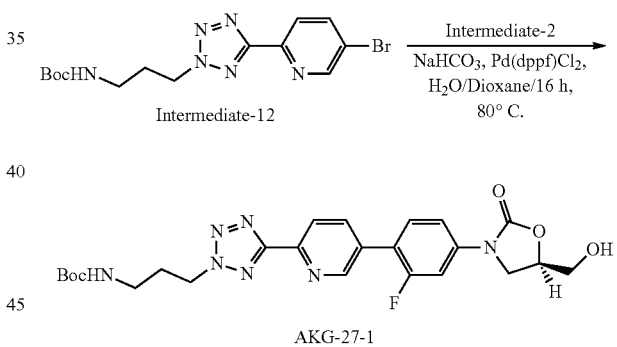

Intermediate-12

AKG-27-1

To a solution of Intermediate-12 (0.83 g, 2.15 mmol), $NaHCO_3$ (0.36 g, 4.31 mmol) and Intermediate-2 (1.24 g, 3.68 mmol) were suspended in 1,4-dioxane (32 mL) and water (8 mL). The mixture was bubbled with $N_2$ for 5 minutes then charged with $Pd(dppf)Cl_2$ (0.078 g, 0.095 mmol). The mixture was stirred at 90° C. for 15 h and then cooled to RT. The mixture was partitioned between EtOAc (2×100 mL) and water. The organic layer was dried on $Na_2SO_4$, filtered, and concentrated. The filtrate was concentrated and purified by silica gel column chromatography on silica gel (DCM/MeOH=20/1) to give AKG-27-1 (0.75 g; 66.9%) as a white solid. $^1H$ NMR (400 MHz, DMSO-$d_6$) δ 8.95 (s, 1H), 8.25 (d, J=8.5 Hz, 1H), 8.21 (d, J=8.4 Hz, 1H), 7.78-7.70 (m, 2H), 7.54 (d, J=8.5 Hz, 1H), 6.93 (s, 1H), 5.26 (t, J=5.0 Hz, 1H), 4.80-4.75 (m, 3H), 4.17 (t, J=9.0 Hz, 1H), 3.91 (t, J=8.5 Hz, 1H), 3.71-3.69 (m, 1H), 3.60-3.59 (m, 1H), 3.06-3.03 (m, 2H), 2.15-2.12 (m, 2H), 1.37 (s, 9H) ppm. MS (ESI+) m/z 514.0 ([M+1]$^+$).

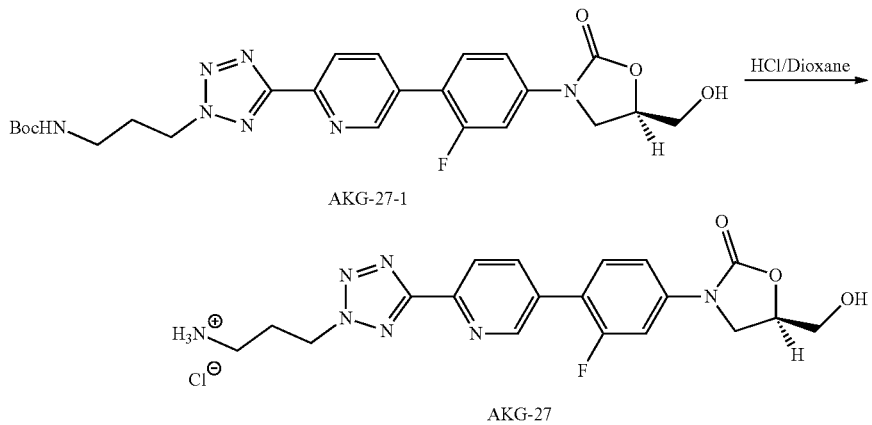

A solution AKG-27-1 (0.9 g, 1.75 mmol) in dry DCM (16 mL) was added HCl in dioxane (4.0 mL) under N2 atmosphere at RT. The reaction mixture was stirred at the same temperature for 6 hours and cooled down RT. The mixture reaction was evaporating the solvent under reduced pressure, gave AKG-27 (0.65 g, 82.5%) as a pale yellow solid. $^1$H NMR (400 MHz, DMSO-$d_6$) δ 8.95 (s, 1H), 8.26-8.20 (m, 5H), 7.77-7.70 (m, 2H), 7.53 (d, J=7.6 Hz, 1H), 4.94 (d, J=6.4 Hz, 2H), 4.77 (s, 1H), 4.51 (s, 2H), 4.16 (t, J=8.8 Hz, 1H), 3.93 (t, J=7.0 Hz, 1H), 3.71 (d, J=12.4 Hz, 1H), 3.60 (d, J=12.4 Hz, 1H), 2.94 (s, 2H), 2.34 (t, J=6.8 Hz, 2H) ppm. MS (ESI+) m/z 414.0 ([M+1]$^+$).

19. Synthesis of AKG-28 to 31

To a solution of (R)-3-(4-bromo-3-fluorophenyl)-5-(hydroxymethyl)oxazolidin-2-one (9 g, 31 mmol) in DCM (100 mL) was added (3.92 g, 34 mmol) and TEA (3.76 g, 37 mmol). The mixture was stirred at RT for 2 h. The mixture was washed with water (2×30 mL) and brine (2×30 mL), dried over Na$_2$SO$_4$, filtered and concentrated to give Intermediate-13 (11.4 g, yield 99%). MS (ESI+) m/z 368 ([M+1]$^+$).

To a solution of Intermediate-13 (11.4 g, 31 mmol) in DMF (200 mL) was added potassium 1,3-dioxoisoindolin-2-ide (6.02 g, 32 mmol). The mixture was stirred at 90° C. overnight. The mixture was cooled to and poured into water (1000 mL) and stirred for 0.5 h. The precipitate was collected and dried in vacuo to give Intermediate-14 (11 g, yield 85%). MS (ESI+) m/z 419 ([M+1]$^+$).

To a solution of Intermediate-14 (11 g, 26.3 mmol) in EtOH (150 mL) was added NH$_2$NH$_2$—H$_2$O (85%, 7.7 g, 131 mmol). The mixture was stirred at 90° C. overnight. The mixture was filtered and rinsed with EtOH (2×50 mL). The filtrate was concentrated to give Intermediate-15 (7.6 g, yield 100%). MS (ESI+) m/z 289 ([M+1]$^+$).

To a solution of Intermediate-15 (7.6 g, 26.4 mmol) in THF (50 mL) and water (50 mL), (Boc)$_2$O (6.9 g, 32 mmol) and K$_2$CO$_3$ (7.29 g, 52.8 mmol) were added and the mixture was stirred at for 2 h. The mixture was diluted with water (100 mL), extracted with EtOAc (3×50 mL). The combined organic extract was washed with brine (2×50 mL), dried over Na$_2$SO$_4$, filtered and concentrated. The residue was purified by FC (Biotage, 80 g silica gel column @ 65 mL/min, eluting with 0-60% EtOAc in petroleum ether for 30 min) to give Intermediate-16 (7.8 g, yield 75%). MS (ESI+) m/z 411 ([M+23]$^+$).

The mixture of Intermediate-16 (7.8 g, 20 mmol), bis(pinacolato)diboron (6.54 g, 30 mmol) and KOAc (2.94 g, 30 mmol) in dioxane (100 mL) was purged with Ar for 10 min and then (Ph$_3$P)$_2$PdCl$_2$ (1.06 g, 1.5 mmol) was added. The mixture was purged with Ar again and stirred at 90° C. overnight. The mixture was cooled to and diluted with water (300 mL), extracted with EtOAc (3×100 mL). The combined extract was washed with brine (2×50 mL), dried over Na$_2$SO$_4$, filtered and concentrated. The residue was purified by FC (Biotage, 80 g silica gel column @65 mL/min, eluting with 0-60% EtOAc in petroleum ether for 30 min) to give Intermediate-18 (6.2 g, yield 70%). MS (ESI+) m/z 459 ([M+23]$^+$).

Procedure C: A mixture of one of Intermediates-5/8/9/10/11 (1.0 eq), one of Intermediates-18/19 (1.5 eq), Pd(dppf)Cl$_2$ DCM (0.1 eq), and K$_3$PO$_4$ (2.0 eq) in dioxane/H$_2$O (10:1, 0.06M) was purged with N$_2$ and stirred at 90° C. overnight. The mixture was diluted with EtOAc, washed with water and brine, dried over anhydrous magnesium sulfate, filtered and concentrated. The residue was purified by FC to give one of the compounds AKG-28-1/AKG-29-1/AKG-30-1/AKG-31-1/AKG-38/AKG-39/AKG-40.

To a solution of one of the compounds AKG-28-1/AKG-29-1/AKG-30-1/AKG-31-1 in DCM (1 mL/100 mg) was added 3N HCl in EtOAc (20 eq). The mixture was stirred at for 2 h and then filtered. The solid was dried in vacuo or lyophilized to give one of the final compounds AKG-28/AKG-29/AKG-30/AKG-31 (yield 35-44% for two steps).

AKG-28

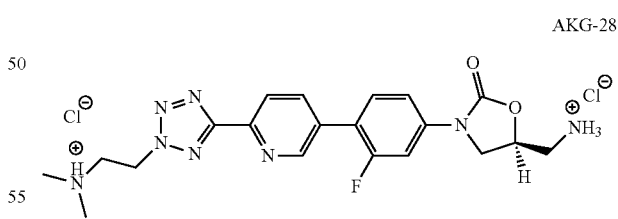

Using procedure C. This product was obtained from Intermediate-5 and Intermediate-18 as a white solid (0.35 g, 35% yield). $^1$H NMR (500 MHz, DMSO-$d_6$) δ 10.53 (s, 1H), 8.97 (s, 1H), 8.37 (s, 3H), 8.29 (d, J=8.5 Hz, 1H), 8.24 (d, J=8.5 Hz, 1H), 7.80 (t, J=8.5 Hz, 1H), 7.69 (dd, J=13.5, 2.0 Hz, 1H), 7.50 (dd, J=8.5, 2.0 Hz, 1H), 5.31 (t, J=6.0 Hz, 2H), 5.04-4.99 (m, 1H), 4.28 (t, J=9.0 Hz, 1H), 3.96 (dd, J=9.0, 6.5 Hz, 1H), 3.84 (s, 2H), 3.28 (s, 2H), 2.87 (s, 6H) ppm. $^{13}$C NMR (126 MHz, D20) S 163.90 (s), 160.30 (s), 158.33 (s), 154.86 (s), 148.55 (s), 142.64 (s), 138.93 (d, J=11.0 Hz), 137.74 (s), 132.43 (s), 130.39 (s), 122.46 (s), 119.03 (s), 114.36 (s), 106.41 (s), 106.18 (s), 70.31 (s), 55.23 (s), 48.07 (s), 47.69 (s), 43.29 (s), 42.19 (s) ppm. MS (ESI+) m/z 427.1 ([M+1]+).

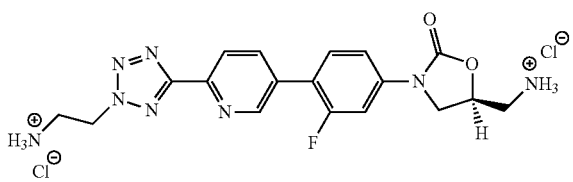

AKG-29

Using procedure C. This product was obtained from Intermediate-8 and Intermediate-18 as a white solid (0.4 g, 44% yield). 1H NMR (400 MHz, DMSO-d6) δ 8.97 (s, 1H), 8.57-8.41 m, 6H), 8.29-8.13 (m, 2H), 7.80 (t, J=9.0 Hz, 1H), 7.69 (dd, J=13.5, 2.5 Hz, 1H), 7.49 (dd, J=8.5, 2.0 Hz, 1H), 5.12-5.03 (m, 3H), 4.28 (t, J=9.0 Hz, 1H), 4.02-3.98 (m, 1H), 3.54-3.51 (m, 2H), 3.33-3.26 (m, 2H). 8.28 (s, 1H), 7.73-7.65 (m, 1H), 7.60 (dd, J=13.6, 2.1 Hz, 1H), 7.54 (t, J=8.9 Hz, 1H), 7.41 (dd, J=8.6, 2.1 Hz, 1H), 6.89 (d, J=9.0 Hz, 1H), 5.25 (t, J=5.6 Hz, 1H), 4.78-4.68 (m, 1H), 4.33 (d, J=13.0 Hz, 2H), 4.12 (t, J=9.0 Hz, 1H), 3.87 (dd, J=8.9, 6.2 Hz, 1H), 3.74-3.64 (m, 1H), 3.62-3.52 (m, 1H), 2.87-2.71 (m, 2H), 2.23 (t, J=7.3 Hz, 2H), 2.11 (s, 6H), 1.72 (d, J=11.5 Hz, 2H), 1.64-1.49 (m, 1H), 1.34 (dd, J=14.3, 7.0 Hz, 2H), 1.18-1.04 (m, 2H) ppm. 13C NMR (101 MHz, D2O) S 161.52, 160.59, 158.12, 154.86, 145.70, 141.05, 140.16, 139.65, 133.57, 130.44, 123.64, 117.70, 114.54, 106.50, 106.22, 70.34, 50.81, 47.68 ppm. MS (ESI+) m/z 399.2 ([M+1]+).

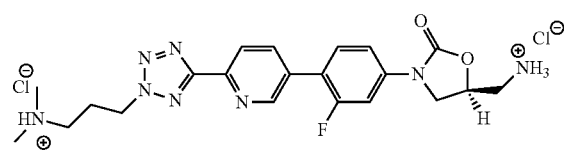

AKG-30

Using procedure C. This product was obtained from Intermediate-10 and Intermediate-18 as a white solid (0.36 g, 40% yield). 1H NMR (400 MHz, DMSO-d6) δ 10.94 (s, 1H), 8.96 (s, 1H), 8.52 (s, 3H), 8.28-8.22 (m, 2H), 7.79 (t, J=8.8 Hz, 1H), 7.69 (dd, J=13.6, 2.0 Hz, 1H), 7.49 (dd, J=8.8, 2.0 Hz, 1H), 5.08-5.01 (m, 1H), 4.93 (t, J=6.8 Hz, 2H), 4.28 (t, J=9.2 Hz, 1H), 4.00 (dd, J=9.2, 6.8 Hz, 1H), 3.29-3.26 (m, 2H), 3.21-3.16 (m, 2H), 2.75 (d, J=4.8 Hz, 6H), 2.49-2.43 (m, 2H) ppm. 13C NMR (101 MHz, D2O) S 162.39 (s), 160.58 (s), 158.11 (s), 154.88 (s), 147.20 (s), 141.66 (s), 139.28 (d, J=11.3 Hz), 132.86 (s), 130.45 (s), 122.90 (s), 118.44 (d, J=12.0 Hz), 114.44 (s), 106.46 (s), 106.17 (s), 70.30 (s), 54.56 (s), 50.62 (s), 47.68 (s), 42.89 (s), 42.16 (s), 23.74 (s) ppm. MS (ESI+) m/z 441 ([M+1]+).

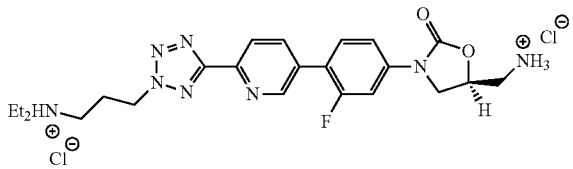

AKG-31

Using procedure C. This product was obtained from Intermediate-11 and Intermediate-18 as a white solid (0.36 g, 42% yield). 1H NMR (400 MHz, DMSO-d6) δ 10.10 (s, 1H), 8.96 (s, 1H), 8.390-8.21 (m, 5H), 7.80 (t, J=8.8 Hz, 1H), 7.69 (dd, J=13.6, 2.0 Hz, 1H), 7.50 (dd, J=8.8, 2.0 Hz, 1H), 5.04-4.97 (m, 1H), 4.94 (t, J=6.8 Hz, 2H), 4.28 (t, J=9.2 Hz, 1H), 3.94 (dd, J=9.6, 6.4 Hz, 1H), 3.31-3.26 (m, 2H), 3.21-3.17 (m, 2H), 3.15-3.12 (m, 4H), 2.46-2.42 (m, 2H), 1.21 (t, J=7.2 Hz, 6H) ppm. 13C NMR (101 MHz, D2O) S 163.04 (s), 160.53 (s), 158.07 (s), 154.84 (s), 147.95 (d, J=5.4 Hz), 142.36 (s), 139.05 (d, J=11.3 Hz), 138.32 (s), 132.44 (s), 130.38 (d, J=4.0 Hz), 122.50 (s), 118.72 (d, J=12.8 Hz), 114.35 (s), 106.37 (s), 106.09 (s), 70.29 (s), 50.65 (s), 48.55 (s), 47.64 (d, J=7.4 Hz), 42.17 (s), 23.05 (s), 8.24 (s) ppm. MS (ESI+) m/z 469 ([M+1]+).

To a solution of Intermediate-15 (7.6 g, 26.4 mmol) in DCM(150 mL) was added triethylamine (TEA, 4.57 g, 6.27 mL, 52.77 mmol, 2.0 equiv) followed by acetyl chloride (AcCl, 2.6 g, 2.74 mL, 39.58 mmol, 1.5 equiv) and 4-N,N-dimethylaminopyridine (DMAP, 0.028 g, 2.64 mmol, 0.01 equiv) at 0-5° C. under N2. The resulting reaction mixture was subsequently stirred at 0-5° C. for 2 h. When TLC and LCMS showed that the reaction was complete, the reaction mixture was quenched with H2O (100 mL). The two layers were separated, and the aqueous layer was then extracted with CH2Cl2 (2×50 mL), and the combined organic extracts were washed with H2O (2×100 mL) and saturated NaCl aqueous solution (100 mL), dried over MgSO4, and concentrated in vacuo. The residue was purified by FC (Biotage, 80 g silica gel column @ 65 mL/min, eluting with 0-60% EtOAc in petroleum ether for 30 min) to give Intermediate-17 (6.5 g, yield 75%). MS (ESI+) m/z 332 ([M+1]+).

To a solution of Intermediate-17 (6.5 g, 19.7 mmol) in 1,4-dioxane (100 mL) was added 1,1'-Bis(diphenylphosphino)ferrocene-palladium(II)dichloride dichloromethane complex (1.61 g, 1.97 mmol), Bis(pinacolato)diboron (10 g, 39.39 mmol) and KOAc (4.83 g, 49.24 mmol). The resulting reaction stirred at 90° C. for 4 h. When TLC and LCMS showed that the reaction was complete, the reaction mixture was cooled to RT before being treated with water (100 mL) and EtOAc (100 mL). The two layers were separated, and the aqueous layer was extracted with EtOAc (2×50 mL). The combined organic extracts were washed with water (2×50 mL) and saturated aqueous NaCl (50 mL), dried over MgSO4, and concentrated in vacuo. The residual brown oil was purified by FC (Biotage, 80 g silica gel column @ 60 mL/min, eluting with 0-100% EtOAc in petroleum ether for 30 min) give Intermediate-19 (6.6 g, yield 88.7%). MS (ESI+) m/z 379 ([M+1]+).

20. Synthesis of AKG-38 to 40.

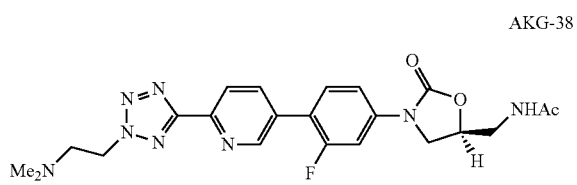 [SMILES: CC(=O)NC[C@H]1CN(c2ccc(-c3ccc(-c4nnn(CCN(C)C)n4)nc3)c(F)c2)C(=O)O1]

AKG-38

Using procedure C. This product was obtained from Intermediate-5 and Intermediate-19 as a white solid (0.48 g, 60% yield). $^1$H NMR (400 MHz, DMSO) δ 8.95 (s, 1H), 8.29-8.19 (m, 3H), 7.77 (t, J=8.8 Hz, 1H), 7.69 (dd, J=13.6, 2.0 Hz, 1H), 7.50 (dd, J=8.8, 2.0 Hz, 1H), 4.89 (t, J=6.0 Hz, 2H), 4.81-4.76 (m, 1H), 4.20 (t, J=9.2 Hz, 1H), 3.82 (dd, J=9.2, 6.8 Hz, 1H), 3.45 (t, J=5.6 Hz, 2H), 2.90 (t, J=6.0 Hz, 2H), 2.19 (s, 6H), 1.85 (s, 3H) ppm. $^{13}$C NMR (101 MHz, DMSO-d$_6$) δ 170.51, 164.17, 154.46, 149.94, 145.62, 140.90, 137.63, 132.07, 131.39, 122.59, 119.25, 114.66, 106.18, 105.90, 72.34, 57.71, 51.45, 47.67, 45.25, 41.87, 22.92 ppm. MS (ESI+) m/z 469.2 ([M+1]$^+$).

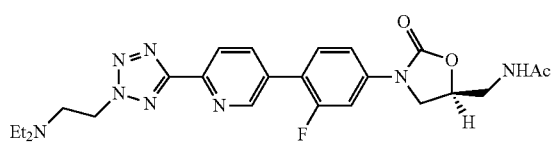

AKG-39

Using procedure C. This product was obtained from Intermediate-9 and Intermediate-19 as a white solid (0.35 g, 40% yield). $^1$H NMR (400 MHz, DMSO) δ 8.95 (s, 1H), 8.29-8.19 (m, 3H), 7.76 (t, J=8.8 Hz, 1H), 7.69 (dd, J=13.6, 2.0 Hz, 1H), 7.50 (dd, J=8.8, 2.0 Hz, 1H), 4.84-4.76 (m, 3H), 4.21 (t, J=9.2 Hz, 1H), 3.82 (dd, J=9.2, 6.4 Hz, 1H), 3.46 (t, J=5.6 Hz, 2H), 3.04 (t, J=5.6 Hz, 2H), 2.50-2.47 (m, 4H), 1.85 (s, 3H), 0.87 (t, J=7.2 Hz, 6H) ppm. $^{13}$C NMR (101 MHz, DMSO-d$_6$) δ 170.50, 164.11, 154.46, 149.91, 145.68, 137.68, 132.04, 131.40, 122.53, 119.27 (d, J=13.3 Hz), 114.65, 106.18, 105.90, 72.34, 52.11, 51.61, 47.67, 46.83, 41.87, 40.63, 40.42, 40.22, 40.01, 39.80, 39.59, 39.38, 22.92, 12.28 ppm. MS (ESI+) m/z 497 ([M+1]$^+$).

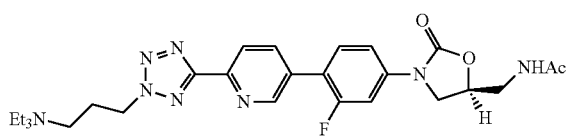

AKG-40

Using procedure C. This product was obtained from Intermediate-11 and Intermediate-19 as a white solid (0.36 g, 50% yield). $^1$H NMR (400 MHz, DMSO-d$_6$) δ 8.95 (s, 1H), 8.31-8.18 (m, 3H), 7.77 (t, J=8.8 Hz, 1H), 7.69 (dd, J=13.6, 2.0 Hz, 1H), 7.50 (dd, J=8.8, 2.0 Hz, 1H), 4.88-4.71 (m, 3H), 4.20 (t, J=9.2 Hz, 1H), 3.81 (dd, J=9.2, 6.4 Hz, 1H), 3.45 (t, J=5.6 Hz, 2H), 2.45 (s, 6H), 2.14 (s, 2H), 1.85 (s, 3H), 0.93 (s, 6H) ppm. $^{13}$C NMR (101 MHz, DMSO-d$_6$) δ 137.70, 131.45, 114.69, 46.79, 41.86, 40.64, 40.43, 40.22, 40.01, 39.80, 39.59, 39.38 ppm. MS (ESI+) m/z 511 ([M+1]$^+$).

Example 2. Assay for In Vitro Activity in *Mycobacterium Tuberculosis*

The broth microdilution MIC method used is described in Collins et al., 1997 and Gruppo et al., 2006. MIC or the minimum inhibitory concentration of the chemical compound which prevents visible growth of a bacteria after overnight incubation.

Briefly, MICs were determined by broth microdilution assay with an Alamar blue endpoint (MABA), as described by Collins et al., 1997 (Collins L, Franzblau S G (1997). Microplate alamar blue assay versus BACTEC 460 system for high-throughput screening of compounds against *Mycobacterium tuberculosis* and *Mycobacterium avium*. AAC. 41(5):1004-1009) and Gruppo et al., 2006 (Gruppo V, Johnson C M, Marietta K S, Scherman H, Zink E E, Crick D C, Adams L B, Orme I M, Lenaerts A J. (2006) Rapid microbiologic and pharmacologic evaluation of experimental compounds against *Mycobacterium tuberculosis*. AAC 50:1245-1250). MABA is a 96-well colorimetric assay in which the redox indicator Alamar blue turns from blue to pink in the presence of mycobacterial growth activity in the broth medium.

Briefly, 7H9 complete media was prepared by adding Middlebrook 4.7 g of 7H9 broth powder (Millipore Sigma Cat #M0178), 2 mL glycerol, and 898 purified water in 1 L flask with mixing until dissolved, and subsequently adding 100 mL of ADC solution (6 g bovine serum albumin, 2 g dextrose, and 3 mg catalase dissolved in 100 mL water) to the same 1 L flask. Compounds were made to a concentration of 10 mg/mL in DMSO and then diluted with DMSO further to 80 μg/mL, or forty times the desired starting concentration of 2 μg/mL. A series of nine 1:2 dilutions was prepared by adding 50 μl of drug solution in the first well to 50 μl of DMSO in the subsequent well and the carrying forward this process to the next eight wells in a drug preparation plate. Stocks of *M.tuberculosis* (M.tb) H$_{34}$Rv and M.tb Erdman strains were diluted from their initial concentration of 3-4×10$^7$ CFU/mL with media to a final concentration of 5×10$^5$ CFU/mL, mixed thoroughly by pipetting up and down with a multi-channel pipettor.

Assay plates were prepared by transferring 100 μl of the 5×10$^5$ CFU/mL inoculated media into all wells. Subsequently, 2.5 μL of each drug dilution from the drug preparation plate was transferred to the corresponding well in the assay plate. Assay plates were subsequently placed in ziplock bags and placed inside an incubator where they were incubated at 37° C. The plates were subsequently read at OD 600 nm on a plate reader on days 3 and 10. After the day ten OD600 reading, 10 μl of Alamar Blue dye was added to each analytical well. On day 12, all assay plates were scanned on a flatbed color scanner. The lowest consecutive antimicrobial concentration (typically two-fold serial dilutions) that does not produce visible color change from blue to pink with Alamar Blue, and/or shows a ≥80% reduction in OD600 relative to drug-free control wells, was regarded as the MIC for these compounds.

Assays were conducted using two unique drug sensitive strains (M.tb Erdman and M.tb H37Rv). MIC assays can also be performed in presence of 4% (w/v) human serum albumin (huSA) (Sigma #A1653) in order to assess potential protein binding (serum shift assay). Generally, a shift in MIC of two wells (4-fold shift in MIC) is considered to be significant. For PA-824 (positive control), a 4-fold shift in MIC is to be expected.

MICs were measured by the Alamar Blue (MABA) readout or by optical density readout (OD600) agreed or differed only by one 2-fold dilution, which is within the limits of the assay. All compounds tested showed consistency in MIC values against both Mtb Erdman and H37Rv, or were within one 2-fold dilution, with the exception of one compound AKG-40; which showed a higher MIC value of 1-2 ug/mL vs Erdman, and an MIC of 0.5 vs H37Rv. This discrepancy could be due to slower growth (lower OD readings) on the Erdman plate.

Linezolid showed an expected MIC value of 2 μg/mL, Tedizolid at 0.25 μg/mL and Bedaquiline at 0.125 μg/mL. These values are consistent with past MIC data and published values (Ruiz et al. Antimicrob. Agents Chemother. 2019, Mar. 27; 63(4), pii: e01939-18, Reddy et al. Antimicrob Agents Chemother. 2010 July; 54(7):2840-6, Torrea et al. J Antimicrob Chemother. 2015 August; 70(8):2300-5). AKG-28 showed an MIC of 0.03-0.015 μg/mL, significantly more active than Tedizolid. Of the oxazolidinone analogues containing an acetamide group, AKG-39 showed an MIC of 0.5 μg/mL, and AKG-40 an MIC of 1-0.5 μg/mL. AKG-38 with an MIC of 0.06 μg/mL also showed several folds greater activity than Tedizolid.

Molecules with an amine group or acetamide group at the C5 position of oxazolidinone were more active (AKG-3 vs Tedizolid, AKG-28 or AKG-38 vs AKG-16, AKG-39 vs AKG-24, AKG-40 vs AKG-26), and compounds with aminoalkyl side chain on the tetrazole showed favorable activity. Substitution of t-butoxycarbonylamino (Boc-NH) group at oxazolidinone position C5 for primary amine (AKG-28-1 vs. AKG-28) or acetamide (AKG-28-1 vs AKG-38) led to the decrease of activity. Compounds containing a dimethylaminoalkyl side chain were particularly superior when compared to aminoethyl or diethylaminoethyl analogs (AKG-16 vs AKG-24, AKG-28 vs AKG-29, AKG-30 vs AKG-31). Likewise, shorter dialkylaminoalkyl side chains (such as ethylene versus propylene) on the tetrazole ring showed greater activity (AKG-16 vs AKG-25, AKG-24 vs AKG-26, AKG-28 vs AKG-30). Analogs with substitutions on the 2' position of the tetrazole were more active than those with substitutions at the 1' position (AKG-16 vs AKG-21, AKG-23 vs AKG-22).

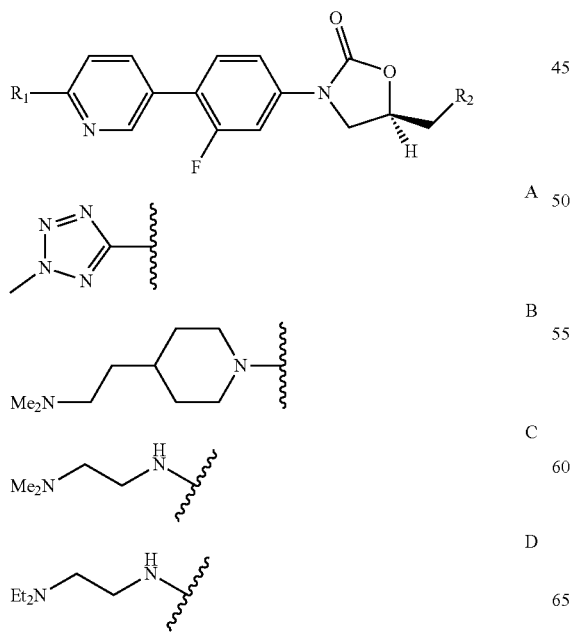

A

B

C

D

-continued

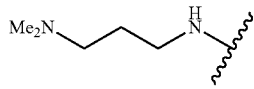

E

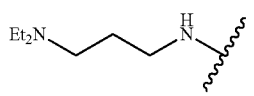

F

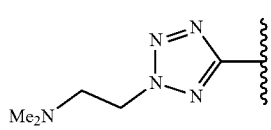

G

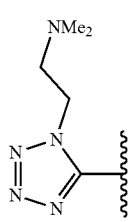

H

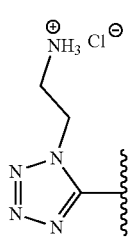

I

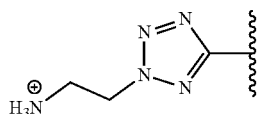

J

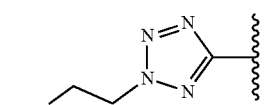

K

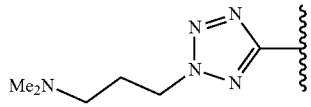

L

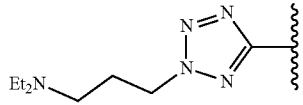

M

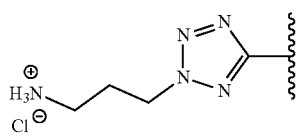

N

TABLE 2

| Compound ID | R₁ | R₂ | Mycobacterium tuberculosis MIC (µg/ml) | |
| --- | --- | --- | --- | --- |
| | | | Erdman | H37Rv |
| Linezolid |  | —NHCOMe | 1 | 1 |
| Sutezolid |  | —NHCOMe | 0.5 | 0.5 |
| Tedizolid |  | —OH | 0.25 | 0.25 |
| AKG-1 | A | —NMe₂ | >8 | >8 |
| AKG-2 | A | —NEt₂ | >8 | >8 |
| AKG-3 | A | —NH₂•HCl | 0.125 | 0.06 |
| AKG-5 | A | —OCO(CH₂)₃NMe₂ | 1 | 1 |
| AKG-6 | A | B | >8 | >8 |
| AKG-7 | A | —O(CH₂)₂NEt₂ | >8 | >8 |
| AKG-8 | A | —N(CH₂)₃NEt₂ | >8 | >8 |
| AKG-9 | A | D | >8 | >8 |
| AKG-11 | B | —OH | 4 | 4 |
| AKG-12 | C | —OH | 4 | 4 |
| AKG-13 | D | —OH | >8 | >8 |
| AKG-14 | E | —OH | 8 | 8 |
| AKG-15 | F | —OH | >8 | >8 |
| AKG-16 | G | —OH | 0.25 | 0.25 |
| AKG-17 | A | —NHCO(CH₂)₂NH₂•HCl | 2 | 2 |
| AKG-18 | A | —NHCO(CH₂)₃NH₂•HCl | 2 | 2 |
| AKG-19 | A | —NH(CH₂)₂NH₂•HCl | >8 | >8 |
| AKG-20 | A | —OCO(CH₂)₂NEt₂ | 0.5 | 0.5 |
| AKG-21 | H | —OH | >8 | >8 |
| AKG-22 | I | —OH | 1 | 0.5 |
| AKG-23 | J | —OH | 0.25 | 0.25 |
| AKG-24 | K | —OH | 1 | 1 |
| AKG-25 | L | —OH | 1 | 1 |
| AKG-26 | M | —OH | 2 | 2 |
| AKG-27 | N | —OH | 0.5 | 0.5 |
| AKG-28 | G | —NH₂•HCl | 0.03 | 0.015 |
| AKG-28-1 | G | —NHCOOCMe₃ | 0.25 | 0.125 |
| AKG-29 | J | —NH₂•HCl | 0.25 | 0.125 |
| AKG-30 | L | —NH₂•HCl | 0.125 | 0.125 |
| AKG-31 | M | —NH₂•HCl | 0.5 | 0.5 |
| AKG-38 | G | —NHCOMe | 0.06 | 0.06 |
| AKG-39 | K | —NHCOMe | 0.5 | 0.5 |
| AKG-40 | M | —NHCOMe | 1 | 0.5 |

Example 3. Assay for In Vitro Cytotoxicity to Human Kidney and Human Hepatocyte Cells Compounds were tested in vitro over a series of 10 dilutions to determine IC50 in African green monkey kidney (Vero; ATCC #CCL81) or human hepatocyte/liver (HepG2; ATCC #HB8065) cells. As these molecules are generally expected to be nontoxic, a positive control of doxorubicin is included in all studies. Data is reported out as the full cell viability curve, as well as a calculation of the actual IC50 value for each compound.

Adherent cells were grown to ~0.80% confluency. The cells were trypsinized by adding 0.25% trypsin-EDTA (Gibco #25200-072) and the cells subsequently spun down, and 5 ml of growth medium (MEM media; Corning #10010 CM) added to disperse the cells. The cell density was determined using a hemocytometer. Growth medium (MEM media containing 10%/FBS; Corning #35015 CV) was added to the cells to adjust to an appropriate concentration of cells. Then, 200 µl of the cells (5,000 cells/well) were added to a 96-well clear flat-bottom plate (Costar #9804) and incubated in the plate at 37° C. in a humidified incubator with 5% $CO_2$ for 24 h.

Prepare serial dilutions of testing compounds using growth medium as solvent (Table 2). These compounds were provided as sterile aqueous solutions of HCl salts with a concentration of 5 mg/ml. For making dilutions, each drug stock was warmed to room temperature, vortexed and was visually inspected for precipitation. If solid drug was present, the stock was heated on a 60° C. water bath and then allowed to cool to near room temperature. Based on the treatment concentrations, 20× working stocks were made by serial dilution. These were further diluted to 1× in the growth media to the highest drug concentration tested of 250 ug/ml.

Compounds were added to the wells at a series of 1:2 dilutions from the initial 250 µg/ml concentration for each compound by aspirating out the old media and replacing it with 200 µl of the drug containing media. The plates were incubated at 37° C. in a humidified incubator with 5% $CO_2$ for 72 h. At the end of the compound incubation period, replace the media in each well with 100 µl of 1× PrestoBlue Cell Viability Reagent (ThermoFisher Cat #A13261). Incubate the plate at 37° C. in a humidified incubator with 5% $CO_2$ 30 min to 2 h. Take readings at 30, 60, and 120 min. Read fluorescence with 560 nm excitation and 590 nm emission using SpectraMax M5 plate reader (Molecular Devices). Correct background by subtracting the RFU of the control containing only the culture medium (background control well) from all sample readings. Calculate the percentage of cytotoxicity using the formula below:

$$\% \text{ Cytotoxicity} = [(RFU_{Medium} - RFU_{Treatment})/RFU_{Medium}] \times 100\%$$

The IC50 was determined using GraphPad Prism using the following formula:

$$Y = 100/(1 + 10^{((\text{Log } IC50 - X) * \text{HillSlope})})$$

TABLE 3

| Compound ID | Cell viability IC50 (µg/ml) | |
| --- | --- | --- |
| Cell line | VERO | HepG2 |
| AKG-1 | 112.6 | 116.0 |
| AKG-2 | 67.9 | 24.5 |
| AKG-3 | 17.8 | 21.2 |
| AKG-5 | 32.5 | 30.8 |
| AKG-6 | 27.4 | 15.5 |
| AKG-7 | 103.6 | 11.2 |
| AKG-9 | 139.3 | 28.1 |
| AKG-11 | 31.9 | 42.8 |
| AKG-12 | 89.1 | 67.6 |
| AKG-13 | 93.9 | 31.8 |
| AKG-14 | 155.8 | 45.6 |
| AKG-15 | 156.2 | 35.6 |
| AKG-16 | 97 | 91 |
| AKG-17 | >250 | 37.3 |
| AKG-18 | >250 | 9.5 |
| AKG-19 | >250 | 42.2 |
| AKG-20 | >250 | 15.1 |
| AKG-21 | >250 | 156.3 |
| AKG-22 | 57.7 | 17.2 |
| AKG-23 | >250 | 7.3 |
| AKG-24 | 31.3 | 11.4 |
| AKG-25 | 182 | 9.4 |
| AKG-26 | 128.5 | 9.0 |
| AKG-27 | 5.6 | 9.0 |
| AKG-28 | 83.0 | 13.4 |
| AKG-29 | 109.9 | 74.4 |
| AKG-30 | 110.5 | 18.9 |
| AKG-31 | 111.5 | 13.2 |
| AKG-38 | 395 | 97 |
| AKG-39 | 201 | 70 |
| AKG-40 | >250 | 113 |

Surprisingly, most of the analogs containing a hydroxyl group on the C5 side chain of the oxazolidinone ring, which mimics the substituent of the active metabolite tedizolid for tedizolid phosphate, were the most hepatotoxic showing single digit IC50 for the HepG2 hepatocyte cell line. Tedizolid is the most active oxazolidinone currently approved for the treatment of MRSA, and has structural similarities to the compounds described here in the tetrazole D-ring, pyridyl C-ring, and the aryl B-ring (See FIG. 6). Here, however, the increased toxicity to hepatocytes results in a comparatively low Selectivity Index for theoxazolidinones with a hydroxyl on the C5 side chain (AKG-23, AKG-25, AKG-26, and AKG-27) when compared to those with an amino or acetamide group at the same position on the C5 side chain (AKG28-31, AKG38-40, and AKG-3).

Example 4. Determination of Selectivity Index

A Selectivity Index (SI) was calculated to determine the relative inhibitory activities of the compounds on the two *Mycobacterium tuberculosis* strains, Erdman and H37Rv, compared to that on mammalian cells, namely, African green monkey kidney (VERO) or human hepatocyte-derived (HepG2) cells, as described in Experimental Examples 2 and 3, respectively. A high SI is preferable as it indicates preferred killing of the bacteria of tuberculosis strains at concentrations of the drug that are less harmful to normal cells in the body. The selectivity index was calculated using the formula below:

$$SI = IC_{50, mammalian} / MIC_{bacteria}.$$

where bacteria are *M. tuberculosis* of either Erdman or H37Rv strains, and mammalian cells are VERO or HepG2 cell lines.

If the IC50 was greater than the highest value tested for the VERO or HepG2 cells, the SI is shown as greater than (>) the ratio calculated using that highest concentration. Likewise, if the MIC for Erdman or H37Rv strains is greater than the highest concentration of drug tested (8 µg/ml), then the SI is shown as less than (<) the ratio calculated using that highest concentration. Calculations where both numbers are above the highest concentrations tested are shown as not determined (nd). The results are shown in TABLE 4. The SI did not correlate directly to the activity of the molecules in either mycobacterial strains or mammalian cell lines, and increased potency in mycobacterial strains did not correlate directly to increased toxicity against the mammalian cell lines. For example, AKG-38 demonstrated nanomolar MIC against both strains of *Mycobacterium tuberculosis*, whereas it was relatively inactive against both VERO and HepG2 cell lines compared to other molecules in the panel, giving it a high SI. This was similarly seen for AKG-28. It is notable that both molecules, AKG-28 and AKG-38, had a dimethylaminoethyl substituent at the 2' position of the tetrazole ring.

TABLE 4

| Compound | Selectivity Index (SI) | | | |
|---|---|---|---|---|
| ID | Erd/VERO | Erd/HepG2 | H37Rv/VERO | H37Rv/HepG2 |
| AKG-1 | <14.1 | <14.5 | <14.1 | 14.5 |
| AKG-2 | <8.5 | <3.1 | <8.5 | 3.1 |
| AKG-3 | 142.4 | 169.6 | 296.7 | 353.3 |
| AKG-5 | 32.5 | 30.8 | 32.5 | 30.8 |
| AKG-6 | 3.4 | <1.9 | <3.4 | 1.9 |
| AKG-7 | 13.0 | <1.4 | <13.0 | 1.4 |
| AKG-9 | <17.4 | <3.5 | <17.4 | 3.5 |
| AKG-11 | 8.0 | 10.7 | 8.0 | 10.7 |
| AKG-12 | 22.3 | 16.9 | 22.3 | 16.9 |
| AKG-13 | <11.7 | <4.0 | <11.7 | <4.0 |
| AKG-14 | 19.5 | 5.7 | 19.5 | 5.7 |
| AKG-15 | <19.5 | <4.5 | <19.5 | <4.5 |
| AKG-16 | 388.0 | 364.0 | 388.0 | 364.0 |
| AKG-17 | >125 | 18.7 | >125 | 18.7 |
| AKG-18 | >125 | 4.8 | >125 | 4.8 |

TABLE 4-continued

| Compound | Selectivity Index (SI) | | | |
|---|---|---|---|---|
| ID | Erd/VERO | Erd/HepG2 | H37Rv/VERO | H37Rv/HepG2 |
| AKG-19 | >31.3 | 5.3 | >31.3 | 5.3 |
| AKG-20 | >500 | 30.2 | >500 | 30.2 |
| AKG-21 | nd | <19.5 | nd | <19.5 |
| AKG-22 | 57.7 | 17.2 | 115.4 | 34.4 |
| AKG-23 | >1000 | 29.2 | >1000 | 29.2 |
| AKG-24 | 31.3 | 11.4 | 31.3 | 11.4 |
| AKG-25 | 182.0 | 9.4 | 182.0 | 9.4 |
| AKG-26 | 64.3 | 4.5 | 64.3 | 4.5 |
| AKG-27 | 11.2 | 18.0 | 11.2 | 18.0 |
| AKG-28 | 2766.7 | 446.7 | 5533.3 | 893.3 |
| AKG-29 | 439.6 | 297.6 | 879.2 | 595.2 |
| AKG-30 | 884.0 | 151.2 | 884.0 | 151.2 |
| AKG-31 | 223.0 | 26.4 | 223.0 | 26.4 |
| AKG-38 | 6583.3 | 1616.7 | 6583.3 | 1616.7 |
| AKG-39 | 402.0 | 140.0 | 402.0 | 140.0 |
| AKG-40 | >250.0 | 113.0 | >500.0 | 226.0 |

In some embodiments, the compounds of interest have a SI index for Erd/HepG2 and H37Rv/HepG2 higher than 100, higher than 200, higher 300, higher than 400, higher than 500, higher than 1000, higher than 1500, higher than 2000, higher than 2500, higher than 3000, higher than 3500, higher than 4000, higher than 4500, higher than 5000, higher than 5500, higher than 6000, higher than 6500, between 100 and 7000, between 100 and 6000, between 100 and 5000, between 100 and 4000, between 100 and 3000, between 100 and 2000, between 100 and 1000, between 100 and 900, between 100 and 800, between 100 and 700, between 100 and 600, between 100 and 500, between 100 and 400, between 100 and 300, between 100 and 200, between 200 and 7000, between 200 and 6000, between 200 and 5000, between 200 and 4000, between 200 and 3000, between 200 and 2000, between 200 and 1000, between 200 and 900, between 200 and 800, between 200 and 700, between 200 and 600, between 200 and 500, between 200 and 400, between 200 and 300, between 300 and 7000, between 300 and 6000, between 300 and 5000, between 300 and 4000, between 300 and 3000, between 300 and 2000, between 300 and 1000, between 300 and 900, between 300 and 800, between 300 and 700, between 300 and 600, between 300 and 500, between 300 and 400. In some embodiments, the compounds of interest have a SI index for Erd/HepG2 and H37Rv/HepG2 ranges from 100 to 1700, 200 to 1700, 300 to 1700.

Compounds with an amino or acetamide groups on the C5 side chain of the oxazolidinone ring and an aminoalkyl group at the 2' position of the tetrazole ring displayed a comparatively higher SI compared to those with a hydroxyl group on the C5 side chain. In addition, the specific tetrazole substitution further improved the SI with a dimethylaminoethyl substitution at the 2' position of the tetrazole ring being preferred (AKG-28 and AKG-38) over methyl, diethylaminoethyl, aminoethyl, or dimethylaminopropyl substitutions at this same position. Moving a dimethyaminoethyl group to position 1' of the tetrazole ring (compound AKG-21 vs. AKG-28) unexpectedly resulted in dramatic loss of activity against *Mycobacterium tuberculosis*.

Example 5. Assay for In Vitro Activity Against Methicillin Resistant *Staphylococcus aureus* (MRSA)

The activity of the lead oxazolidinone inhibitors was measured to demonstrate sufficient potency against the gram positive bacterium methicillin resistant *Staphylococcus aureus* (MRSA) to justify their subsequent delivery in the form of liposomes for the treatment of the same. In some embodiments, the MIC in two of the three evaluated strains of less than 6 µg/mL. In some embodiments, the MIC in two of the three evaluated strains of less than 2 µg/mL less than 2 µg/mL is more preferred.

Three *S. aureus* strains were grown overnight at 37° C. in an ambient atmosphere on trypticase soy agar plates supplemented with 5% sheep blood cells. The cultures were aseptically swabbed and transferred to tubes of sterile water, and the optical density was adjusted to 0.5 at 600 nm. The cultures were then diluted 1:100 to deliver approximately $5 \times 10^5$ cells per well in 120 µL. Following incubation, the MIC of the test article was determined by presence/absence of growth in each well. MIC analyses were performed in triplicate.

Tedizolid showed an MIC of 0.206-0.617 µg/ml, similar to the 0.5 µg/ml described in U.S. Pat. No. 7,816,379. Interestingly, all of the molecules (AKG-3, AKG-28, AKG-29, and AKG-30) with a primary amine modification at $R_Z$ of the oxazolidinone ring showed negligible activity against all three MRSA strains (>50 µg/ml). The molecules with an acetamide group at the same position (AKG-38, AKG-39, and AKG-40) were between 3 and 9-fold less active than tedizolid itself against the three MRSA strains.

TABLE 5

| Compound ID strain | methicillin resistant *Staphylococcus aureus* (MRSA) MIC (µg/ml) | | |
|---|---|---|---|
| | ATCC BAA-1556 | ATCC 43300 | 880 NR-49120 |
| Tedizolid | 0.617 | 0.617 | 0.206 |
| AKG-3 | 50 | 50 | 50 |
| AKG-16 | 1.85 | 1.85 | 1.85 |
| AKG-22 | 1.85-5.55 | 16.67 | 5.55 |
| AKG-28 | >50 | >50 | >50 |
| AKG-29 | 50 | >50 | 50 |
| AKG-30 | >50 | >50 | >50 |
| AKG-38 | 1.85 | 1.85 | 0.617 |
| AKG-39 | 1.85 | 1.85 | 1.85 |
| AKG-40 | 1.85 | 5.55 | 1.85 |

Example 6: Liposome Compositions

General Protocols.

1. The lipid components (phospholipid (PhL), cholesterol, and optionally—a PEG-lipid derivative and/or a lipid fluorescent label were combined in an amount of 100% ethanol equal to one-tenth of a volume (V) calculated to obtain lipid suspension with about 60 mM phospholipid and stirred at the temperature of 65-68° C. until complete dissolution of the lipids.

Neutral phospholipids can include diacylphosphatidylcholines, dialkylphosphatidylcholines, sphingomyelins, and diacylphosphatidylethanolamines. Hydrogenated soyphosphatidylcholine, distearoylphosphatidylcholine, and egg sphingomyelin are some of the preferred phospholipids.

PEG-lipid components may include PEG(Mol. weight 2,000)-distearoylglycerol (PEG-DSG), 1,2-distearoyl-sn-glycero-3-phosphoethanolamine-N-[methoxy(polyethylene glycol)-2000] (PEG-DSPE) or N-palmitoyl-sphingosine-1-{succinyl[methoxy(polyethylene glycol)2000]} (PEG-ceramide). The molecular weight of the PEG-lipid component can also vary from 1,500-6,000 g/mol, but is preferably around 2,000 MW.

Lipid fluorescent labels can include 1,1'-Dioctadecyl-3,3,3',3'-Tetramethylindocarbocyanine-5,5'-Disulfonic Acid (DiIC18(3)-DS), 1,1'-Dioctadecyl-3,3,3',3'-Tetramethylindodicarbocyanine-5,5'-Disulfonic Acid (DiIC8(5)-DS), 1,2-distearoyl-sn-glycero-3-phosphoethanolamine-N-(Cyanine 7) (18:0 Cy7 PE), 1,2-distearoyl-sn-glycero-3-phosphoethanolamine-N-[amino(polyethylene glycol)-2000]-N-(Cyanine 7) (DSPE PEG(2000)-N-Cy7), 1,2-distearoyl-sn-glycero-3-phosphoethanolamine-N-(Cyanine 5) (18:0 Cy5 PE), 1,2-distearoyl-sn-glycero-3-phosphoethanolamine-N-[amino(polyethylene glycol)-2000]-N-(Cyanine 5) (DSPE PEG(2000)-N-Cy5), 1-Oleoyl-2-[12-[(7-nitro-2-1,3-benzoxadiazol-4-yl)amino]dodecanoyl]-sn-Glycero-3-Phosphocholine (18:1-12:0 NBD PC).

2. The ethanolic lipid solution was combined with volume V of the trapping agent solution (0.25-0.5 M ammonium sulfate or 1 N triethylammonium sucrose octasulfate) upon stirring at 65-68° C. until a uniform suspension was obtained.

Potential trapping agents may include but are not limited to diethylammonium or triethylammonium salts of sucrose octasulfate, ammonium sulfate, ammonium citrate, citric acid, dextran sulfate, polyvinylsulfonate, or ammonium salts of inositol hexaphosphate, in the concentrations of 0.1-2 g-equivalents/L (0.1-2 N), preferably 0.2-1.5 N. Ammonium salts are typically employed and may include ammonium itself, monoalkyl-, dialkyl-, or trialkylammonium salts.

3. The lipid suspension was extruded at least three times through a stack of track-etched polycarbonate membranes, typically, two or four membranes with the nominal pore size of 100 nm and one with the nominal pore size 200 nm (Whatman Nuclepore, USA), using a thermobarrel extruder (Lipex, Canada) at 65-68° C., at the pressure of 400-450 psi. When two 100-nm membranes were used in a 100-ml Lipex extruder, the extrusion pressure was typically 260-300 psi. The resulting liposomes have Z-average particle size (diameter) Xz between about 80 and about 130 nm, and PDI less than 0.1.

4. The extruded lipid suspension (known to contain unilamellar and/or oligolamellar liposomes) was chilled in refrigerator (2-8° C.) and filtered through a 0.2-micron Polyethersulfone (PES) membrane filter under positive pressure.

5. An aliquot of the extruded, filtered liposome suspension so made was chromatographed on a gravity-fed Sepharose CL-4B size exclusion column (eluent—Type 1 water), to purify the liposomes from extraliposomal trapping agent. The purified liposomes were collected near the void volume fraction of the column. For a scale-up studies, this step was performed using a tangential flow filtration (TFF) on a hollow fiber cartridge (Repligen Spectrum MicroKros PS or mPES membrane with MWCO of 500 KDa) effecting 8-10 volume exchanges (or until the conductivity of the liposome suspension dropped below 200 µS/cm) with Type 1 or USP "Water for injection" endotoxin-free water.

6. The lipid concentration in a purified extruded liposome preparation was determined using HPLC with UV detection, by measuring the concentration of cholesterol and correcting for the known phospholipid/cholesterol molar ratio Alternatively, a spectrophotometric blue phosphomolybdate method was used to directly quantify the phospholipid content.

7. The drug was dissolved in Type 1 or endotoxin-free pure water in the form of a hydrochloric acid salt (e.g., AKG-3 and AKG-5 were used as monohydrochloride, AKG-28 and AKG-29 were used as dihydrochloride) at the concentration of 5-20 mg/ml of the drug. To the drug prepared in free base form (e.g., AKG-16, AKG-38), an equivalent amount of HCl was added. If necessary, pH of the solution was brought between pH 2.5-5.5, using 1 N NaOH, HCl, or tris(hydroxymethyl)aminomethane (Tris)-base solution, and the solution was filtered through a 0.2-micron PES filter under positive pressure. When necessary, the drug concentration in the stock solution so made was verified by HPLC with UV detection at 305 nm.

8. Purified liposomes of step 5 and the drug stock solution were combined in the presence of an osmotic agent (typically dextrose) and water in the amounts necessary to provide a desired drug-to-phospholipid (DL) ratio, the drug concentration in the range 1.5-3.3 mg/ml, at the osmolality equal to the measured osmolality of the trapping agent solution of step 2. Optionally, a buffer at a desired pH (typically pH 4 to pH 7) was added. In some instances, the amount of added osmotic agent (e.g., dextrose at about 45 g/L) provided osmolality less that the measured osmolality of the trapping agent solution, and the loading was effected at 6-8 mg/ml of the drug.

9. The drug-liposome mixture was incubated with constant agitation at 65-68° C. for about 15-20 min and quickly chilled on ice. After 5-10 min, the mixture was allowed to reach ambient temperature an adjusted to 0.1M NaCl by adding a calculated amount of 3 M NaCl stock solution.

10. The drug-loaded liposomes were purified from the unencapsulated drug by size exclusion chromatography (SEC) on a gravity-feed Sepharose CL-4B column, eluent—10 mM HEPES-buffer pH 7.0 in 140-144 mM NaCl (HBS-7). The liposome fractions were collected near the column void volume. For scale-up studies, the purification and buffer exchange were performed using TFF as described under item 5 above, using 10 volume exchanges with the HBS-7 buffer. In a scaled-up process, about 8 volume exchanges were typically used. Optionally, the purified liposomes were concentrated by continuing the TFF process without buffer feed. The purified, drug-loaded liposomes were aseptically filtered using 0.2-micron sterile PES filter under positive pressure and stored in refrigerator (2-8° C.).

11. The drug and lipid concentrations in the purified drug-loaded liposome preparations were determined by HPLC. Alternatively, a spectrophotometric (blue phosphomolybdate) method was used for phospholipid quantification, and the drug was quantified by UV absorption (302-305 nm) in a liposome sample solubilized in 70% isopropanol-0.1N HCl in the presence of 6.5 mg/ml sodium dodecylsulfate. Encapsulation efficiency was determined as:

$$EE, \% = DL/DL0*100\%$$

where DL0 is drug-to-phospholipid ratio in the liposome loading mixture before SEC or TFF purification, and DL is the drug-to-phospholipid ratio in the drug-loaded liposomes after purification (step 10).

12. The average liposome size (Z-average diameter, Xz) and polydispersity index (PDI) were determined using dynamic laser scattering by a method of cumulants on a Zetasizer mu-V, Zetasizer Nano, or Zetasizer Pro (Malvern Panalytical, US).

Example 7. In Vivo Stability and Blood Clearance of the Liposomes

The stability of drug encapsulation and the blood clearance rates of the liposomes that encapsulate the compounds of the present disclosure was studied in mice according to the following general protocol. Mice of a given laboratory strain (C3H female or CD-1 male) in groups of three were injected with the drug-loaded liposomes via tail vein at the dose of 9 mg of the drug per kg of the body weight. At timepoints 1 and 2, the blood was sampled from the retroorbital sinus, and the animals were sacrificed. Typically, the blood sampling timepoints included 5 min, 1 hour, 6 hours, and 24 hours post injection. The plasma was separated by centrifugation, extracted with acidified isopropanol, optionally containing a solubilizing agent (sodium octanesulfonate), and analyzed for the drug and the lipid (when a liposome the incorporated a lipid label, DiIC18(3)-DS) by HPLC. Blood clearance of the liposomal drug was expressed at percent of injected dose remaining at a given timepoint. In vivo stability of the drug encapsulation was assessed by the percent change (decrease) of DL ratio in the plasma at a given timepoint compared to the pre-injection DL value.

Example 8. Loading of AKG-3, AKG-5, and AKG-16 into Liposomes at Different pH

Trimethylammonium sucrose octasulfate trapping agent solution was prepared by passing a solution of commercial potassium sucrose octasulfate heptahydrate (40.2 g in 145 ml of water) through a 500-ml ion exchange column of Dowex 50 W×8 100-200 mesh in a hydrogen form and titration of the resulting free acid form of sucrose octasulfate with neat triethylamine to pH 6.2. The concentration of triethylammonium sucrose octasulfate (TEA-SOS) (1 N, corresponding to 0.125 M sucrose octasulfate) was estimated from the amount of triethylamine consumed in titration. Residual potassium was estimated using Horiba LAQUATwin K-11 potassium analyzer by the method of additions and was less than 0.1% of the initial potassium amount.

Figure 1:
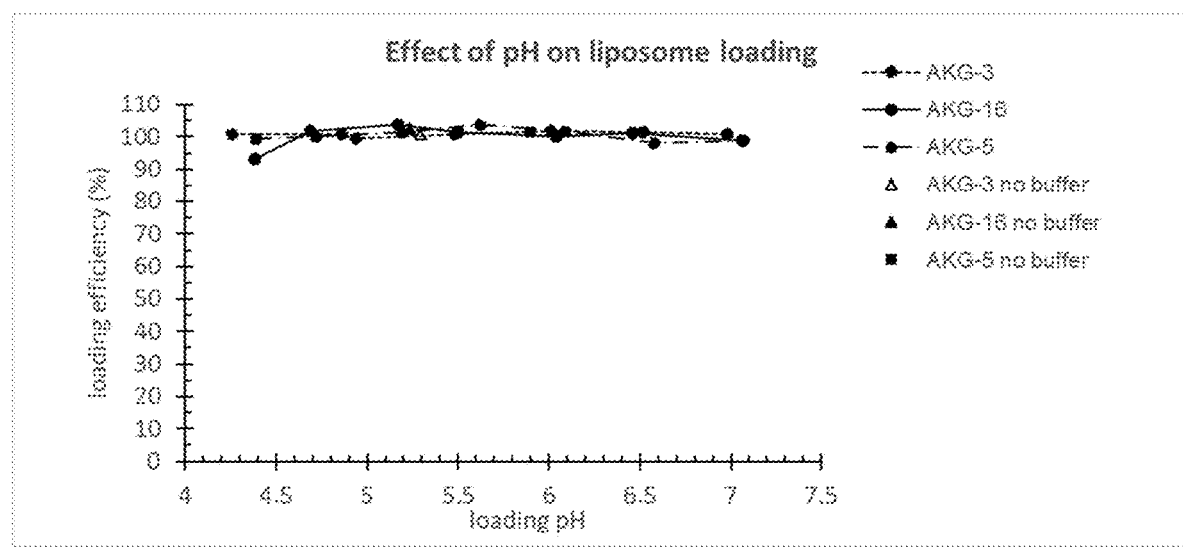
FIG. 1 is a graph showing the effect of pH on the liposome loading of compounds AKG-3, AKG-5, and AKG-16.

Liposomes composed of hydrogenated soy phosphatidylcholine (HSPC) (Lipoid, Germany), cholesterol (3:2 molar ratio), and methoxypoly(ethyleneglycol) ether of 1, 2-distearoylglycerol (PEG-DSG, PEG mol.weight 2000, NOF, Japan) (0.5 mol. % of HSPC) with 1 N trimethylammonium sucrose octasulfate (TEA-SOS) as a trapping agent were prepared essentially as described in the General protocol above. The drug loading step was performed at the DL ratio (DL0) of 500 g/mol PhL in the presence of 16 mM morpholinoethanesulfonic acid (MES) –4 mM sodium citrate buffer having pH in the range of 4.3-7.1, as well as without addition of any buffer substance (pH 5.2-5.9). All drugs were encapsulated into the liposomes with high efficiency (over 98%, except for AKG-16 at pH 4.38, that was loaded with the efficiency of 93.3%) in the whole studied range of pH (FIG. 1). Addition of a buffer substance was not required for efficient encapsulation.

Figure 2A:
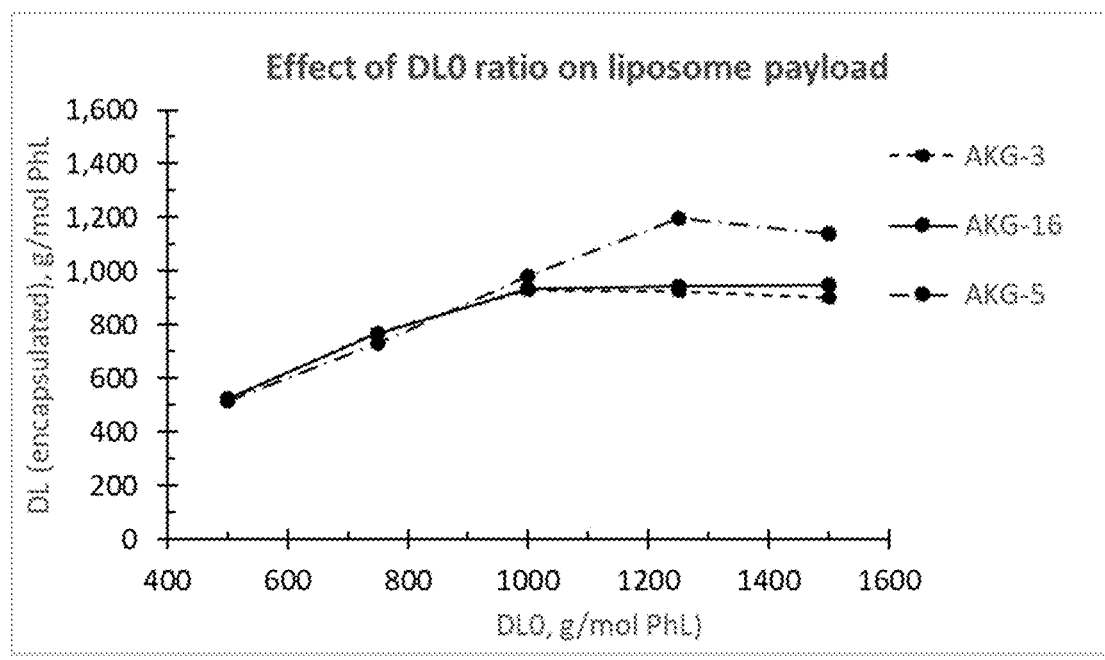
FIG. 2A and FIG. 2B are graphs showing the encapsulation of compounds AKG-3, AKG-5, and AKG-16 into liposomes with TEA-SOS trapping agent at different drug-to-lipid (DL) ratios
Figure 2B:
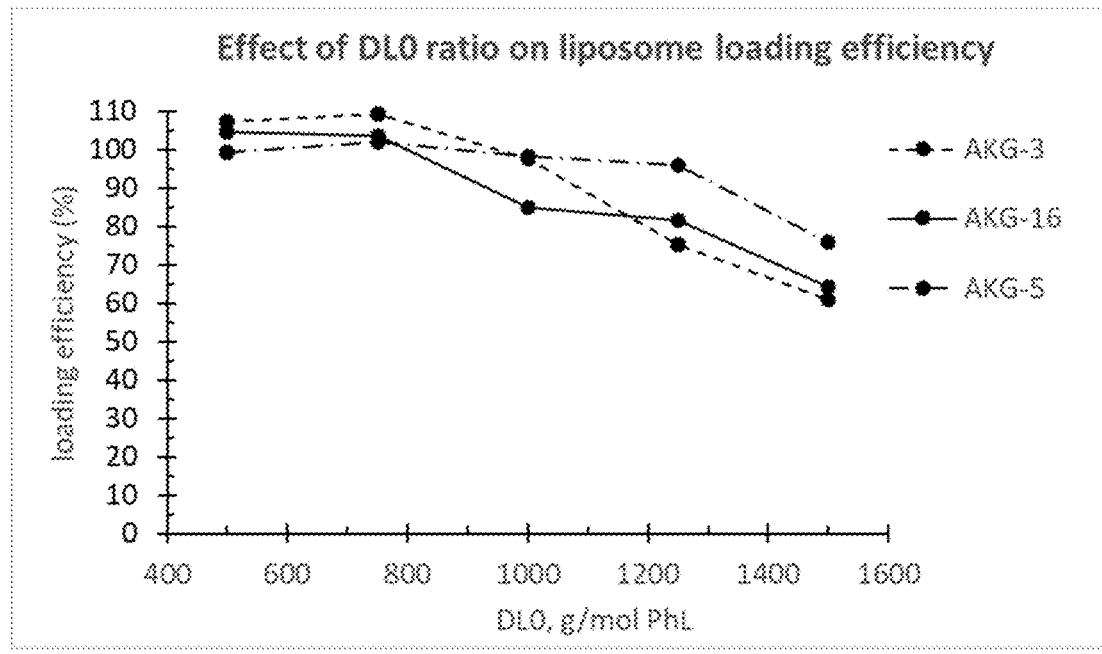
Figure 3A:
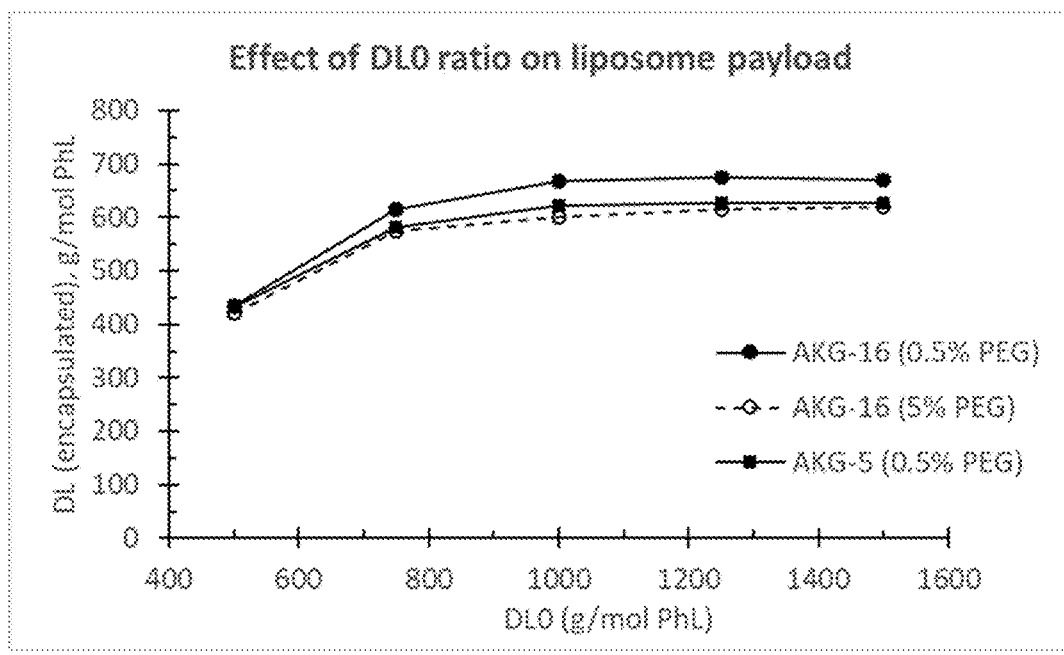
FIG. 3A, FIG. 3B FIG. 3C, and FIG. 3D are graphs showing the encapsulation of compounds AKG-3, AKG-5, and AKG-16 into liposomes with 0.5M ammonium sulfate as a trapping agent at different DL ratios.
Figure 3B:
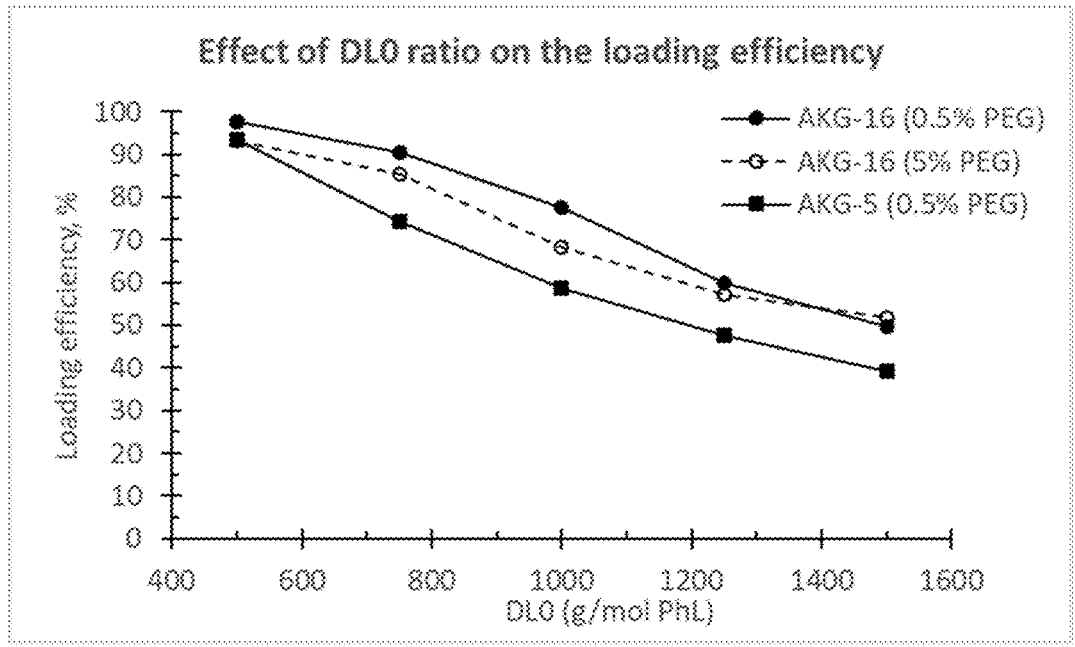
Figure 3C:
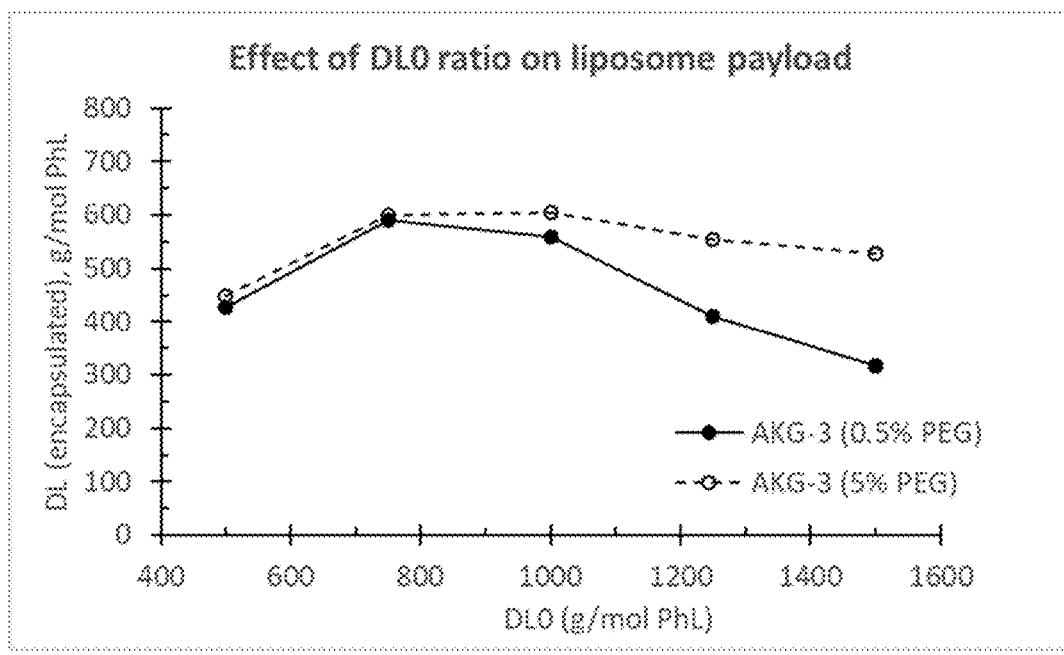
Figure 3D:
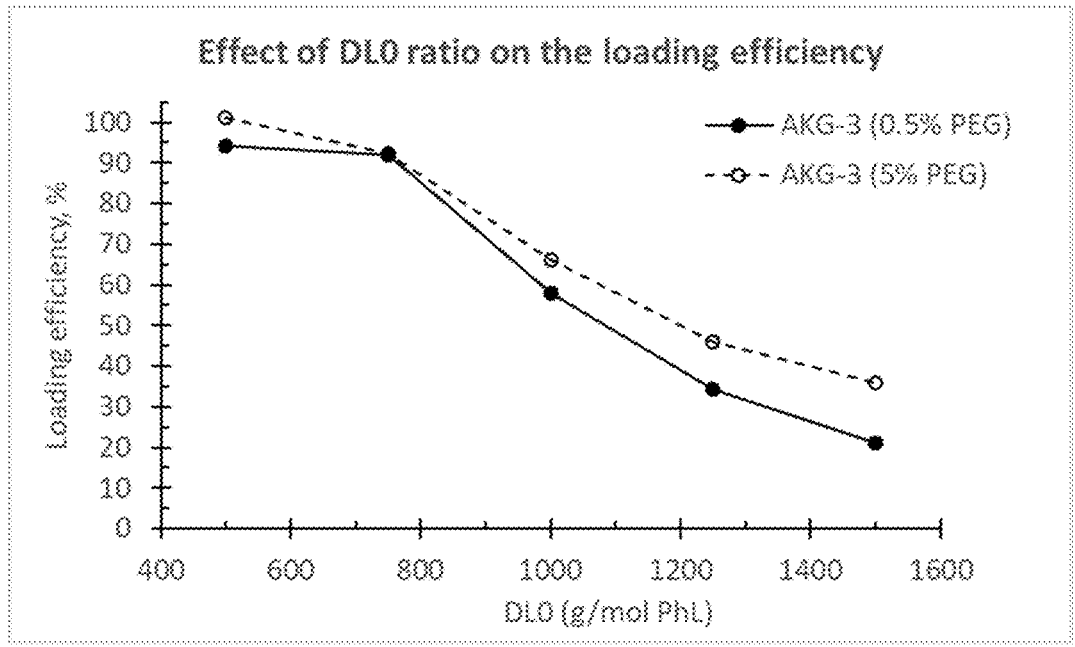

Example 9. Encapsulation of AKG-3, AKG-5, and AKG-16 into Liposomes with TEA-SOS Trapping Agent at Different DL Ratios Liposomes composed of HSPC, cholesterol (3:2 molar ratio), and PEG-DSG (0.5 mol. % of HSPC) with 1 N TEA-SOS as a trapping agent were prepared essentially as described in the General protocol (Example 6). The drug loading step was performed at the DL0 ratios in the range of 750-1500 g/mol PhL without addition of a buffer substance (pH 4.98-6.22). Maximum drug loads for compounds 3, 5, and 16 were observed in the range 900-930 g/mol PhL, 982-1197 g/mol PhL, and 938-951 g/mol PhL, respectively, and the loading efficiencies at or near the maximum drug loads were at least 97.6%, 96.0%, or 85.2%, respectively (FIG. 2A and FIG. 2B).

Example 10. Encapsulation of AKG-3, AKG-5, and AKG-16 into Liposomes with Higher Degree of PEGylation or with 0.25 M Ammonium Sulfate (AS) as a Trapping Agent Liposomes composed of HSPC and cholesterol (3:2 molar ratio) having various PEG-DSG content and trapping agents were prepared according to the General protocol and loaded with compounds AKG-3, AKG-5, and AKG-16, as in Example 9, at DL0 ratios of 250 or 500 g/mol PhL. All three compounds were loaded into the liposomes with high efficiency as shown in the Table 6 below:

TABLE 6

| PEG-DSG, | | | Drug loading efficiency | | |
|---|---|---|---|---|---|
| mol % of PhL | Trapping agent | DL0 ratio g/mol PhL | AKG-3 | AKG-5 | AKG-16 |
| 0.5* | 1N TEA-SOS | 500 | 100.8 | 101.3 | 102.6 |
| 5 | 1N TEA-SOS | 500 | 107.4 | 99.3 | 104.8 |
| 0.5 | 0.25M AS | 250 | 100.4 | 98.5 | 90.6 |
| 0.5 | 0.25M AS | 500 | 80.3 | 97.7 | 82.9 |

*The data for this line are from Example 8, "no added buffer" loading.

Thus, compounds AKG-3, AKG-5, and AKG-16 were effectively loaded into phospholipid-cholesterol liposomes with increased level of PEGylation and with ammonium sulfate as an intraliposomal drug trapping agent. However, the efficiency of loading was reduced with two of the three oxazolidinones (AKG-3 and AKG-16) when loaded at the higher drug-to-lipid ratio of 500 g drug/mol PhL using 0.25 M ammonium sulfate as the trapping agent.

Example 11. Loading of Compounds AKG-3, AKG-5, and AKG-16 into the Liposomes Using 0.5 M AS as a Trapping Agent Liposomes composed of HSPC and cholesterol (3:2 molar ratio) having 0.5 mol % or 5 mol % PEG-DSG (relative to PhL) and 0.5 M ammonium sulfate (AS) as a trapping agent were prepared according to the General protocol and loaded with compounds AKG-3, AKG-5, and AKG-16, as in Example 8, at DL0 ratios in the range of 500-1500 g/mol PhL. The results are shown on FIG. 3A, FIG. 3B, FIG. 3C and FIG. 3D. All three compounds were loaded in both liposomes to the DL ratio of 420-450 g/mol PhL with encapsulation efficiency of 93-100%; maximum drug payloads were as follows:

TABLE 7

| | Maximum encapsulated drug payload, g/mol PhL | |
|---|---|---|
| Drug | 0.5 mol % PEG | 5 mol % PEG |
| AKG-3 | 590 | 600-606 |
| AKG-5 | 627 | nd |
| AKG-16 | 668-675 | 614-619 |

All three compounds tested were loadable into 0.5 M ammonium sulfate liposomes at greater than 500 g drug/mol PhL in preparations with 0.5 mol % PEG-DSG and for compounds AKG-3 and AKG-16, for formulations containing 5 mol % PEG-DSG. These high levels of loading are important in being able to reach sufficient doses of administered drug for the treatment of disease. The loading was significantly improved over Example 10, where the loading efficiency was lower using 0.25 M ammonium sulfate, demonstrating that the higher ammonium sulfate concentration of 0.5 M, despite the higher osmolarity and potential for osmotic burst, is improved with respect to the amount of drug that can be loaded per mol of phospholipid, and preferable for anti-infectives where low toxicity and high dosing can lead to improved outcomes.

Example 12. Loading of Compounds AKG-3, AKG-5, AKG-16, and AKG-28 into Liposomes of Various Compositions Including a Fluorescent Lipid Label Liposomes composed of HSPC and cholesterol (60:40 molar ratio) having 0.5 mol % PEG-DSG (relative to PhL), 0.15 mol. % lipid fluorescent label DiIC18(3)-DS (ThermoFisher, USA), and 0.5 M ammonium sulfate (AS) or 1 N TEA-SOS as trapping agents were prepared according to the General protocol and loaded with compounds AKG-3, AKG-5, and AKG-16, as in Example 11, at pH 4.7-5.8 (no added buffer substance). The liposomes had the following characteristics:

TABLE 8

| Batch ID | Compound | Trapping agent | DL0, g/mol PhL | Encapsulated drug, g/mol PhL | Liposome z-average size, nm | Liposome PDI |
|---|---|---|---|---|---|---|
| 76 | AKG-3 | 1 N TEA-SOS | 500 | 497.0 | 112.7 | 0.008 |
| 85 | AKG-3 | 1 N TEA-SOS | 1000 | 830.7 | 104.3 | 0.111 |
| 78 | AKG-3 | 0.5 M AS | 693 | 632.9 | 104.9 | 0.013 |
| 79 | AKG-5 | 1 N TEA-SOS | 500 | 515.6 | 114.3 | 0.124 |
| 80 | AKG-5 | 1 N TEA-SOS | 1000 | 1003.2 | 110.5 | 0.071 |
| 81 | AKG-5 | 0.5 M AS | 693 | 709.3 | 111.4 | 0.060 |
| 82 | AKG-16 | 1 N TEA-SOS | 500 | 489.2 | 114.8 | 0.046 |
| 86 | AKG-16 | 1 N TEA-SOS | 1000 | 854.2 | 107.6 | 0.097 |
| 84 | AKG-16 | 0.5 M AS | 693 | 708.0 | 112.6 | 0.092 |

All three drugs were efficiently loaded into the liposomes. Degradation of AKG-5 during the liposome loading was detected as an appearance of a second peak on HPLC.

Liposomes composed of various phospholipids (HSPC, distearoylphosphatidylcholine (DSPC, Avanti Polar Lipids, USA), or egg sphingomyelin (ESM, Lipoid, Germany) and cholesterol (60:40 molar ratio), containing various amounts of PEG-DSG or N-methoxypoly(ethyleneglycol)oxycarbonyl-1,2-distearoylphosphatidylethanolamine (PEG-DSPE, PEG mol. weight 2000, Lipoid, Germany), and a lipid fluorescent label DiIC18(3)-DS (0.15 mol. % related to PhL) were prepared with different trapping according to the same General protocol, and loaded with AKG-16 in a similar way. When indicated, the liposome extrusion step of the General protocol was supplemented with extrusion through two stacked polycarbonate membranes with 50 nm pore size. The liposomes had the following characteristics:

TABLE 9

| Batch ID | Phospho-lipid | 50 nm extrusion | PEG-lipid (mol.%) | Trapping agent | DL0 ratio g/mol PhL | Drug load, g/mol PhL | Liposome z-average size, nm | PDI |
|---|---|---|---|---|---|---|---|---|
| 88 | HSPC | no | PEG-DSG (0.5) | 1 N TEA-SOS | 500 | 547.0 | | |
| 90 | DSPC | yes | PEG-DSG (0.5) | 1 N TEA-SOS | 500 | 514.0 | 83.3 | 0.182 |
| 91 | DSPC | yes | PEG-DSG (0.5) | 1 N TEA-SOS | 1000 | 599 | | |
| 93 | HSPC | no | PEG-DSG (5) | 1 N TEA-SOS | 500 | 490.2 | 108.6 | 0.046 |
| 94 | DSPC | no | PEG-DSG (0.5) | 1 N TEA-SOS | 500 | 504.0 | 112.7 | 0.081 |
| 95 | ESM | no | PEG-DSG (0.5) | 1 N TEA-SOS | 500 | 539.9 | 101.3 | 0.074 |
| 97 | HSPC | yes | PEG-DSPE (9.2) | 0.25 M AS | 150 | 128.2 | 81.5 | 0.073 |

Liposomes composed of HSPC and cholesterol (3:2 molar ratio) having 9.2 mol % PEG-DSPE (relative to PhL), 0.15 mol. % lipid label DiIC18(3)-DS, and 0.25 M ammonium sulfate (AS) as a trapping agent were prepared according to the General protocol and Example 12 with additional 50-nm extrusion, and loaded with AKG-28 at the drug-lipid ratio (DL0) 150 g/mol PhL. The liposomes (Batch ID 98) has DL ratio of 73.8 g/mol PhL, Z-average liposome size 77.8 nm, and size polydispersity index (PDI) 0.090.

These studies demonstrate that AKG-3, AKG-5 and AKG-16 could be efficiently loaded into liposomes with range of lipid compositions, including HSPC, DSPC, or ESM as the neutral phospholipid component, or low (0.5 mol %) or high (5 mol %) PEG-lipid content. However, the efficiency was reduced significantly from about 500 g AKG-16/mol PhL to 128 g AKG-16/mol PhL when using 0.25 M AS, as compared to 1 N TEA-SOS. A similar low loading efficiency (i.e. 73.8 g/mol PhL) was observed when loading AKG-28 with 0.25 M AS. This suggests that either TEA-SOS or higher concentrations of AS may be preferable for loading high concentrations of the compounds into liposomes.

Example 13—Blood Persistence and In Vivo Encapsulation Stability of the Liposomes of Example 12 in Mice The study was performed on male CD-1 mice as described in General protocol above.

TABLE 10

| Liposome batch | % ID in plasma (Liposome lipid) | | % initial DL ratio | |
|---|---|---|---|---|
| ID | 5 min | 6 hours | 5 min | 6 hours |
| 88 | 82.4 ± 9.8 | 30.6 ± 7.0 | 89.2 ± 0.6 | 75.6 ± 2.7 |
| 90 | 84.7 ± 1.2 | 35.2 ± 5.1 | 95.9 ± 0.2 | 81.0 ± 2.5 |
| 93 | 85.4 ± 3.5 | 38.2 ± 1.4 | 94.5 ± 0.5 | 82.9 ± 1.1 |
| 94 | 83.1 ± 6.1 | 23.9 1.2 | 97.7 ± 0.5 | 89.2 ± 0.0 |
| 95 | 79.3 ± 3.5 | 36.7 ± 2.0 | 97.9 ± 0.8 | 101.9 ± 8.8 |
| 96 | 80.2 ± 4.3 | 39.7 ± 7.0 | 102.8 ± 1.7 | 99.2 ± 2.8 |
| 97 | 83.5 ± 6.9 | 34.4 ± 2.8 | 88.7 ± 10.8 | 3.7 ± 0.3 |
| 98 | 80.3 ± 6.6 | 43.7 ± 4.7 | 100.2 ± 2.8 | 86.7 ± 1.1 |

These studies demonstrate that liposomes composed of varying neutral phospholipid components (HSPC, DSPC, or SM) and loaded with AKG-16 using the TEA-SOS trapping agent were cleared slowly with more than 30% Injected Dose remaining in plasma at 6 h for most formulation. In addition, most formulations showed good retention of drug, except for Liposome batch ID 97, which include AKG-16 loaded using 0.25 M AS, suggesting that loading of the drug using 0.25 M ammonium sulfate results not only in low loading efficiency as shown in Table 9, but also a low DL ratio (3.7%) at 6 hours due to significant leakage from the liposomes in this formulation.

Figure 4A:
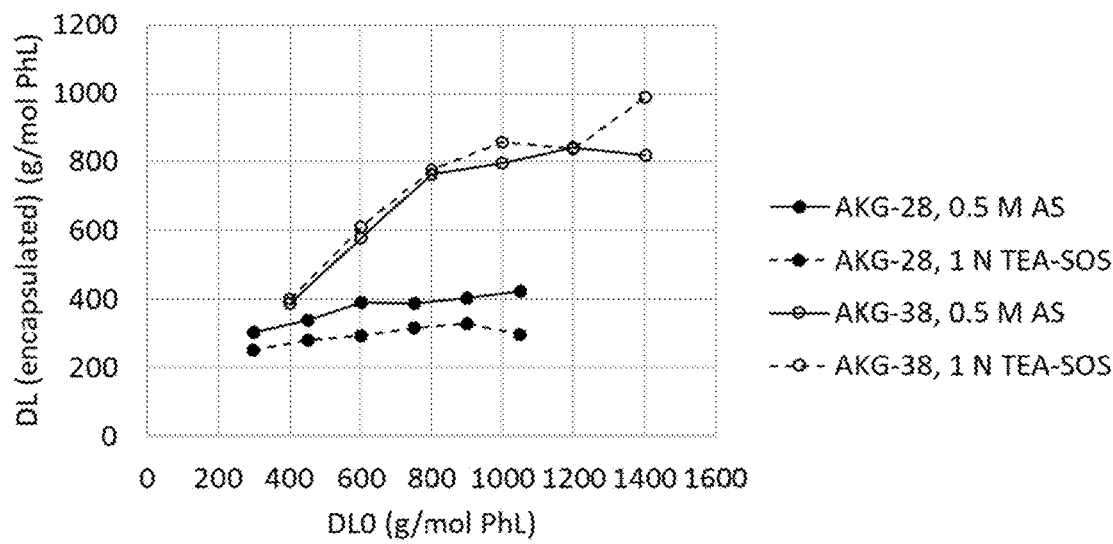
FIG. 4A and FIG. 4B are graphs showing the encapsulation of AKG-28 and AKG-38 with TEA-SOS and ammonium sulfate as trapping agents at different DL0 ratio.
Figure 4B:
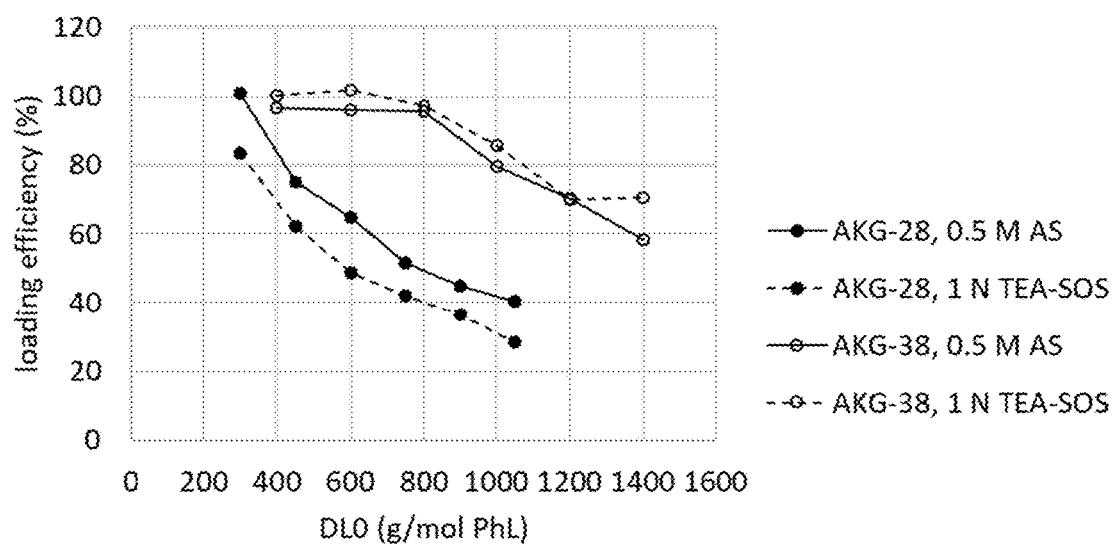
Figure 5A:
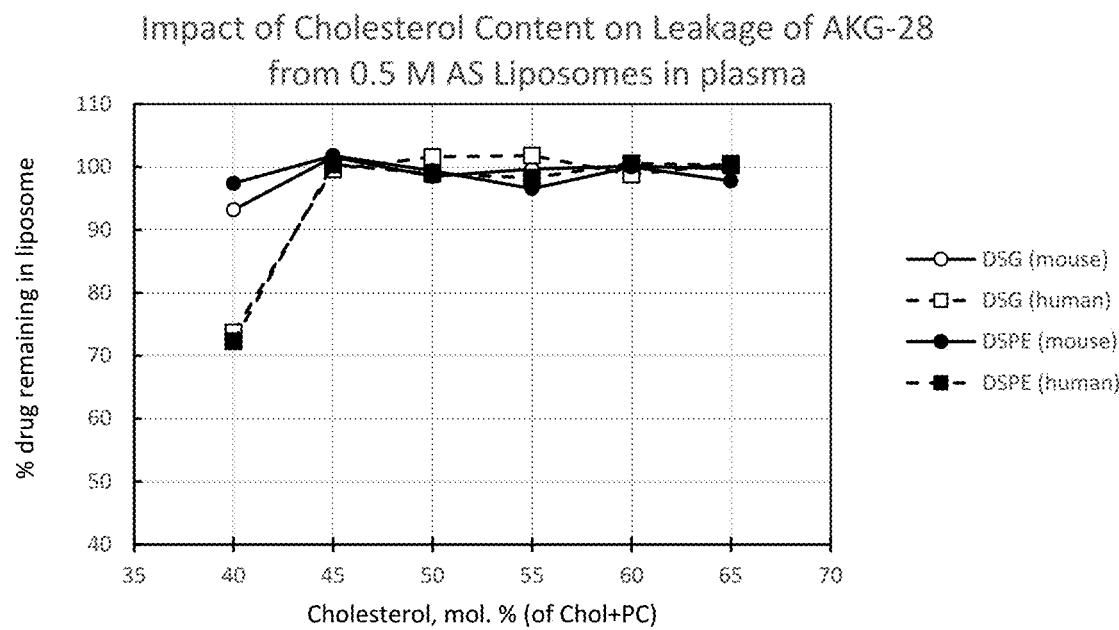
FIG. 5A, FIG. 5B, FIG. 5C, and FIG. 5D are graphs showing the dependence of fast drug leakage from the liposomes encapsulating compounds AKG-28 (FIG. 5A, FIG. 5C) and AKG-38 (FIG. 5B, FIG. 5D) upon in vitro contact with blood plasma of a mouse (denoted "mouse") or a human (denoted "human") as described in Example 19 below. Liposomes contained 5 mol % of PEG(2000)-DSPE (denoted "DSPE") or PEG-DSG (denoted "DSG"). Trapping agents: 0.5M ammonium sulfate (AS) (FIG. 5A, FIG. 5B), IN triethylammonium sucrose octasulfate (TEA-SOS) (FIG. 5C, FIG. 5D).
Figure 5B:
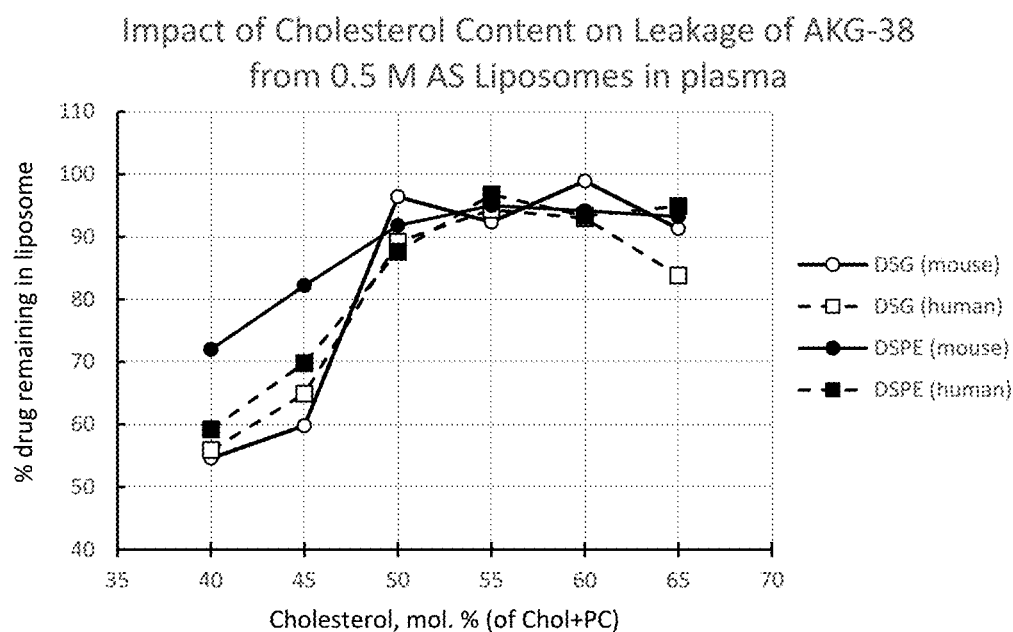
Figure 5C:
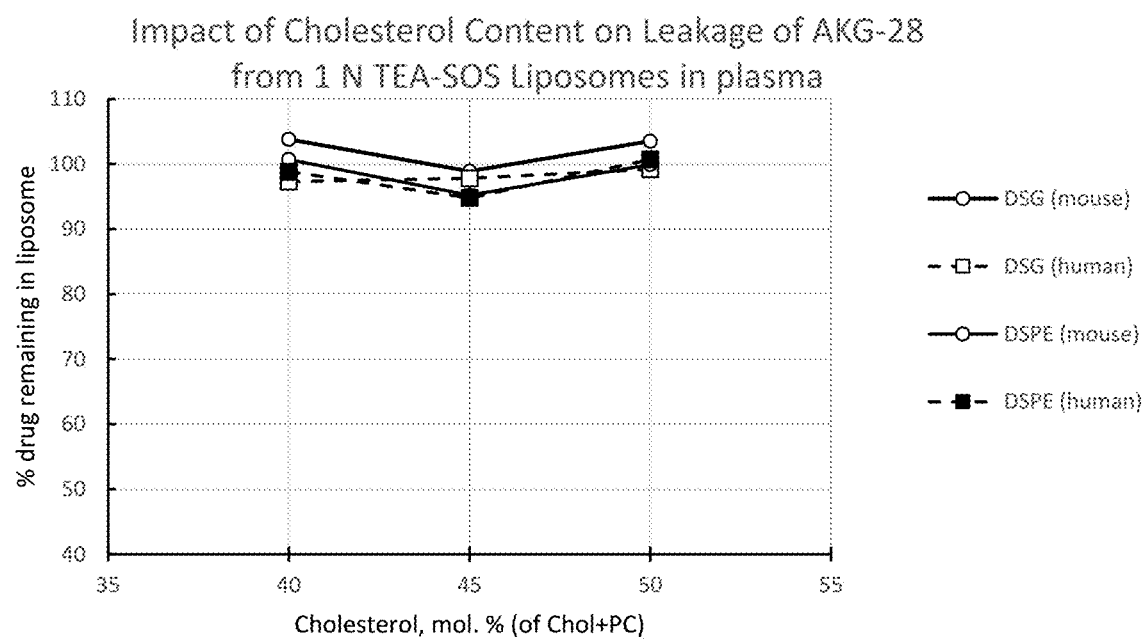
Figure 5D:
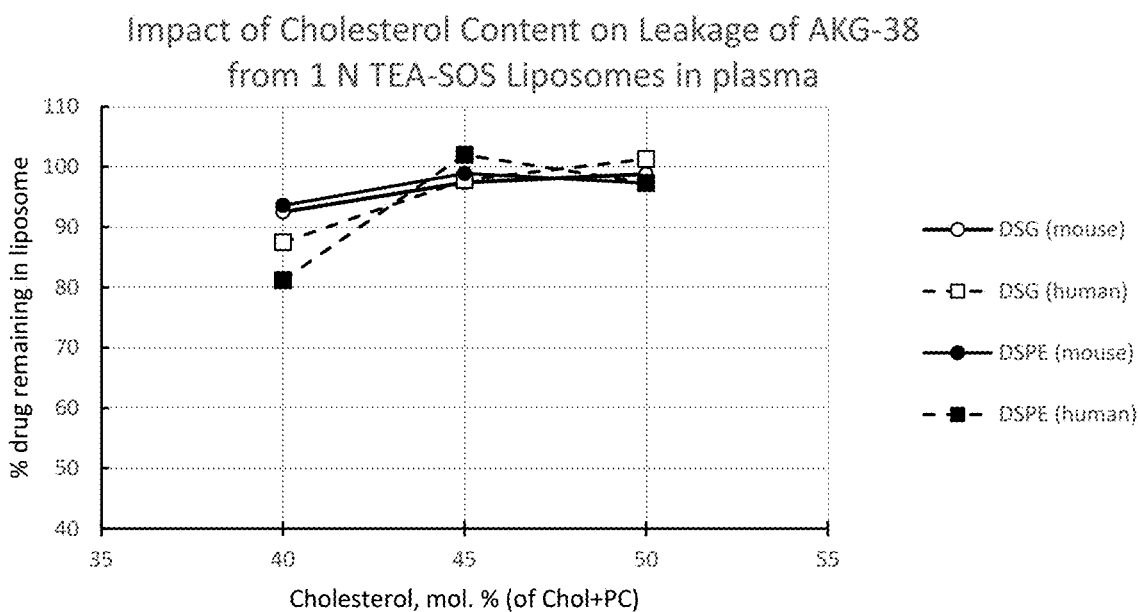

Example 14. Encapsulation of Compounds AKG-28 and AKG-38 into Liposomes with Various Trapping Agents, at Different DL Ratios Liposomes composed of HSPC and cholesterol (3:2 molar ratio) having 0.5 mol % PEG-DSG (relative to PhL), 0.15 mol. % lipid label DiIC18(3)-DS, and 0.5 M ammonium sulfate (AS) or 1 N TEA-SOS as trapping agents were prepared according to the General protocol and loaded with compounds AKG-28 and AKG-38, as in Example 8, at pH 4.95-5.17 (no added buffer substance) and DL0 ratios in the range of 300-1050 g/mol PhL (AKG-28) or 400-1400 g/mol PhL (AKG-38). Using 0.5 M AS, maximum drug loads for compounds AKG-28 and AKG-38 were in the range 404-424 g/mol PhL, and 818-842 g/mol PhL, respectively, and the loading efficiencies of more than 95% were at drug loads of 302 g/mol PhL (quantitative loading) and 387-764 g/mol PhL (95.5-96.7% loading), respectively. Using 1 N TEA-SOS, maximum drug loads for compounds AKG-28 and AKG-38 were in the range 315-328 g/mol PhL, and 989 g/mol PhL, respectively, and the maximum loading efficiencies were 83.5% at the drug load of 250 g/mol PhL, and 400-777 g/mol PhL (more than 97.2% loading), respectively (FIG. 4A and FIG. 4B).

AKG-38 showed nearly quantitative loading between 400 and 800 g AKG-38/mol PhL, while the resulting drug-to-lipid ratio remained flat for AKG-28 over the range of 250-1000 g AKG-28/mol PhL suggesting a lower maximum drug load for AKG-28 than for AKG-38. It should be appreciated that the higher potency previously demonstrated for AKG-28 would allow liposome formulations of AKG-28 to be effective for treating infectious diseases like tuberculosis.

Example 15. Encapsulation of Compounds AKG-28 and AKG-38 into Liposomes with Various Phospholipid Composition, Degree of PEGylation, and Trapping Agents Liposomes composed of a phospholipid (PhL) and cholesterol (3:2 molar ratio), PEG-DSG, and DiIC18(3)-DS (0.15 mol. % of PhL) with 0.5 M AS or 1 N TEA-SOS as trapping agents were prepared according to the General protocol and loaded with compounds AKG-28 and AKG-38 (in the absence of added buffer substance) at DL0 ratios chosen to optimize the drug load and the encapsulation efficiency (EE). The results are in the Tables 10 and 11 below.

This example shows that AKG-28 can be efficiently loaded into liposomes composed of HSPC using either 0.5 M AS or 1 N TEA-SOS as the trapping agent with a maximum drug load between 230-275 g AKG-28/mol PhL. However, formulations containing sphingomyelin as the neutral phospholipid for this compound showed comparably lower loading, with a maximum of only about 110 g AKG-28/mol PhL.

Compound AKG-38 was loaded to significantly higher D/L ratios, between 525-600 g/mol using 0.5 M AS or 1 N TEA-SOS when drug was added at 600 g AKG-38/mol PhL, or more than 735 g/mol when added at 800 g AKG-38/mol PhL. Loading for compound AKG-38 was less sensitive to the presence of sphingomyelin than was AKG-28.

Example 16. Encapsulation of Compounds AKG-16, AKG-28, AKG-29, and AKG-38 into Liposomes with Increased PEGylation and 0.5 M Ammonium Sulfate as Trapping Agent Liposomes composed of HSPC and cholesterol (3:2 molar ratio), PEG-DSG (5 mol. %), and DiIC18(3)-DS (0.15 mol. %) with 0.5 M ammonium sulfate as trapping agent were prepared according to the General protocol and loaded with compounds AKG-16, AKG-28, AKG-29, or AKG-38 (in the absence of added buffer substance) at DL0 ratios chosen to optimize the drug load and the encapsulation efficiency (EE). The results are in the Table 13 below.

TABLE 11

| | | | Encapsulation of compound AKG-28. | | | | | |
|---|---|---|---|---|---|---|---|---|
| Batch ID | PhL | PEG-DSG, mol% of PhL | Trapping agent | DL0 ratio g/mol PhL | Drug load, g/mol PhL | EE, % | Liposome z-average size, nm | Liposome PDI |
| 128 | HSPC | 0.5 | 0.5 M AS | 300 | 265.9 | 88.6 | 116.7 | 0.031 |
| 129 | HSPC | 0.5 | 1 N TEA-SOS | 300 | 273.9 | 91.3 | 115.2 | 0.038 |
| 130 | HSPC | 5 | 1 N TEA-SOS | 300 | 260.4 | 86.8 | 109.2 | 0.031 |
| 131 | ESM | 0.5 | 1 N TEA-SOS | 300 | 109.4 | 36.5 | 109.8 | 0.054 |
| 138 | HSPC | 0.5 | 0.5 M AS | 400 | 260.4 | 65.1 | | |
| 139 | HSPC | 0.5 | 0.5 M AS | 400 | 232.2 | 58.1 | | |

TABLE 12

| | | | Encapsulation of compound AKG-38. | | | | | |
|---|---|---|---|---|---|---|---|---|
| Batch ID | PhL | PEG-DSG, mol% of PhL | Trapping agent | DL0 ratio g/mol PhL | Drug load, g/mol PhL | EE, % | Liposome z-average size, nm | Liposome PDI |
| 132 | HSPC | 0.5 | 0.5 M AS | 600 | 532.1 | 88.7 | 127 | 0.023 |
| 133 | HSPC | 0.5 | 1 N TEA-SOS | 600 | 590.7 | 98.5 | 115.1 | 0.019 |
| 134 | HSPC | 5 | 1 N TEA-SOS | 600 | 565.6 | 94.3 | 110.6 | 0.074 |
| 135 | ESM | 0.5 | 1 N TEA-SOS | 600 | 529.3 | 88.2 | 106.7 | 0.049 |
| 140 | HSPC | 0.5 | 0.5 M AS | 800 | 739.5 | 92.4 | | |
| 141 | HSPC | 0.5 | 1 N TEA-SOS | 800 | 864.0 | 108.0 | | |

TABLE 13

| Batch ID | Compound | DL0 ratio, g/mol PhL | Drug load, g/mol PhL | EE, % |
|---|---|---|---|---|
| 145 | AKG-16 | 600 | 598.9 | 99.8 |
| 142 | AKG-28 | 300 | 292.3 | 97.4 |
| 143 | AKG-29 | 300 | 43.6 | 14.5 |
| 144 | AKG-38 | 600 | 506.2 | 84.4 |

This data shows that all compounds containing a dimethylaminoethyl substituent at the 2 position of the tetrazole ring were efficiently loaded into liposomes at greater than 80%, while AKG-29 with an aminoethyl substituent at the same position was only poorly loaded into liposomes with an efficiency of 14.5% and a final drug load of 43.6 g AKG-29/mol PhL. This illustrates that, despite the presence of titratable amines in all of the compounds tested, compounds with a substituted ammonium (for example, N,N-dimethylaminoethyl group) at the tetrazole ring unexpectedly allowed more efficient drug loading than those with a primary amine (aminoethyl group) at the same position.

Example 17. Blood Persistence and In Vivo Encapsulation Stability of the Liposomes of Examples 15 and 16 in Mice The study was performed on male CD-1 mice as described in General protocol above.

TABLE 14

| Liposome batch | % ID in plasma (Liposome lipid) | | % initial DL ratio | |
|---|---|---|---|---|
| ID | 5 min | 6 hours | 5 min | 6 hours |
| 128 | 80.6 ± 1.3 | 34.9 ± 0.8 | 75.2 ± 1.1 | 67.9 ± 4.0 |
| 129 | 83.6 ± 0.6 | 42.2 ± 3.4 | 95.7 ± 0.9 | 88.7 ± 3.1 |
| 130 | 83.4 ± 11.9 | 54.6 ± 3.8 | 94.4 ± 4.0 | 93.2 ± 1.1 |
| 132 | 83.2 ± 8.3 | 42.4 ± 1.7 | 48.6 ± 0.2 | 29.5 ± 0.5 |
| 133 | 71.3 ± 6.0 | 21.9 ± 8.1 | 97.3 ± 2.6 | 93.2 ± 4.3 |
| 134 | 78.8 ± 2.3 | 46.5 ± 3.2 | 93.8 ± 2.6 | 83.3 ± 4.7 |
| 135 | 77.9 ± 3.6 | 38.7 ± 2.9 | 102.6 ± 2.5 | 102.3 ± 1.8 |
| 142 | 80.9 ± 2.9 | 48.9 ± 2.8 | 52.9 ± 1.1 | 40.0 ± 0.3 |
| 144 | 83.3 ± 5.6 | 42.0 ± 4.4 | 50.4 ± 1.1 | 24.0 ± 0.5 |
| 145 | 80.6 ± 1.3 | 40.3 ± 0.1 | 41.4 ± 1.7 | 13.1 ± 0.0 |

The data showed that the drug in liposome Batch ID 128, 132, 142, 144, and 145, all having 0.5 M AS as a trapping agent, lost 25-60% of the encapsulated drug almost immediately upon contact with blood as shown by the low DL ratio at 5 min, and further decrease of the DL ratio at 6 hours, especially pronounced for AKG-38 and AKG-16-loaded liposomes. Thus, the formulation of 0.5 mol % or 5 mol % PEG-DSG and 40 mol % cholesterol, 0.5 M AS (as a trapping agent) was not able to retain drug as efficiently as the formulations employing 1N TEA-SOS (Liposome Batch ID 129, 130, 133-135), where the % of initial DL ratio at both 5 min and 6 hour time points was greater than 80%.

Example 18. Preparation and Loading of AKG-28 and AKG-38 into Pegylated Liposomes with Varying Ratios of Phospholipid-to-Cholesterol Liposomes containing 5 mol % PEG-DSG or PEG-DSPE (relative to PhL), 0.15 mol. % lipid label DiIC18(3)-DS, and 0.5 M ammonium sulfate (AS) or 1 N TEA-SOS as trapping agents, were prepared according to the General protocol and loaded with compounds AKG-28 and AKG-38, as in Example 8, at pH 5.07-5.82 (no added buffer substance).

In an attempt to stabilize the liposomes having 0.5 M AS at a trapping agent against fast drug release upon contact with blood (as described in Example 17), the liposomes using DSPC (generally known to produce more drug leakage-stable liposomes compared to HSPC) and decreasing proportion of cholesterol (Chol) were prepared and loaded with AKG-28 at DL0 250 g/mol PhL, or with AKG-38 at 600 g/mol PhL (Table 15). Contrary to expectations, decreasing cholesterol content from 40 mol % down to 10 mol % cholesterol resulted in a dramatically reduced encapsulation efficiency for both AKG-28 and AKG-38. Lower cholesterol also destabilized the liposomes against aggregation. At 30 mol. % cholesterol (PhL-cholesterol molar ratio 70:30), AKG-28-containing liposomes made using 1 N TEA-SOS and 5 mol % of either PEG-DSG or PEG-DSPE irreversibly aggregated during the drug loading, as did 30 mol % cholesterol, 5 mol % PEG-DSPE containing formulation of AKG-38, while the 5 mol % PEG-DSG formulation of AKG-38 at 30 mol % cholesterol showed reduced loading efficiency of 77.1%, or 462.4 g/mol PhL

TABLE 15

| Batch ID | Compound | PEG-lipid (lipid portion) | Trapping Agent | Chol (mol %) | Drug load, (g/mol PhL) | EE, (%) |
|---|---|---|---|---|---|---|
| 158 | AKG-28 | DSG | 0.5 M AS | 40 | 231.2 | 92.5 |
| 159 | AKG-28 | DSG | 0.5 M AS | 30 | 173.5 | 69.4 |
| 160 | AKG-28 | DSG | 0.5 M AS | 20 | 116.4 | 46.6 |
| 161 | AKG-28 | DSG | 0.5 M AS | 10 | 92.4 | 36.9 |
| 162 | AKG-28 | DSPE | 0.5 M AS | 30 | 130.5 | 52.2 |
| 166 | AKG-38 | DSG | 0.5 M AS | 40 | 462.8 | 77.1 |
| 167 | AKG-38 | DSG | 0.5 M AS | 30 | 280.2 | 46.7 |
| 168 | AKG-38 | DSG | 0.5 M AS | 20 | 120.0 | 20.0 |
| 169 | AKG-38 | DSG | 0.5 M AS | 10 | 69.8 | 11.6 |
| 170 | AKG-38 | DSPE | 0.5 M AS | 30 | 114.9 | 19.1 |

In contrast, liposomes prepared using HPSC and containing 40 mol % or more of cholesterol, up to 65 mol % of cholesterol (maximum studied), showed excellent encapsulation efficiency over 87% and no liposome aggregation for both AKG-28 (DL0 250 g/mol PhL) and AKG-38 (DL0 500 g/mol PhL), PEG-lipids (PEG-DSG and PEG-DSPE), and trapping agents (AS or TEA-SOS) (Table 16).

In addition, the potential of the optimized formulation to load the current standard of care drug from this class, linezolid, in both 0.5 M AS and 1 N TEA-SOS formulations was evaluated. Tedizolid was not soluble enough in water to perform a transmembrane gradient-assisted loading into liposomes following the general protocol of Example 6. In both cases with linezolid, the encapsulation efficiency was less than 5%, demonstrating that these liposomal formulations of AKG-28 and AKG-38 were dramatically superior in their ability to stably encapsulate drug, when compared to linezolid.

Z-average size ($x_z$) and polydispersity index (PDI) of the liposomes were determined by dynamic light scattering (DLS) cumulants method using Malvern Zetasizer Pro (Malvern Panalytical) at 173° measurement angle.

TABLE 16

| Batch ID | Compound | PEG-lipid (lipid portion) | Trapping Agent | Chol (mol %) | Drug load, (g/mol PhL) | Liposome average size $x_z$, nm | Poly-dispersity index | EE, (%) |
|---|---|---|---|---|---|---|---|---|
| 174 | AKG-28 | DSG | 0.5 M AS | 40 | 249.8 | | | 99.9 |
| 175 | AKG-28 | DSG | 0.5 M AS | 45 | 253.9 | | | 101.6 |
| 176 | AKG-28 | DSG | 0.5 M AS | 50 | 252.6 | | | 101.0 |
| 201 | AKG-28 | DSG | 0.5 M AS | 55 | 228.2 | 107.2 | 0.0495 | 91.3 |
| 202 | AKG-28 | DSG | 0.5 M AS | 60 | 233.0 | 109.4 | 0.0333 | 93.2 |
| 203 | AKG-28 | DSG | 0.5 M AS | 65 | 235.3 | 111.0 | 0.0359 | 94.1 |
| 177 | AKG-28 | DSG | 1 N TEA-SOS | 40 | 223.5 | | | 89.4 |
| 178 | AKG-28 | DSG | 1 N TEA-SOS | 45 | 258.7 | | | 103.5 |
| 179 | AKG-28 | DSG | 1 N TEA-SOS | 50 | 259.5 | | | 103.8 |
| 180 | AKG-38 | DSG | 0.5 M AS | 40 | 440.4 | | | 88.1 |
| 181 | AKG-38 | DSG | 0.5 M AS | 45 | 488.7 | | | 97.7 |
| 182 | AKG-38 | DSG | 0.5 M AS | 50 | 468.4 | | | 93.7 |
| 207 | AKG-38 | DSG | 0.5 M AS | 55 | 460.7 | 109.2 | 0.0034 | 92.1 |
| 208 | AKG-38 | DSG | 0.5 M AS | 60 | 475.1 | 111.3 | 0.0201 | 95.0 |
| 209 | AKG-38 | DSG | 0.5 M AS | 65 | 475.3 | 111.9 | 0.0118 | 95.1 |
| 183 | AKG-38 | DSG | 1 N TEA-SOS | 40 | 505.4 | | | 101.1 |
| 184 | AKG-38 | DSG | 1 N TEA-SOS | 45 | 495.8 | | | 99.2 |
| 185 | AKG-38 | DSG | 1 N TEA-SOS | 50 | 489.4 | | | 97.9 |
| 186 | AKG-28 | DSPE | 0.5 M AS | 40 | 244.4 | 108.9 | 0.0250 | 97.8 |
| 187 | AKG-28 | DSPE | 0.5 M AS | 45 | 241.6 | 107.8 | 0.002 | 96.6 |
| 188 | AKG-28 | DSPE | 0.5 M AS | 50 | 250.4 | 109.1 | 0.0076 | 100.1 |
| 204 | AKG-28 | DSPE | 0.5 M AS | 55 | 223.5 | 117.0 | 0.0037 | 89.4 |
| 205 | AKG-28 | DSPE | 0.5 M AS | 60 | 237.8 | 114.8 | 0.0113 | 95.1 |
| 206 | AKG-28 | DSPE | 0.5 M AS | 65 | 233.0 | 115.1 | 0.0266 | 93.2 |
| 189 | AKG-28 | DSPE | 1 N TEA-SOS | 40 | 244.6 | 109.3 | 0.0480 | 97.8 |
| 190 | AKG-28 | DSPE | 1 N TEA-SOS | 45 | 245.6 | 107.7 | 0.0165 | 98.2 |
| 191 | AKG-28 | DSPE | 1 N TEA-SOS | 50 | 245.0 | 107.9 | 0.0221 | 98.0 |
| 192 | AKG-38 | DSPE | 0.5 M AS | 40 | 434.8 | 115.1 | 0.0040 | 87.0 |
| 193 | AKG-38 | DSPE | 0.5 M AS | 45 | 462.7 | 112.9 | 0.0202 | 92.5 |
| 194 | AKG-38 | DSPE | 0.5 M AS | 50 | 467.0 | 109.4 | 0.0323 | 93.4 |
| 210 | AKG-38 | DSPE | 0.5 M AS | 55 | 463.3 | 114.5 | 0.0183 | 92.7 |
| 211 | AKG-38 | DSPE | 0.5 M AS | 60 | 479.6 | 114.9 | 0.0020 | 95.9 |
| 212 | AKG-38 | DSPE | 0.5 M AS | 65 | 475.0 | 114.2 | 0.0511 | 95.0 |
| 195 | AKG-38 | DSPE | 1 N TEA-SOS | 40 | 503.6 | 109.1 | 0.002 | 100.7 |
| 196 | AKG-38 | DSPE | 1 N TEA-SOS | 45 | 489.8 | 108.5 | 0.0298 | 98.0 |
| 197 | AKG-38 | DSPE | 1 N TEA-SOS | 50 | 481.4 | 107.3 | 0.0395 | 96.3 |
| 229 | Linezolid | DSPE | 0.5 M AS | 55 | 21.0 | | | 4.2 |
| 230 | Linezolid | DSPE | 1 N TEA-SOS | 55 | 19.7 | | | 3.9 |

Example 19. In Vitro Burst Release of Pegylated Liposomes Containing AKG-28 or AKG-38 and Varying Ratios of Phospholipid-to-Cholesterol in the Presence of Plasma The in vitro stability of liposomal formulations of AKG-28 and AKG-38 containing 5 mol % PEG-DSPE or PEG-DSG and varying ratios of HSPC-to-Chol (40-65 mol % Chol) were evaluated for stability in the presence of Mouse CD-1 or human pooled plasma (Lithium-Heparin-stabilized from Innovative Research). The plasma was thawed, if necessary, adjusted to pH 7.4 with 1 N HCl, and sequentially filtered through glass microfiber filters (GF/C), 1 μm polyethersulfone (PES), and 0.22 μm PES filters. Plasma (80 μl) was mixed with liposomal drug formulations (20 μl) in a 0.5 ml Eppendorf tube. The mixture was subsequently incubated for 20 min at 37° C. and then put into chilled water. The mixture (0.1 mL) was chromatographed without delay on a 2 mL Sepharose CL-4B column, eluted with Hepes-buffered saline (pH 7.0) and 0.25 mL of liposomal drug was collected in the void volume fraction. The drug and DiI(3)-DS lipid label were then analyzed by HPLC as described in Example 7, and the % drug remaining encapsulated determined using the following formula:

$(A_d/A_I)/(A_{d,0}/A_{I,0})*100$=% drug remaining encapsulated

Where $A_d$—are of the drug peak, $A_{d,0}$—area of the lipid label peak, $A_{I,0}$—are of the drug peak pre-incubation with plasma, and $A_{I,0}$—are of the lipid label peak pre-incubation.

The results are shown on FIG. 5A, FIG. 5B, FIG. 5C and FIG. 5D. For the liposomes with encapsulated AKG-28 (FIG. 5A), burst release phenomenon (a rapid drop of the DL ratio signifying the drug release from the liposomes) was observed in human plasma for the formulations containing 40 mol. % cholesterol, but not for the formulations with 45 mol. % or more of cholesterol. For the liposomes with encapsulated AKG-38 (FIG. 5B), burst release phenomenon was observed in both human and mouse plasma for the formulations with cholesterol content of 40 mol. % and 45 mol. %, but not at cholesterol content of 50 mol. % or more.

Example 20. In Vitro Plasma Release and In Vivo Pharmacokinetics of 5 Mol % PEG-Lipid Liposomes Containing AKG-38 and 40 or 55 Mol % Cholesterol Three of the liposome formulations of Example 18 using the 0.5 M AS trapping agent were evaluated in a two time point pharmacokinetic study in female CD-1 mice as described in Example 7, measuring percent of the injected dose (% ID) of the liposome lipid remaining in the blood at both 5 min and 6 h, and measuring drug release from the liposomes through determination of the drug-to-lipid ratio (DL). While the liposomes having either 5 mol % PEG-DSG or 5 mol % PEG-DSPE and containing 55 mol % Chol showed more than 95% of the pre-injection D/L ratio at 5 min and >85% at 6 hours, the PEG-DSG formulation containing 40 mol % Chol showed dramatically reduced DL ratios at both 5 min and 6 hours, consistent with the drug leakage data in the presence of plasma in vitro (Table 17). This finding was in contrast with previous experience with drug-loaded liposome formulations, as a number of highly stable liposomal drugs, approved for clinical use, like pegylated liposomal doxorubicin and nanoliposomal irinotecan, contain cholesterol at a ratio of about 40 mol % (see, e.g., Doxil© drug information package insert, updated 08/2019, and Drummond, D. C., et al. (2006). "Development of a highly active nanoliposomal irinotecan using a novel intraliposomal stabilization strategy." Cancer Res. 66(6): 3271-3277)

TABLE 17

| Liposome lot ID | | 180 | 207 | 210 |
|---|---|---|---|---|
| Chol, mol % (of Chol + PC) | | 40 | 55 | 55 |
| PEG-lipid | | DSG | DSG | DSPE |
| D/L ratio post load | | 440.4 ± 8.5 | 460.7 ± 16.2 | 463.3 ± 13.7 |
| Encapsulation eff-cy, % | | 88.1 ± 1.7 | 92.1 ± 3.2 | 92.7 ± 2.7 |
| Plasma stability in vitro, 20 min 37° C. (% drug remaining encapsulated) | Mouse CD1 | 54.6 ± 1.6 | 92.4 ± 0.7 | 95.0 ± 0.8 |
| | Human | 55.9 ± 3.7 | 94.3 ± 0.6 | 96.8 ± 0.9 |
| Two-point PK data (CD-1 mouse, 9 mg/kg iv): | | | | |
| Liposome lipid, % ID | 5 min | 103.4 ± 11.7 | 114.9 ± 14.9 | 104.3 ± 5.6 |
| | 6 hours | 51.1 ± 5.2 | 52.6 ± 3.6 | 50.3 ± 5.7 |
| D/L ratio, % of pre-injection value | 5 min | 60.8 ± 1.2 | 95.1 ± 1.2 | 96.8 ± 0.2 |
| | 6 hours | 30.9 ± 2.4 | 86.6 ± 5.7 | 90.0 ± 4.1 |

Example 21. Inhibition of Mitochondrial Protein Synthesis (MPS) by AKG-3, AKG-16, AKG-22, AKG-28, AKG-29, AKG-30, AKG-38, AKG-39, and AKG-40 and Selectivity for M. tuberculosis (H37Rv) Inhibition Over MPS Inhibition Inhibition of mitochondrial protein synthesis was determined using a colorimetric MitoBiogenesis™ in-cell ELISA kit from AbCam (Catalog #ab11021), as per the manufacturer's instructions. Mitochondrial protein synthesis inhibition has been correlated to important toxicities for linezolid and other oxazolidinones, most notably ocular and peripheral neuropathy, and lactic acidosis (Renslo (2010) Expert Reve Anti Infect Ther 8(5) 565-574; Flanagan et al. (2015) Antimicrob Agents Chemother 59(1) 178-185; Santini et al. (2017) Expert Opin Drug Saf 16(7) 833-843). The levels of two mitochondrial proteins were measured simultaneously, including the mitochondrial DNA-encoded subunit I of Complex IV (COX-1) and the nuclear DNA-encoded 70 kDa subunit of Complex II (SDH-A). The H9C2 rat BDIX heart myoblast cell line was used in these studies in a 384 well plate assay format. Cells were grown in DMEM media with 10% FBS and 1×Glutamine at 37° C. and 5% $CO_2$. Cells were plated at a density of 1,500 cells/well in 384 well plates in 47.5 µl/well. Ten concentrations of each compound, starting at a high concentration of 200 µM and including nine 3-fold dilutions and one replicate per condition, were added to the cells in 2.5 µl and incubated with the cells for five days at 37° C. and 5% $CO_2$. The compounds tested included tedizolid and linezolid controls, as well as AKG-3, AKG-16, AKG-22, AKG-28, AKG-29, AKG-30, AKG-38, AKG-39, and AKG-40.

The MitoBiogenesis In-Cell Elisa was then performed according to the manufacturer's instructions (Abcame Catalog #ab11021) and alkaline phosphatase (AP) developed for detection of SDH-1A at 405 nm in kinetic model for 15 min (20 sec-1 min interval) and HRP developed for detection of COX-I at 600 nm in kinetic mode for 15 min (20 sec-1 min interval) in plate reader. COX-I and SDH-A signals were plotted as a ratio of COX-1/SDH-A against concentration of each compound, and the IC50 were calculated for each of the 9 investigational compounds and two controls.

An MPS selectivity index (SI-MPS) was determined by dividing the MPS 7C50 in ug/ml by the MIC in the drug sensitive H37Rv M. tuberculosis strain as determined in Example 2. Two of the compounds tested, AKG-28 and AKG-29, had an SI-MIPS that was more than ten times higher than that determined for linezolid and more than twenty times higher than determined for tedizolid. Both of these compounds contained a primary amino group at the R2 position of the oxazolidinone ring. Due to its high potency (MIC<0.1) and high selectivity for M. tuberculosis compared to mitochondrial protein synthesis, AKG-28 is excellent candidate for encapsulation in liposomes and treatment of tuberculosis or other mycobacterial diseases.

TABLE 18

| Compound | Tetrazole ring position, $R_1$ (Formula I) | $R_2$ (Formula I) | MIC (H37Rv) (µg/ml) | MPS IC50 (µg/ml) | SI-MPS MPS/H37 |
|---|---|---|---|---|---|
| Linezolid | Not applicable | —$NHCOCH_3$ | 1.00 | 2.157 | 2.16 |
| Tedizolid | 2', $CH_3$— | —OH | 0.25 | 0.143 | 0.57 |
| AKG-3 | 2', $CH_3$— | —$NH_2$ | 0.06 | 0.115 | 1.91 |
| AKG-16 | 2', $(CH_3)_2N(CH_2)_2$— | —OH | 0.25 | 0.244 | 0.98 |
| AKG-22 | 1', $NH_2(CH_2)_2$— | —OH | 0.5 | 1.184 | 2.37 |
| AKG-28 | 2', $(CH_3)_2N(CH_2)_2$— | —$NH_2$ | 0.015 | 0.411 | 27.41 |
| AKG-29 | 2', $NH_2(CH_2)_2$— | —$NH_2$ | 0.125 | 4.11 | 32.80 |
| AKG-30 | 2', $(C_2H_5)_2N(CH_2)_3$— | —$NH_2$ | 0.125 | 0.252 | 2.02 |
| AKG-38 | 2', $(CH_3)_2N(CH_2)_2$— | —$NHCOCH_3$ | 0.06 | 0.041 | 0.69 |
| AKG-39 | 2', $(C_2H_5)_2N(CH_2)_2$— | —$NHCOCH_3$ | 0.5 | 0.060 | 0.12 |
| AKG-40 | 2', $(C_2H_5)_2N(CH_2)_3$— | —$NHCOCH_3$ | 0.5 | 0.064 | 0.13 |

Example 22. Scaled-Up Preparation of Liposomal AKG-28 Lot 275

Lot 267. The general procedure of Example 6 was followed. HSPC (Lipoid AG) 4.95 g (6.30 mmol), cholesterol (Dishman, High purity) 2.98 g (7.71 mmol), and PEG-DSPE (Lipoid AG) 850 mg (0.315 mmol) (HSPC:Chol:PEG-DSPE 45:55:2.25 molar ratio) were combined with 9 ml of absolute ethanol (Sigma, E-7023) and heated with stirring on a 68° C. bath until all lipids dissolved. In a separate container 93.3 g of 0.5 M aqueous ammonium sulfate (0.2-micron filtered) was preheated on a 68° C. bath and poured with stirring into the hot lipid ethanolic solution. The obtained suspension was stirred on a 68° C. bath for 20 min. and extruded eight times at 260-300 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 68° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to less than 200 μS/cm (143 μS/cm after 5.2 volume exchanges). The phospholipid concentration in the post-TFF liposome suspension was determined by blue phosphomolybdate method to be 57.4 mM.

720 mg of AKG-28 (as dihydrochloride salt) in the form of 20 mg/ml aqueous stock solution (adjusted to pH 5.03 with NaOH) were combined with post-TFF liposome suspension to form the loading mixture at drug-to-phospholipid (DL) ratio of 250 g/mol in the presence of 45 mg/ml dextrose and AKG-28 concentration of 6 mg/ml. The mixture was quickly heated to 60-63° C. by external heating under constant stirring, and the incubation continued with stirring on the 65° C. bath. After 20 min. incubation, the mixture was quickly chilled in an ice-water to less than 10° C., and kept at this temperature for about 10 min. After reaching the ambient temperature and adjustment to 0.1 M NaCl, the drug-loaded liposomes were purified by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into 10 mM HEPES-Na buffer pH 7.0, containing 0.144 M NaCl made with endotoxin-free water (HBS-7 buffer) for the total of about 8 volume exchanges. The proportion of unencapsulated drug prior to purification was estimated spectrophotometrically at 305 nm in the pre-concentration diafiltrate and found to be about 0.9% (corresponds to 99.1% loading efficiency). The concentrated, purified liposomes were aseptically passed through 0.2-μm sterile filter and analyzed for the particle size by DLS, and for the drug and phospholipid concentration by spectrophotometry. This procedure was repeated three more times (lots 269, 271, 273). Obtained liposomes had the characteristics shown in TABLE 19.

TABLE 19

| Lot ID | Scale, mg of AKG-28 | DL ratio g AKG-28/ mol PhL | Average particle size Xz, nm | PDI |
|---|---|---|---|---|
| 267 | 720 | 251.9 | 115.4 | 0.0248 |
| 269 | 750 | 248.7 | 112.6 | 0.0282 |
| 271 | 750 | 268.0 | 114.0 | 0.0482 |
| 273 | 766 | 244.9 | 114.7 | 0.0153 |

These lots were combined to obtain lot 275 having 12.0 mg/ml AKG-28 in the liposomal form, particle size Xz 113.7 nm, PDI 0.0417.

Example 23. Scaled-Up Preparation of Liposomal AKG-38 Lot 276

Lot 268. The protocol of Example 22 was used with the following differences: the stock aqueous solution of AKG-38 (as free base) was prepared by dissolving the drug in the equivalent amount of 1 N HCl and adjusting the volume to obtain 20 mg/ml of AG-38 (as free base), pH 5.08. The loading mixture contained 1300 mg of AKG-38 and was prepared at 8 mg/ml of AKG-38 and DL ratio of 450 g/mol phospholipid, and additionally contained 10 mM NaCl. The post-loading liposomes were pre-concentrated to about 22 mg/ml of the drug; the proportion of unencapsulated drug prior to purification was estimated spectrophotometrically at 305 nm in the pre-concentration diafiltrate and found to be about 3.2% (corresponds to 96.8% loading efficiency). The process was repeated three more times (lots 270, 272, 274). Obtained liposomes had the characteristics shown in TABLE 20.

TABLE 20

| Lot ID | Scale mg of AKG-38 | DL ratio g AKG-38/ mol PhL | Average particle size Xz, nm | PDI |
|---|---|---|---|---|
| 268 | 1300 | 445.9 | 114.6 | 0.0419 |
| 270 | 1360 | 444.9 | 114.2 | 0.0456 |
| 272 | 1350 | 463.7 | 115.3 | 0.0245 |
| 274 | 1375 | 437.3 | 115.0 | 0.0349 |

These lots were combined to obtain lot 276 having 22.3 mg/ml AKG-38 in the liposomal form, particle size Xz 113.1 nm, PDI 0.0454.

Example 24. Preparation of "Empty Liposome" Lot 277

2 mmol HSPC, 2.444 mmol cholesterol and 0.1 mmol PEG-DSPE (HSPC:Chol:PEG-DSPE 45:55:2.25 molar ratio) were dissolved in ethanol, formed into liposome suspension and extruded through polycarbonate membranes as described in Example 22, except that instead of 0.5M ammonium sulfate a sulfate salt of non-exchanging cation, 0.13 M sodium sulfate, was taken. The extruded liposomes were purified from extraliposomal sodium sulfate and brought into HBS-7 buffer by TFF buffer exchange using polysulfone hollow fiber cartridge with MWCO 500 KDa for the total of 10 volume exchanges. The purified liposomes had 42.9 mM phospholipid, the particle size Xz 113.7 nm, and PDI 0.0612. They were aseptically passed through 0.2-μm sterile filter and adjusted to 20 mM phospholipid with sterile HBS-7.

Example 25. Liposomal AKG-38 Lot 279

The general procedure of Example 6 was followed. HSPC (Lipoid AG) 13.102 g (16.67 mmol), cholesterol (Dishman, High purity) 7.877 g (20.37 mmol), and PEG-DSPE (Lipoid AG) 2.250 g (0.833 mmol) (HSPC:Chol:PEG-DSPE 45:55:2.25 molar ratio) were combined with 25 ml of absolute ethanol (Sigma, E-7023) and heated with stirring on a 68° C. bath until all lipids dissolved. In a separate container 259.1 g (250 ml) of 0.5 M aqueous ammonium sulfate (0.2-micron filtered) was preheated on a 70° C. bath and poured with stirring into the hot lipid ethanolic solution. The obtained suspension was stirred on a 70° C. bath for at least 20 min. and divided into four portions. Each portion was extruded five times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 129.7 nm) and extruded together through the same membrane stack five more times, resulting in the liposomes of the size Xz 115.9 nm, PDI 0.0212. The liposomes kept overnight in a refrigerator (2-8° C.) and filtered through 0.2-µm polyethersulfone (PES) filter under positive pressure. Phospholipid concentration was found 60.22±0.34 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 180 µS/cm after 5.1 volume exchanges). The phospholipid concentration in the post-TFF liposome suspension was determined by blue phosphomolybdate method to be 54.97±0.32 mM.

AKG-38 (free base) was mixed with 0.95 equivalents of 1 N HCl and made up with endotoxin-free water to obtain 20 mg/ml aqueous stock solution (pH 5.16). The solution was passed through 0.2-µm filter, and the amount of filtrate containing 3958 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.54. The mixture was heated to 61° C. by external heating under constant stirring over the period of 5 min, and the incubation continued with stirring on the 65° C. bath for another 22 min. Then the mixture was transferred into ice-water bath, stirred for 7 minutes to let the temperature drop to 10° C., and kept in the ice-water bath for another 8 min. After being taken out of the ice bath, having reached the ambient temperature, and adjustment to 0.1 M NaCl by addition of 3 M NaCl stock, the drug-loaded liposomes (pH 6.53) were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8 volume exchanges. The concentrated, purified liposomes were aseptically passed through 0.2-µm PES high-flow sterile filter and analyzed for the particle size by DLS, and for the drug and phospholipid concentration by spectrophotometry. The liposomes had the following characteristics: AKG-38 21.1±0.19 mg/ml, DL ratio 454±4.7 g/mol phospholipid, Xz 116.4 nm, PDI 0.0231. Yield of the formulated drug 3834 mg (96.9%).

Example 26. Liposomal AKG-28 Lot 281

The general procedure of Example 6 was followed. Extruded liposomes composed of HSPC, cholesterol, and PEG-DSPE in the molar ratio of 45:55:2.25 containing 0.5 M ammonium sulfate were prepared as described in Example 25. Extraliposomal trapping agent (ammonium sulfate) was removed by TFF exchange for endotoxin-free water on a KrosFlo TFF system using polyethersulfone hollow fiber cartridge with MW cut-off 500 KDa (Spectrum Laboratories) until residual conductivity dropped to 150 µS/cm (4.1 volume exchanges). The phospholipid concentration in the post-TFF liposome suspension was determined by blue phosphomolybdate method to be 55.4 mM.

969.5 mg of AKG-28 (as dihydrochloride salt) in the form of 20 mg/ml aqueous stock solution (adjusted to pH 5.24 with NaOH) were combined with post-TFF liposome suspension to form the loading mixture at drug-to-phospholipid (DL) ratio of 250 g/mol in the presence of 44.5 mg/ml dextrose and AKG-28 concentration of 6 mg/ml. The mixture was heated to 65.4° C. in 2.5 min by external heating under constant stirring, and the incubation continued with stirring on the 65° C. bath. After 20 min. incubation, the mixture was chilled in ice-water to 9.3° C. in 2.75 min, and kept in the ice-water bath for about 10 min. Then the mixture was allowed to reach the ambient temperature and adjusted to 0.1 M NaCl; pH 6.43. 133.4 g of the loading mixture was subjected to purification by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into HBS-7 buffer for the total of 8.1 volume exchanges. The proportion of unencapsulated drug prior to purification was estimated spectrophotometrically at 302 nm in the pre-concentration diafiltrate and found to be about 0.7% (corresponds to 99.3% loading efficiency). The concentrated, purified liposomes were aseptically passed through 0.2-µm sterile filter and analyzed for the particle size by DLS, and for the drug and phospholipid concentration by spectrophotometry. The liposomes had the following characteristics: AKG-28 13.26±0.21 mg/ml, DL ratio 258.2±3.7 g/mol phospholipid, Xz 117.3 nm, PDI 0.0421.

Example 27. Liposomal AKG-38 Lot 285

The general procedure of Example 6 was followed. Extruded liposomes composed of HSPC, cholesterol, and PEG-DSPE in the molar ratio of 45:55:2.25 containing 0.5 M ammonium sulfate were prepared essentially as described in Example 25. Extraliposomal trapping agent (ammonium sulfate) was removed by TFF exchange for endotoxin-free water on a KrosFlo TFF system using polyethersulfone hollow fiber cartridge with MW cut-off 500 KDa (Spectrum Laboratories) until residual conductivity dropped to 138 µS/cm (5.6 volume exchanges). The phospholipid concentration in the post-TFF liposome suspension was determined by blue phosphomolybdate method to be 53.1 mM.

AKG-38 (free base) was mixed with 0.95 equivalents of 1 N HCl and made up with endotoxin-free water to obtain 19.9 mg/ml aqueous stock solution (pH 5.13). The solution was passed through 0.2-µm filter, and the amount of filtrate containing 1400 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.58. The mixture was heated to 63° C. by external heating under constant stirring over the period of 2.25 min, and the incubation continued with stirring on the 65° C. bath for the total of 21 min. Then the mixture was transferred into ice-water bath, stirred for 3 minutes to let the temperature drop to 10.3° C., and kept in the ice-water bath for another 7 min. After being taken out of the ice bath, having reached the ambient temperature, and adjustment to 0.1 M NaCl by addition of 3 M NaCl stock, the drug-loaded liposomes (pH 6.70) were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 7.7 volume exchanges. The concentrated, purified liposomes had AKG-38 concentration of 23.1 mg/ml. The drug concentration was adjusted to 20 mg/ml with HBS-7 buffer, the liposomes were aseptically passed through 0.2-μm PES high-flow sterile filter and analyzed for the particle size by DLS, and for the drug and phospholipid concentration by spectrophotometry. The liposomes had the following characteristics: AKG-38 20.35±0.26 mg/ml, DL ratio 437.8±6.5 g/mol phospholipid, Xz 121.1 nm, PDI 0.0200. Yield of the formulated drug 1355 mg (96.8%).

Example 28. Liposomal AKG-28 Lot 286

Extruded liposomes (HSPC:Chol:PEG-DSPE 45:55:2.25 molar ratio) containing 0.5M ammonium sulfate, free from extraliposomal trapping agent, were obtained as in Example 27.
600 mg of AKG-28 (as dihydrochloride salt) in the form of 20 mg/ml aqueous stock solution (adjusted to pH 5.18 with NaOH) were combined with post-TFF liposome suspension to form the loading mixture at drug-to-phospholipid (DL) ratio of 250 g/mol in the presence of 44.5 mg/ml dextrose and AKG-28 concentration of 6 mg/ml. The mixture was placed on a 65° C. water bath with stirring and reached 60° C. in 4.5 min. The incubation continued with stirring for the total of 20 min, the mixture was chilled in ice-water to 10.0° C. in 2 min, and kept in the ice-water bath for about 10 min. Then the mixture was allowed to reach the ambient temperature and adjusted to 0.1 M NaCl; pH 6.23. 104.6 g of the loading mixture was subjected to purification by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into HBS-7 buffer for the total of 8.3 volume exchanges. The concentrated, purified liposomes were aseptically passed through 0.2-μm sterile filter (chased with HBS-7 buffer) and analyzed for the particle size by DLS, and for the drug and phospholipid concentration by spectrophotometry. The liposomes had the following characteristics: AKG-28 12.05±0.13 mg/ml, DL ratio 239.4 g/mol phospholipid, Xz 120.1 nm, PDI 0.0294. Yield of the formulated drug 555.5 mg (92.6%).

Example 29. Liposomal AKG-38 Lot 292

Lot 288. The general procedure of Example 6 was followed. HSPC (Lipoid AG) 9.17 g (11.67 mmol), cholesterol (Dishman, High purity) 5.51 g (14.26 mmol), and PEG-DSPE (Lipoid AG) 1.575 g (0.583 mmol) were combined with 17.5 ml of absolute ethanol (Sigma, E-7023) and heated with stirring on a 69-70° C. bath until all lipids dissolved. In a separate container 181.4 g (175 ml) of 0.5 M aqueous ammonium sulfate (0.2-micron filtered) was preheated on a 70° C. bath and poured with stirring into the hot lipid ethanolic solution. The obtained suspension was stirred on a 70° C. bath for at least 20 min. and divided into three portions. Each portion was extruded five times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 126.7 nm) and extruded together through the same membrane stack four more times, resulting in the liposomes of the size Xz 119.2 nm, PDI 0.0385. The liposomes kept overnight in a refrigerator (2-8° C.) and filtered through 0.2-μm polyethersulfone (PES) filter under positive pressure. Phospholipid concentration was found 59.08 f 0.44 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 152 μS/cm after 5.4 volume exchanges). The phospholipid concentration in the post-TFF liposome suspension was determined by blue phosphomolybdate method to be 57.76±0.53 mM.

AKG-38 (free base) was mixed with 0.95 equivalents of 1 N HCl and made up with endotoxin-free water to obtain 19.7 mg/ml aqueous stock solution (pH 5.11). The solution was passed through 0.2-μm filter, and the amount of filtrate containing 3509 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.50. The mixture was heated to 61.6° C. by external heating under constant stirring over the period of 5 min, and the incubation continued with stirring on the 65° C. bath for another 20 min. Then the mixture was transferred into ice-water bath, stirred for 7 minutes to let the temperature drop to 10° C., and kept in the ice-water bath for another 8 min. After being taken out of the ice bath, having reached the ambient temperature, and adjustment to 0.1 M NaCl by addition of 3 M NaCl stock, the drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 7.8 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.47±0.38 mg/ml, DL ratio 441.6 g/mol phospholipid, Xz 121.3 nm, PDI 0.0465. Yield of the formulated drug 3375 mg (96.2%).

Lot 289. The process of Ls-288 was repeated using 1506 mg of AKG-38 (as similarly prepared 20.0 mg/ml aqueous stock solution, pH 5.15). The solution was combined with the same post-TFF extruded liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.53. The mixture was heated to 64.3° C. by external heating under constant stirring over the period of 2 min, and the incubation continued with stirring on the 65° C. bath for another 20 min. Then the mixture was transferred into ice-water bath, stirred for 2.75 minutes to let the temperature drop to 9.6° C., and kept in the ice-water bath for another 14 min. After being taken out of the ice bath, the loading mixture was allowed to reach the ambient temperature and adjusted to 0.1 M NaCl with 3 M NaCl stock; pH 6.54. The drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8.1 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.84±0.41 mg/ml, DL ratio 452.7 g/mol phospholipid, Xz 120.3 nm, PDI 0.0522. Yield of the formulated drug 1407 mg (93.4%).

Lot 290. The general procedure of Example 6 was followed. HSPC (Lipoid AG) 7.86 g (10.00 mmol), cholesterol (Dishman, High purity) 4.73 g (12.22 mmol), and PEG-DSPE (Lipoid AG) 1.35 g (0.50 mmol) (HSPC:Chol:PEG-DSPE 45:55:2.25 molar ratio) were combined with 15 ml of absolute ethanol (Sigma, E-7023) and heated with stirring on a 69-70° C. bath until all lipids dissolved. In a separate container 155.5 g (150 ml) of 0.5 M aqueous ammonium sulfate (0.2-micron filtered) were preheated on a 70° C. bath and poured with stirring into the hot lipid ethanolic solution. The obtained suspension was stirred on a 70° C. bath for at least 20 min. and divided into two portions. Each portion was extruded four times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 131.5 nm) and extruded together through the same membrane stack four more times, resulting in the liposomes of the size Xz 122.7 nm, PDI 0.0215. The liposomes were kept overnight in a refrigerator (2-8° C.) and filtered through 0.2-μm polyethersulfone (PES) filter under positive pressure. Phospholipid concentration was found 58.99±0.22 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 146 μS/cm after 5.5 volume exchanges. The phospholipid concentration in the post-TFF liposome suspension was determined by blue phosphomolybdate method to be 56.94±0.41 mM.

AKG-38 (free base) was mixed with 0.95 equivalents of 1 N HCl and made up with endotoxin-free water to obtain 20 mg/ml aqueous stock solution (pH 5.15). The solution was passed through 0.2-μm filter, and the amount of filtrate containing 2315 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8.02 mg/ml, pH 5.52. The mixture was heated to 64.4° C. by external heating under constant stirring over the period of 3.25 min, and the incubation continued with stirring on the 65° C. bath for another 17 min. Then the mixture was transferred into ice-water bath, stirred to let the temperature drop to below 10° C., kept in the ice-water bath for the total of 10 min, allowed to reach the ambient temperature, and adjusted to 0.1 M NaCl with 3 M NaCl stock; pH 6.63. The drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8.0 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.07±0.23 mg/ml, DL ratio 441.6 g/mol phospholipid, Xz 120.4 nm, PDI 0.0395. Yield of the formulated drug 2141 mg (92.5%).

Lot 292. Lots 288 (150.3 g), 289 (61.2 g), and 290 (19.5 g) were combined to give 278.4 g of the lot 292 at 22.5 mg/ml of liposomally formulated AKG-38. All liposomal formulations were stored at 2-8° C.

Example 30. Preparation of Liposomal AKG-28 Lot 235

The general procedure of Example 6 was followed. HSPC (Lipoid AG) 940 mg (1.20 mmol), cholesterol (Dishman, High purity) 568 mg (1.47 mmol), PEG-DSPE (Lipoid AG) 163 mg (0.06 mmol), and 0.0018 mmol of the lipophilic fluorescent label $DiIC_{18}(3)$-DS (AAT Bioquest, USA) (HSPC:Chol:PEG-DSPE:$DiIC_{18}(3)$-DS 45:55:2.25:0.0675 molar ratio, 0.15 mol % DiI3-DS relative to HSPC) were combined in 2 ml of absolute ethanol (Sigma, E-7023) and heated with stirring on a 68° C. bath until all lipids dissolved. In a separate container 20 ml of 0.5 M aqueous ammonium sulfate solution (0.2-micron filtered) was preheated on a 68° C. bath and poured with stirring into the hot lipid ethanolic solution. The obtained suspension was stirred on a 68° C. bath for 20 min. and extruded eight times at 300 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 68° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories)until the conductivity of the retentate drops to 60 μS/cm (10 volume exchanges). The phospholipid concentration in the post-TFF liposome suspension was determined by blue phosphomolybdate method to be 37.56±0.62 mM.

50 mg of AKG-28 (as dihydrochloride salt) in the form of 20 mg/ml aqueous stock solution (adjusted to pH 4.99 with NaOH) were combined with post-TFF liposome suspension to form the loading mixture at drug-to-phospholipid (DL) ratio of 250 g/mol in the presence of 140 mg/ml dextrose and AKG-28 concentration of 3 mg/ml. The mixture (pH 5.53) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.80. Drug-loaded liposomes were purified by TFF using polysulfone hollow fiber cartridge with molecular weight cutoff 500 KD. The liposomes were pre-concentrated by diafiltration to about 5 mg/ml of AKG-28 and purified from any extraliposomal drug by TFF exchange into HBS-7 buffer for the total of about 10 volume exchanges. The purified liposomes were further concentrated two-fold by TFF using syringe-operated small 500 KD hollow fiber cartridge (MicroKros, Spectrum). The concentrated, purified liposomes were aseptically passed through 0.2-μm sterile filter and analyzed for the particle size by DLS, and for the drug and phospholipid concentration by spectrophotometry. The liposomes had the following characteristics: AKG-28 8.22±0.16 mg/ml, DL ratio 257.3±10.3 g/mol phospholipid, liposome size Xz 118.2 nm, PDI 0.0188. Yield of the formulated drug 41.4 mg (82.8%).

Example 31. Preparation of Liposomal AKG-38 Lot 236

Post-TFF extruded liposomes containing 0.5 M ammonium sulfate of Example 30 were used. AKG-38 (free base) was mixed with 0.95 equivalents of 1 N HCl and made up with endotoxin-free water to obtain 20 mg/ml aqueous stock solution (pH 5.11). The solution was passed through 0.2-μm filter, and the amount of filtrate containing 70 mg of the drug was combined with the post-TFF liposome suspension (Example 30) to form the loading mixture at drug-to-phospholipid (DL) ratio of 450 g/mol in the presence of 140 mg/ml dextrose and AKG-38 concentration of 3 mg/ml. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.33. Drug-loaded liposomes were purified by TFF using polysulfone hollow fiber cartridge with molecular weight cutoff 500 KD. The liposomes were pre-concentrated by diafiltration to about 6 mg/ml of AKG-38 and purified from any extraliposomal drug by TFF exchange into HBS-7 buffer for the total of about 10 volume exchanges. The purified liposomes were further concentrated two-fold by TFF using syringe-operated small 500 KD hollow fiber cartridge (MicroKros, Spectrum). The concentrated, purified liposomes were aseptically passed through 0.2-μm sterile filter and analyzed for the particle size by DLS, and for the drug and phospholipid concentration by spectrophotometry. The liposomes had the following characteristics: AKG-38 9.04±0.16 mg/ml, DL ratio 463.9±19.8 g/mol phospholipid, liposome size Xz 119.3 nm, PDI 0.0267. Yield of the formulated drug 56 mg (80%).

Example 32. Retention of Encapsulated Drugs in the Liposomes of the Lots 235 and 236 In Vitro in the Presence of Plasma Retention of the encapsulated drug in the liposomes in the presence of 80% mouse of human blood plasma at 37° C. was determined as described in Example 19 herein. Incubation time was 20 min.

TABLE 21

| Liposome lot ID | 235 | 236 |
| --- | --- | --- |
| Mouse plasma | 100.2 ± 4.3 | 91.0 ± 2.5 |
| Human plasma | 99.6 ± 3.9 | 94.8 ± 2.6 |

These liposomes were stable against burst-release of the drug in contact with blood plasma.

Example 33. Preparation of Liposomal AKG-28 and AKG-38 Lots 231, 232 (HSPC:Cholesterol:PEG-DSPE 45:55:2.25 Molar Ratio, Trapping Agent 0.5 M Ammonium Sulfate)

The general procedure of Example 6 was followed. HSPC (Lipoid AG) 4.255 g (5.41 mmol), cholesterol (Dishman, High purity) 2.56 g (6.62 mmol), and PEG-DSPE (Lipoid AG) 729 mg (0.27 mmol) (HSPC:Cholsterol:PEG-DSPE 45:55:2.25 molar ratio) were combined in 9 ml of absolute ethanol (Sigma, E-7023) and heated with stirring on a 70° C. bath until all lipids dissolved. In a separate container 90 ml of 0.5 M aqueous ammonium sulfate solution (0.2-micron filtered) were preheated on a 70° C. bath and poured with stirring into the hot lipid ethanolic solution. The obtained suspension was stirred on a 70° C. bath for 25 min. and extruded eight times at 260 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until the conductivity of the retentate drops to 60 μS/cm (10 volume exchanges). The phospholipid concentration in the post-TFF liposome suspension was determined by blue phosphomolybdate spectrophotometric method to be 46.97±0.80 mM.

Lot 231. 350 mg of AKG-28 (as dihydrochloride salt) in the form of 20 mg/ml aqueous stock solution (adjusted to pH 5.02 with NaOH) were combined with post-TFF liposome suspension to form the loading mixture at drug-to-phospholipid (DL) ratio of 250 g/mol in the presence of 137.6 mg/ml dextrose and AKG-28 concentration of 2.53 mg/ml. The mixture (pH 5.60) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.68. Drug-loaded liposomes were purified by TFF using polysulfone hollow fiber cartridge with molecular weight cutoff 500 KD. The liposomes were pre-concentrated by diafiltration to about 9 mg/ml of AKG-28 and purified from any extraliposomal drug by TFF exchange into HBS-7 buffer for the total of 10.9 volume exchanges. The purified liposomes were further concentrated to about 12 mg/ml of the drug by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-28 11.42±0.09 mg/ml, DL ratio 247.7±7.1 g/mol phospholipid, liposome size Xz 116.5 nm, PDI 0.0511. Yield of the formulated drug 322.7 mg (92.2%).

Lot 232. AKG-38 (free base) was mixed with 0.95 equivalents of 1 N HCl and made up with endotoxin-free water to obtain 20 mg/ml aqueous stock solution (pH 5.09). The solution was passed through 0.2-μm filter, and the amount of filtrate containing 580 mg of the drug was combined with the post-TFF liposome suspension of this Example to form the loading mixture at drug-to-phospholipid (DL) ratio of 500 g/mol in the presence of 137.6 mg/ml dextrose, AKG-38 concentration of 2.53 mg/ml, pH 5.72. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.40. Drug-loaded liposomes were purified by TFF using polysulfone hollow fiber cartridge with molecular weight cutoff 500 KD. The liposomes were pre-concentrated by diafiltration to about 12 mg/ml of AKG-38 and purified from any extraliposomal drug by TFF exchange into HBS-7 buffer for the total of 8.5 volume exchanges. The purified liposomes were further concentrated two-fold by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-38 16.03±0.07 mg/ml, DL ratio 487.3±13.9 g/mol phospholipid, liposome size Xz 120.0 nm, PDI 0.0069. Yield of the formulated drug 538.9 mg (92.9%)

Example 34. Preparation of liposomal AKG-28 lot 233 (HSPC:cholesterol:PEG-DSG 60:40:3 molar ratio, trapping agent 1 N triethylammonium sucrooctasulfate)

The general procedure of Example 6 was followed. HSPC (Lipoid AG) 1.88 g (2.4 mmol), cholesterol (Dishman, High purity) 619 mg (1.6 mmol), and PEG-DSG (Sunbright GS-020, NOF, Japan) 312 mg (0.12 mmol) were combined in 3 ml of absolute ethanol and heated with stirring on a 67° C. bath until all lipids dissolved. In a separate container 31.5 g (30 ml) of 1 N aqueous triethylammonium sucrooctasulfate solution (0.2-micron filtered, pH 6.20, see Example 8) were preheated on a 65° C. bath and poured with stirring into the hot lipid ethanolic solution. The obtained suspension was stirred on a 65° C. bath for 5 min, and extruded three times at 400 psi through the stack of four 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 65° C. water. The resulting extruded liposomes were kept overnight in a refrigerator (2-8° C.) and filtered through 0.2-μm polyethersulfone (PES) filter under positive pressure. 9.2 g of the extruded liposomes were purified from the extraliposomal trapping agent (TEA-SOS) by TFF buffer exchange for endotoxin-free water on a KrosFlo TFF system using polysulfone hollow fiber cartridge with MW cut-off 500 KDa (Spectrum Laboratories) until the conductivity of the retentate drops to 21 μS/cm (14.5 volume exchanges). The phospholipid concentration in the post-TFF liposome suspension was determined by blue phosphomolybdate spectrophotometric method to be 31.32±0.85 mM.

140 mg of AKG-28 (as dihydrochloride salt) in the form of 20 mg/ml aqueous stock solution (adjusted to pH 5.02 with NaOH) were combined with post-TFF liposome suspension to form the loading mixture at drug-to-phospholipid (DL) ratio of 250 g/mol in the presence of 116.1 mg/ml dextrose and AKG-28 concentration of 2.52 mg/ml. The mixture (pH 5.43) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.80. Drug-loaded liposomes were purified by TFF using polysulfone hollow fiber cartridge with molecular weight cutoff 500 KD. The liposomes were pre-concentrated by diafiltration to about 9 mg/ml of AKG-28 and purified from any extraliposomal drug by TFF exchange into HBS-7 buffer for the total of 10.9 volume exchanges. The purified liposomes were further concentrated to about 12 mg/ml of the drug by continuing TFF diafiltration without buffer feed. The concentrated, purified liposomes were aseptically passed through 0.2-μm sterile filter (chased with HBS-7 buffer) and analyzed for the particle size by DLS, and for the drug and phospholipid concentration by spectrophotometry. The liposomes had the following characteristics: AKG-28 10.64±0.20 mg/ml, DL ratio 246.8±11.7 g/mol phospholipid, liposome size Xz 116.3 nm, PDI 0.0022. Yield of the formulated drug 118.2 mg (84.4%).

Example 35. Preparation of Liposomal AKG-38 Lot 234 (HSPC:Cholesterol:PEG-DSPE 45:55:2.25 Molar Ratio, Trapping Agent 1 N Triethylammonium Sucrooctasulfate)

The general procedure of Example 6 was followed. HSPC (Lipoid AG) 3.30 g (4.20 mmol), cholesterol (Dishman, High purity) 1.985 g (5.13 mmol), and PEG-DSPE (Lipoid AG) 567 mg (0.21 mmol) (HSPC:Cholsterol:PEG-DSPE 45:55:2.25 molar ratio) were combined in 7 ml of absolute ethanol (Sigma, E-7023) and heated with stirring on a 70° C. bath until all lipids dissolved. In a separate container 10 ml of 1 N aqueous triethylammonium sucrooctasulfate (TEA-SOS) solution (0.2-micron filtered) were preheated on a 70° C. bath and poured with stirring into the hot lipid ethanolic solution. The obtained suspension was stirred on a 70° C. bath for 10 min. and extruded eight times at 260 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. The resulting extruded liposomes were kept overnight in a refrigerator (2-8° C.) and filtered through 0.2-μm polyethersulfone (PES) filter under positive pressure. Phospholipid concentration was 54.6 mM. 11.33 g of the extruded liposomes were purified from the extraliposomal trapping agent (TEA-SOS) by TFF buffer exchange for endotoxin-free water on a KrosFlo TFF system using polysulfone hollow fiber cartridge with MW cut-off 500 KDa (Spectrum Laboratories) until the conductivity of the retentate drops to 64 μS/cm (13.8 volume exchanges). The phospholipid concentration in the post-TFF liposome suspension was determined by blue phosphomolybdate spectrophotometric method to be 28.67±1.01 mM.

AKG-38 (free base) was mixed with 0.95 equivalents of 1 N HCl and made up with endotoxin-free water to obtain 20 mg/ml aqueous stock solution (pH 5.09). The solution was passed through 0.2-μm filter, and the amount of filtrate containing 250 mg of the drug was combined with the post-TFF liposome suspension of this Example to form the loading mixture at drug-to-phospholipid (DL) ratio of 500 g/mol in the presence of 116.4 mg/ml dextrose, AKG-38 concentration of 2.53 mg/ml, pH 5.24. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.60. Drug-loaded liposomes were purified by TFF using polysulfone hollow fiber cartridge with molecular weight cutoff 500 KD. The liposomes were pre-concentrated by diafiltration to about 10 mg/ml of AKG-38 and purified from any extraliposomal drug by TFF exchange into HBS-7 buffer for the total of 8.0 volume exchanges. The purified liposomes were further concentrated approximately two-fold by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-38 15.71±0.33 mg/ml, DL ratio 518.6±18.4 g/mol phospholipid, liposome size Xz 114.3 nm, PDI 0.0284. Yield of the formulated drug 235.7 mg (94.3%).

Example 36. Effect of Osmotic Agent Concentration on the Loading Efficiency of AKG-28 and AKG-38 into the Liposomes and Drug Retention by the Liposomes in Plasma The general protocol of Example 6 was followed. Extruded liposomes containing 0.5 M ammonium sulfate and the lipid composition of HPSC, cholesterol, PEG-DSPE, and DiIC18(3)-DS (fluorescent lipid label) in the molar ratio of 45:55:2.25:0.0675 were prepared as described in Example 30. The liposomes were purified from the extraliposomal ammonium sulfate by TFF exchange for endotoxin-free "water for injection" (WFI)-quality water (Hyclone) using syringe-operated MicroKros polysulfone hollow fiber cartridge (MWCO 500 KDa, Spectrum Laboratories) (13.8 volume exchanges, residual conductivity 88 µS/cm, phospholipid concentration 55.4 mM). The liposomes were loaded with AKG-28 or AKG-38 by incubation of the drugs (prepared as aqueous 20 mg/ml stocks as described in Examples 30 and 31) with the purified extruded liposomes in aqueous solution in a 65° C. water bath for 20 min in the presence of various concentrations of osmotic agent (dextrose), at the drug concentration 2.22 mg/ml and DL ratio of 250 g/mol phospholipid (AKG-28) or 450 g/mol phospholipid (AKG-38). Unencapsulated drug was removed by size-exclusion chromatography on Sepharose CL-4B, eluent HBS-7 buffer, and the loading (encapsulation) efficiency was determined from the results of drug and phospholipid analysis. The osmotic agent concentration was expressed both in absolute terms and as percent of the 168 mg/ml dextrose concentration determined to be isoosmotic to the 0.5 M ammonium sulfate solution used to form the liposomes. Contrary to expectations from the general consensus in the liposome field, the drugs were effectively loaded into the liposomes of the disclosure (encapsulation efficiency more than 85%, and mostly more than 90%) even under hypoosmotic conditions (i.e., at the osmolality of the extraliposomal solution lower than that of the intraliposomal trapping agent solution), down to complete absence of the added osmotic balance agent (dextrose) (Table 22). Moreover, upon exposure to blood plasma under the conditions of in vitro plasma release assay described in Example 19, the drug encapsulation in the liposomes loaded at the lowest concentrations of the osmotic agent was at least as stable as in those loaded at nearly complete (86.3%) osmotic balance.

The results show that liposomes with 55 mol % Chol, 45 mol % PC, PEG-DSPE at 5 mol % of HSPC, and 0.5 M AS trapping agent load both AKG-28 (TABLE 22) and AKG-38 (TABLE 23) at 250 or 500 g/mol PhL with efficiency >85%, mostly >90%, under hypoosmotic conditions up to zero percent dextrose, and the liposomes loaded under hypoosmotic conditions efficiently retain the drug in the presence of blood plasma.

TABLE 22

| Lot ID | Dextrose, g/L | % Osmotic with balance 0.5 M AS | Output DL ratio, g/mol PhL | Encapsulation efficiency, % | % drug retained in liposomes, 80% plasma, 20 min, 37° C. | |
|---|---|---|---|---|---|---|
| | | | | | Mouse | Human |
| 237 | 144.9 | 86.3 | 243.1 ± 7.5 | 97.2 ± 3.0 | 98.8 ± 4.6 | 98.0 ± 4.0 |
| 238 | 130.4 | 77.6 | 243.1 ± 4.9 | 97.2 ± 2.0 | | |
| 239 | 115.9 | 69.0 | 253.1 ± 5.2 | 101.2 ± 2.1 | | |
| 240 | 86.9 | 51.8 | 246.1 ± 3.5 | 98.4 ± 1.4 | | |
| 241 | 58.0 | 34.5 | 253.7 ± 8.1 | 101.5 ± 3.3 | | |
| 242 | 29.0 | 17.3 | 246.5 ± 5.4 | 98.6 ± 2.2 | 99.4 ± 4.3 | 100.3 ± 4.9 |
| 243 | 0 | 0 | 249.2 ± 5.4 | 99.7 ± 2.2 | 100.6 ± 4.3 | 102.2 ± 4.8 |

TABLE 23

| Lot ID | Dextrose, g/L | % Osmotic with balance 0.5 M AS | Output DL ratio, g/mol PhL | Encapsulation efficiency, % | % drug retained in liposomes, 80% plasma, 20 min, 37° C. | |
|---|---|---|---|---|---|---|
| | | | | | Mouse | Human |
| 244 | 144.9 | 86.3 | 464.9 ± 14.6 | 93.0 ± 2.9 | 82.0 ± 2.4 | 86.8 ± 2.8 |
| 245 | 130.4 | 77.6 | 463.5 ± 18.2 | 92.7 ± 3.6 | | |
| 246 | 115.9 | 69.0 | 453.2 ± 8.7 | 90.6 ± 1.7 | | |
| 247 | 86.9 | 51.8 | 459.8 ± 13.8 | 92.0 ± 02.8 | | |
| 248 | 58.0 | 34.5 | 466.1 ± 14.5 | 93.2 ± 2.9 | 85.0 ± 3.3 | 89.6 ± 3.7 |
| 249 | 29.0 | 17.3 | 455.8 ± 12.9 | 91.2 ± 2.6 | 89.7 ± 3.1 | 92.8 ± 3.0 |
| 250 | 0 | 0 | 433.1 ± 17.7 | 86.6 ± 3.5 | 93.8 ± 3.5 | 91.2 ± 3.2 |

Example 37. Single Dose Pharmacokinetic Studies of the Total Form (Encapsulated+Released Drug) of Ls-AKG28 & Ls-AKG38 in Rats This study was performed to evaluate the PK of AKG28 and AKG 38 administered as a single dose Ls-AKG28 and Ls-AKG38 in rats. The study was performed on male Sprague-Dawley rats using IV administration of liposomal AKG-38 (Ls-AKG38) at 20, 40, or 80 mg per kg of the body weight or liposomal AKG-28 (Ls-AKG28) at 10, 20, and 40 mg per kg of the body weight. Ls-AKG28 (Lot 275) and Ls-AKG38 (Lot 276) were prepared as described in Examples 22 and 23, respectively. For comparison, Linezolid at 50 mg/kg of the body weight was administered orally as a gavage formulated with 0.5% methyl cellulose and acidified to pH 3-4 (Sigma M0430) at a concentration of 20 mg/mL. For plasma drug measurements, 0.5 ml blood was collected in lithium heparin tubes at 5 min, 15 min, 1 h, 3 h, 6 h, 24 h, 48 h, and 72 h. The samples were centrifuged and the resultant plasma was separated and transferred to duplicate clear polypropylene tubes, frozen immediately over dry ice, and stored at −80° C. until analysis. The plasma concentration in rats was determined by HPLC. Non-compartment PK analyses were performed using Phoenix Win-Nonlin (Version 7.0). For Ls-AKG28 and Ls-AKG38, this PK software was used to estimate the plasma maximum concentration ($C_{max}$), plasma maximum concentration divided by dose ($C_{max}$/dose), time of $C_{max}$ ($T_{max}$), last measured concentration ($C_{last}$), time of last measured concentration (T1/2), area-under the plasma concentration versus time curve from 0 h to last time point ($AUC_{0-last}$) and 0 h to infinity ($AUC_{0-inf}$), $AUC_{0-last}$ divided by dose ($AUC_{0-last}$/dose), clearance (CL), volume of distribution (Vd), and elimination half-life (T1/2). For linezolid, this PK software was used to estimate the same PK parameters except for apparent clearance (CL/F) and apparent volume of distribution (Vd/F).

Figure 7:
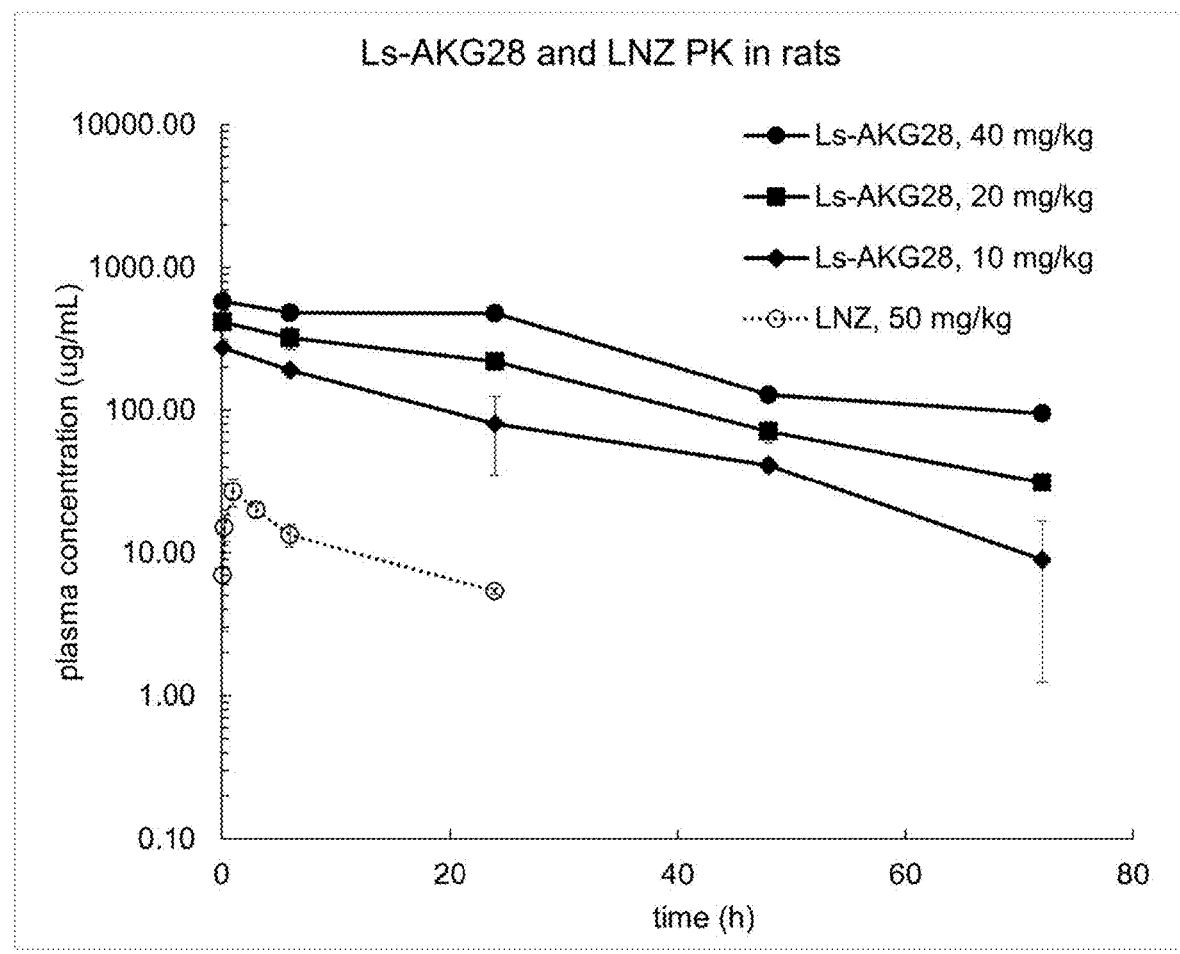
FIG. 7 is a graph showing the plasma concentration versus time profiles for total drug in Sprague-Dawley rats after administration of a single intravenous dose (IV×1) of Ls-AKG28 at 10 mg/kg (diamonds), 20 mg/kg (squares), and 40 mg/kg (circles). Plasma concentration versus time profiles of linezolid at 50 mg/kg (single oral dose, PO×1) in 5% methyl cellulose (pH 3-4) was also included for comparison. The mean and SD concentration are presented at each time point.

The plasma concentration versus time profiles for total drug after administration of Ls-AKG28 at 10, 20, and 40 mg/kg single IV dose (IV×1) are presented in FIG. 7. The summary of plasma PK parameters for total drug after administration of Ls-AKG28 at 10, 20, and 40 mg/kg IV×1 are presented in TABLE 24.

At all doses the plasma concentration versus time profiles for Ls-AKG28 were detectable from 5 min to 72 h. Based on the results of Cmax/dose and AUC/dose, the plasma PK of Ls-AKG28 is linear (dose proportional) after administration of 10, 20, and 40 mg/kg. At all doses the plasma clearance (CL) of Ls-AKG38 (~2.59 mL/h/kg) was greater than Ls-AKG28 (~1.67 mL/h/kg). At the same dose (20 or 40 mg/kg), the Vd of Ls-AKG28 was greater than for Ls-AKG38.

TABLE 24

Summary of plasma PK parameters for total drug after administration of Ls-AKG28 at 10, 20, and 40 mg/kg IV.

| PK Parameter | Linezolid | Ls-AKG28 | | |
|---|---|---|---|---|
| Total AKG28 | 50 mg/kg | 10 mg/kg | 20 mg/kg | 40 mg/kg |
| $C_{max}$ [µg/mL] | 26.73 | 272.23 | 413.83 | 577.70 |
| $C_{max}$/Dose [µg/mL]/[mg/kg] | 0.53 | 27.22 | 20.69 | 14.44 |
| $T_{max}$ [hr] | 1.0 | 0.083 | 0.083 | 0.083 |
| $C_{last}$ [µg/mL] | 5.35 | 8.95 | 31.05 | 94.89 |
| $T_{last}$ [hr] | 24.0 | 72 | 72 | 72 |
| $AUC_{0-last}$ [hr * µg/mL] | 282.01 | 5,565.17 | 11,287.31 | 20,712.25 |
| $AUC_{0-last}$/Dose [hr * µg/mL]/[mg/kg] | 5.64 | 556.52 | 564.37 | 517.81 |
| $AUC_{0-inf}$ [hr * µg/mL] | 373.53 | 5,764.67 | 12,143.11 | 24,218.25 |
| Clearance [mL/hr/kg] | 133.86 | 1.73 | 1.64 | 1.65 |
| Vd [mL/kg] | 2,291.26 | 38.66 | 45.40 | 61.03 |
| $T_{1/2}$ [hr] | 11.86 | 15.45 | 19.11 | 25.61 |

Figure 8:
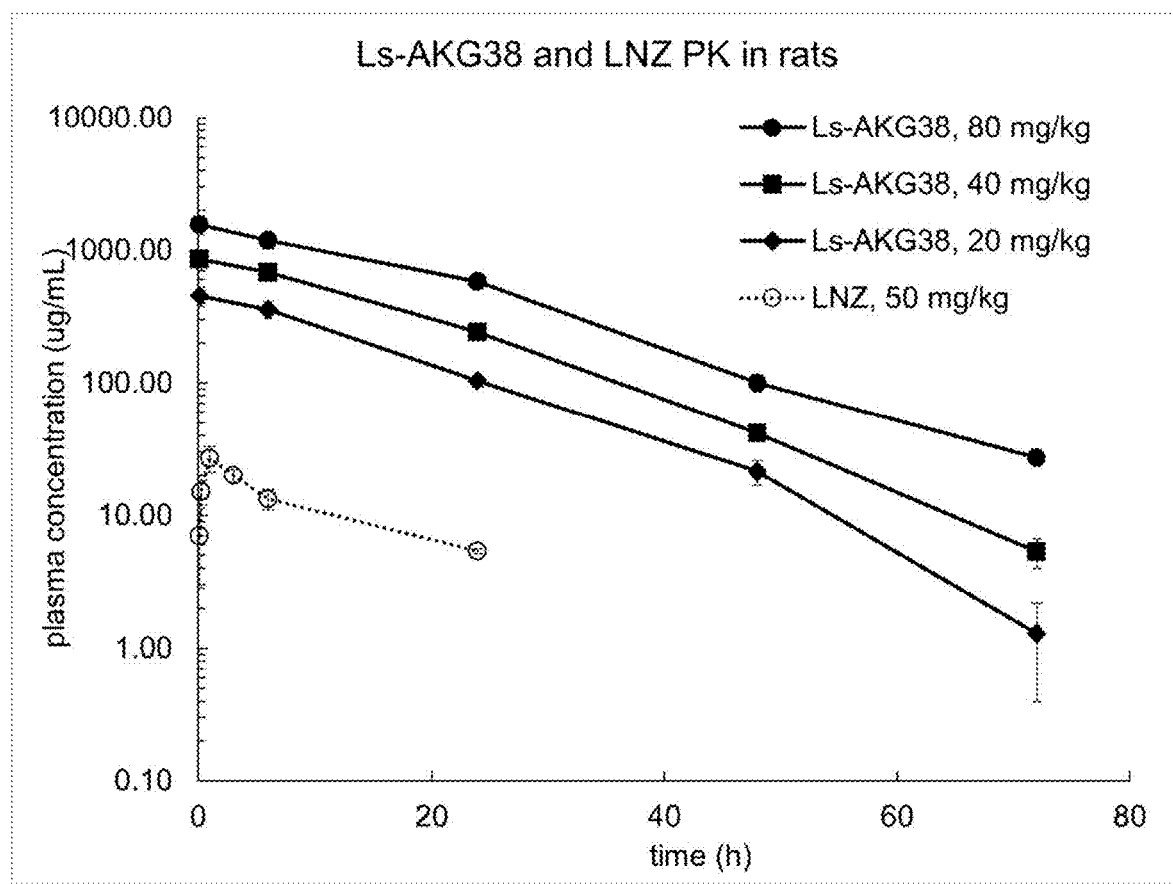
FIG. 8 is a graph showing the plasma concentration versus time profiles for total drug in Sprague-Dawley rats after administration of a single intravenous dose (IV×1) of Ls-AKG38 at 20 mg/kg (diamonds), 40 mg/kg (squares), and 80 mg/kg (diamonds). Plasma concentration versus time profiles of linezolid at 50 mg/kg (single oral dose, PO×1) in 5% methyl cellulose (pH 3-4) was also included for comparison. The mean and SD concentration are presented at each time point.

The plasma concentration versus time profiles for total drug after administration of Ls-AKG38 at 20, 40, and 80 mg/kg IV×1 are presented in FIG. 8.

The summary of plasma PK parameters for total drug after administration of Ls-AKG38 at 20, 40, and 80 mg/kg IV×1 are presented in TABLE 25.

At all doses the plasma concentration versus time profiles for Ls-AKG38 were detectable from 5 min to 72 h. Based on the results of Cmax/dose and AUC/dose, the plasma PK of Ls-AKG38 is linear (dose proportional) after administration of 20, 40, and 80 mg/kg. At all doses the plasma clearance (CL) of Ls-AKG38 (~2.59 mL/h/kg) was greater than Ls-AKG28 (~1.67 mL/b/kg). At the same dose (20 or 40 mg/kg), the Vd of Ls-AKG28 was greater than for Ls-AKG38.

TABLE 25

Summary of plasma PK parameters for total drug after administration of Ls-AKG38 at 20, 40, and 80 mg/kg IV.

| PK Parameter | Linezolid | Ls-AKG28 | | |
|---|---|---|---|---|
| Total AKG28 | 50 mg/kg | 10 mg/kg | 20 mg/kg | 40 mg/kg |
| $C_{max}$ [µg/mL] | 26.73 | 452.84 | 856.42 | 1,555.85 |
| $C_{max}$/Dose [µg/mL]/[mg/kg] | 0.53 | 22.64 | 21.41 | 19.44 |
| $T_{max}$ [hr] | 1.0 | 0.083 | 0.083 | 0.083 |
| $C_{last}$ [µg/mL] | 5.35 | 1.29 | 5.29 | 27.14 |
| $T_{last}$ [hr] | 24.0 | 72 | 72 | 72 |
| $AUC_{0-last}$ [hr * µg/mL] | 282.01 | 7,532.62 | 15,402.45 | 31,313.26 |
| $AUC_{0-last}$/Dose [hr * µg/mL]/[mg/kg] | 5.64 | 376.63 | 385.06 | 391.42 |
| $AUC_{0-inf}$ [hr * µg/mL] | 373.53 | 7,548.80 | 15,468.95 | 31,784.91 |
| Clearance [mL/hr/kg] | 133.86 | 2.65 | 2.59 | 2.52 |
| Vd [mL/kg] | 2,291.26 | 33.26 | 32.48 | 43.74 |
| $T_{1/2}$ [hr] | 11.86 | 8.70 | 8.71 | 12.05 |

The plasma concentration versus time profiles for total drug after administration of Ls-AKG28 at 10, 20, and 40 mg/kg IV×1 and Ls-AKG38 at 20, 40, and 80 mg/kg IV×1 are presented in FIG. 7 and FIG. 8, respectively. In the single IV dose studies, at all doses the plasma conc vs time profiles for Ls-AKG28 and Ls-AKG38 were detectable from 5 min to 72 h. The plasma PK of Ls-AKG28 is linear (dose proportional) after administration of 10, 20, and 40 mg/kg. The plasma PK of Ls-AKG38 is linear (dose proportional) after administration of 20, 40, and 80 mg/kg. At all doses the plasma clearance (CL) of Ls-AKG38 (~2.59 mL/h/g) was greater than Ls-AKG28 (~1.67 mL/h/kg). At the same dose (20 or 40 mg/kg), the Vd of Ls-AKG28 was greater than for Ls-AKG38. The total plasma PK exposure of Ls-AKG28 at 40 mg/kg and Ls-AKG38 were ~73-fold and ~110-fold higher than plasma PK of linezolid (using AUC from 0 to last).

The plasma AUC and the drug persistence in circulation were much greater for both liposome formulations compared to linezolid. The PK of both liposome formulations has a linear dose dependence as seen by the values for AUC/dose are very similar each for Ls-AKG28 and Ls-AKG38.

Figure 9A:
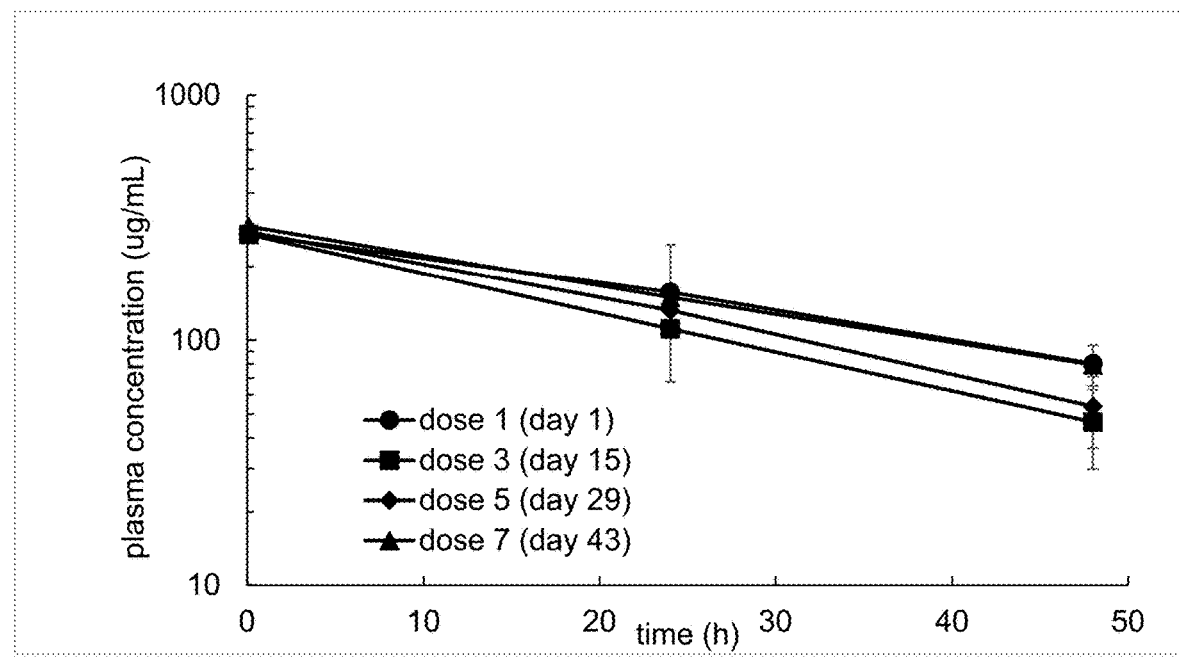
FIG. 9A, FIG. 9B, and FIG. 9C are graphs showing the plasma concentration versus time profiles for total drug in Sprague-Dawley rats after administration of Ls-AKG28 at 10 mg/kg (FIG. 9A), 20 mg/kg (FIG. 9B), and 40 mg/kg (FIG. 9C), IV×1, on day 1 (circles), day 15 (squares), day 29 (diamonds), and day 43 (triangles). The mean and SD concentration are presented at each time point.
Figure 9B:
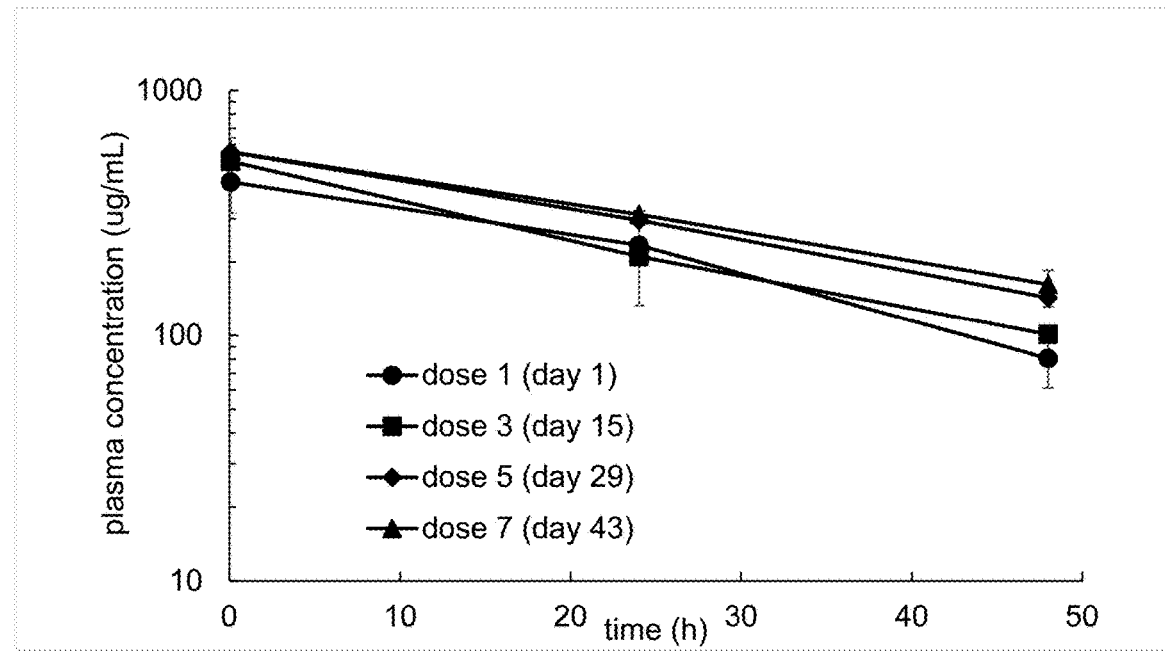
Figure 9C:
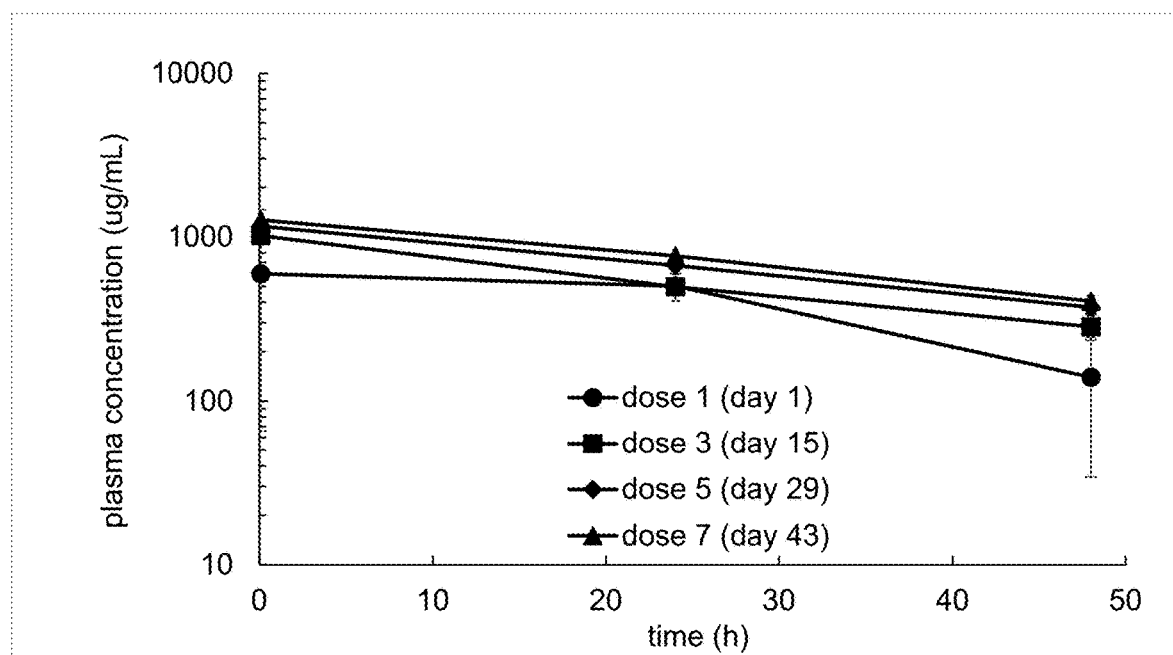

Example 38. Plasma Pharmacokinetics (PK) of the Total Form of (Encapsulated+Released Drug) Ls-AKG28 and Ls-AKG38 after Multiple IV Doses in Sprague-Dawley Rats This study was performed to evaluate the PK of AKG28 and AKG 38 administered at escalating doses of Ls-AKG28 and Ls-AKG38, weekly for a total of eight weeks in rats. The study was performed on Sprague-Dawley rats using IV administration. Ls-AKG28 (Lot 275) and Ls-AKG38 (Lot 276) were prepared as described in Examples 22 and 23, respectively The plasma concentration in rats was determined by HPLC. The plasma concentration versus time profiles for total drug after administration of Ls-AKG28 at 10, 20, and 40 mg/kg IV×1 on days 1, 15, 29, and 43 are presented in TABLE 26 and FIG. 9A, FIG. 9B, and FIG. 9C. The summary of plasma PK parameters for total drug after administration of Ls-AKG28 at 10, 20, and 40 mg/kg IV×1 on days 1, 15, 29, and 43 are presented in TABLE 26. All of the data in FIG. 9A, FIG. 9B, and FIG. 9C was used to generate the PK parameter results in TABLE 26.

In the single and multi-dose PK studies, the plasma disposition of Ls-AKG28 were similar after the first dose. For Ls-AKG28 at 10 mg/kg, the plasma Cmax and AUC were similar on days 1, 15, 29, and 43. For Ls-AKG28 at 20 mg/kg, the plasma Cmax and AUC increase on days 29 and 43. For Ls-AKG28 at 40 mg/kg, the plasma Cmax and AUC increase after doses on days 1 to 43.

Figure 10A:
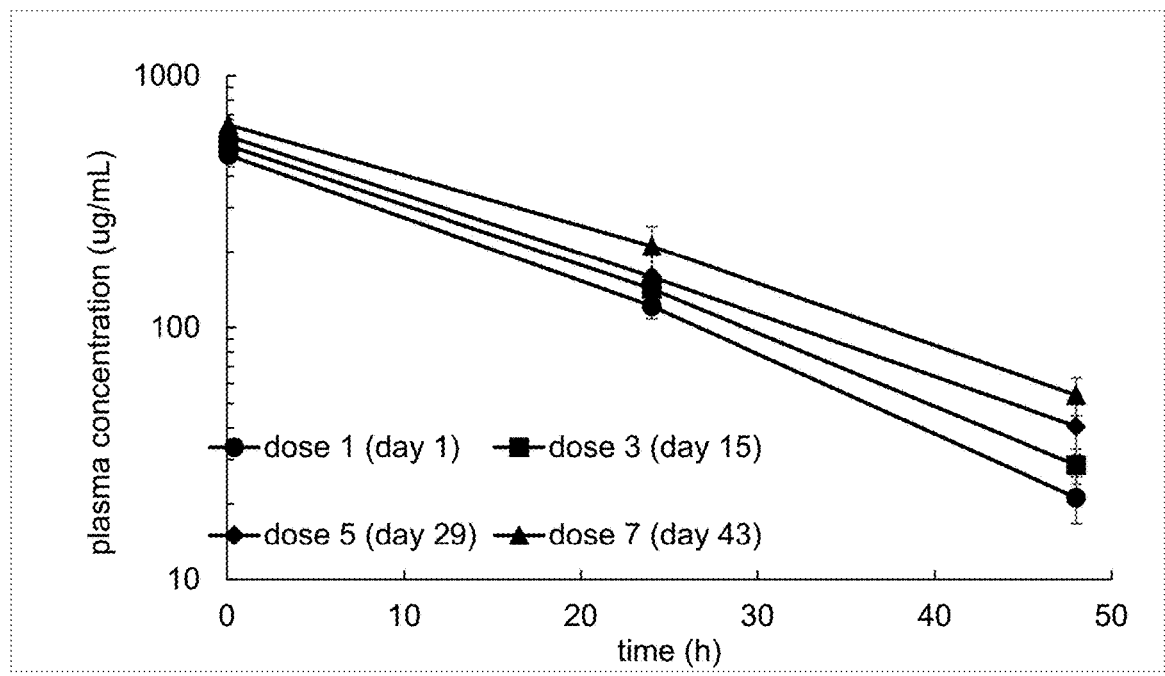
FIG. 10A, FIG. 10B, and FIG. 10C are graphs showing the plasma concentration versus time profiles for total drug in Sprague-Dawley rats after administration of Ls-AKG38 at 20 mg/kg (FIG. 10A), 40 mg/kg (FIG. 10B), and 80 mg/kg (FIG. 10C), IV×1, on day 1 (circles), day 15 (squares), day 29 (diamonds), and day 43 (triangles). The mean and SD concentration are presented at each time point.
Figure 10B:
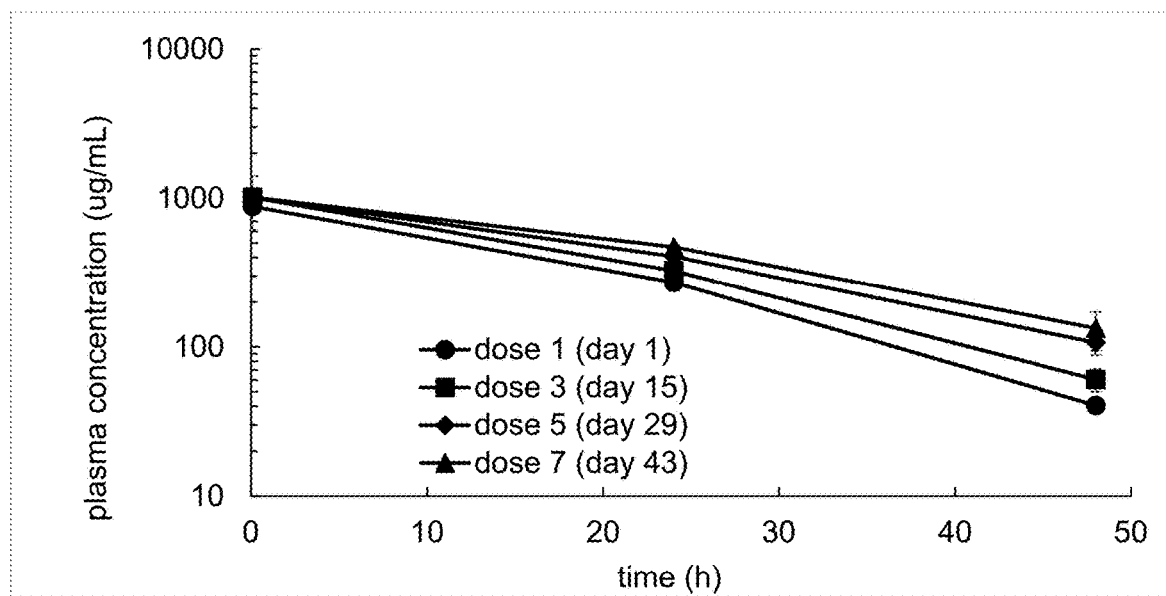
Figure 10C:
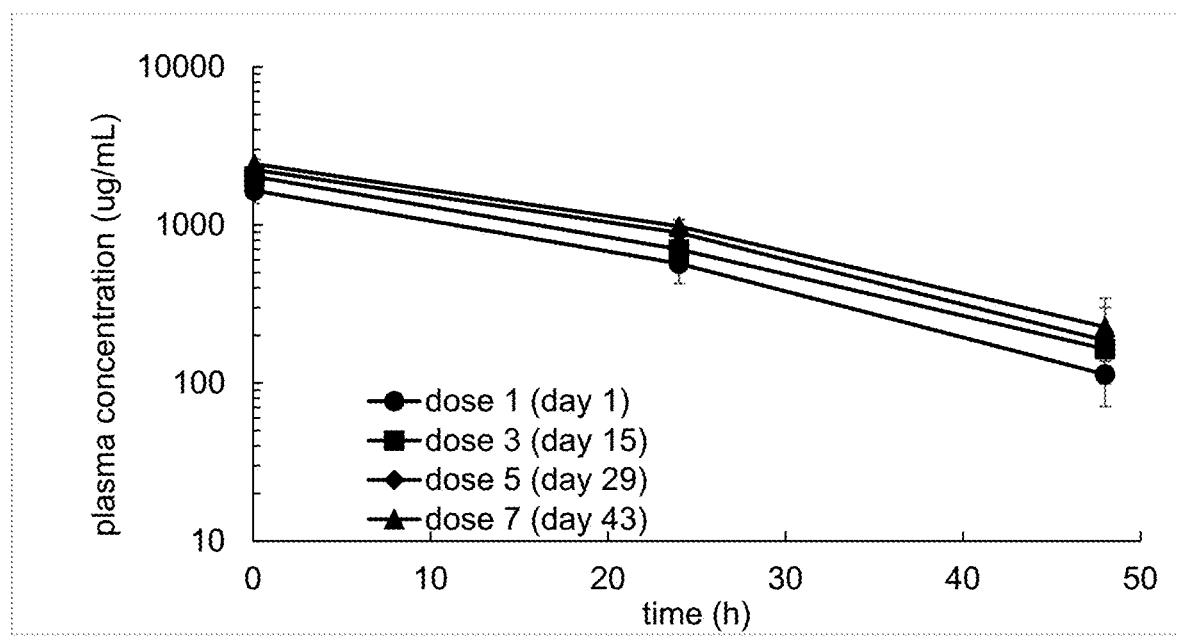

The plasma concentration versus time profiles for total drug after administration of Ls-AKG38 at 20, 40, and 80 mg/kg IV×1 on days 1, 15, 29, and 43 are presented in TABLE 27 and FIG. 10A, FIG. 10B, and FIG. 10C. The summary of plasma PK parameters for total drug after administration of Ls-AKG38 at 20, 40, and 80 mg/kg IV×1 on days 1, 15, 29, and 43 are presented in TABLE 27. In the single and multi-dose PK studies, the plasma disposition of Ls-AKG38 were similar after the first dose. For Ls-AKG38 at 20, 40, and 80 mg/kg, the plasma Cmax and AUC increase from days 1 to 43. Given the concern for accelerated blood clearance (ABC) for pegylated liposomes containing non-cytotoxic drug payloads, the lack of increased clearance at later cycles was surprising, and suggests liposomes containing AKG-28 or AKG-38 can be chronically dosed in mammals.

TABLE 26

Summary of plasma PK parameters for total drug after administration of Ls-AKG28 at 10, 20, and 40 mg/kg IV × 1 on days 1, 15, 29, and 43.

| | $C_{max}$ [μg/mL] | $AUC_{0\text{-}last}$ [hr * μg/mL] | Clearance [mL/hr/kg] | Vd [mL/kg] | $T_{1/2}$ [hr] |
|---|---|---|---|---|---|
| Ls-AKG28 (10 mg/kg)-d1 | 271.28 | 7,766.70 | 0.92 | 36.01 | 27.27 |
| Ls-AKG28 (10 mg/kg)-d15 | 270.78 | 6,093.17 | 1.36 | 36.94 | 18.83 |
| Ls-AKG28 (10 mg/kg)-d29 | 277.67 | 6,807.48 | 1.19 | 34.84 | 20.23 |
| Ls-AKG28 (10 mg/kg)-d43 | 292.14 | 7,780.12 | 0.93 | 34.37 | 25.48 |
| Ls-AKG28 (20 mg/kg)-d1 | 423.81 | 11,133.88 | 1.49 | 42.87 | 19.99 |
| Ls-AKG28 (20 mg/kg)-d15 | 514.07 | 11,757.75 | 1.36 | 39.97 | 20.41 |
| Ls-AKG28 (20 mg/kg)-d29 | 560.15 | 14,997.08 | 1.00 | 35.06 | 24.31 |
| Ls-AKG28 (20 mg/kg)-d43 | 561.51 | 15,702.04 | 0.91 | 35.13 | 26.73 |
| Ls-AKG28 (40 mg/kg)-d1 | 596.89 | 19,970.35 | 1.63 | 53.70 | 22.88 |
| Ls-AKG28 (40 mg/kg)-d15 | 1,018.25 | 26,606.26 | 1.07 | 40.29 | 26.02 |
| Ls-AKG28 (40 mg/kg)-d29 | 1,163.03 | 33,635.70 | 0.81 | 34.14 | 29.19 |
| Ls-AKG28 (40 mg/kg)-d43 | 1,269.07 | 37,580.42 | 0.73 | 30.78 | 29.17 |

TABLE 27

Summary of plasma PK parameters for total drug after administration of Ls-AKG38 at 20, 40, and 80 mg/kg IV × 1 on days 1, 15, 29, and 43.

| | $C_{max}$ [μg/mL] | $AUC_{0\text{-}last}$ [hr*μg/ mL] | Clearance [mL/ hr/kg] | Vd [mL/ kg] | $T_{1/2}$ [hr] |
|---|---|---|---|---|---|
| Ls-AKG38 (10 mg/kg) - d1 | 485.39 | 7,702.72 | 2.49 | 38.12 | 10.61 |
| Ls-AKG38 (10 mg/kg) - d15 | 529.93 | 8,792.21 | 2.16 | 35.41 | 11.36 |
| Ls-AKG38 (10 mg/kg) - d29 | 576.14 | 9,875.80 | 1.89 | 34.05 | 12.52 |
| Ls-AKG38 (10 mg/kg) - d43 | 639.70 | 12,053.96 | 1.53 | 29.59 | 13.43 |
| Ls-AKG38 (20 mg/kg) - d1 | 880.03 | 15,364.53 | 2.50 | 38.91 | 10.78 |
| Ls-AKG38 (20 mg/kg) - d15 | 1,011.05 | 18,314.30 | 2.07 | 35.16 | 11.78 |
| Ls-AKG38 (20 mg/kg) - d29 | 1,017.30 | 21,373.77 | 1.69 | 35.96 | 14.74 |
| Ls-AKG38 (20 mg/kg) - d43 | 1,013.54 | 23,414.28 | 1.51 | 35.57 | 16.38 |
| Ls-AKG38 (40 mg/kg) - d1 | 1,648.38 | 31,180.74 | 2.41 | 43.10 | 12.40 |
| Ls-AKG38 (40 mg/kg) - d15 | 2,025.67 | 38,874.97 | 1.90 | 36.31 | 13.21 |
| Ls-AKG38 (40 mg/kg) - d29 | 2,231.92 | 45,921.63 | 1.62 | 31.15 | 13.36 |
| Ls-AKG38 (40 mg/kg) - d43 | 2,428.35 | 50,694.28 | 1.45 | 29.22 | 13.99 |

Example 39. Pharmacokinetic Studies of Drug and Liposome Lipid of Ls-AKG28 and Ls-AKG38 in CD-1 Mice This study was designed to determine the blood pharmacokinetic parameters for both drug and liposome lipid and the stability of drug retention in the liposomes of the liposome formulations of AKG-28 and AKG-38 in the blood plasma in vivo. The study was performed on male CD-1 (20-22 g) mice as described in General protocol above in Example 7, (5 mice per time point). Ls-AKG28 (Lot 235) and Ls-AKG38 (Lot 236) were prepared as described in Examples 30 and 31, respectively. The liposomes at the dose of 50 mg/kg (Ls-AKG28) or 90 mg/kg (Ls-AKG38) were injected in the lateral tail vein at time 0 and the blood was sampled at 0.083, 1, 3, 6, 24, and 48 hours post injection. The plasma concentration of AKG-28, AKG-38, and a fluorescent liposome lipid label ($DiIC_{18}(3)$-DS) was determined by HPLC. Plasma concentration of the liposome phospholipid was calculated from the fluorescent label quantification using liposome lots 235 and 236 as standards. Because the tissue affinity of non-encapsulated oxazolidinone drugs is expected to be many times higher than that of the liposome-encapsulated ones (as supported, for example, by the Vd of 2,291.26 mL/kg of non-encapsulated oxazolidinone, linezolid, in comparison with the Vd of 33.27-43.74 mL/kg for liposome-encapsulated AKG-28 in rats, see Example 37), the plasma drug concentration could be attributed predominantly to liposome-associated drug, and the plasma drug-liposome lipid (DL) ratio normalized to the original (pre-injection) DL value was taken as the measure of drug retention by the liposomes. Non-compartment PK analyses were performed using Summit Research Services, PK Solutions 2.0. For Ls-AKG28 and Ls-AKG38, this PK software was used to estimate the plasma maximum concentration ($C_{max}$), plasma maximum concentration divided by dose ($C_{max}$/dose), time of Cmax ($T_{max}$), last measured concentration ($C_{last}$), time of last measured concentration (Tim), area-under the plasma concentration versus time curve from 0 h to last time point ($AUC_{0\text{-}last}$) and 0 h to infinity ($AUC_{0\text{-}inf}$), $AUC_{0\text{-}last}$ divided by dose ($AUC_{0\text{-}last}$/dose), clearance (CL), volume of distribution (Vd), and elimination half-life.

The plasma concentration versus time profiles for drug after administration of Ls-AKG28 (FIG. 11A) and Ls-AKG38 (FIG. 11B) are presented. The summary of plasma PK parameters for Ls-AKG28 and Ls-AKG38 drug in plasma are presented in TABLE 28 and of the liposomal phospholipid is presented in TABLE 29. Dynamics of the DL ratio indicative of the stability of the drug encapsulation in vivo is presented in FIG. 11C and TABLE 30.

Ls-AKG28 has a near perfect in vivo stability with an undetectable loss of drug up to 48 hours after IV injection in mice. The half-life of drug release for Ls-AKG28 is 866.3 h using a monoexponential equation ($R^2=0.822$). Ls-AKG28 has a faster drug release rate. The half-life of drug release for Ls-AKG38 is 22.9 h using a monoexponential equation ($R^2=0.950$).

TABLE 28

Summary of plasma PK parameters for the drug after administration of Ls-AKG28 and Ls-AKG38.

| PK Parameter | Ls-AKG28 | Ls-AKG38 |
|---|---|---|
| $C_{max}$ [mg/L] | 1261.1 | 2320.3 |
| $C_{max}$ / Dose [mg/L]/[mg/kg] | 25.22 | 25.78 |
| $T_{max}$ [hr] | 0.083 | 0.083 |
| $C_{last}$ [mg/L] | 81.17 | 41.48 |
| $T_{last}$ [hr] | 48 | 48 |
| $AUC_{0\text{-}last}$ [hr*mg/L] | 19,820 | 30,346 |
| $AUC_{0\text{-}last}$ / Dose [hr*mg/L]/[mg/kg] | 396.4 | 337.2 |
| $AUC_{0\text{-}inf}$ [hr*mg/L] | 21,156 | 45,114 |
| Clearance [mL/hr/kg] | 2.35 | 2.93 |
| Vd [mL/kg] | 42.13 | 30.12 |
| $T_{1/2}$ [hr] | 12.42 | 7.14 |

TABLE 29

Summary of plasma PK parameters for liposomal phospholipid after administration of Ls-AKG28 and Ls-AKG38.

| PK Parameter | Ls-AKG28 | Ls-AKG38 |
|---|---|---|
| $C_{max}$ [mg/L] | 0.00485 | 0.00493 |
| $C_{max}$ / Dose [mg/L]/[mg/kg] | 24.87 | 25.54 |
| $T_{max}$ [hr] | 0.083 | 0.083 |
| $C_{last}$ [mg/L] | 0.00033 | 0.00041 |
| $T_{last}$ [hr] | 48 | 48 |
| $AUC_{0\text{-}last}$ [hr*mg/L] | 0.0769 | 0.0817 |
| $AUC_{0\text{-}last}$ / Dose [hr*mg/L]/[mg/kg] | 394.3 | 421.1 |
| $AUC_{0\text{-}inf}$ [hr*mg/L] | 0.0826 | 0.0979 |
| Clearance [mL/hr/kg] | 2.34 | 2.17 |
| Vd [mL/kg] | 43.3 | 41.0 |
| $T_{1/2}$ [hr] | 12.82 | 13.09 |

TABLE 30

Plasma drug to liposomal phospholipid ratio of Ls-AKG28 and Ls-AKG38 after IV administration in mice.

| | Ls-AKG28 drug to phospholipid ratio | | Ls-AKG38 drug to phospholipid ratio | |
|---|---|---|---|---|
| Time (h) | (%) of original | Standard deviation | (%) of original | Standard deviation |
| 0.083 | 101.1 | 1.75 | 101.7 | 4.29 |
| 1 | 102.4 | 2.10 | 97.6 | 1.56 |
| 3 | 101.9 | 1.27 | 94.2 | 4.20 |
| 6 | 101.2 | 0.89 | 97.4 | 2.08 |
| 24 | 98.7 | 1.92 | 63.3 | 2.36 |
| 48 | 98.4 | 2.54 | 22.7 | 1.75 |

Example 40. Pharmacokinetic Studies of Ls-AKG28 & Ls-AKG38 Drug in Mice after Multiple Doses of the Liposomes the Presence of ABC Effect The generation of anti-PEG antibodies has been shown to cause faster clearance of the liposomes containing PEG-lipid conjugates (pegylated liposomes) after repeated multiple injections (Ishida et al. Journal of Controlled Release 105 (2005) 305-317; Laverman et al. JPET 298 (2001) 607-612), a phenomenon known as accelerated blood clearance (ABC) effect. This study was performed to determine if there is an ABC effect after multiple repeated administration of various doses of Ls-AKG28 and Ls-AKG38 having various compositions. The liposomes were prepared according to Examples 33-35, lots 231, 232, 233, and 234. This study was performed on male CD-1 mice as generally described in Example 7. Five mice were used per group. The plasma concentration of AKG-28 and AKG-38 in mice was determined by HPLC. Mice were injected with the indicated dose and formulation once per week for a total of 4 injections. The drug was measured in the plasma at the 6 h time point after the $1^{st}$ and $4^{th}$ doses (FIG. 12). None of the groups tested had a significant accelerated clearance of the $4^{th}$ injection (2-tailed, unequal variance t-test all p values >0.05). This data confirms that these liposomal oxazolidinones can be dosed chronically for multiple weekly cycles with no significant negative impact on drug exposure.

TABLE 31

Plasma drug concentration for Ls-AKG28 and Ls-AKG38 for liposomal phospholipid after administration of Ls-AKG28 and Ls-AKG38. Abbreviations: SOS, 1 N TEA-SOS; AS, 0.5 M ammonium sulfate; Chol, cholesterol content as mol % of the sum of cholesterol and HSPC; DL, drug-to-lipid ratio, g/mol liposome phospholipid; % ID-percent of injected dose, average per group; SD- standard deviation.

| group | drug | trapping agent | Chol (mol%) | DL ratio | Injected dose (mg/kg) | 1st dose % ID | 1st dose SD | 4th dose % ID | 4th dose SD |
|---|---|---|---|---|---|---|---|---|---|
| 1 | AKG-28 | SOS | 40 | 266.9 | 65 | 61.99 | 7.20 | 55.71 | 13.88 |
| 2 | AKG-28 | SOS | 40 | 266.9 | 90 | 55.74 | 6.73 | 63.23 | 11.07 |
| 3 | AKG-28 | AS | 55 | 252.5 | 65 | 56.15 | 18.3 | 70.17 | 3.91 |
| 4 | AKG-28 | AS | 55 | 252.5 | 90 | 62.90 | 3.41 | 67.11 | 7.67 |
| 5 | AKG-38 | SOS | 55 | 538.1 | 90 | 54.67 | 6.49 | 51.57 | 8.55 |
| 6 | AKG-38 | SOS | 55 | 538.1 | 120 | 58.53 | 9.52 | 56.79 | 6.29 |
| 7 | AKG-38 | AS | 55 | 524.5 | 90 | 53.57 | 1.20 | 44.25 | 8.66 |
| 8 | AKG-38 | AS | 55 | 524.5 | 120 | 55.39 | 7.99 | 48.95 | 8.66 |

This data shows that after four cycles of treatment, the blood clearance rate of liposomal AKG-28 or liposomal AKG-38 of the disclosure did not increase, in contrast to what has been previously reported for other pegylated liposomes not containing a cytotoxic drug associated with the liposome.

Example 41. Dose-Dependent Tolerability of Liposomal AKG-28 and Liposomal AKG-38 in CD-1 Mice The aim of this studies was to evaluate tolerability of Ls-AKG28 and Ls-AKG38 injected as a single agent at different doses in mice. Female CD-1 mice of 20-22 grams (5 per each group) were administered with Ls-AKG28 (50, 65, 90 or 100 mg/kg/dose) or Ls-AKG38 (50, 90, 120 or 200 mg/kg/dose) by intravenous injection (tail vein) once weekly for 4 weeks. The liposomal formulations (Ls-AKG28 lot 231 and Ls-AKG38 lot 232) were prepared as described previously in Example 33. The control group was injected once weekly for 4 weeks with an equal volume of HEPES buffered saline (HBS, pH 7). The body weights were measured 3 times a week throughout the study and data were presented as a percentage of body weight change relative to the body weight measured at day zero.

The animals were humanely euthanized at the end of the study (72 hours post last treatment) using $CO_2$ inhalation. Blood samples were collected by a cardiac puncture and transferred to EDTA prefilled microtainers for hematology analysis (Homological ADVIA 120/2120i Analyzer) and to microtainers prefilled with lithium heparin for plasma separation. Plasma was separated from the cell fraction by centrifugation at 10000 rpm for 5 min and used for the biochemistry analysis (Cobas 6000 Analyzer). Tissue samples (liver, spleen, kidney, ling, heart, small intestine, and column) were collected in 50 ml tubes prefilled with 10% buffered formalin, which was replaced with 70% ethanol after 24 hrs. The tissues were embedded in paraffin, sectioned, stained with hematoxylin and eosin (H&E) and evaluated for histopathology by a board-certified veterinary pathologist.

As shown in FIG. 13A and FIG. 13B, there was no significant impact on the mice body weight observed for both Ls-AKG28 and Ls-AKG38 when treating for a total of four weekly doses at doses up to 90 mg/kg for Ls-AKG28, and 200 mg/kg for Ls-AKG38 relative to the saline control group.

Relative to the control group, there was no significant decrease in red blood cells count and hematocrit (FIG. 13C) in the mice treated with high doses of Ls-AKG38 (90, 120 and 200 mg/kg) relative to the saline control group. No such effect was observed in mice treated with Ls-AKG28. A significant decrease in the platelet count relative to the control group was found in the mice treated with Ls-AKG28 at the highest dose of 90 mg/kg (FIG. 13C), but still less than 25% reduction compared to saline controls. Treatment with either Ls-AKG28 or Ls-AKG38 did not significantly affect the white blood cell (WBC) count or that of blood liver enzymes (ALT and AST).

The histopathology analysis showed no test article-related findings in animals that received 50 and 65 mg/kg Ls-AKG28 (FIG. 13D). There were test article-related findings, that consisted of minimal vacuolization of macrophages (including Kupffer cells), in the liver, spleen, and kidney of animals that received 90 mg/kg LS-AKG28. Treatment with Ls-AKG38 was associated with test article-related findings in the liver and spleen at doses of 90 mg/kg and 120 mg/kg.

In the liver, there was minimal to mild vacuolation and hypertrophy of Kupffer cells at 50 and 90 mg/kg, moderate vacuolation and hypertrophy of Kupffer cells at 50 and 120 mg/kg, and minimal multifocal aggregation of vacuolated macrophages at 90 mg/kg and 120 mg/kg.

Treatment at the highest does of Ls-AKG38 (200 mg/kg) was associated with minimally increased extramedullary hematopoiesis (EMH) in the liver and spleen, minimal to mild multifocal mixed cell infiltrates and minimal individual hepatocellular necrosis in the liver and minimal focal hepatocellular necrosis (FIG. 13D). These microscopic findings were not considered test article-related due to their common occurrence as a background finding in this species.

Overall, both Ls-AKG28 and Ls-AKG38 monotherapy show good in vivo tolerability in mice even when the liposomal drugs were injected at the highest evaluated dose for each, 90 and 200 mg/kg for Ls-AKG28 and Ls-AKG38, respectively.

Example 42. In Vivo Tolerability of Ls-AKG28 and Ls-AKG38 Combined with BDQ/PMD or BDQ/PMD/MOX in Mice In this example in vivo tolerability of liposomal oxazolidinones was evaluated in combination with therapeutically relevant anti-TB drugs. The three drug regimens of bedaquiline, pretomanid, and linezolid (BDQ/PMD/LNZ or BPL) or bedaquiline, pretomanid, and moxifloxacin (BDQ/PMD/MOXI or BPM) have shown strong activity in the clinic when treating multidrug resistant tuberculosis (Conradie et al (2020) N Engl J Med 382(10) 893-902 and Tweed et al. (2019) Lancet Respir Med 7(12) 1048-1058), although the BPL regimen has been limited by toxicities primarily related to the addition of linezolid (Conradie et al (2020) N Engl J Med 382(10) 893-902). Here, we evaluated the safety and tolerability of two liposomal oxazolidinones, Ls-AKG28 and Ls-AKG38, when used as a part of both regimens, either by replacing linezolid in the BPL regimen, or through addition to the BPM regimen. CD-1 mice (5 per each group) were treated with either Ls-AKG28 (lot 231) or Ls-AKG38 (lot 232) alone or together with bedaquiline (BDQ) and pretomanid (PMD) combination. Ls-AKG28 (Lot 231) and Ls-AKG38 (Lot 232) were prepared as described in Example 33. Additionally, mice were co-treated with a triple combination of BDQ, PMD and moxifloxacin (MOXI) and liposomal oxazolidinones.

Ls-AKG28 (50 mg/kg/dose) and Ls-AKG38 (90 mg/kg/dose) were administered by intravenous injection via a tail vein once weekly for 4 weeks. Combination of BDQ, PMD and MOXI (25/100/100 mg/kg/dose respectively) was given by oral gavage daily, five times a week for 4 weeks. As an additional control, mice were treated with only BDQ/PMD/MOX or BDQ/PMD (25/100 mg/kg/dose respectively) plus linezolid (LNZ) given orally at 100 mg/kg/dose daily, five times a week for 4 weeks. The body weight measurements, tissue collection and analysis were conducted as described previously in Example 41.

As demonstrated in FIG. 14A and FIG. 14B, no significant effect of either Ls-AKG28 or Ls-AKG38 co-treated in combination with BDQ/PMD (BP) or BDQ/PMD/MOX (BPM) on the mice body weight was observed during the study. Both Ls-AKG28 and LsAKG38 show good tolerability in combination with BDQ/PMD or BDQ/PMD/MOX and did not affect hematology or blood biochemistry in the treated mice (FIG. 14C).

The histopathology data (FIG. 14D) showed no treatment related changes in case of Ls-AKG28 combined with BDQ/

PMD. Ls-AKG28+BDQ/PMD/MOX combination has minimal events associated with mixed cell and mononuclear cell infiltration in lung and heart. Treatment with Ls-AKG38 as a monotherapy was associated with minimal test article-related findings in the liver (inflammatory infiltration and hepatocellular necrosis). Administration of Ls-AKG38+ BDQ/PMD did not show any treatment related findings and combination of Ls-AKG38+BDQ/PMD/MOX was associated with minimal mixed cell infiltration in lung. Animals treated with BDQ/PMD/LNZ combination were associated with the treated-related finding of inflammatory infiltration in the liver, minimal hepatocellular necrosis and infiltration of vacuolated macrophages in the lung. Therefore, both Ls-AKG28 (50 mg/kg/dose) and Ls-AKG38 (90 mg/kg/dose) administered once weekly for 4 weeks showed good tolerability in mice in combination with BDQ/PMD or BDQ/PMD/MOX.

Example 43. Effect of Dose Scheduling on Tolerability of Ls-AKG28 and Ls-AKG38 Combined with BDQ/PMD in Mice In this study in vivo tolerability of Ls-AKG28 (50 mg/kg/dose) or Ls-AKG38 (100 mg/kg/dose) administered twice a week was compared with Ls-AKG28 (100 mg/kg/dose) or Ls-AKG38 (200 mg/kg/dose) given once a week. The liposomes were prepared according to Example 25 (Ls-AKG38, lot 279) and Example 26 (Ls-AKG28, lot 281). Both liposomal drugs were injected into CD-1 female mice (5 per each group) alone or in combination with BDQ/PMD (BP). BDQ/PMD (25 and 100 mg/kg/dose respectively) was given by oral gavage daily, five times a week for 4 weeks. The control group was injected once weekly for 4 weeks with HEPES buffered saline (HBS, pH 7). Blood and tissue samples were collected and analyzed as described above in Examples 41 and 42.

Both monotherapy and combination treatment of mice with Ls-AKG28 or Ls-AKG38 administered twice a week or once a week at higher dose did not affect neither body weight (FIG. 15A and FIG. 15B) or blood cell count and biochemistry (FIG. 15C).

Histopathology analysis of collected tissues (FIG. 15D) showed minimal interstitial mixed cell infiltrates composed of macrophages and neutrophils in 2 out of 5 mice that received Ls-AKG28 at 50 mg/kg (2qw) and mild interstitial mixed cell infiltrates in 1 out of 5 animals that received Ls-AKG28 at 100 mg/kg (1qw).

In the lungs of mice that received Ls-AKG28+BP at 50 mg/kg (1qw) there were minimal interstitial infiltrates composed of macrophages (1 out of 5 animals) or mixed (macrophages and neutrophils) inflammatory cells (3 out of 5 mice). In mice that received Ls-AKG28+BP at 100 mg/kg (1qw) there were minimal interstitial mixed cell infiltrates in 4 out of 5 animals. In addition, there were minimal multifocal foreign body granulomas associated with pale basophilic foreign material in the lungs of 2 out of 5 animals that received Ls-AKG28+BP at 100 mg/kg (1qw). These microscopic findings were not considered test article-related due to their common occurrence as a background finding in this species included minimal multifocal mixed cell infiltrates and minimal individual hepatocellular necrosis in the liver of 1 out of 5 animals that received Ls-AKG28+BP at 50 mg/kg (2qw).

The similar microscopic findings associated with Ls-AKG38 treatment (alone or in combination) were not considered to be test article related included minimally increased extramedullary hematopoiesis (EMH) in the liver and spleen, minimal to mild multifocal mixed cell infiltrates and minimal individual hepatocellular necrosis in the liver, minimal focal hepatocellular necrosis, minimal focal foreign body granuloma (associated with pale basophilic foreign material) in the lung, and minimal mixed cell infiltrates in the lung. Due to their minimal to mild nature, sporadic incidence, presence in the saline control group, and occurrence as common background findings in this species, these findings were not considered treatment related.

Therefore, both Ls-AKG28 and Ls-AKG38 (alone or in combination with BDQ/PMD) administered twice a week at doses 50 mg/kg and 100 mg/kg respectively or at doubled doses of 100 mg/kg and 200 mg/kg once a week were well tolerated in mice and did not affected body weight, hematology, or histopathology of the treated animals.

Example 44. In Vivo Tolerability of Ls-AKG28 and Ls-AKG38 in Rats

The objectives of this study were to determine the potential toxicity of Ls-AKG28 (lot 275) and Ls-AKG38 (lot 276) in rats. Ls-AKG28 (Lot 275) and Ls-AKG38 (Lot 276) were prepared as described in Examples 22 and 23, respectively. Male Sprague-Dawley rats were administered with Ls-AKG28 (10, 20 or 40 mg/kg/dose) or LsAKG-38 (20, 40 or 80 mg/kg/dose) by intravenous injection (tail vein) once weekly for 8 weeks. The control group was injected once weekly for 8 weeks with an equal volume of HEPES buffered saline (HBS, pH 7). Before the endpoint of the study animals were humanely euthanized by exsanguination from the abdominal aorta following isoflurane anesthesia. Blood and tissue samples were collected for evaluation of clinical pathology parameters. Representative samples of tissues were collected and preserved in 10% neutral buffered, embedded in paraffin, sectioned, mounted on glass slides, stained with hematoxylin and eosin, and evaluated for histopathology by a board-certified veterinary pathologist. Blood hematology analysis was performed using Homological ADVIA 120/2120i Analyzer and blood biochemistry was analyzed using Cobas 6000 Analyzer.

The following parameters and end points were also evaluated: mortality and moribundity check, clinical observations, body weights, food consumption, nerve conduction velocity (NCV) and muscle action potential (MAP), functional observation battery (FOB).

Nerve Conduction Velocity (NCV) and Muscle Action Potential (MAP) were conducted on week 8. During the recording sessions, the animals were anesthetized with isoflurane. Caudal nerve NCV measures the speed of conduction in the caudal nerve, which runs along the central bone of the tail. This nerve is approximately 50% longer than any other nerve in the rat and it is especially vulnerable to a length-dependent distal axonopathy. NCV was measured over a distance of 50 mm and is sensitive to nodal and transmembrane currents, the structure and mean cross-sectional diameter of the responding axons and the integrity of the associated myelin sheaths. The amplitude of the evoked response reflects the number and synchrony of the activated fibers. Data were recorded with the active recording electrode positioned approximately 10 mm below the hair line on the tail (determined visually) and the stimulating cathode 50 mm further distal. The amplitude and the onset latency of the signal were recorded, and velocity was calculated by dividing the distance between the stimulating cathode and the active electrode by the absolute onset latency of the initial depolarizing current.

Digital nerve NCV measures the speed of conduction in the sensory digital nerve. The digital nerve is the distal extreme of the sciatic nerve innervating the dorsal surface of the hind paw. Nerve conduction velocity is sensitive to the nodal and transmembrane currents, structure and mean cross-sectional diameter of the responding axons and the integrity of the associated myelin sheaths. Data were recorded with the active recording electrode positioned at the ankle behind the lateral malleolus and the stimulating cathode at the base of the second digit of the hind paw. The amplitude and the onset latency of the signal were recorded, and velocity was calculated by dividing the distance between the stimulating cathode and the active electrode by the absolute onset latency of the initial depolarizing current.

Tibial motor conduction (onset latency) measures the response properties of the intrinsic muscles of the rat hind paw following stimulation of the motor fibers at the distal portion of the tibial nerve. Data were recorded with the active electrode positioned in a lateral dorsal muscle of the hind paw (equivalent to the extensor digitorum *brevis* muscle in humans) and the stimulating cathode positioned proximal to the ankle, behind the lateral malleolus. The speed of nerve conduction in the motor axons was estimated from the onset latency of the induced compound muscle action potential (CMAP). The amplitude of the CMAP was determined at the peak of the response following supramaximal stimulation of the associated nerve.

There were no Ls-AKG28, Ls-AKG38-related unscheduled deaths, clinical observations, or effects on body weights (FIG. 16A and FIG. 16B), NCV and MAP (TABLE 34), FOB (TABLE 35), food consumption, coagulation parameters, organ weights or macroscopic findings (data is not shown). The greatest decline nerve conductance velocity for the caudal or left digital nerves in any liposomal treatment group was less than 5%, despite a 16.5-fold increase in potency adjusted dose (based on free drug potency against *M. tuberculosis* Erdmann strain in Example 2) for Ls-AKG28 or Ls-AKG38 compared to linezolid.

Administration of Ls-AKG28 and Ls-AKG38 at doses >20 mg/kg resulted in a statistically significant decrease of platelet count (difference up to 20% compared to control group). No additional effects on the other hematological and blood biochemistry parameters were observed (TABLE 32, TABLE 33)

Administration of Ls-AKG28 by intravenous injection to male Sprague-Dawley rats once weekly for 8 weeks at doses >10 mg/kg/dose resulted in spleen, kidney, and liver microscopic findings (Table 36). The spleen had minimal to moderate macrophage vacuolation with basophilic granules and minimal to mild accumulation of basophilic material in rats given 20 or 40 mg/kg/dose. The kidneys of rats given 40 mg/kg/dose had minimal glomerular mesangial cell vacuolation. The liver had minimal centrilobular single cell necrosis and minimal to mild centrilobular hepatocellular degeneration at all doses.

TABLE 32

Impact of liposomal AKG-28 and AKG-38 on level of liver enzymes in blood following treatment for eight weekly doses in male Sprague Dawley rats.

| Group | ALT (U/L) | AST (U/L) |
|---|---|---|
| saline | 105.7 ± 23.0 | 52.2 ± 9.2 |
| Ls-AKG28 (10 mg/kg) | 89.5 ± 16.5 | 37.7 ± 9.4 |
| Ls-AKG28 (20 mg/kg) | 97.5 ± 20.3 | 38.0 ± 8.1 |
| Ls-AKG28 (40 mg/kg) | 98.5 ± 10.5 | 56.3 ± 16.8 |

TABLE 32-continued

Impact of liposomal AKG-28 and AKG-38 on level of liver enzymes in blood following treatment for eight weekly doses in male Sprague Dawley rats.

| Group | ALT (U/L) | AST (U/L) |
|---|---|---|
| Ls-AKG38 (10 mg/kg) | 98.7 ± 14.0 | 38.8 ± 10.2 |
| Ls-AKG38 (20 mg/kg) | 92.0 ± 23.6 | 38.2 ± 8.1 |
| Ls-AKG38 (40 mg/kg) | 93.3 ± 9.4 | 45.8 ± 10.1 |

TABLE 33

Impact of liposomal AKG-28 and AKG-38 on blood cell counts and hematocrit (HCT) following treatment for eight weekly doses in male Sprague Dawley rats.

| Group | RBC ($10^6$/μl) | HCT (%) | WBC ($10^3$/μl) | PLT ($10^3$/μl) |
|---|---|---|---|---|
| saline | 52.2 ± 9.2 | 8.11 ± 0.48 | 9.92 ± 3.13 | 1234 ± 113 |
| Ls-AKG28 (10 mg/kg) | 37.7 ± 9.4 | 8.13 ± 0.26 | 9.26 ± 1.10 | 1143 ± 88 |
| Ls-AKG28 (20 mg/kg) | 38.0 ± 8.1 | 8.26 ± 0.35 | 8.83 ± 1.30 | 1089 ± 118 |
| Ls-AKG28 (40 mg/kg) | 56.3 ± 16.8 | 8.15 ± 0.34 | 8.79 ± 2.44 | 973 ± 66 |
| Ls-AKG38 (10 mg/kg) | 38.8 ± 10.2 | 7.74 ± 0.41 | 10.46 ± 1.62 | 1090 ± 50 |
| Ls-AKG38 (20 mg/kg) | 38.2 ± 8.1 | 7.90 ± 0.39 | 7.23 ± 1.18 | 1039 ± 75 |
| Ls-AKG38 (40 mg/kg) | 45.8 ± 10.1 | 7.65 ± 0.43 | 9.37 ± 3.56 | 984 ± 74 |

TABLE 34

Impact of liposomal AKG-28 and AKG-38 on nerve conductance following treatment for eight weekly doses in male Sprague Dawley rats.

| Group | Caudal NCV (m/sec) | Left Digital NCV (m/sec) | Left Tibial MAP (msec) |
|---|---|---|---|
| saline | 48.7 ± 2.7 | 31.5 ± 1.8 | 1.675 ± 0.099 |
| Ls-AKG28 (10 mg/kg) | 49.6 ± 1.9 | 32.6 ± 2.3 | 1.678 ± 0.092 |
| Ls-AKG28 (20 mg/kg) | 49.1 ± 2.3 | 32.3 ± 4.6 | 1.707 ± 0.124 |
| Ls-AKG28 (40 mg/kg) | 46.8 ± 3.4 | 33.9 ± 2.2 | 1.667 ± 0.078 |
| Ls-AKG38 (10 mg/kg) | 47.6 ± 1.8 | 32.7 ± 1.8 | 1.680 ± 0.055 |
| Ls-AKG38 (20 mg/kg) | 45.6 ± 2.6 | 32.9 ± 3.2 | 1.752 ± 0.084 |
| Ls-AKG38 (40 mg/kg) | 48.6 ± 4.8 | 31.0 ± 1.7 | 1.717 ± 0.153 |

TABLE 35

Impact of liposomal AKG-28 and AKG-38 on nerve functional observational battery following treatment for eight weekly doses in male Sprague Dawley rats.

| Group | Hindlind Splay (cm) | Hindlimb Grip Mean (g) | Forelimb Grip Mean (g) |
|---|---|---|---|
| saline | 11.10 ± 1.50 | 670.2 ± 68.9 | 1274.8 ± 132.9 |
| Ls-AKG28 (10 mg/kg) | 11.20 ± 2.00 | 715.9 ± 50.9 | 1335.2 ± 153.0 |
| Ls-AKG28 (20 mg/kg) | 12.20 ± 1.50 | 695.7 ± 125.9 | 1331.9 ± 117.1 |
| Ls-AKG28 (40 mg/kg) | 11.50 ± 1.60 | 709.9 ± 61.9 | 1140.2 ± 169.9 |
| Ls-AKG38 (10 mg/kg) | 12.10 ± 1.30 | 741.5 ± 92.9 | 1373.6 ± 107.2 |
| Ls-AKG38 (20 mg/kg) | 11.70 ± 2.70 | 740.9 ± 74.6 | 1281.6 ± 114.8 |
| Ls-AKG38 (40 mg/kg) | 11.40 ± 2.60 | 737.6 ± 75.7 | 1350.1 ± 147.7 |

TABLE 36

Summary of microscopic findings in tissues following treatment for eight weekly doses with liposomal AKG-28 and AKG-38 in male Sprague Dawley rats.

| Group | 1 | 2 | 3 | 4 | 5 | 6 | 7 | 8 |
|---|---|---|---|---|---|---|---|---|
| Test material | linezolid | | Ls-AKG28 | | | Ls-AKG38 | | |
| Dose (mg/kg/dose) | 0 | 50 | 10 | 20 | 40 | 20 | 40 | 80 |
| No. Animals per Group | 6 | 6 | 6 | 6 | 6 | 6 | 6 | 6 |
| Liver (No. Examined) | 6 | 6 | 6 | 6 | 6 | 6 | 6 | 6 |
| Degeneration, hepatocellular, centrilobular | (0)[a] | (0) | (1) | (3) | (6) | (1) | (4) | (6) |
| Minimal | 0 | 0 | 1 | 3 | 2 | 1 | 3 | 1 |
| Mild | 0 | 0 | 0 | 0 | 4 | 0 | 1 | 5 |
| Single cell necrosis, centrilobular | (0) | (2) | (3) | (4) | (6) | (4) | (5) | (6) |
| Minimal | 0 | 2 | 3 | 4 | 6 | 4 | 5 | 6 |
| Spleen (No. Examined) | 6 | 6 | 6 | 6 | 6 | 6 | 6 | 6 |
| Vacuolation, macrophages | (0) | (0) | (0) | (6) | (6) | (0) | (0) | (0) |
| Minimal | 0 | 0 | 0 | 1 | 0 | 0 | 0 | 0 |
| Mild | 0 | 0 | 0 | 2 | 0 | 0 | 0 | 0 |
| Moderate | 0 | 0 | 0 | 3 | 6 | 0 | 0 | 0 |
| Accumulation, basophilic material | (0) | (0) | (0) | (4) | (6) | (0) | (0) | (0) |
| Minimal | 0 | 0 | 0 | 1 | 0 | 0 | 0 | 0 |
| Mild | 0 | 0 | 0 | 3 | 6 | 0 | 0 | 0 |
| Kidney (No. Examined) | 6 | 6 | 6 | 6 | 6 | 6 | 6 | 6 |
| Vacuolation, mesangial cell, glomerular | (0) | (0) | (0) | (0) | (6) | (0) | (0) | (0) |
| Minimal | 0 | 0 | 0 | 0 | 6 | 0 | 0 | 0 |

[a]Numbers in parentheses represent the number of animals with the finding.

Administration of Ls-AKG38 at doses >20 mg/kg/dose resulted in liver microscopic findings of minimal centrilobular single cell necrosis and minimal to mild centrilobular hepatocellular degeneration at all doses.

In comparison, the Ls-AKG28 and Ls-AKG38 dosed rats had an increased incidence of liver single cell necrosis at all doses compared to linezolid dosed rats. The liver of Ls-AKG28 and Ls-AKG38 dosed rats had a similar incidence and severity of centrilobular hepatocellular degeneration at all doses. The Ls-AKG28 dosed rats also had vacuolated macrophages and basophilic material in the spleen at 20 or 40 mg/kg/dose and glomerular mesangial cell vacuolation in the kidneys at 40 mg/kg/dose.

In conclusion, administration of Ls-AKG28 by multiple intravenous injections over 8 weeks was well tolerated in rats at levels of 10, 20 and 40 mg/kg/dose. Administration of Ls-AKG38 by multiple intravenous injections over 8 weeks was well tolerated in rats at levels of 20, 40 and 80 mg/kg/dose. Example 2 showed that AKG-28 is 33-fold more potent, and AKG-38 17-fold more potent, in killing *M. tuberculosis* in vitro (Erdmann strain) than linezolid. Thus, when corrected for potency, the rats are showing no significant neuropathy (changes to nerve conductance velocity), elevation of liver enzymes, reduced red blood cell counts or hematocrit, or reductions in body weight at linezolid-equivalent doses of 1320-1336 mg/kg, which is 16.5-fold higher than the clinically relevant dose of 80 mg/kg for linezolid.

Example 45. Efficacy of Liposomal AKG-28 and AKG-38 in Combination with Bedaquiline and Pretomanid, or with Bedaquiline (B), Pretomanid (Pa), and Moxifloxacin (M) in Kramnik (C3HeB/FeJ Mouse Mode of Pulmonary *M. tuberculosis* Infection The C3HeB/FeJ (Kramnik) mouse infection model exhibits advanced, hypoxic, caseating granulomas in lungs after TB infection (Driver E., et al., Antimicrobial Agents and Chemotherapy, 2012, vol. 56, p. 3181-3195). The lung pathology observed in C3HeB/FeJ mice resembles more closely the heterogeneity in lesion pathology and bacterial populations as seen in TB patients and was used to evaluate the efficacy of liposomal AKG-28 and AKG-38 at moderate weekly doses of 50 and 90 mg/kg. Ls-AKG28 (Lot 275) and Ls-AKG38 (Lot 276) were prepared as described in Examples 22 and 23, respectively. The lung pathology in C3HeB/FeJ mice shows three different types of lesions that were classified as caseous necrotic lesions delineated by a collagen rim (Type I), fulminant neutrophilic alveolitis (Type II), and cellular lesions (Type III) (see Irwin et al. (2015) Dis Model Mech 8, 591-602). 8-10-week-old C3HeB/FeJ female mice were infected with LDA (Low Dose Aerosol infection). A Glas-Col Inhalation Exposure System was utilized to infect the mice with a target of ~50-75 bacilli/mouse (Erdman strain). Five mice per aerosol run were sacrificed day 1 post-infection to determine bacterial uptake.

At 8 weeks post-infection, 8 mice were sacrificed to determine bacterial load in the lungs and spleens at the start of therapy. Mice were weighed prior to sacrifice. Gross pathology observations of the lungs and spleens were made. Whole lungs and spleens were extracted and frozen at −80° C. Previously frozen tissues were recovered and homogenized in 1×PBS using a Precellys homogenizer. Lung and spleen homogenates were plated on 7H11 agar quad plates. Enumeration of CFU occurred after 3-5 weeks incubation at 37° C. in a dry-air incubator. Therapy was administered via oral gavage or intraperitoneal (i.p.) injection, starting 8 weeks post-infection and continuing for 4-6 consecutive weeks (M-F for gavage, once weekly for i.p. injection). Bedaquiline (B), Pretomanid (Pa), moxifloxacin (M), and linezolid (L) were given 5 days per week for 4 or 6 weeks in total, 200 µL/dose, by gavage. Bedaquiline (25 mg/kg) was dosed first, then pretomanid (100 mg/kg), given no less than one hour later. Moxifloxacin (100 mg/kg) or linezolid (100 mg/kg) were given 4 hours later than the pretomanid dose. The liposomal formulations were given once per week for 4 or 6 weeks in total.

Daily observations of the mice were made at the time of dosing and weights were taken at least once per week. The sacrifices occurred 2 weeks after the four or six week treatment had been completed. Eight mice per treatment group were weighed prior to sacrifice. Whole lungs and spleens were aseptically harvested for all treatment groups. Gross pathology observations of the lungs and spleens were diagrammed. Lungs were photographed for gross lesion analysis. Whole lungs and spleens were frozen at −80° C. Previously frozen tissues were recovered and homogenized in either 1×PBS or 10% Bovine Serum Albumin (BSA) in 1×PBS (to avoid drug carry-over, *see below for explanation) using a Precellys homogenizer. Lung and spleen homogenates were plated on 7H11 agar or charcoal containing 7H11 quad plates, after homogenization and serially diluted in 1×PBS or 10% BSA. Enumeration of CFU occurred after 5 weeks incubation at 37° C. in a dry-air incubator.

Addition of Ls-AKG28 to BPaM treatment resulted in a further 0.64 log 10 CFU reduction vs. BPaM in lungs, while BPaM+Ls-AKG38 treatment gave a further log 10CFU reduction of 0.25 versus BPaM after 4 weeks of treatment. The substitution of either Ls-AKG28 or Ls-AKG38 for linezolid (L) in the NIX (BPaL) regimen resulted in improved efficacy over BPaL at six weeks of treatment. At 6 weeks of treatment, the substitution of Ls-AKG38 for linezolid in the BPaL regimen did significantly improve efficacy compared the BPaL treated group. Specifically, BPaL treatment for 6 weeks resulted in a 4.18 log 10 CFU reduction, with plates for one of 8 animals having no CFU. BPa+Ls-AKG28 treatment for 6 weeks resulted in a 4.68 log 10 CFU reduction, which was not a statistically significant difference from BPaL. BPa+Ls-AKG38 treatment for 6 weeks resulted in a 5.26 log 10 CFU reduction, with plates for 2 of 8 animals having no CFU. This was a statistically significant reduction vs. BPaL (p=0.04, Dunnett's test).

In the spleen at 6 weeks of treatment, substitution of either liposomal formulation for linezolid in the NIX regimen resulted in a slight improvement in lung efficacy relative to the BPaL treated group. Treatment for 6 weeks with the NIX regimen resulted in a 3.56 log 10 CFU reduction, with plates for 3 of 8 animals showing no CFU. Treatment for 6 weeks with BPa+Ls-AKG28 resulted in a 4.18 log 10 CFU reduction, with plates for 5 of 8 mice showing no CFU. Treatment for 6 weeks with BPa+Ls-AKG38 resulted in a 04.38 log 7 CFU reduction, with plates for 6 of 8 mice showing no CFU. CFU loads in the spleens of mice on 6 weeks of drug treatment were low and approaching the lower limit of detection of 0.66 log 10 CFU.

TABLE 37

Lung Log CFU

| Treatment | Doses | 4 week (Log CFU) | 6 week (Log CFU) |
|---|---|---|---|
| Untreated | | 7.71 ± 0.65 | |
| BPaM | 25/100/100 mg/kg | 3.05 ± 0.31 | |
| BPaM + Ls-AKG28 | 25/100/100/50 mg/kg | 2.41 ± 0.37 | |
| BPaM + Ls-AKG38 | 25/100/100/90 mg/kg | 2.80 ± 0.57 | |
| BPaL | 25/100/100 mg/kg | | 2.83 ± 1.28 |
| BPa + Ls-AKG28 | 25/100/100/50 mg/kg | | 2.33 ± 0.95 |
| BPa + Ls-AKG38 | 25/100/100/90 mg/kg | | 1.75 ± 0.59* |

*2/8 mice had no measurable CFU; all mice were listed at the detection limit of 0.96 log CFU.

TABLE 38

Spleen Log CFU

| Treatment | Doses | 4 week (Log CFU) | 6 week (Log CFU) |
|---|---|---|---|
| Untreated | | 5.36 ± 0.48 | |
| BPaM | 25/100/100 mg/kg | 2.07 ± 0.65 | |
| BPaM + Ls-AKG28 | 25/100/100/50 mg/kg | 1.15 ± 0.45 | |
| BPaM + Ls-AKG38 | 25/100/100/90 mg/kg | 1.85 ± 0.96 | |
| BPaL | 25/100/100 mg/kg | | 1.56 ± 0.82* |
| BPa + Ls-AKG28 | 25/100/100/50 mg/kg | | 0.94 ± 0.45** |
| BPa + Ls-AKG38 | 25/100/100/90 mg/kg | | 0.74 ± 0.23*** |

*3/8 mice had no measurable CFU
**5/8 mice had no measurable CFU;.
***6/8 mice had no measurable CFU; all mice were listed at the detection limit of 0.66 log CFU. all mice that had no measurable CFU were listed at the detection limit of 0.66 log CFU. This shows that Ls-AKG38 and Ls-AKG28 are more active than linezolid when combined with bedaquiline and pretomanid at a moderate and highly tolerable dose of both drug after only six weeks of treatment. As Example 42 and 43 show, both Ls-AKG28 and Ls-AKG38 can be safely dosed in this combination at doses at least twice as high as those used in this study. It also shows that when Ls-AKG28 is added to a regimen of BPaM there is a further decrease in CFU in both lungs and spleen at this same highly tolerable dose.

Example 46. Efficacy of Monotherapy with Liposomal AKG-28 in Balb/c Model of Pulmonary *Mycobacterium tuberculosis* Infection The schedule and dose dependent efficacy of Ls-AKG28 was determined in comparison to free linezolid at clinically relevant doses of 50 and 100 mg/kg in a chronic Balb/c model of tuberculosis. In the chronic Balb/c mouse model, the bacterial load in lungs reaches a steady state 4-5 weeks after *M. tuberculosis* infection (Lenaerts et al. (2005) AAC 49(6) 2294-2301). Ls-AKG28 (Lot 286) was prepared as described in Example 28. 6-8 week old Balb/c female mice were obtained from Jackson Laboratories, and the mice were infected with a LDA (Low Dose Aerosol infection), using the Glas-Col Inhalation Exposure System to infect the mice with ~50-100 bacilli/mouse of *M. tuberculosis* Erdman.

Mice (n=3) were sacrificed day 1 post-infection to determine bacterial uptake. Whole lungs were aseptically harvested in Precellys tubes (Bertin cat #KT03961-1-396.7) and homogenized in 4 ml of 1×PBS using a Precellys tissue homogenizer. Undiluted homogenate was transferred to two large 7H11 agar plates (150×15 mm) and the plates were incubated in sealed zip top bags at 37° C. in a dry-air incubator for at least 21 days until colonies could be enumerated. At Day 28 post-aerosol infection, mice (n=5) were sacrificed to determine bacterial load in the lungs and spleens at the start of therapy. Mice were weighed prior to sacrifice. Gross pathology observations of the lungs and spleens were made. Lungs (divided into left lobe and upper right [cranial] lobes)+accessory lobe) and spleens were aseptically harvested and frozen at −80° C. Lower right lung lobes [caudal] were collected in 4% paraformaldehyde (PFA) for histology. Previously frozen tissues were recovered and homogenized in 1×PBS using a Precellys homogenizer. Lung and spleen homogenates were plated on 7H11 agar quad plates. Enumeration of CFU occurs after 3-5 weeks incubation at 37° C. in a dry-air incubator.

Linezolid in 5% PEG-200(Sigma P3015, lot MKBW3119V)/95% (0.5%) methylcellulose (Sigma M0430, lot 031M0051) was administered via oral gavage (200 uL per mouse) is started day 28 post-aerosol infection (Mon) and continued for 2-8 weeks 5 of 7 days per week. Ls-AKG28 was administered by injection i.p, once or twice per week at doses of 50 or 100 mg/kg. The final sacrifice occurred 3 days following the last day of dosing for mice treated with drug for 2, 4 or 8 weeks. Mice were weighed prior to sacrifice. Gross pathology observations of the lungs and spleens were made. Lungs (divided into left lobe, upper right lobes+accessory lobe) and spleens were aseptically harvested and frozen at −80° C. Lower right lung lobes were collected in 4% PFA for histology. Previously frozen tissues were recovered and homogenized in 10% Bovine Serum Albumin (BSA) in 1×PBS to avoid drug carry-over. After homogenization, lung and spleen homogenates were serially diluted in 1×PBS and 10% BSA and then plated on 7H11 agar or charcoal containing 7H11 quad plates. Enumeration of CFU occurred after 3-5 weeks incubation at 37° C. in a dry-air incubator.

The reduction in Lung CFU counts is shown in TABLE 39 and in Spleen CFU counts in TABLE 40. Treatment with Ls-AKG28 at 50 mg/kg twice weekly or once weekly at 100 mg/kg results in a 1.5 Log 10 CFU reduction after only two weeks in the lungs, compared to less than 0.15 Log 10 CFU reduction for linezolid at 100 mg/kg (q1×5). This reduction was nearly 3 Log 10 CFU in the spleen at two weeks for Ls-AKG28. At eight weeks, all of the mice treated with Ls-AKG28 were completely sterile (or below the detection limit of 1.13 in lungs and 0.66 in spleen) at eight weeks compared to 2.45 log 10 CFU in lungs and 3.15 log 10 CFU in spleen for linezolid at the higher 100 mg/kg dose of linezolid. This monotherapy activity is surprising for an oxazolidinone in the absence of an active combination partner like bedaquiline, and a relatively short period of time in only eight weeks. For example, at eight weeks of treatment, linezolid monotherapy showed log 10 CFU counts in the 4-6 range for Balb/c and C3HeB/FeJ mice (Lanoix et al. (2015) Dis Models Mech. 8, 603-610), and activity remains modest even up to 1000 mg/kg/week at schedules ranging from 3-14 doses/week (Bigelow et al (2021) J Infec. Dis. 223(11) 1855-1864).

TABLE 39

Lung Log CFU

| Treatment | Dose, schedule | 2 week (Log CFU) | 4 week (Log CFU) | 8 week (Log CFU) |
|---|---|---|---|---|
| Untreated | | 5.71 ± 0.15 | 5.47 ± 0.19 | |
| Linezolid | 50 mg/kg, q1x5 | | 4.61 ± 0.31 | |
| | 100 mg/kg, q1x5 | 5.58 ± 0.10 | 4.17 ± 0.21 | 2.45 ± 0.37 |
| Ls-AKG28 | 50 mg/kg, | | 3.81 ± 0.33 | |
| Ls-AKG28 | 50 mg/kg, | 4.01 ± 0.20 | 2.30 ± 0.57 | |
| Ls-AKG28 | 100 mg/kg, | 4.09 ± 0.34 | 2.65 ± 0.70 | 1.13 ± 0.00* |

*6/6 mice had no measurable CFU; all mice were listed at the detection limit of 1.13 log CFU.

TABLE 40

Spleen Log CFU

| Treatment | Dose, schedule | 2 week (Log CFU) | 4 week (Log CFU) | 8 week (Log CFU) |
|---|---|---|---|---|
| Untreated | | 5.08 ± 0.31 | 4.77 ± 0.21 | |
| Linezolid | 50 mg/kg, q1x5 | | 4.32 ± 0.28 | |
| | 100 mg/kg, q1x5 | 4.53 ± 0.25 | 3.90 ± 0.28 | 3.15 ± 0.27 |
| Ls-AKG28 | 50 mg/kg, | | 1.74 ± 0.65 | |
| Ls-AKG28 | 50 mg/kg, | 1.71 ± 0.59 | 0.67 ± 0.02* | |
| Ls-AKG28 | 100 mg/kg, | 2.25 ± 0.82 | 1.07 ± 0.93** | 0.66 ± 0.00*** |

*4/5 mice had no measurable CFU
**1/6 mice had no measurable CFU;.
***6/6 mice had no measurable CFU; all mice were listed at the detection limit of 0.66 log CFU. all mice that had no measurable CFU were listed at the detection limit of 0.66 log CFU.

Example 47. Efficacy of Liposomal AKG-38 in Rabbit Endocarditis Model of Methicillin-Resistant *Staphylococcus aureus* (MRSA)

*Staphylococcus aureus* infections, especially involving the endovascular system (e.g., IE; cardiac and hemodialysis device infections, etc) are prevalent, and are associated with unacceptably high morbidity, mortality and post-therapy relapse rates. This is particularly true when such infections are caused by multi-drug-resistant strains of MRSA. Moreover, even when MRSA strains have minimal inhibitory concentrations (MICs) for vancomycin (the "workhouse" anti-MRSA agent) within the accepted Clinical Standards Laboratory Institute (CLSI) "susceptible" range (i.e., ≤2 ug/ml), clinical outcomes remain suboptimal.

A prototypical high-inoculum endovascular biofilm MRSA infection model, left-sided aortic valve rabbit IE, was employed in female New Zealand white rabbits of six months of age and 2.2-2.5 kg. Rabbits underwent general anesthesia with an intramuscular injection of xylazine and ketamine. They then had their fur clipped over the right carotid artery to expose skin. The cut-down site over the right carotid artery was locally anesthetized with 1% lidocaine. A cut-down was then performed to expose the right carotid artery. This was isolated, proximally ligated, then cannulated retrograde with a polyethylene catheter, across the aortic valve into the left ventricle, where it was then tied in-place and left indwelling for the duration of the study. For left-sided IE at 48 h after catheter placement (to induce sterile aortic valve and ventricular vegetations), animals had IE induced by an IV challenge of ~2×10$^5$ cfu of the MW2 strain. The MRSA strain MW-2 (USA 400—clonal complex [CC] 1) used: i) is clinically-derived; ii) is genome-sequenced; iii) represents a common hospital-acquired MRSA clonotypes; iv) is virulent in the experimental IE model; and v) is daptomycin (DAP)-susceptible in vitro. Infection spreads from the heart valve infected vegetations to kidneys and spleen.

Liposomal AKG-38 (Ls-AKG38) was given, in separate animal groups, either once (in combination therapy with DAP) or twice (once in combination therapy with DAP; then a second infusion at the time of the post-DAP treatment sacrifice in a "relapse group of animals" not receiving further DAP therapy) at a dose of 40 mg/kg/dose. Ls-AKG38 (Lot 292) was prepared as described in Example 29. The first Ls-AKG38 infusions will follow the first DAP iv dose by ~1 h. The DAP was given at a sublethal dose of 2 mg/kg daily for four days, either alone or in combination with Ls-AKG38.

Animals were humanely euthanized, and key target organs sterilely removed and quantitatively cultured (blood, cardiac vegetations; kidneys and spleen for left-sided IE) on either day 6 (DAP alone or DAP+single dose of Ls-AKG38) or day 12 (DAP+two doses of Ls-AKG38 on days 1 and 6). Quantitative target tissue cultures were performed by standard preparation of sterilely removed organs by weighing, homogenization, serial dilutions and plate cultures. Serial dilution of blood and quantitative cultures were performed similarly. Data for blood cultures and each target organ for the different treatment groups were calculated as mean and median $\log_{10}$ cfu/ml or $\log_{10}$ cfu/gm of tissue (f SD), respectively.

Preliminary data from a left ventricular endocarditis model of MRSA in rabbits is shown below in Table 41. Daptomycin alone or Daptomycin plus a single dose of Ls-AKG38 showed no significant efficacy on day 6 post inoculation. Surprisingly, a second injection of Ls-AKG38 resulted in remarkably efficacy on day 12, including sterilization in 4/5 rabbits in all five tissues, and a more than 6 Log reduction in CFU in multiple organs. This data suggests that endocarditis could effectively be treated with Ls-AKG38 following discontinuation of daily daptomycin.

TABLE 41

| | Vegetations | Kidneys | Spleen | Liver | Lungs |
|---|---|---|---|---|---|
| Control (4) | 7.45 ± 0.60 | 5.93 ± 0.54 | 5.71 ± 0.85 | 5.03 ± 0.51 | 4.73 ± 0.46 |
| Daptomycin | 8.13 ± 0.17 | 6.90 ± 0.61 | 7.43 ± 0.38 | 6.77 ± 0.90 | 6.37 ± 0.64 |
| Daptomycin (relapse) | 9.18 ± 0.22 | 8.11 ± 0.49 | 7.91 ± 0.54 | 7.65 ± 0.26 | 8.00 ± 0.66 |
| Daptomycin + Ls-AKG38 (1 dose) | 8.26 ± 0.66 | 6.70 ± 0.83 | 5.65 ± 0.61 | 5.75 ± 0.83 | 5.97 ± 0.77 |
| Daptomycin + Ls-AKG38 (2 doses) | 1.14 ± 0.97 (4/5 sterile) | 1.05 ± 0.69 (4/5 sterile) | 0.89 ± 0.08 (5/5 sterile) | 0.93 ± 0.46 (4/5 sterile) | 1.18 ± 0.61 (4/5 sterile) |

Example 48. Activity of AKG-28 and AKG-38 in Various Species of Nontuberculosis Mycobacteria In Vitro MIC testing was performed by microbroth dilution method (Obregon-Henao et al. (2015) Antimicrobial Agents Chemother 59, 6904-6912) using Mueller Hinton (MH) broth (Cation Adjusted) to the calcium and magnesium ion concentration recommended in the CLSI standard M7-A7 (Becton Dickinson). MIC testing also was performed using the microbroth dilution method using 7H9 broth (Sigma-Aldrich) (Shang et al. (2011) PLoS One 6, e24726; Chan et al. (2010) Am J Respir Cell Mol Biol 43, 287-393). The goal was to optimize the ability to detect more compounds with activity against NTMs by using different broths in our microbroth dilution method. NTMs were grown on 7H11 agar plates (Sigma-Aldrich) for 3-25 days at 35-37° C. in ambient air (depending on bacterial strain). The CFUs were taken from the agar plates and placed in either MH broth with 0.05% tween-80 and grown at 35-37° C. in ambient air until the optical density (OD) absorbance taken after 7 days of growth is an (OD) 0.08-0.1 (0.5 McFarland Standard). The bacterial cell suspensions were then confirmed by preparing them in saline, matching the (OD) 0.08-0.1 (0.5 McFarland Standard).

The broth (MH) 180 µl was added to the first column in the 96 well plates. Then 100 µl of the broth (MH) was added to the other columns in the 96 well plate. Compounds are made using 1.28 mg/mL in DMSO and used immediately for test range 64-0.062 µg/ml and 20 µl of compound added to the first column of wells and 100 µl serially diluted. Finally, 100 µl NTM cell suspension was added in all the wells except the media only control wells. QC agents specific for each organism 1) bacteria only negative control 2) media only negative control 3) or tedizolid positive drug control 4) optional E. coli control.

RGMs were assayed for ODs on day 3. After that, the plate is assayed by using the Resazurin Microtiter Assay Plate method as recommended by the Clinical and Laboratories Standards Institute (Brown-Elliott et al. (2012) Clin Microbiol Rev vol. 25(3), p. 545-582). Briefly, the method used the addition of resazurin (7-Hydroxy-3H-phenoxazin-3-one 10-oxide) to the MIC 96 well plate. Resazurin is a blue dye, itself weakly fluorescent until it is irreversibly reduced to the pink colored and highly red fluorescent resorufin. It was used as an oxidation-reduction indicator in bacterial cell viability MIC assays.

The results show the both AKG-28 and AKG-38 were generally more potent than tedizolid in a range of different NTM species and strains. This included in M.avium, M. chelonae, M. abscessus and M. kansasii. Only in M. massiliense was tedizolid more active in all three strains evaluated.

TABLE 42

| NTM Species | Strain | AKG-28 MIC (µg/mL) | AKG-38 MIC (µg/mL) | Tedizolid MIC (µg/mL) |
|---|---|---|---|---|
| M. avium sbsp. avium | 2285 S | 0.125 | 0.125 | 0.25 |
| M. avium sbsp. avium | 3993 | 0.125 | 0.125 | 0.25 |
| M. avium sbsp. avium | 2285 R | 0.06 | 0.06 | 0.25 |
| M. chelonae | 49 | 0.06 | 0.06 | 0.25 |
| M. chelonae | 69 | 0.5 | 0.5 | 2 |
| M. chelonae | 35752 | 0.125 | 0.06 | 0.125 |

TABLE 42-continued

| NTM Species | Strain | AKG-28 MIC (µg/mL) | AKG-38 MIC (µg/mL) | Tedizolid MIC (µg/mL) |
|---|---|---|---|---|
| M. abscessus sbsp. abscessus | 21 | 0.25 | 0.06 | 0.5 |
| M. abscessus sbsp. abscessus | 1948 | 0.125 | 0.06 | 0.5 |
| M. abscessus sbsp. abscessus | 1513 | 32 | 32 | 4 |
| M. massiliense | CIP 108297 | 1 | 0.5 | 0.25 |
| M. massiliense | CRM0019 | 0.25 | 0.25 | 0.06 |
| M. massiliense | M154 | 0.25 | 0.25 | 0.06 |
| M. kansasii | 662 | >32 | >32 | >32 |
| M. kansasii | 824 | 0.125 | 0.06 | 0.25 |
| M. kansasii | 732 | 0.125 | 0.03 | 0.25 |
| M. kansasii | MK13D6 | 0.125 | 0.03 | 0.25 |
| M. kansasii | WT171017 | 0.125 | 0.03 | 0.125 |

Example 49. Activity of Selected Compounds Against Drug Resistant Strains of Mycobacterium tuberculosis In Vitro Compounds of the present disclosure showing activity against drug-susceptible strains of M. tuberculosis were further evaluated for activity against several multidrug resistant (MDR) clinical isolate strains M70, M28, M94, M14 (Cheng A. F., et al., 2004, Antimicrob. Agents Chemother. v. 48, p. 596-601) and TN5904 (Palanisamay G. S., et al., 2008, Tuberculosis (Edinb.) vol. 88 p. 295-306). These strains are characterized by the following resistance features: TABLE 43. Drug resistance features of the M. tuberculosis MDR strains used in the study. (Abbreviations: R—resistant; S—susceptible; STR—streptomycin, MNN—isoniazid; RIF—rifampin, EMB—ethambutol, PZA—pyrazinamide.

TABLE 43

| Strain\Drug | STR | INH | RIF | EMB | PZA |
|---|---|---|---|---|---|
| M70 | R | R | R | S | R |
| M28 | S | R | R | R | R |
| M14 | R | R | S | S | R |
| M94 | R | R | S | S | S |
| TN5904 | R | R | R | S | R |

MIC of the test compounds, including comparators/resistance controls (RIF, INH, STR, moxifloxacin (MOX), and Linezolid (LNZ)) was determined using broth microdilution method with an Alamar Blue endpoint (MABA) essentially as described in Example 2, with the following modifications. Test compounds and comparators serially diluted by the factor of two in DMSO were added to the wells of a 96-well assay plate containing 100 µL of ADC-supplemented 7H9-glycerol medium. The compounds were diluted in DMSO so as to keep the compound concentration in the desired range and the final DMSO concentration in the well at 2% (M70, M28, M94) or 2.5% (M14, TN5904), except that due to low solubility in DMSO, STR was serially diluted and added as aqueous solution. Bacterial stocks of MDR strains and of the susceptible H37Rv strain (positive control) were taken from the cold storage, thawed and diluted with 7H9-ADC-glycerol medium to provide for the bacterial density of $10^6$ CFU/mL (H37Rv, TN5904), $2 \times 10^6$ CFU/mL (M70, M14), or 3×10⁶ CFU/mL (M28, M94), and 50 μL of the diluted bacterial stocks were added to the compound-containing medium in the wells. The ranges of final drug concentrations in the wells are shown in the Table below. The plates were sealed in Ziplock bags, incubated at 37° C., and monitored for the bacterial growth by periodic optical density reading at 600 nm (OD600). On Day 14 (if OD600 reached or exceeded 0.40) or Day 17 15 μL of Alamar Blue solution was added to the wells, the incubation was continued, and the color of the incubation mixtures was documented three days later (seven days in the case of slow growing M28 strain). The lowest consecutive antimicrobial concentration of the two-fold serial dilutions that did not produce visible color change with Alamar Blue relative to drug-free control wells, was regarded as the MIC for these compounds. The OD600-based MIC determination (>80% OD600 reduction relative to the drug-free control wells) was in agreement with the MABA results. A shift in MIC of two wells (4-fold) was considered significant. The results are summarized in TABLE 44 below.

TABLE 44

Minimum inhibitory concentrations (MIC) of various compounds in drug-susceptible and drug-resistant strains of *M. tuberculosis* in vitro (MABA assay).

| Compound | Concentration range, μg/mL | MIC, μg/mL in *M. tuberculosis* strain: | | | | |
| --- | --- | --- | --- | --- | --- | --- |
| | | H37Rv | M70 | M28 | M94 | M14 | TN5904 |
| RIF | 8-0.03 | 0.06 | >8 | >8 | 0.125 | 0.06 | >8 |
| INH | 2-0.008 | 0.06 | >2 | >2 | >2 | >2 | 2 |
| MOX | 8-0.03 | 0.125 | 1 | 2 | 0.125 | 0.125 | 0.125 |
| STR | 8-0.03 | 0.5 | 2 | 0.125 | >8 | >8 | 1 |
| LNZ | 8-0.03 | 2 | 0.5 | 0.5 | 0.5 | 0.5 | 1 |
| AKG-3 | 4-0.015 | 0.125 | ≤0.015 | 0.06 | 0.06 | 0.03 | 0.06 |
| AKG-16 | 8-0.03 | 0.25 | 0.125 | 0.25 | 0.06 | 0.06 | 0.06 |
| AKG-28 | 1-0.004 | 0.03 | ≤0.004 | 0.015 | 0.015 | 0.015 | 0.015 |
| AKG-29 | 8-0.03 | 0.25 | ≤0.03 | 0.125 | 0.125 | 0.06 | 0.06 |
| AKG-38 | 4-0.015 | 0.03 | ≤<0.015 | 0.03 | 0.03 | 0.03 | 0.03 |
| AKG-39 | 8-0.03 | 0.5 | 0.125 | 0.5 | 1 | 0.5 | 0.25 |

The comparator/control compounds RIF, IHN, MOX, and STR showed the expected in vitro activity against the DR-TB/MDR-TB strains as well as H37Rv. Within the margin of variance of typical MIC assays, all tested compounds of the present disclosure were at least as active against the MDR-TB strains as they were against drug-susceptible strain H37Rv. The highest activity was shown by AKG-28, followed by AKG-38 and AKG-3. Compounds AKG-28 and AKG-38 stood out as the most active ones compared even to their structurally close analogs.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

What is claimed is:

1. A compound of Formula I or a pharmaceutically acceptable salt thereof:

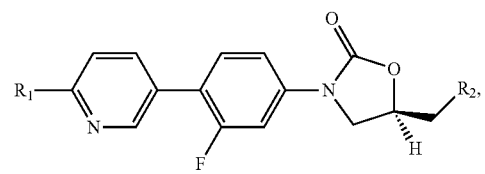

Formula I wherein
$R_1$ is a tetrazole ring substituted at position 2' with an aminoalkyl, and
$R_2$ is an amine.

2. The compound of claim 1, wherein $R_1$ is a tetrazole ring substituted at position 2' with a primary aminoalkyl group.

3. The compound of claim 1, wherein $R_1$ is a tetrazole ring substituted at position 2' with a mono-alkyl-substituted (secondary) aminoalkyl group.

4. The compound of claim 1, wherein $R_1$ is a tetrazole ring substituted at position 2' with a di-alkyl-substituted (tertiary) aminoalkyl group.

5. The compound of claim 1, wherein $R_1$ is a tetrazole ring substituted at position 2' with an alkyl-substituted aminoalkyl group where the amine nitrogen atom and the alkyl chain that substitutes for amine hydrogens form a heterocycle.

6. The compound of claim 1, wherein $R_2$ is $NH_2$.

7. The compound of claim 2, wherein $R_2$ is $NH_2$.

8. The compound of claim 3, wherein $R_2$ is $NH_2$.

9. The compound of claim 4, wherein $R_2$ is $NH_2$.

10. The compound of claim 5, wherein $R_2$ is $NH_2$.

11. The compound of claim 1, wherein $R_1$ is selected from the group consisting of:

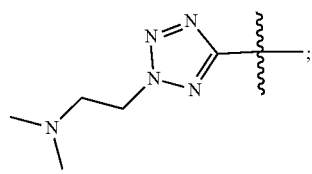

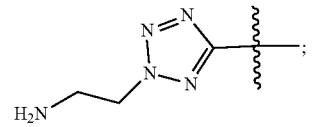

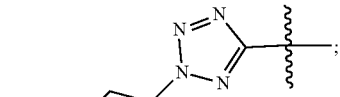

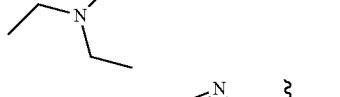

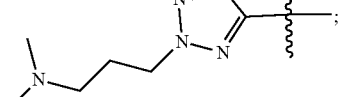; and

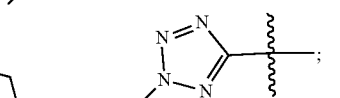

12. The compound of claim 7, wherein $R_1$ is

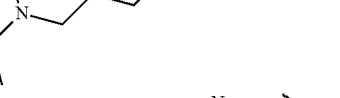

13. The compound of claim 9, wherein $R_1$ is

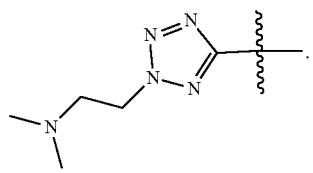 [SMILES: *c1nnn(CCN(C)C)n1]

14. The compound of claim 9, wherein $R_1$ is

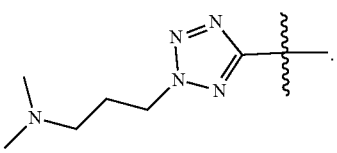 [SMILES: *c1nnn(CCCN(C)C)n1]

15. The compound of claim 9, wherein $R_1$ is

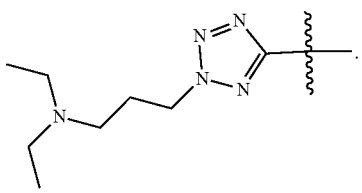 [SMILES: *c1nnn(CCCN(CC)CC)n1]

16. A free base form of a compound of Formula I:

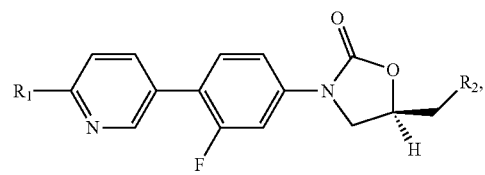

Formula I wherein $R_1$ is a tetrazole ring substituted at position 2' with a di-alkyl-substituted (tertiary) aminoalkyl, and $R_2$ is $NH_2$.

17. The compound of claim 16, wherein $R_1$ is a tetrazole ring substituted at position 2' with a dimethylaminoethyl.

18. The compound of claim 16, wherein $R_1$ is

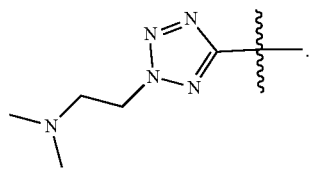 [SMILES: *c1nnn(CCN(C)C)n1]

19. The compound of claim 16, wherein $R_1$ is

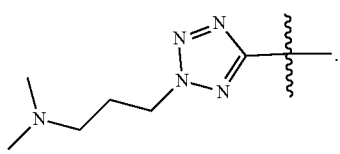

20. The compound of claim 16, wherein $R_1$ is

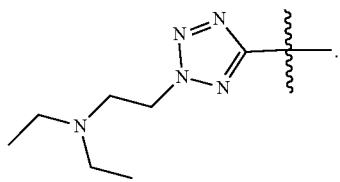 [SMILES: *c1nnn(CCN(CC)CC)n1]

21. The compound of claim 16, wherein $R_1$ is

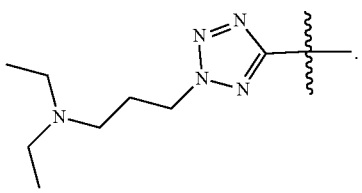 [SMILES: *c1nnn(CCCN(CC)CC)n1]

22. A hydrochloric acid salt of a compound of Formula I:

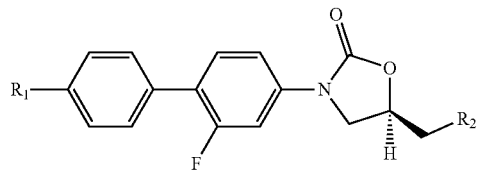

wherein
$R_1$ is selected from the group consisting of:

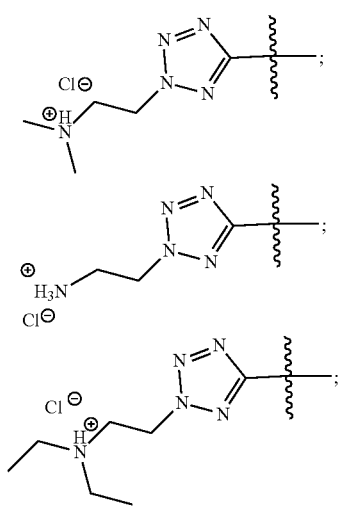

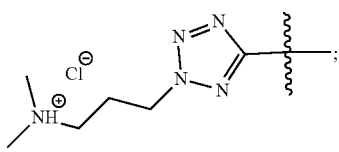

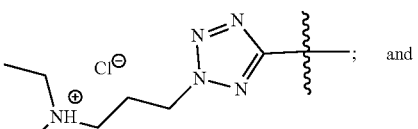

and

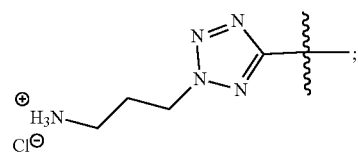

and $R_2$ is $NH_3^+Cl^-$.

23. The compound of claim 22, wherein the compound is

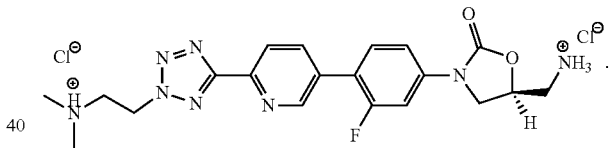

AKG-28

24. The compound of claim 22, wherein the compound is

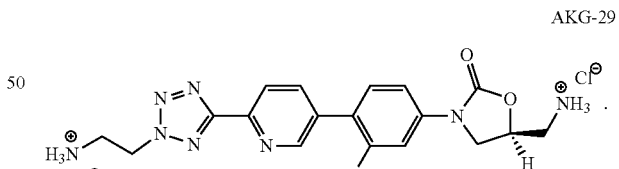

AKG-29

25. The compound of claim 22, wherein the compound is

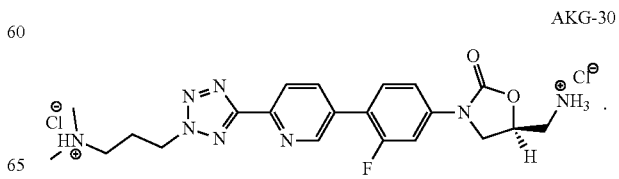

AKG-30

26. The compound of claim 22, wherein the compound is
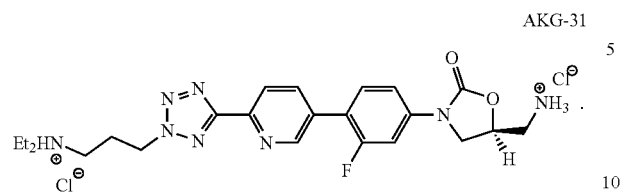
AKG-31
* * * * *